(12) United States Patent
Bostick et al.

(10) Patent No.: US 8,980,589 B2
(45) Date of Patent: *Mar. 17, 2015

(54) MUTANT DELTA-9 ELONGASES AND THEIR USE IN MAKING POLYUNSATURATED FATTY ACIDS

(75) Inventors: Michael W. Bostick, Wilmington, DE (US); Hongxian He, Wilmington, DE (US); Yougen Li, Pennington, NJ (US); Quinn Qun Zhu, West Chester, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 142 days.

This patent is subject to a terminal disclaimer.

(21) Appl. No.: 13/218,591

(22) Filed: Aug. 26, 2011

(65) Prior Publication Data

US 2012/0226062 A1    Sep. 6, 2012

Related U.S. Application Data

(60) Provisional application No. 61/377,248, filed on Aug. 26, 2010.

(51) Int. Cl.
| | |
|---|---|
| C12P 21/06 | (2006.01) |
| C12P 7/64 | (2006.01) |
| C12N 9/10 | (2006.01) |
| C12N 15/81 | (2006.01) |

(52) U.S. Cl.
CPC ............ C12N 9/1029 (2013.01); C12N 15/815 (2013.01); C12P 7/6472 (2013.01); C12Y 203/01016 (2013.01)
USPC .......... 435/134; 435/183; 435/193; 536/23.1; 536/23.2

(58) Field of Classification Search
None
See application file for complete search history.

(56) References Cited

U.S. PATENT DOCUMENTS

| 7,645,604 B2 | 1/2010 | Damude et al. |
| 7,794,701 B2 | 9/2010 | Damude et al. |
| 2007/0118929 A1 | 5/2007 | Damude et al. |
| 2008/0254195 A1 | 10/2008 | Damude et al. |
| 2009/0320161 A1 | 12/2009 | McGonigle et al. |
| 2010/0317072 A1 | 12/2010 | Hong et al. |

FOREIGN PATENT DOCUMENTS

| WO | 02077213 A2 | 10/2002 |
| WO | 2004057001 A2 | 7/2004 |
| WO | 2005012316 A2 | 2/2005 |
| WO | 2005083093 A2 | 9/2005 |
| WO | 2007061742 A1 | 5/2007 |

OTHER PUBLICATIONS

Related Application U.S. Appl. No. 13/218,708, filed Aug. 26, 2011.
Related Application U.S. Appl. No. 13/218,673, filed Aug. 26, 2011.
NCBI Genbank Accession No. AAL37626, Long Chain Polyunsaturated Fatty Acid Elongation Enzyme (*Isochrysis galbana*), Mar. 9, 2006.
Qi, B. et al., The Variant 'His-Box' of the C18-Delta 9-PUFA-Specific Elongase Igase1 From *Isochrysis Galbana* is Essential for Optimum Enzyme Activity, FEBS Letters, vol. 547 (2003), pp. 137-139.
International Search Report, PCT International Application PCT/US2011/049361, Mailed Dec. 9, 2011.
Related International Application, PCT International Application No. PCT/US2011/049403, Filed Aug. 26, 2011.
Related International Application, PCT International Application No. PCT/US2011/04938, Filed Aug. 26, 2011.

*Primary Examiner* — Richard Hutson

(57) ABSTRACT

Mutant delta-9 elongases having the ability to convert linoleic acid [18:2, LA] to eicosadienoic acid [20:2, EDA] and/or α-linolenic [18:3, ALA] to eicosatrienoic acid [20:3, ETrA] are disclosed herein. Isolated nucleic acid fragments and recombinant constructs comprising such fragments encoding mutant delta-9 elongases, along with a method of making long chain polyunsaturated fatty acids ["PUFAs"] using these mutant delta-9 elongases in oleaginous yeast are also disclosed.

14 Claims, 15 Drawing Sheets

```
              290       300       310       320       330       340       350
               |    .    |    .    |    .    |    .    |    .    |    .    |    .    |
Cd_elo    LSALG-----PSMQKFLWWKKYITMLQLVQFVLATYHTARSLYVKCPSP----------VRMEWALI 239
Om_elo    LSAV------PALRPYLWWRKYITQVQLIQFPLTMSQTICAVIWPCDFP----------RGWLYFQI 236
Mp_elo1   LAATLGKNEKLARRKYLWWGKYLITQLQMFQFVLNMIQAYYDIKANSPYP---------QFLIQILF 256
Pp_elo1   LAACLRSSPKLENKYLFWGRYLTQFQMPQFMLMLVQAYYDMKTNAPYP----------QWLIKILF 258
Mp_d5e    LAATVARDEKRRKYLFWGKYLTIIQMLQFLSFIGQAIYAMWFFBYYP-----------KGFGRMLP 318
Ot_elo1   LSTLIGKEDPKRSMYLWWGRHLTQMQMLQFFFNVLQALYCAS-FSTYP-----------KFLSKILL 263
Pav_elo2  MALLG-------WSCPWKRYLTQAQLVQFCICLAHSTWAAV-TGAYP-----------WRICLVEY 234
Ps_elo1   MALLG-------WSCPWKRYLTQAQLVQFCICLAHATWAAA-TGVYP-----------FHICLVEI 256
Ot_elo2   MSALG-------IRCPWKRYITQAQMLQFVIVFABAVFVLR-QKHCP-----------VTLPWAQM 250
Ea_d9e    TRLIK-------INPPMPKNLITSMQIIQFMVGPYIVWKYRNVPCYRQDG--------MRMFAWIFNY 228
Bg_elo1   TRLIK-------INPPMPKSLITSKQIIQPNVGFYIVWKYRNIPCYRQDG--------MRMFGWFFNY 228
E389_d9e  TRIMK-------MNPPMPKQLITAMQITQFMVGFYLVWYYKDIPCYRKDP--------MRMLAWIFNY 232
Ig_d9e    LITAAG------VSPKA-KPLITDAMQICQPVGGFLLVWDYINVPCFNSDK--------GKLFSWAPNY 232
Tp_elo2   LALIL-------YSCPWKRYLTQAQLLQFTSVVVTGCTGYTHYHKGADETQPSLGTYFCCGVQV 273
Tp_elo1   ICMHTADSKTGKSLPIWWKSSLITAFQLLQFTIMSQATYLVFHGCDKVS---------LRITIVYP 245
Ma_d6e    RSAAG-------VRIWWRQYLSTTLQIVQFVLDLGFIYFCAYTYFAPTYFPWAPNVGKCAGTEGAALRGC 265
Th_elo2   RPFPEG------LRPLITQLQTVQFIFSIGIHTAIYWHYDCEPLVHT-----------HFWBYVTPY 243
Trace_1   LXXXXXeaXXXXaxdldWXqKatrXfQtfQPEXXXXfsKXXXXXXXXXXP--------XXfXXXXXf 323
Trace_2   MXXLG-------fsCPWKRYaTQAQfaQFFIfABKXdXXX-sXXfP-----------fsaXfXaf 260
Trace_3   XsXXX-------fsfXXXXXKlLITAMQIKQfXKGPfaVWKYKsaPCdssDX--------XqfLXWXFNY 249
Trace_4   XXXXXXXkagahgaaKffqXXaTXXQasQFXXXfXXXXfXXXXXXXXXXaXXXXXXfhXXXXXXf 285
                                  |----TM3----|
```

FIG. 3E

```
              360         370         380         390         400         410         420
       ....|....|....|....|....|....|....|....|....|....|....|....|....|....|....|....|
Cl_elo         LYAFSFILLFSNFYMHAYIKKSRRGK----ENGSRG-------KGGVSNGKEKLHANGKTD-------------- 289
Om_elo         FYVITLIALFSNFYIQTYKKHLVSQKKEYHQKKEYHQKKPAKIKSKKAE---------------------------- 295
Mp_elo1        YMISLLALFGNFYVHKYVSAPAKPAKIKSKKAE------------------------------------------- 290
Pp_elo1        YMISLLFLFGNFYVQKYIKP--SDGKQGAKTE-------------------------------------------- 290
Mp_d5e         FYSVSLLAFFGNFFVKKYSNA----SQPKTVKVE------------------------------------------ 348
Ot_elo1        VYMMSLLGLFGHFYYSKHIAA----AKLQKKQQ------------------------------------------- 292
Pav_elo2       WVMVSMLVLFTRFYRQAYAKE----AKAKBAKK-------LAQEASQAKAVKAE---------------------- 277
Ps_elo2        WVMVSMLYLFTKFYNSAYKGA----AKGAAASSNG-----AAAPSGAKPKSIKAN--------------------- 302
Ot_elo2        FVMTNMLVLFGNFYLKAYSNK----SRGDGASSVKPAETTRAPSVRRTRSRKID---------------------- 300
Ea_d9e         WYVGTVLLLFLNFYVQTYIRK----PRKNRGKKE------------------------------------------ 258
Eg_elo1        FYVGTVLCLFLNFYVQTYIVR----KHKGAKKIQ------------------------------------------ 258
E389_d9e       WYVGTVLLLPINFYVKSYVFP----KPKTADKKVQ----------------------------------------- 263
Ig_d9e         AYVGSVFLLFCHEFQDNLAT-----KKSAKAGKQL----------------------------------------- 263
Tp_elo2        FEMVSLFVLFSIFYKRSYSKKNKSGGKDSKKNDDGNNEDQCHKAMKDISEGAKEVGHAAKDAGKLVATA------- 343
Tp_elo1        VSLLSLFFLFAQFFVQSYMAP----KKKKSA--------AKAAEKRGSNFTPKTVKSGGSPKKPSKSKHI------ 272
Ma_d6e         GLLSSYLLLFINFYRITYNAK----AKAAEKRGSNFTPKTVKSGGSPKKPSKSKHI-------------------- 317
Th_elo2        LFVVPFLILFLNFYLQQYVLAP---AKTKKA--------------------------------------------- 271
Trace_1        fYXfsfaxfFXsFdfsXXXXXXsXXXXsXXXXXsXXXsXhsaphqXXhasXXssXXqXsXXqXk------------ 382
Trace_2        dVMXsMLfLFXsFYXsAYXKX----XqhXXAsXXXhksXXXAsXXXAXsXXsXXAXsXXsXqXXKKs--------- 310
Trace_3        XYVGsVffLFfsPdfssXaXX----XXsXXXXXXX----------------------------------------- 280
Trace_4        XXfXffLFXXfdXXsYXXXXqshXfKXXsXXsXsXssfqshXsXXsXXXssXahqhhqkhhqaahsh--------- 355
                                  *
                           |_____TM4_____|
```

FIG. 3F

| | | |
|---|---|---|
| Ct_elo | | 289 |
| Om_elo | | 295 |
| Mp_elo1 | | 290 |
| Pp_elo1 | | 290 |
| Mp_d5e | | 348 |
| Ot_elo1 | | 292 |
| Pav_elo2 | | 277 |
| Ps_elo2 | | 302 |
| Ot_elo2 | | 300 |
| Ea_d9e | | 258 |
| Eg_elo1 | | 258 |
| E389_d9e | | 263 |
| Ig_d9e | | 263 |
| Tp_elo2 | SKAVRKGTRVTGAM | 358 |
| Tp_elo1 | | 272 |
| Ma_d6e | | 317 |
| Th_elo2 | | 271 |
| Trace_1 | | 382 |
| Trace_2 | | 310 |
| Trace_3 | | 280 |
| Trace_4 | sqhaqqgbaqashhf | 370 |

FIG. 3G

Abbreviations

Ct_elo = SEQ ID NO:43
Om_elo = SEQ ID NO:44
Mp_elo1 = SEQ ID NO:45
Pp_elo1 = SEQ ID NO:46
Mp_d5e = SEQ ID NO:47
Ot_elo1 = SEQ ID NO:48
Pav_elo2 = SEQ ID NO:49
Ps_elo2 = SEQ ID NO:50
Ot_elo2 = SEQ ID NO:51
Ea_d9e = SEQ ID NO:12
Eg_d9e = SEQ ID NO:8
E398_d9e = SEQ ID NO:4
Ig_d9e = SEQ ID NO:2
Tp_elo2 = SEQ ID NO:52
Tp_elo1 = SEQ ID NO:53
Ma_d6e = SEQ ID NO:54
Th_elo2 = SEQ ID NO:55

FIG. 3H

MUTANT DELTA-9 ELONGASES AND THEIR USE IN MAKING POLYUNSATURATED FATTY ACIDS

This application claims the benefit of U.S. Provisional Application No. 61/377,248, filed Aug. 26, 2010, which is herein incorporated by reference in its entirety.

FIELD OF THE INVENTION

This invention is in the field of biotechnology. More specifically, this invention pertains to the creation of polynucleotide sequences encoding mutant delta-9 fatty acid elongases and the use of these elongases in making long-chain polyunsaturated fatty acids ["PUFAs"].

BACKGROUND OF THE INVENTION

A variety of different hosts including plants, algae, fungi, stramenopiles and yeast are being investigated as means for commercial polyunsaturated fatty acid ["PUFA"] production. Genetic engineering has demonstrated that the natural abilities of some hosts (even those natively limited to linoleic acid ["LA"; 18:2 omega-6] and α-linolenic acid ["ALA"; 18:3 omega-3] fatty acid production) can be substantially altered to result in high-level production of various long-chain omega-3/omega-6 PUFAs. Whether this is the result of natural abilities or recombinant technology, production of arachidonic acid ["ARA"; 20:4 omega-6], eicosapentaenoic acid ["EPA"; 20:5 omega-3], docosapentaenoic acid ["DPA"; 22:5 omega-3] and docosahexaenoic acid ["DHA"; 22:6 omega-3] may all require expression of a delta-9 elongase gene.

Characterized delta-9 elongases have the ability to convert LA to eicosadienoic acid ["EDA"; 20:2 omega-6], and ALA to eicosatrienoic acid ["ETrA"; 20:3 omega-3]. However, only a few delta-9 elongases have been identified. These include the delta-9 elongases from *Isochrysis galbana* ["IgD9e"] (SEQ ID NOs:1 and 2; PCT Publications No. WO 2002/077213, No. WO 2005/083093, No. WO 2005/012316 and No. WO 2004/057001; GenBank Accession No. AAL37626), *Eutreptiella* sp. CCMP389 ["E389D9e"] (SEQ ID NOs:3 and 4; U.S. Pat. No. 7,645,604), *Euglena gracilis* ["EgD9e"] (SEQ ID NOs:7 and 8; U.S. Pat. No. 7,645,604) and *Euglena anabaena* ["EaD9e"] (SEQ ID NOs:11 and 12; U.S. Pat. No. 7,794,701). Although U.S. Pat. No. 7,645,604 identified seven motifs that were conserved between and among EgD9e, E389D9e and IgD9e elongases, only a single study has been performed with IgD9e in attempt to identify important amino acid residues to delta-9 elongase functionality (Qi, B., et al., *FEBS Lett.*, 547:137-139 (2003)). There are no crystal structures available from delta-9 elongases to guide genetic evolution of the protein and little is known about the relationship between delta-9 elongase sequence, structure and function. Despite this lack of knowledge, there remains a need for delta-9 elongase genes that are efficiently expressed with high enzyme activities in production host cells capable of making PUFAs.

New delta-9 elongase mutants having high activity that are well suited for integration into PUFA biosynthetic pathways in commercially useful host cells have been discovered. Surprisingly and unexpectedly, it was found that specific point mutations resulted in delta-9 elongase mutants whose enzymatic activity was from 96% to 145% of the wildtype enzyme, based on the conversion of LA to EDA.

SUMMARY OF THE INVENTION

In a first embodiment, the invention concerns an isolated polynucleotide comprising:

(a) a nucleotide sequence encoding a mutant polypeptide having delta-9 elongase activity and having an amino acid sequence as set forth in SEQ ID NO:22, wherein SEQ ID NO:22 differs from SEQ ID NO:10 by at least one amino acid mutation, said mutation(s) selected from the group consisting of:
  i) a L35F mutation;
  ii) a L35M mutation;
  iii) a L35G mutation;
  iv) a L35G mutation and at least one other mutation selected from the group consisting of: S9A, S9D, S9G, S9I, S9K, S9Q, Q12K, A21D, A21T, A21V, V32F, Y84C, Q107E, L108G, G127L, W132T, M143N, M143W, L161T, L161Y, W168G, I179M, I179R, C236N, Q244N, A254W and A254Y;
  v) L35G, W132T and I179R mutations;
  vi) L35G, S9D, Y84C and I179R mutations;
  vii) L35G, A21V, L108G and I179R mutations;
  viii) L35G, Y84C, I179R and Q244N mutations;
  ix) L35G, A21V, W132T, I179R and Q244N mutations;
  x) K58R and I257T mutations;
  xi) a D98G mutation;
  xii) L130M and V243A mutations; and,
  xiii) any combination comprising at least two mutations, wherein the mutations are selected from the group consisting of: K58R, L35F, L35G, L35M, S9A, S9D, S9G, S9I, S9K, S9Q, Q12K, A21D, A21T, A21V, V32F, Y84C, D98G, Q107E, L108G, G127L, L130M, W132T, M143N, M143W, L161T, L161Y, W168G, I179M, I179R, C236N, V243A, Q244N, A254W, A254Y and I257T;

(b) a complement of the nucleotide sequence of part (a), wherein the complement and the nucleotide sequence consist of the same number of nucleotides and are 100% complementary.

The isolated polynucleotide may have a nucleotide sequence selected from the group consisting of SEQ ID NO:28, SEQ ID NO:31, SEQ ID NO:34, SEQ ID NO:37, SEQ ID NO:40, SEQ ID NO:58, SEQ ID NO:61, SEQ ID NO:86, SEQ ID NO:95, SEQ ID NO:96, SEQ ID NO:97, SEQ ID NO:100, SEQ ID NO:103, SEQ ID NO:106 and SEQ ID NO:109.

In a second embodiment, the invention concerns a mutant polypeptide having delta-9 elongase activity encoded by the isolated polynucleotide of claim 1. The mutant polypeptide may have a protein sequence selected from the group consisting of: SEQ ID NO:29, SEQ ID NO:32, SEQ ID NO:35, SEQ ID NO:38, SEQ ID NO:41, SEQ ID NO:59, SEQ ID NO:62, SEQ ID NO:87, SEQ ID NO:101, SEQ ID NO:104, SEQ ID NO:107 and SEQ ID NO:110.

In a third embodiment, the mutant polypeptide will have delta-9 elongase activity at least about functionally equivalent to the delta-9 elongase activity of the polypeptide as set forth in SEQ ID NO:10. Preferably, the percent substrate conversion of linoleic acid to eicosadienoic acid of the mutant polypeptide is at least 110% when compared to the percent substrate conversion of linoleic acid to eicosadienoic acid of the polypeptide as set forth in SEQ ID NO:10 (i.e., corresponding in at least a 10% improvement in activity), and more preferably, the percent substrate conversion of linoleic acid to eicosadienoic acid of the mutant polypeptide is at least 120% (i.e., corresponding in at least a 20% improvement in activity). In a fourth embodiment, the invention concerns a recombinant construct comprising the isolated polynucleotide of claim 1, operably linked to at least one regulatory sequence.

In a fifth embodiment, the invention concerns a transformed cell comprising the isolated polynucleotide of the invention. The transformed cell may preferably be selected from the group consisting of: plants, bacteria, yeast, algae, euglenoids, stramenopiles, oomycetes and fungi.

In a sixth embodiment, the invention concerns a transformed oleaginous yeast producing at least about 25% of its dry cell weight as oil, comprising:
  (a) at least one recombinant DNA construct comprising the isolated polynucleotide of the invention; and,
  (b) at least one recombinant DNA construct comprising an isolated polynucleotide operably linked to at least one regulatory sequence, the construct encoding a polypeptide selected from the group consisting of: delta-4 desaturase, delta-5 desaturase, delta-8 desaturase, delta-6 desaturase, delta-9 desaturase, delta-12 desaturase, delta-15 desaturase, delta-17 desaturase, $C_{14/16}$ elongase, $C_{16/18}$ elongase, $C_{18/20}$ elongase and $C_{20/22}$ elongase;
wherein the transformed oleaginous yeast may produce a long-chain polyunsaturated fatty acid selected from the group consisting of: arachidonic acid, eicosadienoic acid, eicosapentaenoic acid, eicosatetraenoic acid, eicosatrienoic acid, dihomo-γ-linolenic acid, docosatetraenoic acid, docosapentaenoic acid and docosahexaenoic acid.

More particularly, the transgenic oleaginous yeast of the invention is *Yarrowia lipolytica*.

In a seventh embodiment, the invention concerns a method for producing a polyunsaturated fatty acid comprising:
  a) providing an oleaginous yeast comprising:
    i) a recombinant construct, operably linked to at least one regulatory sequence, wherein said recombinant construct comprises an isolated polynucleotide encoding a mutant polypeptide having delta-9 elongase activity and having an amino acid sequence as set forth in SEQ ID NO:22, wherein SEQ ID NO:22 differs from SEQ ID NO:10 by at least one amino acid mutation, said mutation(s) selected from the group consisting of:
      (a) a L35F mutation;
      (b) a L35M mutation;
      (c) a L35G mutation;
      (d) a L35G mutation and at least one other mutation selected from the group consisting of: S9A, S9D, S9G, S9I, S9K, S9Q, Q12K, A21D, A21T, A21V, V32F, Y84C, Q107E, L108G, G127L, W132T, M143N, M143W, L161T, L161Y, W168G, I179M, I179R, C236N, Q244N, A254W and A254Y;
      (e) L35G, W132T and I179R mutations;
      (f) L35G, S9D, Y84C and I179R mutations;
      (g) L35G, A21V, L108G and I179R mutations;
      (h) L35G, Y84C, I179R and Q244N mutations;
      (i) L35G, A21V, W132T, I179R and Q244N mutations;
      (j) K58R and I257T mutations;
      (k) a D98G mutation;
      (l) L130M and V243A mutations; and,
      (m) any combination comprising at least two mutations, wherein the mutations are selected from the group consisting of: K58R, L35F, L35G, L35M, S9A, S9D, S9G, S9I, S9K, S9Q, Q12K, A21D, A21T, A21V, V32F, Y84C, D98G, Q107E, L108G, G127L, L130M, W132T, M143N, M143W, L161T, L161Y, W168G, I179M, I179R, C236N, V243A, Q244N, A254W, A254Y and I257T; and,
    ii) a source of substrate fatty acid selected from the group consisting of linoleic acid and alpha-linolenic acid;
  b) growing the yeast of step (a) under conditions wherein the recombinant construct encoding a mutant polypeptide having delta-9 elongase activity is expressed and the substrate fatty acid is converted to product fatty acid, wherein linoleic acid is converted to eicosadienoic acid and alpha-linolenic acid is converted to eicosatrienoic acid; and,
  c) optionally recovering the product fatty acid of step (b).

In an eighth embodiment, the invention concerns microbial oil obtained from the oleaginous yeast of the invention.

In a ninth embodiment, the invention concerns a recombinant microbial host cell producing an oil comprising at least 22.5 weight percent of eicosapentaenoic acid measured as a weight percent of dry cell weight, said recombinant microbial host cell comprising at least one mutant delta-9 elongase polypeptide of the invention.

BIOLOGICAL DEPOSITS

The following biological material has been deposited with the American Type Culture Collection (ATCC), 10801 University Boulevard, Manassas, Va. 20110-2209, and bears the following designation, accession number and date of deposit.

| Biological Material | Accession No. | Date of Deposit |
|---|---|---|
| *Yarrowia lipolytica* Y8412 | ATCC PTA-10026 | May 14, 2009 |

The biological material listed above was deposited under the terms of the Budapest Treaty on the International Recognition of the Deposit of Microorganisms for the Purposes of Patent Procedure. The listed deposit will be maintained in the indicated international depository for at least 30 years and will be made available to the public upon the grant of a patent disclosing it. The availability of a deposit does not constitute a license to practice the subject invention in derogation of patent rights granted by government action.

*Yarrowia lipolytica* Y9502 was derived from *Yarrowia lipolytica* Y8412, according to the methodology described in U.S. Pat. Appl. Pub. No. 2010-0317072-A1.

BRIEF DESCRIPTION OF THE DRAWINGS AND SEQUENCE LISTINGS

FIG. 1 is an alignment of the delta-9 elongases of *Isochrysis galbana* ["IgD9e"] (SEQ ID NO:2), *Eutreptiella* sp. CCMP389 ["E389D9e"] (SEQ ID NO:4), *Euglena gracilis* ["EgD9e"] (SEQ ID NO:8) and *Euglena anabaena* ["EaD9e"] (SEQ ID NO:12) using Vector NTI®'s AlignX program (Invitrogen Corporation, Carlsbad, Calif.).

FIGS. 3A, 3B, 3C, 3D, 3E, 3F, 3G and 3H are an alignment of seventeen fatty acid elongases from *Ciona intestinalis* (SEQ ID NO:43), *Oncorhynchus mykiss* (SEQ ID NO:44), *Marchantia polymorpha* (SEQ ID NO:45), *Physcomitrella patens* (SEQ ID NO:46), *Marchantia polymorpha* (SEQ ID NO:47), *Ostreococcus tauri* (SEQ ID NO:48), *Pavlova* sp. CCMP459 (SEQ ID NO:49), *Pavlova salina* (SEQ ID NO:50), *Ostreococcus tauri* (SEQ ID NO:51), *Euglena anabaena* (SEQ ID NO:12), *Euglena gracilis* (SEQ ID NO:8), *Eutreptiella* sp. CCMP389 (SEQ ID NO:4), *Isochrysis galbana* (SEQ ID NO:2), *Thalassiosira pseudonana* (SEQ ID NO:52), *Thalassiosira pseudonana* (SEQ ID NO:53), *Mortierella alpina* (SEQ ID NO:54) and *Thraustochytrium* sp. FJN-10 (SEQ ID NO:55) using a ClustalW method of alignment.

Figure 4A:
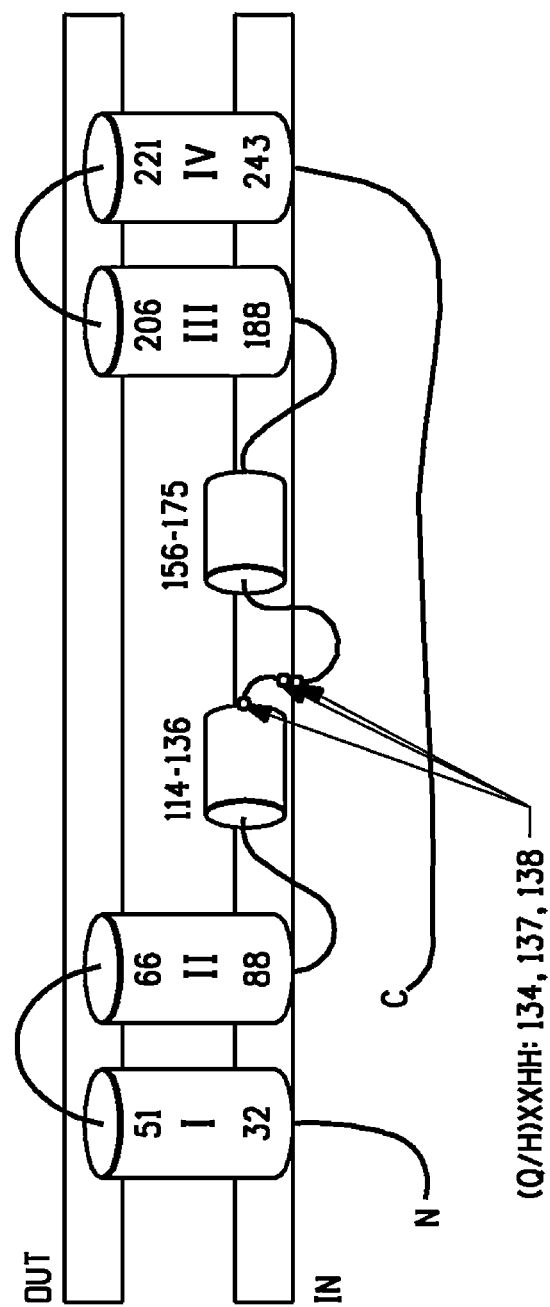

FIG. 4A shows a membrane topology model of EgD9eS; each vertical cylinder indicates a membrane-spanning segment, while each horizontal cylinder indicates a hydrophobic stretch that lies in or near the inner membrane leaflet.

Figure 4B:
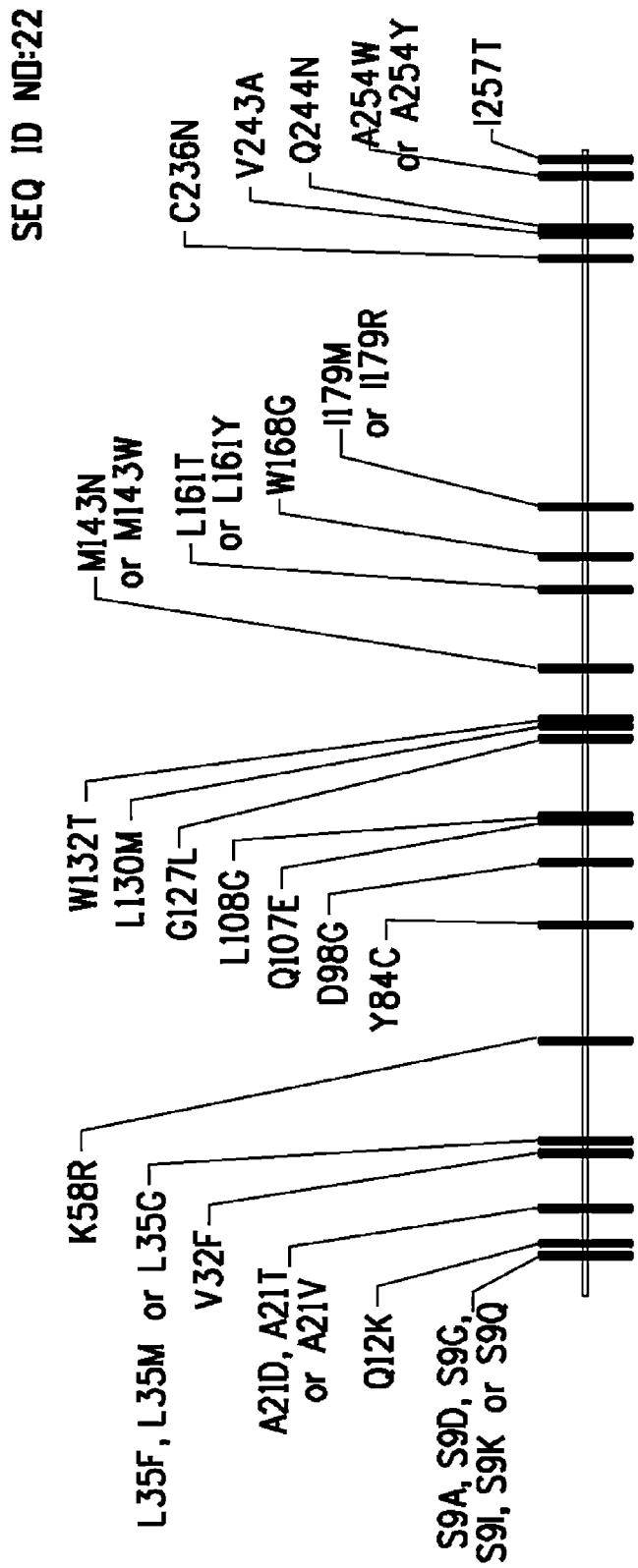

FIG. 4B shows a representation of the synthetic mutant delta-9 elongase, derived from *Euglena gracilis* (i.e., "EgD9eS-mutant consensus"; SEQ ID NO:22) optionally comprising: a L35F mutation; a L35M mutation; a L35G mutation; a L35G mutation and at least one other mutation selected from the group consisting of: S9A, S9D, S9G, S9I, S9K, S9Q, Q12K, A21 D, A21T, A21V, V32F, Y84C, Q107E, L108G, G127L, W132T, M143N, M143W, L161T, L161Y, W168G, I179M, I179R, C236N, Q244N, A254W and A254Y; L35G, A21V, L108G and I179R mutations; L35G, W132T and I179R mutations; L35G, S9D, Y84C and I179R mutations; L35G, Y84C, I179R and Q244N mutations; L35G, A21V, W132T, I179R and Q244N mutations; K58R and I257T mutations; a D98G mutation; L130M and V243A mutations; and, any combination comprising at least two mutations, wherein the mutations are selected from the group consisting of: K58R, L35F, L35G, L35M, S9A, S9D, S9G, S9I, S9K, S9Q, Q12K, A21D, A21T, A21V, V32F, Y84C, D98G, Q107E, L108G, G127L, L130M, W132T, M143N, M143W, L161T, L161Y, W168G, I179M, I179R, C236N, V243A, Q244N, A254W, A254Y and I257T.

Figure 5A:
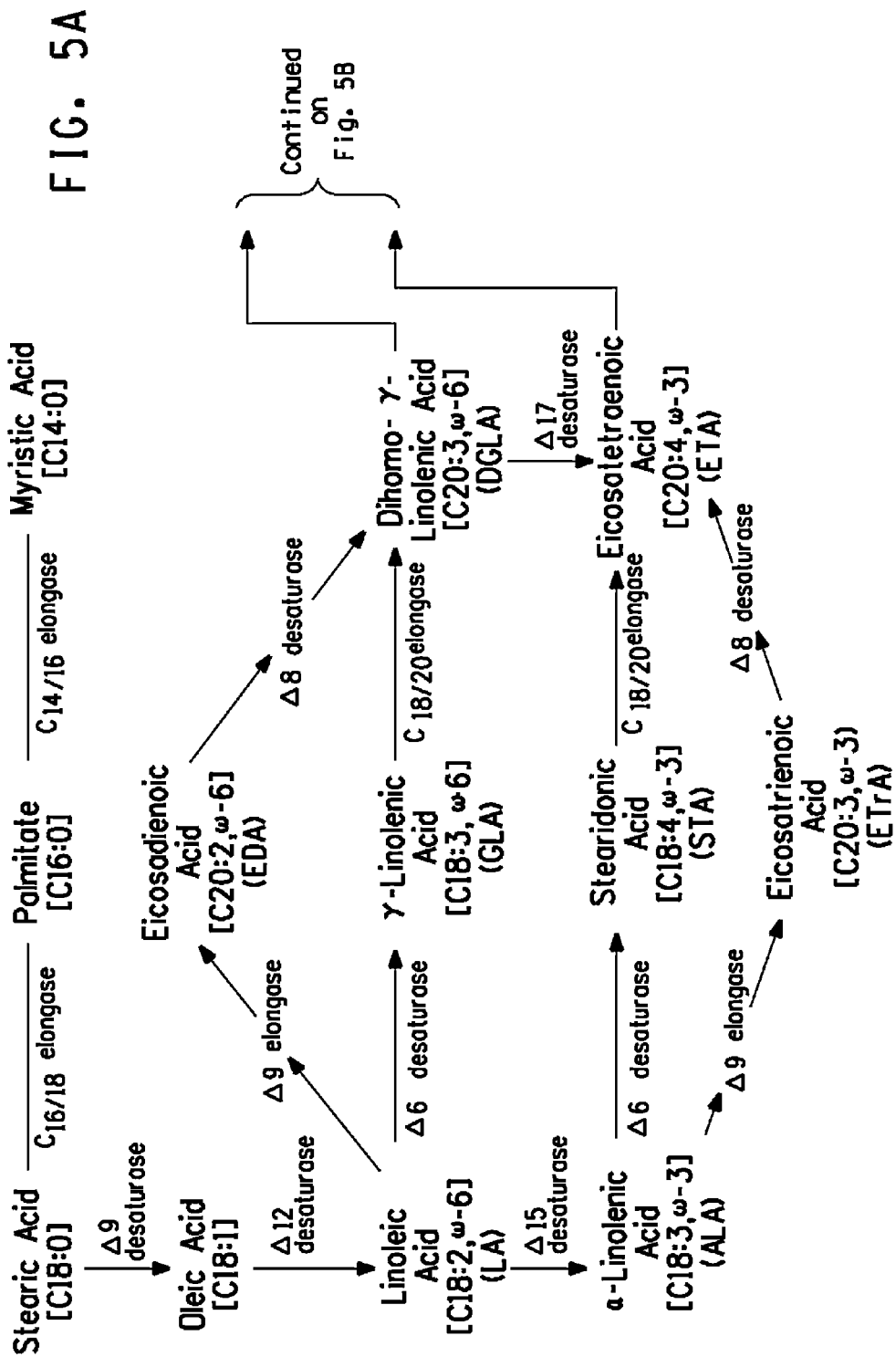
Figure 5B:
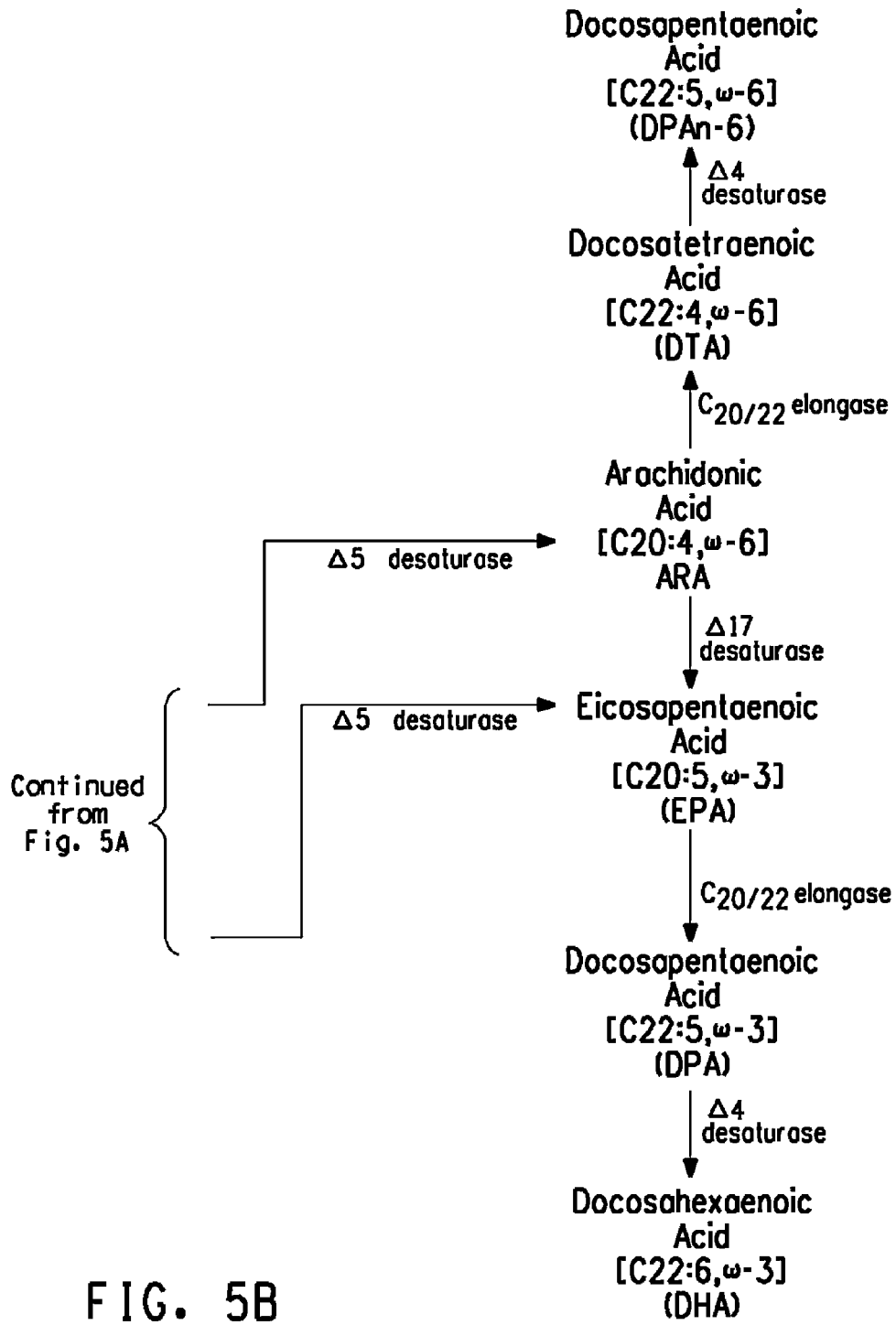

FIG. 5A and FIG. 5B illustrate the omega-3 and omega-6 fatty acid biosynthetic pathway, and should be viewed together.

Figure 6:
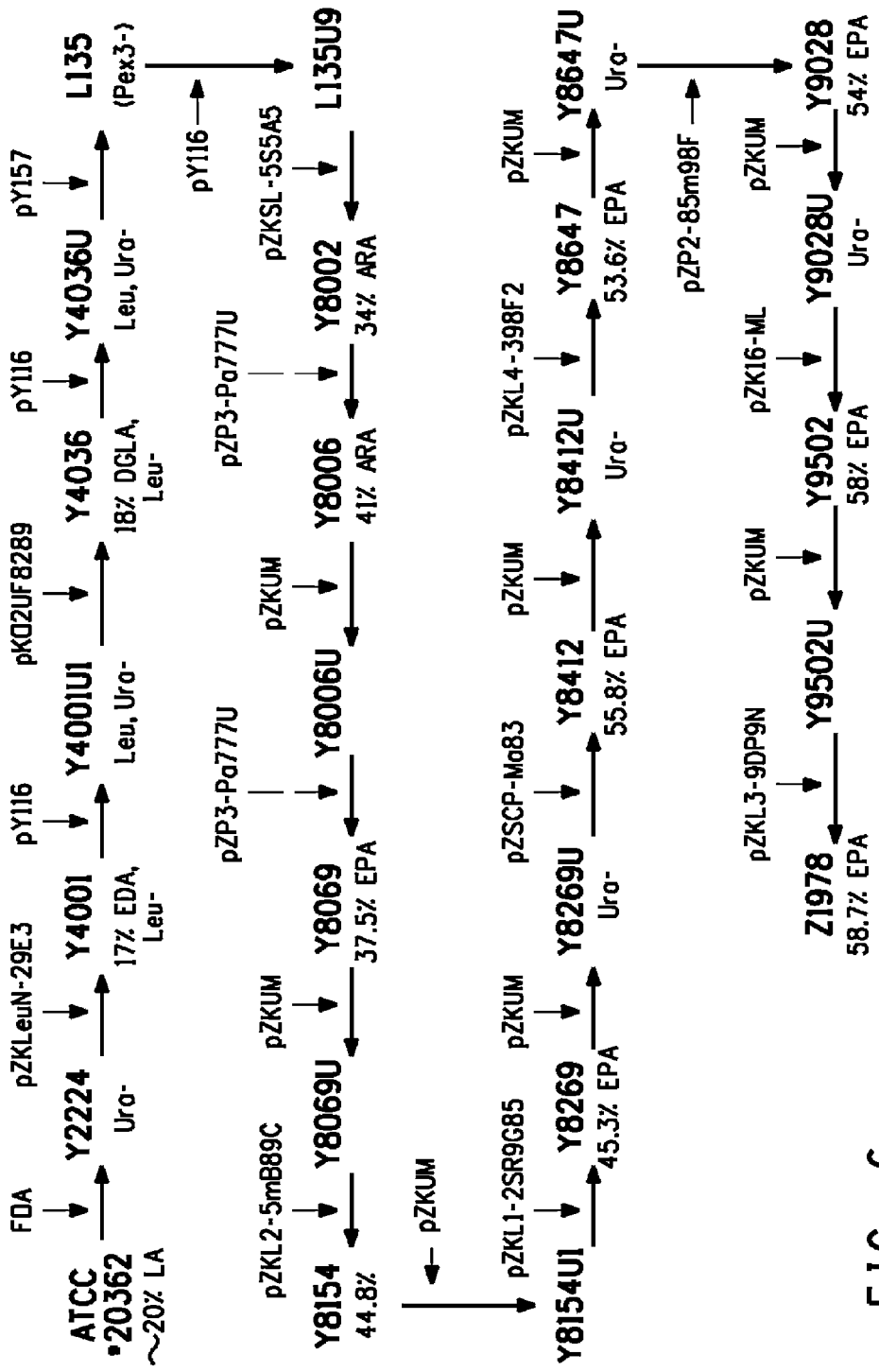

FIG. 6 diagrams the development of *Yarrowia lipolytica* strain Z1978, producing greater than 58.7% EPA in the total lipid fraction.

FIG. 7 provides plasmid maps for the following: (A) pZKUM; and, (B) pZKL3-9DP9N.

The invention can be more fully understood from the following detailed description and the accompanying sequence descriptions, which form a part of this application.

The following sequences comply with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1-111 are ORFS encoding genes, proteins (or portions thereof), primers or plasmids, as identified in Table 1.

TABLE 1

Summary Of Nucleic Acid And Protein SEQ ID Numbers

| Description | Nucleic acid SEQ ID NO. | Protein SEQ ID NO. |
|---|---|---|
| *Isochrysis galbana* delta-9 elongase ("IgD9e") | 1 (1064 bp) | 2 (263 AA) |
| *Eutreptiella* sp. CCMP389 delta-9 elongase ("E389D9e") | 3 (792 bp) | 4 (263 AA) |
| Synthetic delta-9 elongase, derived from *Eutreptiella* sp. CCMP389 delta-9 elongase, codon-optimized for expression in *Yarrowia lipolytica* ("E389D9eS") | 5 (792 bp) | 6 (263 AA) |
| *Euglena gracilis* delta-9 elongase ("EgD9e") | 7 (777 bp) | 8 (258 AA) |
| Synthetic delta-9 elongase, derived from *Euglena gracilis*, codon-optimized for expression in *Yarrowia lipolytica* ("EgD9eS") | 9 (777 bp) | 10 (258 AA) |
| *Euglena anabaena* delta-9 elongase ("EaD9e") | 11 (774 bp) | 12 (258 AA) |
| Synthetic delta-9 elongase, derived from *Euglena anabaena*, codon-optimized for expression in *Yarrowia lipolytica* ("EaD9eS") | 13 (774 bp) | 14 (258 AA) |
| Delta-9 Elongase Motif #1: Y-N-X-(L or F)-$X_4$-S-$X_2$-S-F | — | 15 |
| Delta-9 Elongase Motif #2: F-Y-X-S-K-$X_2$-(E or D)-Y-X-D-(T or S)-$X_2$-L | — | 16 |
| Delta-9 Elongase Motif #3: L-(Q or H)-X-F-H-H-X-G-A | — | 17 |
| Delta-9 Elongase Motif #4: M-Y-X-Y-Y-X$_7$-(K or R or N)-F | — | 18 |
| Delta-9 Elongase Motif #5: K-X-L-(I or L or M)-T-$X_2$-Q | — | 19 |
| Delta-9 Elongase Motif #6: W-X-F-N-Y-X-Y | — | 20 |
| Delta-9 Elongase Motif #7: Y-X-G-X-V-$X_2$-L-F | — | 21 |
| Synthetic mutant delta-9 elongase, derived from *Euglena gracilis* ("EgD9eS-mutant consensus") optionally comprising: a L35F mutation; a L35M mutation; a L35G mutation; a L35G mutation and at least one other mutation selected from the group consisting of: S9A, S9D, S9G, S9I, S9K, S9Q, Q12K, A21D, A21T, A21V, V32F, Y84C, Q107E, L108G, G127L, W132T, M143N, M143W, L161T, L161Y, W168G, I179M, I179R, C236N, Q244N, A254W and A254Y; L35G, A21V, L108G and I179R mutations; L35G, W132T and I179R mutations; L35G, S9D, Y84C and I179R mutations; L35G, Y84C, I179R and Q244N mutations; L35G, A21V, W132T, I179R and Q244N mutations; K58R and I257T mutations; a D98G mutation; L130M and V243A mutations; and, any combination comprising at least two mutations, wherein the mutations are | — | 22 (258 AA) |

TABLE 1-continued

Summary Of Nucleic Acid And Protein SEQ ID Numbers

| Description | Nucleic acid SEQ ID NO. | Protein SEQ ID NO. |
|---|---|---|
| selected from the group consisting of: K58R, L35F, L35G, L35M, S9A, S9D, S9G, S9I, S9K, S9Q, Q12K, A21D, A21T, A21V, V32F, Y84C, D98G, Q107E, L108G, G127L, L130M, W132T, M143N, M143W, L161T, L161Y, W168G, I179M, I179R, C236N, V243A, Q244N, A254W, A254Y and I257T | | |
| His-rich motif: Q)(X)$_2$HH | — | 23 |
| His-rich motif: H(X)$_2$HH | — | 24 |
| Plasmid pZUFmEgD9ES | 25 (7769 bp) | — |
| Primer pZUFm__6980__012208f | 26 | — |
| Primer pZUFm__40__012208r | 27 | — |
| Synthetic mutant delta-9 elongase, derived from *Euglena gracilis* ("EgD9eS-L35F") | 28 (777 bp) | 29 (258 AA) |
| Plasmid pZuFmEgD9ES-L35F | 30 (7769 bp) | — |
| Synthetic mutant delta-9 elongase, derived from *Euglena gracilis* ("EgD9eS-K58R/I257T") | 31 (777 bp) | 32 (258 AA) |
| Plasmid pZuFmEgD9ES-K58R/I257T | 33 (7769 bp) | — |
| Synthetic mutant delta-9 elongase, derived from *Euglena gracilis* ("EgD9eS-L130M/V243A$_1$") | 34 (777 bp) | 35 (258 AA) |
| Plasmid pZuFmEgD9ES-L130M/V243A$_1$ | 36 | — |
| Synthetic mutant delta-9 elongase, derived from *Euglena gracilis* ("EgD9eS-D98G") | 37 (777 bp) | 38 (258 AA) |
| Plasmid pZuFmEgD9ES-D98G | 39 (7769 bp) | — |
| Synthetic mutant delta-9 elongase, derived from *Euglena gracilis* ("EgD9eS-L130M/V243A$_2$") | 40 (777 bp) | 41 (258 AA) |
| Plasmid pZuFmEgD9ES-L130M/V243A$_2$ | 42 (7769 bp) | — |
| *Ciona intestinalis* elongase (GenBank Accession No. AAV67802) | — | 43 (289 AA) |
| *Oncorhynchus mykiss* elongase (GenBank Accession No. AAV67803) | — | 44 (295 AA) |
| *Marchantia polymorpha* elongase (GenBank Accession No. AAT85662) | — | 45 (290 AA) |
| *Physcomitrella patens* elongase (GenBank Accession No. AAL84174) | — | 46 (290 AA) |
| *Marchantia polymorpha* elongase (GenBank Accession No. BAE71130) | — | 47 (348 AA) |
| *Ostreococcus tauri* elongase (GenBank Accession No. AAV67797) | — | 48 (292 AA) |
| *Pavlova* sp. CCMP459 elongase (GenBank Accession No. AAV33630) | — | 49 (277 AA) |
| *Pavlova saline* elongase (GenBank Accession No. AAY15135) | — | 50 (302 AA) |
| *Ostreococcus tauri* elongase (GenBank Accession No. AAV67798) | — | 51 (300 AA) |
| *Thalassiosira pseudonana* elongase (GenBank Accession No. AAV67800) | — | 52 (358 AA) |
| *Thalassiosira pseudonana* elongase (GenBank Accession No. AAV67799) | — | 53 (272 AA) |
| *Mortierella alpina* GenBank elongase (Accession No. AAF70417) | — | 54 (318 AA) |
| *Thraustochytrium* sp. FJN-10 elongase (GenBank Accession No. ABC18314) | — | 55 (271 AA) |
| Primer EgD9E__102__053008f | 56 | — |
| Primer EgD9E__760__053008r | 57 | — |
| Synthetic mutant delta-9 elongase, derived from *Euglena gracilis* ("EgD9eS-L35G") | 58 (777 bp) | 59 (258 AA) |
| Plasmid pZuFmEgD9ES-L35G | 60 (7769 bp) | — |
| Synthetic mutant delta-9 elongase, derived from *Euglena gracilis* ("EgD9eS-L35M/Q107E") | 61 (777 bp) | 62 (258 AA) |
| Plasmid pZuFmEgD9ES-L35M/Q107E | 63 (7769 bp) | — |
| Primers | 64-85 | — |
| Synthetic mutant delta-9 elongase, derived from *Euglena gracilis* ("EgD9eS-A21V/L35G/L108G/I179R") | 86 (777 bp) | 87 (258 AA) |
| Plasmid pZuFmEgD9ES-A21V/L35G/L108G/I179R | 88 (7769 bp) | — |
| Plasmid pZKUM | 89 (4313 bp) | — |

TABLE 1-continued

Summary Of Nucleic Acid And Protein SEQ ID Numbers

| Description | Nucleic acid SEQ ID NO. | Protein SEQ ID NO. |
|---|---|---|
| Plasmid pZKL3-9DP9N | 90 (13565 bp) | — |
| *Yarrowia lipolytica* delta-9 desaturase gene (GenBank Accession No. XM_501496) | 91 (1449 bp) | 92 (482 AA) |
| *Yarrowia lipolytica* choline-phosphate cytidylyl-transferase gene (GenBank Accession No. XM_502978) | 93 (1101 bp) | 94 (366 AA) |
| Synthetic mutant delta-9 elongase, derived from *Euglena gracilis* ("EgD9eS-L35G") | 95 (777 bp) | — |
| Synthetic mutant delta-9 elongase, derived from *Euglena gracilis* ("EgD9eS-L35G") | 96 (777 bp) | — |
| Synthetic mutant delta-9 elongase, derived from *Euglena gracilis* ("EgD9eS-L35G") | 97 (777 bp) | — |
| Primer FBAIN-F | 98 | — |
| Primer Y1026 | 99 | — |
| Synthetic mutant delta-9 elongase, derived from *Euglena gracilis* ("EgD9eS-L35G/W132T/I179R") | 100 (777 bp) | 101 (258 AA) |
| Plasmid pZuFmEgD9ES-L35G/W132T/I179R | 102 (7769 bp) | — |
| Synthetic mutant delta-9 elongase, derived from *Euglena gracilis* ("EgD9eS-S9D/L35G/Y84C/I179R") | 103 (777 bp) | 104 (258 AA) |
| Plasmid pZuFmEgD9ES-S9D/L35G/Y84C/I179R | 105 (7769 bp) | — |
| Synthetic mutant delta-9 elongase, derived from *Euglena gracilis* ("EgD9eS-L35G/Y84C/I179R/Q244N") | 106 (777 bp) | 107 (258 AA) |
| Plasmid pZuFmEgD9ES-L35G/Y84C/I179R/Q244N | 108 (7769 bp) | — |
| Synthetic mutant delta-9 elongase, derived from *Euglena gracilis* ("EgD9eS-A21V/L35G/W132T/I179R/Q244N") | 109 (777 bp) | 110 (258 AA) |
| Plasmid pZuFmEgD9ES-A21V/L35G/W132T/I179R/Q244N | 111 (7769 bp) | — |

DETAILED DESCRIPTION OF THE INVENTION

All patents, patent applications, and publications cited herein are incorporated by reference in their entirety.

In this disclosure, a number of terms and abbreviations are used. Amino acids are identified by either the one-letter code or the three-letter codes for amino acids, in conformity with the IUPAC-IYUB standards described in *Nucleic Acids Research*, 13:3021-3030 (1985) and in the *Biochemical Journal*, 219 (2):345-373 (1984), which are herein incorporated by reference.

The following definitions are provided.

"Open reading frame" is abbreviated "ORF".

"Polymerase chain reaction" is abbreviated "PCR".

"American Type Culture Collection" is abbreviated "ATCC".

"Polyunsaturated fatty acid(s)" is abbreviated "PUFA(s)".

"Triacylglycerols" are abbreviated "TAGs".

"Total fatty acids" are abbreviated as "TFAs".

"Fatty acid methyl esters" are abbreviated as "FAMEs".

As used herein the term "invention" or "present invention" is intended to refer to all aspects and embodiments of the invention as described in the claims and specification herein and should not be read so as to be limited to any particular embodiment or aspect.

The term "fatty acids" refers to long chain aliphatic acids (alkanoic acids) of varying chain lengths, from about $C_{12}$ to $C_{22}$, although both longer and shorter chain-length acids are known. The predominant chain lengths are between $C_{16}$ and $C_{22}$. The structure of a fatty acid is represented by a simple notation system of "X:Y", where X is the total number of carbon ["C"] atoms in the particular fatty acid and Y is the number of double bonds. Additional details concerning the differentiation between "saturated fatty acids" versus "unsaturated fatty acids", "monounsaturated fatty acids" versus "polyunsaturated fatty acids" ["PUFAs"], and "omega-6 fatty acids" ["ω-6" or "n-6"] versus "omega-3 fatty acids" ["ω-3" or "n-3"] are provided in U.S. Pat. No. 7,238,482, which is hereby incorporated herein by reference.

Nomenclature used to describe PUFAs herein is given in Table 2. In the column titled "Shorthand Notation", the omega-reference system is used to indicate the number of carbons, the number of double bonds and the position of the double bond closest to the omega carbon, counting from the omega carbon, which is numbered 1 for this purpose. The remainder of the Table summarizes the common names of omega-3 and omega-6 fatty acids and their precursors, the abbreviations that will be used throughout the specification and the chemical name of each compound.

TABLE 2

Nomenclature of Polyunsaturated Fatty Acids And Precursors

| Common Name | Abbreviation | Chemical Name | Shorthand Notation |
|---|---|---|---|
| Myristic | — | tetradecanoic | 14:0 |
| Palmitic | Palmitate | hexadecanoic | 16:0 |
| Palmitoleic | — | 9-hexadecenoic | 16:1 |
| Stearic | — | octadecanoic | 18:0 |
| Oleic | — | cis-9-octadecenoic | 18:1 |

TABLE 2-continued

Nomenclature of Polyunsaturated Fatty Acids And Precursors

| Common Name | Abbreviation | Chemical Name | Shorthand Notation |
|---|---|---|---|
| Linoleic | LA | cis-9,12-octadecadienoic | 18:2 ω-6 |
| γ-Linolenic | GLA | cis-6,9,12-octadecatrienoic | 18:3 ω-6 |
| Eicosadienoic | EDA | cis-11,14-eicosadienoic | 20:2 ω-6 |
| Dihomo-γ-Linolenic | DGLA | cis-8,11,14-eicosatrienoic | 20:3 ω-6 |
| Arachidonic | ARA | cis-5,8,11,14-eicosatetraenoic | 20:4 ω-6 |
| α-Linolenic | ALA | cis-9,12,15-octadecatrienoic | 18:3 ω-3 |
| Stearidonic | STA | cis-6,9,12,15-octadecatetraenoic | 18:4 ω-3 |
| Eicosatrienoic | ETrA | cis-11,14,17-eicosatrienoic | 20:3 ω-3 |
| Eicosa-tetraenoic | ETA | cis-8,11,14,17-eicosatetraenoic | 20:4 ω-3 |
| Eicosa-pentaenoic | EPA | cis-5,8,11,14,17-eicosapentaenoic | 20:5 ω-3 |
| Docosa-tetraenoic | DTA | cis-7,10,13,16-docosatetraenoic | 22:4 ω-6 |
| Docosa-pentaenoic | DPAn-6 | cis-4,7,10,13,16-docosapentaenoic | 22:5 ω-6 |
| Docosa-pentaenoic | DPA | cis-7,10,13,16,19-docosapentaenoic | 22:5 ω-3 |
| Docosa-hexaenoic | DHA | cis-4,7,10,13,16,19-docosahexaenoic | 22:6 ω-3 |

Although the omega-3/omega-6 PUFAs listed in Table 2 are the most likely to be accumulated in the oil fractions of microbial and plant hosts using the methods described herein, this list should not be construed as limiting or as complete.

The term "oil" refers to a lipid substance that is liquid at 25° C.; the oil is hydrophobic but is soluble in organic solvents. In oleaginous organisms, oil constitutes a major part of the total lipid. "Oil" is composed primarily of triacylglycerols ["TAGs"] but may also contain other neutral lipids, phospholipids and free fatty acids. The fatty acid composition in the oil and the fatty acid composition of the total lipid are generally similar; thus, an increase or decrease in the concentration of PUFAs in the total lipid will correspond with an increase or decrease in the concentration of PUFAs in the oil, and vice versa.

"Neutral lipids" refer to those lipids commonly found in cells in lipid bodies as storage fats and are so called because at cellular pH, the lipids bear no charged groups. Generally, they are completely non-polar with no affinity for water. Neutral lipids generally refer to mono-, di-, and/or triesters of glycerol with fatty acids, also called monoacylglycerol ["MAG"], diacylglycerol ["DAG"] or triacylglycerol, respectively, or collectively, acylglycerols. A hydrolysis reaction must occur to release free fatty acids from acylglycerols.

The term "triacylglycerols" ["TAGs"] refers to neutral lipids composed of three fatty acyl residues esterified to a glycerol molecule. TAGs can contain long chain PUFAs and saturated fatty acids, as well as shorter chain saturated and unsaturated fatty acids.

The term "total fatty acids" ["TFAs"] herein refer to the sum of all cellular fatty acids that can be derivitized to fatty acid methyl esters ["FAMEs"] by the base transesterification method (as known in the art) in a given sample, which may be the biomass or oil, for example. Thus, total fatty acids include fatty acids from neutral lipid fractions (including DAGs, MAGs and TAGs) and from polar lipid fractions (including, e.g., the phosphatidylcholine ["PC"] and phosphatidylethanolamine ["PE"] fractions) but not free fatty acids.

The term "total lipid content" of cells is a measure of TFAs as a percent of the dry cell weight ["DCW"], although total lipid content can be approximated as a measure of FAMEs as a percent of the DCW ["FAMEs % DCW"]. Thus, total lipid content ["TFAs % DCW"] is equivalent to, e.g., milligrams of total fatty acids per 100 milligrams of DCW.

The concentration of a fatty acid in the total lipid is expressed herein as a weight percent of TFAs ["% TFAs"], e.g., milligrams of the given fatty acid per 100 milligrams of TFAs. Unless otherwise specifically stated in the disclosure herein, reference to the percent of a given fatty acid with respect to total lipids is equivalent to concentration of the fatty acid as % TFAs (e.g., % EPA of total lipids is equivalent to EPA % TFAs).

In some cases, it is useful to express the content of a given fatty acid(s) in a cell as its weight percent of the dry cell weight ["% DCW"]. Thus, for example, EPA % DCW would be determined according to the following formula: (EPA % TFAs)*(TFAs % DCW)]/100. The content of a given fatty acid(s) in a cell as its weight percent of the dry cell weight ["% DCW"] can be approximated, however, as: (EPA % TFAs)* (FAMEs % DCW)]/100.

The terms "lipid profile" and "lipid composition" are interchangeable and refer to the amount of individual fatty acids contained in a particular lipid fraction, such as in the total lipid or the oil, wherein the amount is expressed as a weight percent of TFAs. The sum of each individual fatty acid present in the mixture should be 100.

The term "PUFA biosynthetic pathway" refers to a metabolic process that converts oleic acid to omega-6 fatty acids such as LA, EDA, GLA, DGLA, ARA, DTA and DPAn-6 and omega-3 fatty acids such as ALA, STA, ETrA, ETA, EPA, DPA and DHA. This process is well described in the literature (e.g., see U.S. Pat. No. 7,932,077). Briefly, this process involves elongation of the carbon chain through the addition of carbon atoms and desaturation of the molecule through the addition of double bonds, via a series of special elongation and desaturation enzymes termed "PUFA biosynthetic pathway enzymes" that are present in the endoplasmic reticulum membrane. More specifically, "PUFA biosynthetic pathway enzymes" refer to any of the following enzymes (and genes which encode said enzymes) associated with the biosynthesis of a PUFA, including: delta-4 desaturase, delta-5 desaturase, delta-6 desaturase, delta-12 desaturase, delta-15 desaturase, delta-17 desaturase, delta-9 desaturase, delta-8 desaturase, delta-9 elongase, $C_{14/16}$ elongase, $C_{16/18}$ elongase, $C_{18/20}$ elongase and/or $C_{20/22}$ elongase.

The term "delta-9 elongase/delta-8 desaturase pathway" will refer to a PUFA biosynthetic pathway that minimally includes at least one delta-9 elongase and at least one delta-8 desaturase, thereby enabling biosynthesis of DGLA and/or ETA from LA and ALA, respectively, with EDA and/or ETrA as intermediate fatty acids. With expression of other desaturases and elongases, ARA, DTA, DPAn-6, EPA, DPA and DHA may also be synthesized.

The term "desaturase" refers to a polypeptide that can desaturate, i.e., introduce a double bond, in one or more fatty acids to produce a fatty acid or precursor of interest. Despite use of the omega-reference system throughout the specification to refer to specific fatty acids, it is more convenient to indicate the activity of a desaturase by counting from the carboxyl end of the substrate using the delta-system. Of particular interest herein are: delta-8 desaturases, delta-5 desaturases, delta-17 desaturases, delta-12 desaturases, delta-4 desaturases, delta-6 desaturases, delta-15 desaturases and delta-9 desaturases.

The term "elongase" refers to a polypeptide that can elongate a substrate fatty acid carbon chain to produce a fatty acid 2 carbons longer than the fatty acid substrate that the elongase acts upon. The process of elongation occurs in a multi-step mechanism in association with fatty acid synthase, as described in U.S. Pat. No. 7,659,120. Examples of reactions catalyzed by elongase systems are the conversion of LA to EDA, ALA to ETrA, GLA to DGLA, STA to ETA, ARA to DTA and EPA to DPA. In general, the substrate selectivity of elongases is somewhat broad but segregated by both chain length and the degree and type of unsaturation. For example, a $C_{14/16}$ elongase will utilize a $C_{14}$ substrate (e.g., myristic acid), a $C_{16/18}$ elongase will utilize a $C_{16}$ substrate (e.g., palmitate), a $C_{18/20}$ elongase will utilize a $C_{18}$ substrate (e.g., GLA, STA, LA and ALA) and a $C_{20/22}$ elongase [also referred to as a delta-5 elongase or C20 elongase] will utilize a $C_{20}$ substrate (e.g., ARA, EPA). For the purposes herein, two distinct types of $C_{18/20}$ elongases can be defined: a delta-6 elongase will catalyze conversion of GLA and STA to DGLA and ETA, respectively, while a delta-9 elongase is able to catalyze the conversion of LA and ALA to EDA and ETrA, respectively.

The term "EgD9e" refers to a delta-9 elongase (SEQ ID NO:8) isolated from *Euglena gracilis*, encoded by SEQ ID NO:7 herein. Similarly, the term "EgD9eS" refers to a synthetic delta-9 elongase derived from *E. gracilis* that is codon-optimized for expression in *Yarrowia lipolytica* (i.e., SEQ ID NOs:9 and 10). Further details concerning EgD9e and EgD9eS are described in U.S. Pat. No. 7,645,604.

For the purposes herein, the term "EaD9e" refers to a delta-9 elongase (SEQ ID NO:12) isolated from *Euglena anabaena*, encoded by SEQ ID NO:11 herein. Similarly, the term "EaD9eS" refers to a synthetic delta-9 elongase derived from *E. anabaena* that is codon-optimized for expression in *Y. lipolytica* (i.e., SEQ ID NOs:13 and 14). Further details concerning EaD9e and EaD9eS are described in U.S. Pat. No. 7,794,701.

The term "E389D9e" refers to a delta-9 elongase (SEQ ID NO:4) isolated from *Eutreptiella* sp. CCMP389, encoded by SEQ ID NO:3 herein. Similarly, the term "E389S9eS" refers to a synthetic delta-9 elongase derived from *Eutreptiella* sp. CCMP389 that is codon-optimized for expression in *Y. lipolytica* (i.e., SEQ ID NOs:5 and 6). Further details concerning E389D9e and E389D9eS are described in U.S. Pat. No. 7,645,604.

The term "IgD9e" refers to a delta-9 elongase (SEQ ID NO:2; NCBI Accession No. AAL37626 (GI 17226123)) isolated from *Isochrysis galbana*, encoded by SEQ ID NO:1 herein.

The term "conserved domain" or "motif" means a set of amino acids conserved at specific positions along an aligned sequence of evolutionarily related proteins. While amino acids at other positions can vary among homologous proteins, amino acids that are highly conserved at specific positions indicate these amino acids may be important in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

Figure 1:
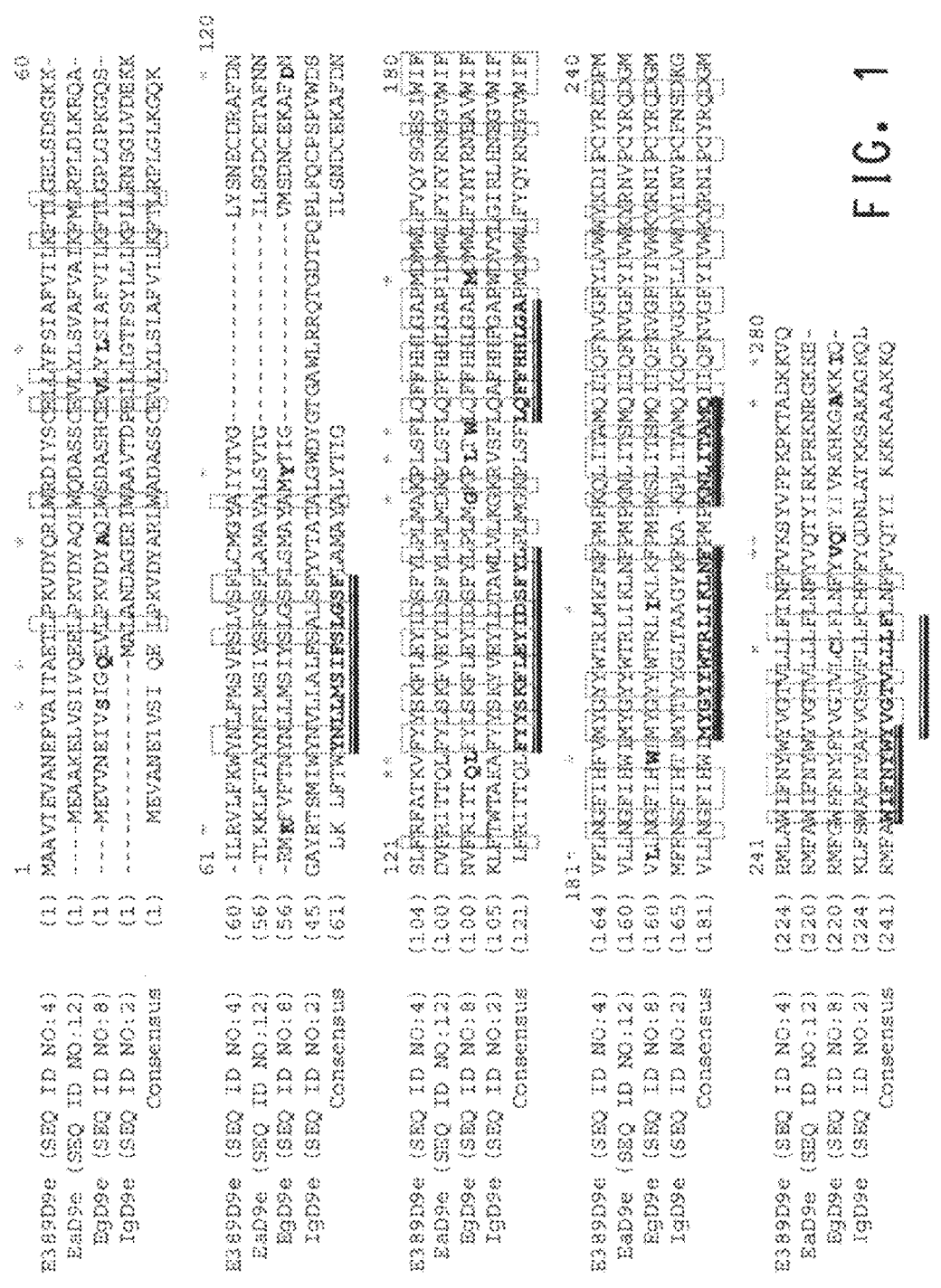

Delta-9 elongase motifs are described in U.S. Pat. No. 7,645,604 and include: Y-N-X-(L or F)-X$_4$-S-X$_2$-S-F (SEQ ID NO:15); F-Y-X-S-K-X$_2$-(E or D)-Y-X-D-(T or S)-X$_2$-L (SEQ ID NO:16); L-(Q or H)-X-F-H-H-X-G-A (SEQ ID NO:17); M-Y-X-Y-Y-X$_7$-(K or R or N)-F (SEQ ID NO:18); K-X-L-(I or L or M)-T-X$_2$-Q (SEQ ID NO:19); W-X-F-N-Y-X-Y (SEQ ID NO:20); and Y-X-G-X-V-X$_2$-L-F (SEQ ID NO:21); wherein X can be any amino acid and the underlined amino acids may be unique to delta-9 elongases. Multiple alignment of the amino acid sequences of IgD9e (SEQ ID NO:2), EgD9e (SEQ ID NO:8), E389D9e (SEQ ID NO:4) and EaD9e (SEQ ID NO:12) using default parameters of Vector NTI®'s AlignX program (Invitrogen Corporation, Carlsbad, Calif.) is shown in FIG. 1. The delta-9 elongase motifs of U.S. Pat. No. 7,645,604, conserved among all of the aligned sequences, are shown in the Figure as underlined, bolded text within the consensus sequence.

The term "mutant EgD9eS" refers to a delta-9 elongase of the present invention that has at least one nucleotide or amino acid mutation with respect to the synthetic delta-9 elongase derived from *Euglena gracilis* that is codon-optimized for expression in *Yarrowia lipolytica* (i.e., EgD9eS [SEQ ID NOs:9 and 10]). Although "mutations" may include any deletions, insertions and point mutations (or combinations thereof), in preferred embodiments the mutant EgD9eS is set forth in SEQ ID NO:22 (FIG. 4B), wherein SEQ ID NO:22 differs from SEQ ID NO:10 by at least one amino acid mutation, said mutation(s) selected from the group consisting of: a) a L35F mutation; b) a L35M mutation; c) a L35G mutation; d) a L35G mutation and at least one other mutation selected from the group consisting of: S9A, S9D, S9G, S9I, S9K, S9Q, Q12K, A21D, A21T, A21V, V32F, Y84C, Q107E, L108G, G127L, W132T, M143N, M143W, L161T, L161Y, W168G, I179M, I179R, C236N, Q244N, A254W and A254Y; e) L35G, A21V, L108G and I179R mutations; f) L35G, W132T and I179R mutations; g) L35G, S9D, Y84C and I179R mutations; h) L35G, Y84C, I179R and Q244N mutations; i) L35G, A21V, W132T, I179R and Q244N mutations; j) K58R and I257T mutations; k) a D98G mutation; l) L130M and V243A mutations; and, m) any combination comprising at least two mutations, wherein the mutations are selected from the group consisting of: K58R, L35F, L35G, L35M, S9A, S9D, S9G, S9I, S9K, S9Q, Q12K, A21D, A21T, A21V, V32F, Y84C, D98G, Q107E, L108G, G127L, L130M, W132T, M143N, M143W, L161T, L161Y, W168G, I179M, I179R, C236N, V243A, Q244N, A254W, A254Y and I257T. For each substitution listed, the first letter corresponds to the amino acid in EgD9eS (SEQ ID NO:10) and the second letter corresponds to the amino acid found in the same position in the mutant (SEQ ID NO:22), i.e., L35F indicates a change from Leu [L] in EgD9eS at position 35 to Phe [F] in the EgD9eS mutant. This nomenclature is used throughout the specification to refer to mutations within the delta-9 elongase proteins described herein; similar notation is used to describe substitutions within the nucleotide sequence (i.e., C62T indicates a change from cytosine [C] in EgD9eS (SEQ ID NO:9) at position 62 to thymine [T] in the EgD9eS mutant).

A mutant EgD9eS is "at least about functionally equivalent" to EgD9eS when enzymatic activity (and optionally, specific selectivity) of the mutant EgD9eS sequence is comparable to that of EgD9eS, despite differing polypeptide sequences. Thus, a functionally equivalent mutant EgD9eS sequence will possess delta-9 elongase activity that is not substantially reduced with respect to that of EgD9eS when the "conversion efficiency" of each enzyme is compared (i.e., a mutant EgD9eS will have at least about 50%, preferably at least about 75%, more preferably at least about 85%, and most preferably at least about 95% of the enzymatic activity of EgD9eS). In more preferred embodiments, the mutant EgD9eS will have increased enzymatic activity (and optionally, specific selectivity) when compared to that of EgD9eS (i.e., at least about 101-150%, more preferably at least about 151-200% and most preferably at least about 201-250% of the enzymatic activity of EgD9eS). Although preferred ranges are described above, useful examples of conversion efficiencies relative to EgD9eS include any integer percentage from 50% to at least 250%, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 101%, 102%, 103%, 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, 150%, etc. up to and including 250%.

The terms "conversion efficiency" and "percent substrate conversion" refer to the efficiency by which a particular enzyme (e.g., a delta-9 elongase) can convert substrate to product. The conversion efficiency is measured according to the following formula: ([product]/[substrate+product])*100, where 'product' includes the immediate product and all products in the pathway derived from it. Thus, "LA to EDA conversion efficiency" refers to the conversion efficiency by which the substrate, LA, is converted to the product, EDA.

Generally, the term "oleaginous" refers to those organisms that tend to store their energy source in the form of oil (Weete, In: Fungal Lipid Biochemistry, 2nd Ed., Plenum, 1980). During this process, the cellular oil content of oleaginous microorganisms generally follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.*, 57:419-25 (1991)). For the purposes of the present application and when used with respect to microorganisms, the term "oleaginous" refers to those microorganisms that can accumulate at least about 25% of their DCW as oil.

The term "oleaginous yeast" refers to those oleaginous microorganisms classified as yeasts that can make oil, i.e., wherein the oil can accumulate in excess of about 25% of their DCW. Examples of oleaginous yeast include, but are no means limited to, the following genera: *Yarrowia, Candida, Rhodotorula, Rhodosporidium, Cryptococcus, Trichosporon* and *Lipomyces*. The ability to accumulate oil in excess of about 25% of the DCW of the yeast may be through efforts of recombinant engineering or through the natural abilities of the organism.

The term "conservative amino acid substitution" refers to a substitution of an amino acid residue in a given protein with another amino acid, without altering the chemical or functional nature of that protein. For example, it is well known in the art that alterations in a gene that result in the production of a chemically equivalent amino acid at a given site (but do not affect the structural and functional properties of the encoded, folded protein) are common. For the purposes herein, "conservative amino acid substitutions" are defined as exchanges within one of the following five groups:
 1. Small aliphatic, nonpolar or slightly polar residues: Ala [A], Ser [S], Thr [T] (Pro [P], Gly [G]);
 2. Polar, negatively charged residues and their amides: Asp [D], Asn [N], Glu [E], Gln [Q];
 3. Polar, positively charged residues: His [H], Arg [R], Lys [K];
 4. Large aliphatic, nonpolar residues: Met [M], Leu [L], Ile [I], Val [V](Cys [C]); and,
 5. Large aromatic residues: Phe [F], Tyr [Y], Trp [W].

Thus, Ala, a slightly hydrophobic amino acid, may be substituted by another less hydrophobic residue (e.g., Gly). Similarly, changes which result in substitution of one negatively charged residue for another (e.g., Asp for Glu) or one positively charged residue for another (e.g., Lys for Arg) can also be expected to produce a functionally equivalent product. As such, conservative amino acid substitutions generally maintain: 1) the structure of the polypeptide backbone in the area of the substitution; 2) the charge or hydrophobicity of the molecule at the target site; or, 3) the bulk of the side chain. Additionally, in many cases, alterations of the N-terminal and C-terminal portions of the protein molecule would also not be expected to alter the activity of the protein.

The term "non-conservative amino acid substitution" refers to an amino acid substitution that is generally expected to produce the greatest change in protein properties. Thus, for example, a non-conservative amino acid substitution would be one whereby: 1) a hydrophilic residue is substituted for/by a hydrophobic residue (e.g., Ser or Thr for/by Leu, Ile, Val); 2) a Cys or Pro is substituted for/by any other residue; 3) a residue having an electropositive side chain is substituted for/by an electronegative residue (e.g., Lys, Arg or H is for/by Asp or Glu); or, 4) a residue having a bulky side chain is substituted for/by one not having a side chain (e.g., Phe for/by Gly). Sometimes, non-conservative amino acid substitutions between two of the five groups will not affect the activity of the encoded protein.

The term "silent mutation" refers to a mutation in a DNA sequence that does not result in an amino acid change in the encoded polypeptide. These mutations often occur as a result of the degeneracy of the genetic code, wherein more than one codon may specify an amino acid. For example, TCT, TCA, TCG and TCC all encode the amino acid Ser; thus, a TCT to TCA mutation in the DNA sequence will only be detected by sequencing the gene (or its mRNA), since there is no alteration in the amino acid in the synthesized protein (i.e., Ser).

The terms "polynucleotide", "polynucleotide sequence", "nucleic acid sequence", "nucleic acid fragment" and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.*, 215: 403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The disclosure herein teaches the complete amino acid and nucleotide sequence encoding particular elongases. The skilled artisan, having the benefit of the sequences as reported herein, may now use all or a substantial portion of the disclosed sequences for purposes known to those skilled in this art. Accordingly, the complete sequences as reported in the accompanying Sequence Listing, as well as substantial portions of those sequences as defined above, are encompassed in the present disclosure.

The term "complementary" is used to describe the relationship between nucleotide bases that are capable of hybridizing to one another. For example, with respect to DNA, adenosine is complementary to thymine and cytosine is complementary to guanine. Accordingly, isolated nucleic acid fragments that are complementary to the complete sequences as reported in the accompanying Sequence Listing, as well as those substantially similar nucleic acid sequences, are encompassed in the present disclosure.

The terms "homology", "homologous", "substantially similar" and "corresponding substantially" are used interchangeably herein. They refer to nucleic acid fragments or polypeptides that have similar, but not identical sequence. These terms sometimes also refer to modifications of the nucleic acid fragments (e.g., via deletion or insertion of one or more nucleotides) that do not substantially alter the functional properties of the resulting nucleic acid fragment relative to the initial, unmodified fragment. It is therefore understood, as those skilled in the art will appreciate, that the invention encompasses more than the specific exemplary sequences.

"Sequence identity" or "identity" in the context of nucleic acid or polypeptide sequences refers to the nucleic acid bases or amino acid residues in two sequences that are the same when aligned for maximum correspondence over a specified comparison window.

Thus, "percentage of sequence identity" or "percent identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity.

Methods to determine "percent identity" and "percent similarity" are codified in publicly available computer programs. Percent identity and percent similarity can be readily calculated by known methods, including but not limited to those described in: 1) *Computational Molecular Biology* (Lesk, A. M., Ed.) Oxford University: NY (1988); 2) *Biocomputing: Informatics and Genome Projects* (Smith, D. W., Ed.) Academic: NY (1993); 3) *Computer Analysis of Sequence Data, Part I* (Griffin, A. M., and Griffin, H. G., Eds.) Humania: NJ (1994); 4) *Sequence Analysis in Molecular Biology* (von Heinje, G., Ed.) Academic (1987); and, 5) *Sequence Analysis Primer* (Gribskov, M. and Devereux, J., Eds.) Stockton: NY (1991).

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" and the "Clustal W method of alignment" (described by Higgins and Sharp, *CABIOS*, 5:151-153 (1989); Higgins, D. G. et al., *Comput. Appl. Biosci.*, 8:189-191 (1992)) and found in the MegAlign™ (version 8.0.2) program of the LASERGENE bioinformatics computing suite (DNASTAR Inc.). After alignment of the sequences using either Clustal program, it is possible to obtain a "percent identity" by viewing the "sequence distances" table in the program.

For multiple alignments using the Clustal V method of alignment, the default values correspond to GAP PENALTY=10 and GAP LENGTH PENALTY=10. Default parameters for pairwise alignments and calculation of percent identity of protein sequences using the Clustal V method are KTUPLE=1, GAP PENALTY=3, WINDOW=5 and DIAGONALS SAVED=5. For nucleic acids, these parameters are KTUPLE=2, GAP PENALTY=5, WINDOW=4 and DIAGONALS SAVED=4.

Default parameters for multiple alignment using the Clustal W method of alignment correspond to GAP PENALTY=10, GAP LENGTH PENALTY=0.2, Delay Divergent Seqs(%)=30, DNA Transition Weight=0.5, Protein Weight Matrix=Gonnet Series, DNA Weight Matrix=IUB.

The "BLASTN method of alignment" is an algorithm provided by the National Center for Biotechnology Information ["NCBI"] to compare nucleotide sequences using default parameters, while the "BLASTP method of alignment" is an algorithm provided by the NCBI to compare protein sequences using default parameters.

It is well understood by one skilled in the art that many levels of sequence identity are useful in identifying polypeptides, from other species, wherein such polypeptides have the same or similar function or activity. Suitable nucleic acid fragments, i.e., isolated polynucleotides according to the disclosure herein, encode polypeptides that are at least about 70-85% identical, while more preferred nucleic acid fragments encode amino acid sequences that are at least about 85-95% identical to the amino acid sequences reported herein. Although preferred ranges are described above, useful examples of percent identities include any integer percentage from 80%, 81%, 82%, 83%, 84%, 85%, 86%, 87%, 88%, 89%, 90%, 91%, 92%, 93%, 94%, 95%, 96%, 97%, 98% or 99%. Also, of interest is any full-length or partial complement of this isolated nucleotide fragment.

Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

"Codon degeneracy" refers to the nature in the genetic code permitting variation of the nucleotide sequence without affecting the amino acid sequence of an encoded polypeptide. Accordingly, described herein is any nucleic acid fragment that encodes all or a substantial portion of the amino acid sequence encoding the instant delta-9 elongase polypeptides as set forth in EgD9eS-L35F (SEQ ID NO:29), EgD9eS-K58R/I257T (SEQ ID NO:32), EgD9eS-L130M/V243A$_1$ (SEQ ID NO:35), EgD9eS-D98G (SEQ ID NO:38), EgD9eS-L130M/V243A$_2$ (SEQ ID NO:41), EgD9eS-L35G (SEQ ID NO:59), EgD9eS-L35M/Q107E (SEQ ID NO:62), EgD9eS-A21V/L35G/L108G/I179R (SEQ ID NO:87), EgD9eS-L35G/W132T/I179R (SEQ ID NO:101), EgD9eS-L35G/S9D/Y84C/I179R (SEQ ID NO:104), EgD9eS-L35G/Y84C/I179R/Q244N (SEQ ID NO:107), EgD9eS-L35G/A21V/W132T/I179R/Q244N (SEQ ID NO:110) and EgD9eS-mutant consensus (SEQ ID NO:22). The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These oligonucleotide building blocks are annealed and then ligated to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available. For example, the codon usage profile for *Yarrowia lipolytica* is provided in U.S. Pat. No. 7,125,672.

"Gene" refers to a nucleic acid fragment that expresses a specific protein, and that may refer to the coding region alone or may include regulatory sequences upstream and/or downstream to the coding region (e.g., 5' untranslated regions upstream of the transcription start site of the coding region, 3' non-coding regions). "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene that is introduced into the host organism by gene transfer. Foreign genes can comprise native genes inserted into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence which codes for a specific amino acid sequence. "Regulatory sequences" refer to nucleotide sequences located upstream of the coding sequence's transcription start site, 5' untranslated regions and 3' non-coding regions, and which may influence the transcription, RNA processing or stability, or translation of the associated coding sequence. Regulatory sequences may include, but are not limited to: promoters, enhancers, silencers, 5' untranslated leader sequence, introns, polyadenylation recognition sequences, RNA processing sites, effector binding sites and stem-loop structures.

"Promoter" refers to a DNA sequence capable of controlling the expression of a coding sequence or functional RNA. In general, a promoter sequence is located 5' upstream of a coding sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of cell growth and/or development, or in response to different environmental conditions. Promoters that cause a gene to be expressed at almost all stages of development are commonly referred to as "constitutive promoters". It is further recognized that since in most cases the exact boundaries of regulatory sequences (especially at their 5' end) have not been completely defined, DNA fragments of some variation may have identical promoter activity.

The terms "3' non-coding sequences", "transcription terminator", "terminator" and "termination sequences" refer to DNA sequences located 3' downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript. A RNA transcript is referred to as the mature RNA when it is a RNA sequence derived from post-transcriptional processing of the primary transcript. "Messenger RNA" or "mRNA" refers to the RNA that is without introns and that can be translated into protein by the cell. "cDNA" refers to a DNA that is complementary to, and synthesized from, a mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (U.S. Pat. No. 5,107,065).

The term "operably linked" refers to the association of nucleic acid sequences on a single nucleic acid fragment so that the function of one is affected by the other. For example, a promoter is operably linked with a coding sequence when it is capable of affecting the expression of that coding sequence, i.e., the coding sequence is under the transcriptional control of the promoter. Coding sequences can be operably linked to regulatory sequences in a sense or antisense orientation.

The term "recombinant" refers to an artificial combination of two otherwise separated segments of sequence, e.g., by chemical synthesis or by the manipulation of isolated segments of nucleic acids by genetic engineering techniques.

The term "expression", as used herein, refers to the transcription and stable accumulation of sense (mRNA) or antisense RNA. Expression also includes translation of mRNA into a protein (either precursor or mature).

"Transformation" refers to the transfer of a nucleic acid molecule into a host organism, resulting in genetically stable inheritance. The nucleic acid molecule may be a plasmid that replicates autonomously, for example, or it may integrate into the genome of the host organism. Host organisms containing the transformed nucleic acid fragments are referred to as "transgenic" or "recombinant" or "transformed" or "transformant" organisms.

The terms "plasmid" and "vector" refer to an extra chromosomal element often carrying genes that are not part of the central metabolism of the cell, and usually in the form of circular double-stranded DNA fragments. Such elements may have autonomously replicating sequences, genome integrating sequences, phage or nucleotide sequences, and may be linear or circular, of a single- or double-stranded DNA or RNA, derived from any source, in which a number of nucleotide sequences have been joined or recombined into a unique construction which is capable of introducing an expression cassette(s) into a cell.

The term "expression cassette" refers to a fragment of DNA containing a foreign gene and having elements in addition to the foreign gene that allow for expression of that gene in a foreign host. Generally, an expression cassette will comprise the coding sequence of a selected gene and regulatory sequences preceding (5' non-coding sequences) and following (3' non-coding sequences) the coding sequence that are required for expression of the selected gene product. Thus, an expression cassette is typically composed of: 1) a promoter sequence; 2) a coding sequence (i.e., ORF); and, 3) a terminator that usually contains a polyadenylation site in eukaryotes. The expression cassette(s) is usually included within a vector, to facilitate cloning and transformation. Different expression cassettes can be transformed into different organisms including bacteria, yeast, plants and mammalian cells, as long as the correct regulatory sequences are used for each host.

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a recombinant DNA construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments described herein. The skilled artisan will also recognize that different independent transformation events will result in different levels and patterns of expression (Jones et al., *EMBO J.*, 4:2411-2418 (1985); De Almeida et al., *Mol. Gen. Genetics*, 218:78-86 (1989)), and thus that multiple events must be screened in order to obtain strains or lines displaying the desired expression level and pattern. Such screening may be accomplished by Southern analysis of DNA, Northern analysis of mRNA expression, Western and/or Elisa analyses of protein expression, formation of a specific product, phenotypic analysis or GC analysis of the PUFA products, among others.

The terms "host cell" and "host organism" are used interchangeably herein and refer to any organism such as a microorganism or a plant (i.e., an oilseed plant) that is capable of receiving foreign or heterologous genes and capable of expressing those genes. A "recombinant host cell" refers to a host cell that has been recombinantly engineered.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1) the GCG suite of programs (Wisconsin Package Version 9.0, Genetics Computer Group (GCG), Madison, Wis.); 2) BLASTP, BLASTN, BLASTX (Altschul et al., *J. Mol. Biol.*, 215:403-410 (1990)); 3) DNASTAR (DNASTAR, Inc. Madison, Wis.); 4) Sequencher (Gene Codes Corporation, Ann Arbor, Mich.); and, 5) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within this description, whenever sequence analysis software is used for analysis, the analytical results are based on the "default values" of the program referenced, unless otherwise specified. As used herein "default values" will mean any set of values or parameters that originally load with the software when first initialized.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory: Cold Spring Harbor, N.Y. (1989); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987).

New mutant delta-9 elongase enzymes and genes encoding the same that may be used for the manipulation of biochemical pathways for the production of healthful PUFAs are disclosed herein.

FIGS. 5A and 5B together set forth multiple alternate pathways for production of a specific omega-3/omega-6 fatty acid(s). All pathways require the initial conversion of oleic acid to linoleic acid ["LA"], the first of the omega-6 fatty acids, by a delta-12 desaturase. Then, using the "delta-9 elongase/delta-8 desaturase pathway" and LA as substrate, long-chain omega-6 fatty acids are formed as follows: 1) LA is converted to eicosadienoic acid ["EDA"] by a delta-9 elongase; 2) EDA is converted to dihomo-γ-linolenic acid ["DGLA"] by a delta-8 desaturase; 3) DGLA is converted to arachidonic acid ["ARA"] by a delta-5 desaturase; 4) ARA is converted to docosatetraenoic acid ["DTA"] by a $C_{20-22}$ elongase; and, 5) DTA is converted to docosapentaenoic acid ["DPAn-6"] by a delta-4 desaturase.

The "delta-9 elongase/delta-8 desaturase pathway" can also use alpha-linolenic acid ["ALA"] as substrate to produce long-chain omega-3 fatty acids as follows: 1) LA is converted to ALA, the first of the omega-3 fatty acids, by a delta-15 desaturase; 2) ALA is converted to eicosatrienoic acid ["ETrA"] by a delta-9 elongase; 3) ETrA is converted to eicosatetraenoic acid ["ETA"] by a delta-8 desaturase; 4) ETA is converted to eicosapentaenoic acid ["EPA"] by a delta-5 desaturase; 5) EPA is converted to docosapentaenoic acid ["DPA"] by a $C_{20/22}$ elongase; and, 6) DPA is converted to docosahexaenoic acid ["DHA"] by a delta-4 desaturase. Optionally, omega-6 fatty acids may be converted to omega-3 fatty acids. For example, ETA and EPA are produced from DGLA and ARA, respectively, by delta-17 desaturase activity.

Alternate pathways for the biosynthesis of omega-3/omega-6 fatty acids utilize a delta-6 desaturase and $C_{18/20}$ elongase, that is, the "delta-6 desaturase/delta-6 elongase pathway". More specifically, LA and ALA may be converted to GLA and stearidonic acid ["STA"], respectively, by a delta-6 desaturase; then, a $C_{18/20}$ elongase converts GLA to DGLA and/or STA to ETA. Downstream PUFAs are subsequently formed as described above.

It is contemplated that the particular functionalities required to be introduced into a specific host organism, to enable or enhance the organism's ability to produce omega-3/omega-6 fatty acids, will depend on the host cell (and its native PUFA profile and/or desaturase/elongase profile), the availability of substrate, and the desired end product(s). A discussion of these considerations, as well as factors that affect the identification and selection of specific genes encoding desaturase and elongase enzymes (e.g., delta-6 desaturases, $C_{18/20}$ elongases, delta-5 desaturases, delta-17 desaturases, delta-15 desaturases, delta-9 desaturases, delta-12 desaturases, $C_{14/16}$ elongases, $C_{16/18}$ elongases, delta-9 elongases, delta-8 desaturases, delta-4 desaturases and $C_{20/22}$ elongases), can be found in U.S. Pat. No. 7,238,482 and U.S. Pat. No. 7,932,077.

One aspect of particular relevance to the invention herein, however, is the conversion efficiency of each particular desaturase and/or elongase that is to be expressed in a specific host organism. More specifically, since each enzyme rarely functions with 100% efficiency to convert substrate to product, the final lipid profile of unpurified oils produced in a host cell will typically be a mixture of various PUFAs consisting of the desired omega-3/omega-6 fatty acid, as well as various upstream intermediary PUFAs. Thus, each enzyme's conversion efficiency is often considered, when optimizing biosynthesis of a desired fatty acid.

Once fatty acids are synthesized within an organism (including saturated and unsaturated fatty acids and short-chain and long-chain fatty acids), they may be incorporated into TAGs. TAGs are the primary storage unit for fatty acids.

Commonly owned U.S. Pat. Pub. No. 2007-0118929-A1 and U.S. Pat. No. 7,645,604 both disclose a *Euglena gracilis* delta-9 elongase ("EgD9e"; SEQ ID NOs:7 and 8 herein) able to elongate LA to EDA. Furthermore, a synthetic delta-9 elongase derived from *E. gracilis* and codon-optimized for expression in *Yarrowia lipolytica* was also disclosed in U.S. Pat. No. 7,645,604 ("EgD9eS"; SEQ ID NOs:9 and 10 herein). Specifically, in addition to modification of the translation initiation site, 117 bp of the 777 bp coding region were modified (15.1%) and 106 codons were optimized (yet the protein sequence encoded by the codon-optimized gene [i.e., SEQ ID NO:10] is identical to that of the wildtype protein sequence [i.e., SEQ ID NO:8]). EgD9eS was determined to be about 16.2% more efficient elongating LA to EDA than the wildtype EgD9e when expressed in *Y. lipolytica*.

Methods for synthesizing sequences and bringing sequences together are well established in the literature. And, many techniques are commonly employed to obtain mutations of naturally occurring genes (wherein such mutations may include deletions, insertions and point mutations, or combinations thereof). The present work was conducted with the goal of identifying suitable mutation(s) within EgD9eS that would increase the LA to EDA conversion efficiency of the enzyme when it was expressed in the oleaginous yeast, *Yarrowia lipolytica*. Increased conversion efficiency was desirable as a means to increase the overall rate and quantity of PUFA biosynthesis. A variety of mutations are described herein; all such mutant proteins and nucleotide sequences encoding them that are derived from the wildtype (i.e., SEQ ID NO:8) and synthetic codon-optimized (SEQ ID NO:10) delta-9 elongase described supra are within the scope of the present invention.

Although delta-9 elongases contain several conserved sequences (FIG. 1; i.e., SEQ ID NOs:15-21), only a portion of one of these motifs has been previously studied to determine its role in optimal enzymatic function. Specifically, Qi, B., et al. (*FEBS Lett.*, 547:137-139 (2003)) examined the variant histidine-box ["His-box"] of the *Isochrysis galbana* delta-9 elongase ["IgD9e"], the first PUFA-specific elongase identified with delta-9 elongase activity. Since IgD9e was the only known PUFA-specific elongase (at the time) to possess a Gln-Xaa-Xaa-His-His ["QxxHH"; SEQ ID NO:23] motif, instead of the highly conserved His-Xaa-Xaa-His-His ["HxxHH"; SEQ ID NO:24] motif present in delta-6 elongases, a series of mutations were performed to replace the Gln with His, Ala or Phe residues and assay the mutant proteins for activity upon expression in *Saccharomyces cerevisiae*. Qi et al. determined that all of the substitutions resulted in lower delta-9 elongase activity and thus it was concluded that "the glutamine residue in the histidine box . . . appears to be essential for optimum enzyme catalysis".

Based on the sole study above and the lack of any crystal structures from delta-9 elongases, a rationale targeted approach to identify suitable mutations within delta-9 elongases was not ideal. Libraries of mutant sequences encoding delta-9 elongases were synthetically engineered by error-prone PCR ["ePCR"], using EgD9eS (SEQ ID NO:9) as a template, wherein EgD9eS was contained within a plasmid construct comprising a chimeric FBAINm::EgD9eS::Pex20 gene. The ePCR libraries were then transformed into *Yarrowia lipolytica*, and screened for improved delta-9 elongase activity based on GC analyses and the production of EDA.

Many clones were identified that resulted in a completely non-functional mutant delta-9 elongase (i.e., having no detectable delta-9 elongase activity) or a mutant delta-9 elongase having substantially decreased delta-9 elongase activity with respect to the non-mutant wildtype enzyme, EgD9eS. Surprisingly, however, various mutations that resulted in an improved LA to EDA conversion efficiency [calculated as ([EDA]/[LA+EDA])*100] were identified. Specifically, five transformant strains were identified comprising four different mutant delta-9 elongase genes (i.e., comprising a K58R/I257T mutation, a L35F mutation, a D98G mutation and a L130M/V243A mutation, respectively, when compared to the protein sequence of EgD9eS [SEQ ID NO:10]), wherein the delta-9 elongase conversion activity ranged from 105% to 117% (Table 3, infra), corresponding to a 5-17% improvement. Thus, this work demonstrated that the delta-9 elongase activity of EgD9eS could indeed be improved by protein engineering.

The initial data obtained from the above EgD9eS ePCR libraries was then utilized to rationally identify two different amino acid residues within EgD9eS that were appropriate targets for the creation of site-saturation libraries (i.e., residues 35 and 107). Again, the effect of each mutation on the delta-9 elongase activity of the resulting mutant EgD9eS protein was screened, thus enabling identification of two additional mutations that resulted in an improved LA to EDA conversion efficiency. Specifically, transformant strains were identified comprising either a L35G mutation or a L35M/Q107E mutation within the mutant delta-9 elongase, wherein the delta-9 elongase conversion activity was either 142%-145% or 132% relative to EgD9eS (Table 3, infra), corresponding to a 32-45% improvement.

Following identification of the L35G mutation, a subsequent library targeting 50 different amino acid residues was created using SlonoMax® technology and the EgD9eS-L35G gene as a target. Twenty-five different mutations were identified, each in combination with the L35G mutation, which resulted in delta-9 elongase conversion activity from 96% to 141% when compared to the parent elongase, i.e., EgD9eS-L35G (Table 3, infra), corresponding to a −4% to 41% improvement.

Finally, recent work has attempted to combine (or "stack") multiple beneficial mutations identified within the SlonoMax® library, thereby "stacking" appropriate individual amino acid mutations within the synthetic codon-optimized EgD9eS sequence. Thus, for example, a mutant delta-9 elongase comprising A21V, L35G, W132T, I179R and Q244N mutations with respect to SEQ ID NO:10 [EgD9eS] has been demonstrated to result in 123% delta-9 elongase conversion activity relative to EgD9eS (Table 3, infra) corresponding to a 23% improvement.

Instead, it is contemplated that many of the above conservative and non-conservative amino acid substitutions (i.e., mutations) may be used in any combination with one another. And, all such mutant proteins and nucleotide sequences encoding them that are derived from EgD9e and/or EgD9eS as described herein are within the scope of the present invention.

For example, the experimental strategy applied in the present work was largely based on identifying additional conservative and non-conservative amino acid substitutions that could be "stacked" into EgD9eS-L35G and convey a further benefit to the delta-9 elongase conversion efficiency, when compared to that of either the synthetic codon-optimized EgD9eS or EgD9eS-L35G. Although a variety of mutant delta-9 elongases were identified comprising two mutations with respect to EgD9eS, only five mutants have been characterized from the combinatorial library, each hav-

TABLE 3

Summary Of Mutants Having Increased Delta-9 Elongase Activity

| Method of Library Generation | Resulting Amino Acid Substitution | Designation For Mutant Gene | Relative Activity |
|---|---|---|---|
| ePCR | L35F | EgD9eS-L35F | 115%$^a$ |
| | K58R and I257T | EgD9eS-K58R/I257T | 105%$^a$ |
| | L130M and V243A | EgD9eS-L130M/V243A | 106%-111%$^a$ |
| | D98G | EgD9eS-D98G | 117%$^a$ |
| Site-Saturation | L35G | EgD9eS-L35G | 142%-145%$^a$ |
| | L35M and Q107E | EgD9eS-L35M/Q107E | 132%$^a$ |
| SlonoMax ® | L35G and S9A | EgD9eS-L35G/S9A | 126%$^b$ |
| | L35G and S9D | EgD9eS-L35G/S9D | 141%$^b$ |
| | L35G and S9G | EgD9eS-L35G/S9G | 129%$^b$ |
| | L35G and S9I | EgD9eS-L35G/S9I | 113%$^b$ |
| | L35G and S9K | EgD9eS-L35G/S9K | 122%$^b$ |
| | L35G and S9Q | EgD9eS-L35G/S9Q | 111%$^b$ |
| | L35G and Q12K | EgD9eS-L35G/Q12K | 123%$^b$ |
| | L35G and A21D | EgD9eS-L35G/A21D | 118%$^b$ |
| | L35G and A21T | EgD9eS-L35G/A21T | 110%$^b$ |
| | L35G and A21V | EgD9eS-L35G/A21V | 118%$^b$ |
| | L35G and V32F | EgD9eS-L35G/V32F | 104%$^b$ |
| | L35G and Y84C | EgD9eS-L35G/Y84C | 144%$^b$ |
| | L35G and L108G | EgD9eS-L35G/L108G | 104%$^b$ |
| | L35G and G127L | EgD9eS-L35G/G127L | 104%$^b$ |
| | L35G and W132T | EgD9eS-L35G/W132T | 100%$^b$ |
| | L35G and M143N | EgD9eS-L35G/M143N | 96%$^b$ |
| | L35G and M143W | EgD9eS-L35G/M143W | 106%$^b$ |
| | L35G and L161T | EgD9eS-L35G/L161T | 131%$^b$ |
| | L35G and L161Y | EgD9eS-L35G/L161Y | 119%$^b$ |
| | L35G and W168G | EgD9eS-L35G/W168G | 115%$^b$ |
| | L35G and I179M | EgD9eS-L35G/I179M | 104%$^b$ |
| | L35G and I179R | EgD9eS-L35G/I179R | 141%$^b$ |
| | L35G and C236N | EgD9eS-L35G/C236N | 102%$^b$ |
| | L35G and Q244N | EgD9eS-L35G/Q244N | 134%$^b$ |
| | L35G and A254W | EgD9eS-L35G/A254W | 112%$^b$ |
| | L35G and A254Y | EgD9eS-L35G/A254Y | 116%$^b$ |
| Combinatorial | L35G and W132T and I179R | EgD9eS-L35G/W132T/I179R | 110%$^a$ |
| | S9D and L35G and Y84C and I179R | EgD9eS-S9D/L35G/Y84C/I179R | 108%$^a$ |
| | A21V and L35G and L108G and I179R | EgD9eS-A21V/L35G/L108G/I179R | 104%$^a$ |
| | L35G and Y84C and I179R and Q244N | EgD9eS-L35G/Y84C/I179R/Q244N | 111%$^a$ |
| | A21V and L35G and W132T and I179R and Q244N | EgD9eS-A21V/L35G/W132T/I179R/Q244N | 123%$^a$ |

$^a$"Relative Activity" refers to the delta-9 elongase activity of each mutant EgD9eS with respect to the delta-9 elongase activity of EgD9eS, set forth as SEQ ID NO: 10.
$^b$"Relative Activity" refers to the delta-9 elongase activity of each mutant EgD9eS with respect to the delta-9 elongase activity of EgD9eS-L35G, set forth as SEQ ID NO: 59.

It will be appreciated by one of skill in the art that the useful mutant delta-9 elongases of the present invention are not limited to the 37 mutation combinations described above.

ing three to five mutations with respect to EgD9eS. It is expected that various other mutants could be identified having at least about functionally equivalent activity or improved delta-9 elongase conversion efficiency with respect to either EgD9eS or EgD9eS-L35G, and having 2, 3, 4, 5, 6 or more mutations with respect to EgD9eS.

Alternatively, one of skill in the art could readily use, for example, EgD9eS-D98G as a template (i.e., instead of EgD9eS-L35G) and determine which mutations selected from the group consisting of K58R, L35F, L35G, L35M, S9A, S9D, S9G, S9I, S9K, S9Q, Q12K, A21D, A21T, A21V, V32F, Y84C, Q107E, L108G, G127L, L130M, W132T, M143N, M143W, L161T, L161Y, W168G, I179M, I179R, C236N, V243A, Q244N, A254W, A254Y and I257T could be advantageously "stacked", thereby yielding a final mutant delta-9 elongase with 2, 3, 4, 5, 6 or more mutations with respect to EgD9eS.

Thus, in one embodiment, the present invention concerns an isolated polynucleotide, as represented in FIG. 4B, comprising:
  a) a nucleotide sequence encoding a mutant polypeptide having delta-9 elongase activity and having an amino acid sequence as set forth in SEQ ID NO:22, wherein SEQ ID NO:22 differs from SEQ ID NO:10 by at least one amino acid mutation, said mutation(s) selected from the group consisting of:
    i) a L35F mutation;
    ii) a L35M mutation;
    iii) a L35G mutation;
    iv) a L35G mutation and at least one other mutation selected from the group consisting of: S9A, S9D, S9G, S9I, S9K, S9Q, Q12K, A21D, A21T, A21V, V32F, Y84C, Q107E, L108G, G127L, W132T, M143N, M143W, L161T, L161Y, W168G, I179M, I179R, C236N, Q244N, A254W and A254Y;
    v) L35G, A21V, L108G and I179R mutations;
    vi) L35G, W132T and I179 mutations; vii) L35G, S9D, Y84C and I179R mutations;
    viii) L35G, Y84C, I179R and Q244N mutations;
    ix) L35G, A21V, W132T, I179R and Q244N mutations;
    x) K58R and I257T mutations;
    xi) a D98G mutation;
    xii) L130M and V243A mutations; and,
    xiii) any combination comprising at least two mutations, wherein the mutations are selected from the group consisting of: K58R, L35F, L35G, L35M, S9A, S9D, S9G, S9I, S9K, S9Q, Q12K, A21D, A21T, A21V, V32F, Y84C, D98G, Q107E, L108G, G127L, L130M, W132T, M143N, M143W, L161T, L161Y, W168G, I179M, I179R, C236N, V243A, Q244N, A254W, A254Y and I257T; and,
  b) a complement of the nucleotide sequence of part (a), wherein the complement and the nucleotide sequence consist of the same number of nucleotides and are 100% complementary.

In some embodiments, the mutant polypeptide of the invention herein may have a protein sequence selected from the group consisting of: SEQ ID NO:29, SEQ ID NO:32, SEQ ID NO:35, SEQ ID NO:38, SEQ ID NO:41, SEQ ID NO:59, SEQ ID NO:62, SEQ ID NO:87, SEQ ID NO:101, SEQ ID NO:104, SEQ ID NO:107 and SEQ ID NO:110, although these examples are not limiting to the invention herein.

Neither the methodology used to produce the mutant polypeptides of the invention nor the methodology used to identify the mutant polypeptides of the invention should be considered a limitation herein.

For example, in vitro mutagenesis and selection or error prone PCR (Leung et al., *Techniques*, 1:11-15 (1989); Zhou et al., *Nucleic Acids Res.*, 19:6052-6052 (1991); Spee et al., *Nucleic Acids Res.*, 21:777-778 (1993); Melnikov et al., *Nucleic Acids Res.*, 27(4):1056-1062 (Feb. 15, 1999)) could be employed as a means to obtain mutations of naturally occurring delta-9 elongase genes, wherein the mutations may include deletions, insertions and point mutations, or combinations thereof. The principal advantage of error-prone PCR is that all mutations introduced by this method will be within the desired elongase gene, and any change may be easily controlled by changing the PCR conditions. Alternatively, in vivo mutagenesis may be employed using commercially available materials such as the *E. coli* XL1-Red strain and *Epicurian coli* XL1-Red mutator strain from Stratagene (La Jolla, Calif.; see also, Greener and Callahan, *Strategies*, 7:32-34 (1994)). This strain is deficient in three of the primary DNA repair pathways (mutS, mutD and mutT), resulting in a mutation rate 5000-fold higher than that of wildtype. In vivo mutagenesis does not depend on ligation efficiency (as with error-prone PCR); however, a mutation may occur at any region of the vector and the mutation rates are generally much lower.

It is also contemplated that a mutant delta-9 elongase with altered or enhanced delta-9 elongase activity may be constructed using the method of "gene shuffling" (U.S. Pat. No. 5,605,793; U.S. Pat. No. 5,811,238; U.S. Pat. No. 5,830,721; and U.S. Pat. No. 5,837,458). The method of gene shuffling is particularly attractive due to its facile implementation and high rate of mutagenesis. The process of gene shuffling involves the restriction of a gene of interest into fragments of specific size in the presence of additional populations of DNA regions of both similarity to (or difference to) the gene of interest. This pool of fragments will denature and then reanneal to create a mutated gene. The mutated gene is then screened for altered activity. Any of these methods may be used to create delta-9 elongase mutant enzymes having improved activity.

Alternately, the skilled person will be able to envision additional screens for the selection of genes encoding proteins having delta-9 elongase activity. For example, elongase activity may be demonstrated by assays in which a preparation containing an enzyme is incubated with a suitable form of substrate fatty acid and analyzed for conversion of this substrate to the predicted fatty acid product. Alternatively, a DNA sequence proposed to encode an elongase protein may be incorporated into a suitable vector construct and thereby expressed in cells of a type that do not normally have an ability to elongate a particular fatty acid substrate. Activity of the elongase encoded by the DNA sequence can then be demonstrated by supplying a suitable form of substrate fatty acid to cells transformed with a vector containing the elongase-encoding DNA sequence and to suitable control cells (e.g., transformed with the empty vector alone). In such an experiment, detection of the predicted fatty acid product in cells containing the elongase-encoding DNA sequence and not in control cells establishes the elongase activity.

It will be appreciated by one of skill in the art that useful mutant delta-9 elongases are not limited to the mutations described above. Instead, the results suggest that similar experimentation could be performed using a variety of alternate delta-9 elongases as the parent (i.e., from a different genus, species, etc.), to thereby engineer various mutant delta-9 elongases having increased delta-9 elongase activity. Preferably, the delta-9 elongase subjected to mutagenesis would comprise at least one of the seven delta-9 elongase motifs described in U.S. Pat. No. 7,645,604 and set forth as SEQ ID NOs:15, 16, 17, 18, 19, 20 and 21. Most likely, a suitable parent delta-9 elongase would be at least about 35%-50% identical to EgD9eS, where those sequences that are at least about 50%-65% identical are particularly suitable and those sequences that are at least about 65%-80% identical are most preferred. Although preferred ranges are described above, useful examples of percent sequence identities include any integer percentage from 35% to 100%, such as 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. It will be appreciated that a mutant enzyme having increased delta-9 elongase activity can be useful to enable increased production of omega-3/omega-6 fatty acids.

For example, one could readily improve the delta-9 elongase activity of the delta-9 elongases of *Isochrysis galbana* (i.e., IgD9e [SEQ ID NO:2]; ~35% sequence identity to EgD9eS), *Eutreptiella* sp. CCMP389 (i.e., E389D9e [SEQ ID NO:4]; ~60% sequence identity to EgD9eS) and *Euglena anabaena* (i.e., EaD9e [SEQ ID NO:12]; ~60% sequence identity to EgD9eS), as it would be likely these genes would tolerate mutations in a manner similar to that observed in *E. gracilis*. Although it may be desirable to initiate mutagenesis by creation of e.g., error prone PCR libraries for any of these parent molecules, one could also reasonably predict that improved mutants could be identified based on mutation of amino acid residues sharing homology with those sites in EgD9eS. An alignment of IgD9e, E389D9e, EgD9e and EaD9e is shown in FIG. 1, prepared using default parameters of the Vector NTI® AlignX program (Invitrogen Corporation, Carlsbad, Calif.). The underlined, bolded text within the consensus sequence has been previously discussed with respect to the motif sequences that may be indicative of delta-9 elongase activity. Bolded residues within the EgD9e sequence of SEQ ID NO:8 (which is identical in sequence to that of EgD9eS, as set forth in SEQ ID NO:10) indicate residues that were mutated in the present application to result in a mutant elongase having improved delta-9 elongase activity. The locations of these mutations are also highlighted with an asterisk over each row of the alignment. Based on analysis of this alignment, one of skill in the art would hypothesize that modification at any of the residues described below in Table 4 may also result in improved delta-9 elongase activity in EaD9e, E389D9e and IgD9e, respectively. Thus, for example, amino acid residue 13 of SEQ ID NO:4 [E389D9e] (i.e., Ala [A]) aligns with amino acid residue 9 of SEQ ID NO:10 [EgD9eS] (i.e., Ser [S]); thus, one would predict that substitution of the Ala in E389D9e may result in a mutant E389D9e elongase having increased delta-9 activity, in a manner similar to that observed in EgD9eS, when the Ser was substituted with an Ala, Asp, Gly, Ile, Lys or Gln. Identification of the most preferred substitution at each amino acid residue could be determined experimentally.

TABLE 4

Residue Sites Predicted To Improve Delta-9 Elongase Activity In EaD9e, E389D9e And IgD9e, Based on Residue Sites Identified In EgD9eS

| Mutation Observed To Improve Delta-9 Elongase Activity In EgD9eS | Corresponding Amino Acid Residue Where Mutation Is Predicted To Improve Delta-9 Elongase Activity | | |
|---|---|---|---|
| | In EaD9e (SEQ ID NO: 12) | In E389D9e (SEQ ID NO: 4) | In IgD9e (SEQ ID NO: 2) |
| S9A, S9D, S9G, S9I, S9K, S9Q | S9 | A13 | — |
| Q12K | Q12 | A16 | — |

TABLE 4-continued

Residue Sites Predicted To Improve Delta-9 Elongase Activity In EaD9e, E389D9e And IgD9e, Based on Residue Sites Identified In EgD9eS

| Mutation Observed To Improve Delta-9 Elongase Activity In EgD9eS | Corresponding Amino Acid Residue Where Mutation Is Predicted To Improve Delta-9 Elongase Activity | | |
|---|---|---|---|
| | In EaD9e (SEQ ID NO: 12) | In E389D9e (SEQ ID NO: 4) | In IgD9e (SEQ ID NO: 2) |
| A21D, A21T, A21V | A21 | Q25 | E9 |
| V32F | V32 | L36 | I20 |
| L35F, L35G, L35M | L35 | F39 | G23 |
| K58R | K58 | R62 | R48 |
| Y84C | S84 | Y88 | G74 |
| D98G | N98 | D102 | D103 |
| Q107E | Q107 | K111 | K112 |
| L108G | L108 | V112 | A113 |
| G127L | D127 | A131 | G132 |
| L130M | L130 | L134 | V135 |
| W132T | F132 | F136 | F137 |
| M143N, M143W | I143 | M147 | W148 |
| L161T, L161Y | L161 | F165 | F166 |
| W168G | W168 | F172 | T173 |
| I179M, I179R | I179 | M183 | A184 |
| C236N | L236 | L240 | L240 |
| V243A | V243 | V247 | Y247 |
| Q244N | Q244 | K248 | Q248 |
| A254W, A254Y | R254 | A258 | K258 |
| I257T | K257 | K261 | K261 |

It is expected that introduction of chimeric genes encoding the mutant delta-9 elongases described herein, having increased delta-9 elongase activity with respect to that of EgD9eS, under the control of the appropriate promoters will result in increased production of EDA and/or ETrA in the transformed host organism, respectively. As such, methods for the direct production of PUFAs are described herein, wherein said methods comprise exposing a fatty acid substrate (i.e., LA and/or ALA) to a mutant elongase enzyme described herein (e.g., SEQ ID NO:22]), such that the substrate is converted to the desired fatty acid product (i.e., EDA and/or ETrA, respectively).

More specifically, described herein is a method for producing a polyunsaturated fatty acid comprising:

a) providing an oleaginous yeast comprising:

i) a recombinant construct, operably linked to at least one regulatory sequence, wherein said recombinant construct comprises an isolated polynucleotide encoding a mutant polypeptide having delta-9 elongase activity and having an amino acid sequence as set forth in SEQ ID NO:22, wherein SEQ ID NO:22 differs from SEQ ID NO:10 [EgD9eS] by at least one amino acid mutation, said mutation(s) selected from the group consisting of:

(a) a L35F mutation;

(b) a L35M mutation;

(c) a L35G mutation;

(d) a L35G mutation and at least one other mutation selected from the group consisting of: S9A, S9D, S9G, S9I, S9K, S9Q, Q12K, A21D, A21T, A21V, V32F, Y84C, Q107E, L108G, G127L, W132T, M143N, M143W, L161T, L161Y, W168G, I179M, I179R, C236N, Q244N, A254W and A254Y;

(e) L35G, A21V, L108G and I179R mutations;
(f) L35G, W132T and I179 mutations;
(g) L35G, S9D, Y84C and I179R mutations;
(h) L35G, Y84C, I179R and Q244N mutations;
(i) L35G, A21V, W132T, I179R and Q244N mutations;
(j) K58R and I257T mutations;
(k) a D98G mutation;
(l) L130M and V243A mutations; and,
(m) any combination comprising at least two mutations, wherein the mutations are selected from the group consisting of: K58R, L35F, L35G, L35M, S9A, S9D, S9G, S9I, S9K, S9Q, Q12K, A21D, A21T, A21V, V32F, Y84C, D98G, Q107E, L108G, G127L, L130M, W132T, M143N, M143W, L161T, L161Y, W168G, I179M, I179R, C236N, V243A, Q244N, A254W, A254Y and I257T; and,
ii) a source of substrate fatty acid selected from the group consisting of linoleic acid and alpha-linolenic acid;
b) growing the yeast of step (a) under conditions wherein the recombinant construct encoding a mutant polypeptide having delta-9 elongase activity is expressed and the substrate fatty acid is converted to product fatty acid, wherein linoleic acid is converted to eicosadienoic acid and alpha-linolenic acid is converted to eicosatrienoic acid, and;
c) optionally recovering the product fatty acid of step (b).

Alternatively, each mutant delta-9 elongase gene and its corresponding enzyme product described herein may be used to increase production of various omega-6 and omega-3 PUFAs (see FIG. 5A and FIG. 5B; U.S. Pat. No. 7,238,482 and U.S. Pat. Pub. No. 2009-0093543-A1). Increased production of omega-3/omega-6 PUFAs occurs wherein the fatty acid substrate is converted into the desired fatty acid product, via means of an intermediate step(s) or pathway intermediate(s). Thus, it is contemplated that the mutant delta-9 elongases described herein may be expressed in conjunction with additional genes encoding enzymes of the PUFA biosynthetic pathway (e.g., delta-6 desaturases, $C_{18/20}$ elongases, delta-17 desaturases, delta-8 desaturases, delta-15 desaturases, delta-9 desaturases, delta-12 desaturases, $C_{14/16}$ elongases, $C_{16/18}$ elongases, delta-9 elongases, delta-5 desaturases, delta-4 desaturases, $C_{20/22}$ elongases) to result in higher levels of production of longer-chain omega-3/omega-6 fatty acids (e.g., DGLA, ETA, ARA, EPA, DTA, DPAn-6, DPA and/or DHA).

Preferably, the delta-9 elongases described herein will be expressed in conjunction with at least one delta-8 desaturase. However, the particular genes included within a particular expression cassette will depend on the host cell (and its PUFA profile and/or desaturase/elongase profile), the availability of substrate and the desired end product(s).

The use of a mutant delta-9 elongase for increased production of omega-3/omega-6 PUFAs is demonstrated herein in Example 11, wherein strain Z1978 of *Yarrowia lipolytica* was constructed to produce about 58.7% EPA relative to the total lipids with 38.3% total lipid content ["TFAs % DCW"]. In this specific example, the mutant delta-9 elongase is assumed to have functioned to increase delta-9 elongase activity in the delta-9 elongase/delta-8 desaturase pathway.

Thus, one aspect of the invention herein concerns a recombinant microbial host cell producing oil comprising at least 22.5 weight percent of EPA measured as a weight percent of DCW, said recombinant microbial host cell comprising at least one mutant delta-9 elongase polypeptide of the invention.

The mutant delta-9 elongase genes and gene products described herein may be produced in a variety of heterologous host cells, particularly in cells selected from the group consisting of: plants, bacteria, yeast, algae, euglenoids, stramenopiles, oomycetes and fungi. In general, one of skill in the art may assume that the mutant delta-9 elongases of the present invention will be suitable for expression in any host cell that is capable of expressing the wildtype EgD9e or codon-optimized EgD9eS delta-9 elongases from which the mutants were derived, or in hosts in which homologs of delta-9 elongases have been expressed.

U.S. Pat. No. 7,645,604 describes plant expression systems, cassettes, vectors and transformation methods thereof for expression of EgD9e and EgD9eS and the discussion therein is incorporated by reference in its entirety herein. Particularly preferred plants in which the mutant delta-9 elongases may be expressed include oilseed plants (e.g., soybean, *Brassica* species, sunflower, maize, cotton, flax and safflower).

Similarly, U.S. Pat. No. 7,645,604 also describes microbial expression systems, cassettes, vectors and transformation methods thereof for expression of EgD9e and EgD9eS. The discussion therein should be considered in combination with the following. In particular, the mutant delta-9 elongase genes and gene products described herein may also be produced in heterologous microbial host cells, particularly in the cells of oleaginous yeasts (e.g., *Yarrowia lipolytica*). Expression in recombinant microbial hosts may be useful for the production of various PUFA pathway intermediates, or for the modulation of PUFA pathways already existing in the host for the synthesis of new products heretofore not possible using the host.

Microbial expression systems and expression vectors containing regulatory sequences that direct high level expression of foreign genes are well known to those skilled in the art. Any of these could be used to construct chimeric genes for production of any of the gene products of the instant sequences. These chimeric genes could then be introduced into appropriate microorganisms via transformation to provide high-level expression of the encoded proteins.

Vectors (e.g., constructs, plasmids) and DNA expression cassettes useful for the transformation of suitable microbial or plant host cells are well known in the art. The specific choice of sequences present in the construct is dependent upon the desired expression products (supra), the nature of the host cell and the proposed means of separating transformed cells versus non-transformed cells. Typically, however, the vector contains at least one expression cassette, a selectable marker and sequences allowing autonomous replication or chromosomal integration. Suitable expression cassettes typically comprise a promoter, the coding sequence of a selected gene, and a terminator. It is most preferred when both control regions are derived from genes from the transformed host cell.

Promoters useful for driving expression of the instant delta-9 elongase ORFS in the desired microbial host cell or plant cell are numerous and known to those skilled in the art. Virtually any promoter (i.e., native, synthetic, or chimeric) capable of directing expression of these genes in the selected host cell is suitable. Expression in a host cell can be accomplished in an induced or constitutive fashion. Induced expression can be accomplished by inducing the activity of a regulatable promoter operably linked to the gene of interest, while constitutive expression can be achieved by the use of a constitutive promoter operably linked to the gene of interest.

As an example, U.S. Pat. Pub. No. 2009-0093543-A1 describes promoters for use in *Yarrowia lipolytica*. Any one of a number of promoters can be used, depending upon whether constitutive or induced transcription is desired, the efficiency of the promoter in expressing the ORF of interest, the ease of construction and the like.

Nucleotide sequences surrounding the translational initiation codon 'ATG' have been found to affect expression in yeast cells. If the desired polypeptide is poorly expressed in yeast, the coding region of exogenous genes can be modified to include an efficient yeast translation initiation sequence to obtain optimal gene expression. For expression in yeast, this can be done by site-directed mutagenesis of an inefficiently expressed gene or by fusing it in-frame to an endogenous yeast promoter, preferably a highly expressed promoter. Alternatively, the consensus translation initiation sequence of the host can be engineered into heterologous genes for their optimal expression.

The terminator can be derived from the 3' region of the gene from which the promoter was obtained or from a different gene. A large number of terminators are known and function satisfactorily in a variety of hosts, when utilized both in the same and different genera and species from which they were derived. The terminator usually is selected more as a matter of convenience rather than because of any particular property. Terminators may be derived from various genes native to the preferred hosts. The terminator can also be synthetic, as one of skill in the art can utilize available information to design and synthesize a terminator. A terminator may be unnecessary, but is highly preferred.

Merely inserting a gene into a cloning vector does not ensure its expression at the desired rate, concentration, amount, etc. In response to the need for high level expression, many specialized expression vectors have been created by adjusting certain properties that govern transcription, RNA stability, translation, protein stability and location, oxygen limitation and secretion from the microbial host cell or a plant cell. These properties include: the nature of the relevant transcriptional promoter and terminator sequences; the number of copies of the cloned gene (wherein additional copies may be cloned within a single expression construct and/or additional copies may be introduced into the host cell by increasing the plasmid copy number or by multiple integration of the cloned gene into the genome); whether the gene is plasmid-borne or integrated into the host cell genome; the final cellular location of the synthesized foreign protein; the efficiency of translation and correct folding of the protein in the host organism; the intrinsic stability of the mRNA and protein of the cloned gene within the host cell; and, the codon usage within the cloned gene. Each of these may be used in the methods and host cells described herein, to further optimize expression of the mutant delta-9 elongases described herein.

Once a DNA cassette (e.g., comprising a chimeric gene comprising a promoter, ORF and terminator) suitable for expression in an appropriate host cell has been obtained, it is placed in a plasmid vector capable of autonomous replication in a host cell, or it is directly integrated into the genome of the host cell. Integration of expression cassettes can occur randomly within the host genome or can be targeted through the use of constructs containing regions of homology with the host genome sufficient to target recombination within the host locus. All or some of the transcriptional and translational regulatory regions can be provided by the endogenous locus where constructs are targeted to an endogenous locus.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene(s) of interest may be introduced into a microbial host cell or plant host cell by any standard technique. These techniques include transformation (e.g., lithium acetate transformation [*Methods in Enzymology*, 194:186-187 (1991)]), protoplast transformation, bolistic impact, electroporation, microinjection, or any other method that introduces the gene(s) of interest into the host cell.

For convenience, a host cell that has been manipulated by any method to take up a DNA sequence, for example, in an expression cassette, is referred to herein as "transformed", "transformant" or "recombinant" (as these terms will be used interchangeably herein). The transformed host will have at least one copy of the expression construct and may have two or more, depending upon whether the expression cassette is integrated into the genome, amplified, or is present on an extrachromosomal element having multiple copy numbers.

The transformed host cell can be identified by selection for a marker contained on the introduced construct. Alternatively, a separate marker construct may be co-transformed with the desired construct, as many transformation techniques introduce many DNA molecules into host cells.

Typically, transformed hosts are selected for their ability to grow on selective media, which may incorporate an antibiotic or lack a factor necessary for growth of the untransformed host, such as a nutrient or growth factor. An introduced marker gene may confer antibiotic resistance, or encode an essential growth factor or enzyme, thereby permitting growth on selective media when expressed in the transformed host. Selection of a transformed host can also occur when the expressed marker can be detected, either directly or indirectly. Additional selection techniques are described in U.S. Pat. No. 7,238,482, U.S. Pat. No. 7,259,255 and U.S. Pat. No. 7,932,077.

Following transformation, substrates suitable for the instant mutant delta-9 elongases (and, optionally other PUFA enzymes that are co-expressed within the host cell) may be produced by the host either naturally or transgenically, or they may be provided exogenously.

Microbial host cells for expression of the instant genes and nucleic acid fragments may include hosts that grow on a variety of feedstocks, including simple or complex carbohydrates, fatty acids, organic acids, oils, glycerol and alcohols, and/or hydrocarbons over a wide range of temperature and pH values. Based on the needs of the Applicants' Assignee, the elongases described herein have been expressed in an oleaginous yeast, and in particular *Yarrowia lipolytica*. It is contemplated that because transcription, translation and the protein biosynthetic apparatus are highly conserved, any bacteria, yeast, algae, euglenoid, stramenopiles, oomycetes and/or fungus will be a suitable microbial host for expression of the present nucleic acid fragments.

Preferred microbial hosts, however, are oleaginous organisms, such as oleaginous yeasts. These organisms are naturally capable of oil synthesis and accumulation, wherein the oil can comprise greater than about 25% of the dry cell weight ["DCW"], more preferably greater than about 30% of the DCW, more preferably greater than about 40% of the DCW, more preferably greater than about 50% of the DCW, and most preferably greater than about 60% of the DCW. Genera typically identified as oleaginous yeast include, but are not limited to: *Yarrowia, Candida, Rhodotorula, Rhodospo-* ridium, *Cryptococcus, Trichosporon* and *Lipomyces*. More specifically, illustrative oil-synthesizing yeasts include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis*, and *Yarrowia lipolytica* (formerly classified as *Candida lipolytica*). In alternate embodiments, a non-oleaginous organism can be genetically modified to become oleaginous, e.g., yeast such as *Saccharomyces cerevisiae* (see, Int'l. App. Pub. No. WO 2006/102342).

Thus, in one embodiment here, an oleaginous yeast is provided comprising: (a) a first recombinant DNA construct comprising an isolated polynucleotide encoding a mutant delta-9 elongase polypeptide, operably linked to at least one regulatory sequence; and, (b) at least one additional recombinant DNA construct comprising an isolated polynucleotide, operably linked to at least one regulatory sequence, encoding a polypeptide selected from the group consisting of: delta-4 desaturase, delta-5 desaturase, delta-8 desaturase, delta-6 desaturase, delta-9 desaturase, delta-12 desaturase, delta-15 desaturase, delta-17 desaturase, $C_{14/16}$ elongase, $C_{16/18}$ elongase, $C_{18/20}$ elongase and $C_{20/22}$ elongase.

Most preferred is the oleaginous yeast *Yarrowia lipolytica*. In a further embodiment, most preferred are the *Y. lipolytica* strains designated as ATCC #20362, ATCC #8862, ATCC #18944, ATCC #76982 and/or LGAM S(7)1 (Papanikolaou S., and Aggelis G., *Bioresour. Technol.*, 82(1):43-9 (2002)).

Specific teachings applicable for transformation of oleaginous yeasts (i.e., *Yarrowia lipolytica*) via integration techniques based on linearized fragments of DNA include U.S. Pat. No. 4,880,741 and U.S. Pat. No. 5,071,764 and Chen, D. C. et al. (*Appl. Microbiol. Biotechnol.*, 48(2):232-235 (1997)). Specific teachings applicable for engineering ARA, EPA and DHA production in *Y. lipolytica* are provided in U.S. Pat. No. 7,588,931, U.S. Pat. No. 7,932,077 and U.S. Pat. Pub No. 2009-0093543-A1, and U.S. Pat. No. 7,550,286, respectively.

Other preferred microbial hosts include oleaginous bacteria, algae, euglenoids, stramenopiles, oomycetes and/or fungi. Within this broad group of microbial hosts, of particular interest are microorganisms that synthesize omega-3/omega-6 fatty acids, or those that can be genetically engineered for this purpose (e.g., other yeast such as *Saccharomyces cerevisiae*). Thus, for example, transformation of *Mortierella alpina* (which is commercially used for production of ARA) with any of the present delta-9 elongase genes under the control of inducible or regulated promoters could yield a transformant organism capable of synthesizing increased quantities of EDA; this could be converted to increased quantities of DGLA if a delta-8 desaturase gene was co-expressed. The method of transformation of *M. alpina* is described by Mackenzie et al. (*Appl. Environ. Microbiol.*, 66:4655 (2000)). Similarly, methods for transformation of Thraustochytriales microorganisms (e.g., *Thraustochytrium, Schizochytrium*) are disclosed in U.S. Pat. No. 7,001,772.

Irrespective of the host selected for expression of the mutant delta-9 elongases described herein, multiple transformants must be screened in order to obtain a strain displaying the desired expression level and pattern. Such screening may be accomplished by Southern analysis of DNA blots (Southern, *J. Mol. Biol.*, 98:503 (1975)), Northern analysis of mRNA expression (Kroczek, *J. Chromatogr. Biomed. Appl.*, 618(1-2):133-145 (1993)), Western and/or Elisa analyses of protein expression, phenotypic analysis or GC analysis of the PUFA products.

The transformed microbial host cell is grown under conditions that optimize expression of chimeric desaturase and elongase genes and produce the greatest and most economical yield of desired PUFAs. In general, media conditions may be optimized by modifying the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. Microorganisms of interest, such as oleaginous yeast (e.g., *Yarrowia lipolytica*) are generally grown in a complex medium such as yeast extract-peptone-dextrose broth ["YPD"] or a defined minimal media that lacks a component necessary for growth and thereby forces selection of the desired expression cassettes (e.g., Yeast Nitrogen Base (DIFCO Laboratories, Detroit, Mich.)).

Fermentation media for the methods and host cells described herein must contain a suitable carbon source such as are taught in U.S. Pat. No. 7,238,482 and U.S. Pat. Pub. No. 2011-0059204-A1. Suitable sources of carbon in the methods and host cells described herein encompass a wide variety of sources with the preferred ones being sugars (e.g., glucose, invert sucrose, fructose and combinations thereof), glycerols, and/or fatty acids.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the oleaginous host and promotion of the enzymatic pathways necessary for PUFA production. Particular attention is given to several metal ions, such as $Fe^{+2}$, $Cu^{+2}$, $Mn^{+2}$, $Co^{+2}$, $Zn^{+2}$ and $Mg^{+2}$, that promote synthesis of lipids and PUFAs (Nakahara, T. et al., *Ind. Appl. Single Cell Oils*, D. J. Kyle and R. Colin, eds. pp 61-97 (1992)).

Preferred growth media for the methods and host cells described herein are common commercially prepared media, such as Yeast Nitrogen Base (DIFCO Laboratories, Detroit, Mich.). Other defined or synthetic growth media may also be used and the appropriate medium for growth of the transformant host cells will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in oleaginous yeast (e.g., *Yarrowia lipolytica*). This approach is described in U.S. Pat. No. 7,238,482, as are various suitable fermentation process designs (i.e., batch, fed-batch and continuous) and considerations during growth.

PUFAs may be found in the host microorganisms and plants as free fatty acids or in esterified forms such as acylglycerols, phospholipids, sulfolipids or glycolipids, and may be extracted from the host cells through a variety of means well-known in the art. One review of extraction techniques, quality analysis and acceptability standards for yeast lipids is that of Z. Jacobs (*Critical Reviews in Biotechnology*, 12(5/6): 463-491 (1992)). A brief review of downstream processing is also available by A. Singh and O. Ward (*Adv. Appl. Microbiol.*, 45:271-312 (1997)).

In general, means for the purification of PUFAs may include extraction (e.g., U.S. Pat. No. 6,797,303 and U.S. Pat.

No. 5,648,564) with organic solvents, sonication, supercritical fluid extraction (e.g., using carbon dioxide), saponification and physical means such as presses, bead beaters, or combinations thereof. See U.S. Pat. No. 7,238,482 for additional details.

The market place currently supports a large variety of food and feed products, incorporating omega-3 and/or omega-6 fatty acids (particularly e.g., ALA, GLA, ARA, EPA, DPA and DHA). It is contemplated that the microbial or plant biomass comprising long-chain PUFAs, partially purified biomass comprising PUFAs, purified oil comprising PUFAs, and/or purified PUFAs made by the methods and host cells described herein will impart health benefits, upon ingestion of foods or feed improved by their addition. More specifically, these oils containing omega-3 and/or omega-6 fatty acids can be added to: food analogs, meat products, cereal products, baked foods, snack foods and dairy products, to name a few. See U.S. Pat. Pub. No. 2009-0093543-A1, which is hereby incorporated herein by reference.

These compositions may also impart health benefits by being added to medical foods including medical nutritionals, dietary supplements, infant formula and pharmaceuticals. One of skill in the art will understand the amount of these oils to be added to food, feed, dietary supplements, nutriceuticals, pharmaceuticals, and other ingestible products as to impart health benefits. Health benefits from ingestion of these oils are described in the art, known to the skilled artisan and continuously being investigated. Such an amount will be referred to herein as an "effective" amount and will depend on, among other things, the nature of the ingested products containing these oils and the physical conditions they are intended to address.

EXAMPLES

The present invention is further described in the following Examples, which illustrate reductions to practice of the invention but do not completely define all of its possible variations.

General Methods

Standard recombinant DNA and molecular cloning techniques used in the Examples are well known in the art and are described by: 1) Sambrook, J., Fritsch, E. F. and Maniatis, T., *Molecular Cloning: A Laboratory Manual*; Cold Spring Harbor Laboratory: Cold Spring Harbor, N.Y. (1989) (Maniatis); 2) T. J. Silhavy, M. L. Bennan, and L. W. Enquist, Experiments with Gene Fusions; Cold Spring Harbor Laboratory: Cold Spring Harbor, N.Y. (1984); and, 3) Ausubel, F. M. et al., Current Protocols in Molecular Biology, published by Greene Publishing Assoc. and Wiley-Interscience (1987).

Materials and methods suitable for the maintenance and growth of microbial cultures are well known in the art. Techniques suitable for use in the following examples may be found as set out in Manual of Methods for General Bacteriology (P. Gerhardt, R. G. E. Murray, R. N. Costilow, E. W. Nester, W. A. Wood, N. R. Krieg and G. B. Phillips, Eds), American Society for Microbiology: Washington, D.C. (1994)); or by Thomas D. Brock in Biotechnology: A Textbook of Industrial Microbiology, 2$^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.), New England Biolabs (Ipswich, Mass.), or Sigma Chemical Company (St. Louis, Mo.), unless otherwise specified. *E. coli* strains were typically grown at 37° C. on Luria Bertani ["LB"] plates.

General molecular cloning was performed according to standard methods (Sambrook et al., supra). Sequence editing was performed in Sequencher (Gene Codes Corp., Ann Arbor, Mich.). All sequences represent coverage at least two times in both directions. Comparisons of genetic sequences were accomplished using DNASTAR software (DNASTAR Inc., Madison, Wis.) or similar software created in-house (E.I. duPont de Nemours & Co., Inc., Wilmington, Del.).

The meaning of abbreviations is as follows: "sec" means second(s), "min" means minute(s), "h" means hour(s), "d" means day(s), "µl" means microliter(s), "mL" means milliliter(s), "L" means liter(s), "µM" means micromolar, "mM" means millimolar, "M" means molar, "mmol" means millimole(s), "µmole" means micromole(s), "g" means gram(s), "µg" means microgram(s), "ng" means nanogram(s), "U" means unit(s), "bp" means base pair(s) and "kB" means kilobase(s).

Nomenclature For Expression Cassettes: The structure of an expression cassette will be represented by a simple notation system of "X::Y::Z", wherein X describes the promoter fragment, Y describes the gene fragment, and Z describes the terminator fragment, which are all operably linked to one another Transformation And Cultivation Of *Yarrowia lipolytica*: *Yarrowia lipolytica* strains with ATCC Accession Nos. #20362, #76982 and #90812 were purchased from the American Type Culture Collection (Rockville, Md.). *Y. lipolytica* strains were typically grown at 28-30° C. in several media, according to the recipes shown below. Agar plates were prepared as required by addition of 20 g/L agar to each liquid media, according to standard methodology.

YPD agar medium (per liter): 10 g of yeast extract [Difco], 20 g of Bacto peptone [Difco], and 20 g of glucose.

Basic Minimal Media ["MM"] (per liter): 20 g glucose, 1.7 g yeast nitrogen base without amino acids, 1.0 g proline, and pH 6.1 (do not need to adjust).

Minimal Media+5-Fluoroorotic Acid ["MM+5-FOA"] (per liter): 20 g glucose, 6.7 g Yeast Nitrogen base, 75 mg uracil, 75 mg uridine and appropriate amount of FOA (Zymo Research Corp., Orange, Calif.), based on FOA activity testing against a range of concentrations from 100 mg/L to 1000 mg/L (since variation occurs within each batch received from the supplier).

High Glucose Media ["HGM"] (per liter): 80 glucose, 2.58 g $KH_2PO_4$ and 5.36 g $K_2HPO_4$, pH 7.5 (do not need to adjust).

Fermentation medium ["FM"] (per liter): 6.70 g/L Yeast nitrogen base, 6.00 g $KH_2PO_4$, 2.00 g $K_2HPO_4$, 1.50 g $MgSO_4$*$7H_2O$, 20 g glucose and 5.00 g Yeast extract (BBL).

Transformation of *Y. lipolytica* was performed as described in U.S. Pat. Pub. No. 2009-0093543-A1, hereby incorporated herein by reference.

Example 1

Construction of *Yarrowia lipolytica* Expression Vector pZUFmEgD9ES, Comprising a Synthetic Delta-9 Elongase Gene (Derived from *Euglena gracilis*), Codon-Optimized for Expression in *Yarrowia lipolytica* ["EgD9eS"]

Figure 2:
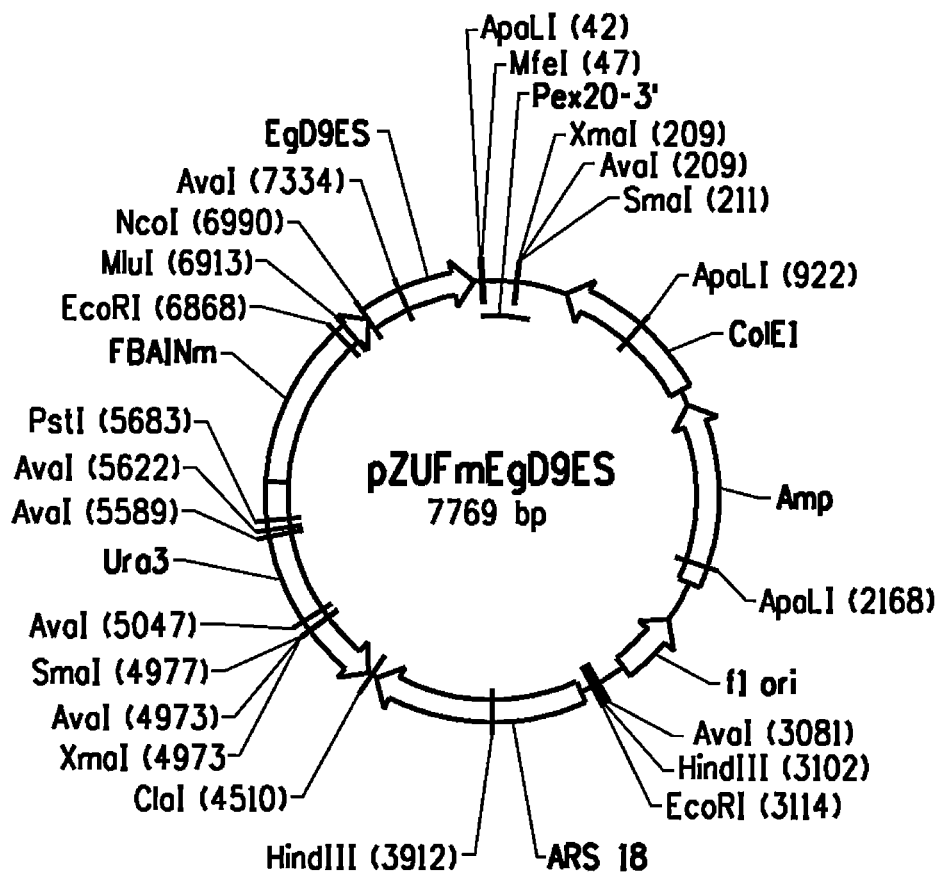
FIG. 2 is a plasmid map of pZUFmEgD9ES.

The construction of *Y. lipolytica* vector pZUFmEgD9ES (FIG. 2; SEQ ID NO:25), comprising a chimeric FBAINm:: EgD9eS::Pex20 gene, wherein EgD9eS is a synthetic delta-9 elongase derived from *E. gracilis* and codon-optimized for expression in *Yarrowia*, is described in Example 8 of U.S. Pat.

No. 7,645,604, hereby incorporated herein by reference. The nucleotide sequence of EgD9eS (SEQ ID NO:9) differs from the nucleotide sequence of the wild type *E. gracilis* delta-9 elongase ("EgD9e"; SEQ ID NO:7), since 117 bp of the 777 bp coding region were modified (15.1%) and 106 codons were optimized (40.9%), in addition to modification of the translation initiation site (yet the protein sequence encoded by the codon-optimized gene [i.e., SEQ ID NO:10] is identical to that of the wildtype protein sequence [i.e., SEQ ID NO:8]).

Example 2

Generalized Method for Analyzing *Yarrowia lipolytica* Transformants Comprising Mutant Delta-9 Elongases with Increased Delta-9 Elongase Conversion Efficiency The present Example describes generalized means to analyze lipid profiles within pZUFmEgD9ES transformant organisms of *Y. lipolytica* strain Y2224 (a FOA resistant mutant from an autonomous mutation of the Ura3 gene of wildtype *Yarrowia* strain ATCC #20362 [isolation described in Example 7 of Intl. App. Pub. No. WO 2008/073367]), expressing either the non-mutant EgD9eS gene (SEQ ID NO:9 (referred to as either the "control" or "wildtype") or various mutated EgD9eS genes, created in error prone polymerase chain reaction ["ePCR"] libraries (Example 3), site-saturation libraries (Example 5), SlonoMax® libraries (Example 7), or combinatorial libraries (Example 9) (described infra).

Transformation of Mutant Libraries into *Escherichia coli* and *Yarrowia lipolytica*

DNA from each mutant library was transformed into *E. coli* Top 10 electro-competent cells (Cat. No. C404052, Invitrogen, Carlsbad, Calif.) by electroporation. The transformed cells were spread onto Luria-Bertani ["LB"] agar plates with 100 mg/L ampicillin and grown in a 37° C. incubator overnight. Plasmid DNA was extracted from the transformant *E. coli* cells using a QIAprep® Spin Miniprep kit (Qiagen Inc., Valencia, Calif.) following the manufacturer's protocol.

The DNA molecules were then transformed into *Y. lipolytica* strain Y2224 as described in the General Methods, and the transformants were selected on MM plates. After 2 days growth at 30° C., transformants selected on MM plates were picked and re-streaked onto fresh MM plates.

Quick Screen Plate Assay

A quick screen "plate assay" was used for the preliminary functional analysis of each mutant library. For this plate assay, transformant *Yarrowia* cells from the re-streaked MM plates above were analyzed directly from the media plate. Fatty acid methyl esters ["FAMEs"] were prepared using trimthylsulphonium hydroxide ["TMSH"].

The TMSH was prepared from trimethylsulfonium iodide ["TMSI"], after conversion to a solution of the hydroxide by reaction with silver oxide in methanol. Specifically, 4.4 g TMSI were mixed in 100 mL MeOH and allowed to incubate in a 50° C. water bath for 1 hr; then, 5 g Ag$_2$O were added to the solution and stirred for 4 hr at room temperature. The final solution was filtered before use. TMSH causes base-catalyzed transesterification of O-acyl lipids (i.e., TAG) and esterification of free fatty acids (A. H. El-Hamdy & W. W. Christie, *J. of Chromatography*, 630:438-441 (1993)).

Using a 1 µl loop, cells were taken directly from the re-streaked MM plate and suspended in 50 µl TMSH in a gas chromatogram ["GC"] vial with a 0.35 mL insert. Heptane (150 µl) was then added to the vial insert, the vial was capped and then incubated for 20 min at room temperature with agitation. Subsequently, 1 µl from the heptane layer was injected into a Hewlett Packard 7890 GC fitted with an Omegawax 320 fused silica capillary column (Supelco Inc., Bellefonte, Pa.) for GC analysis of FAMEs. Retention times were compared to those for methyl esters from commercial standards (Standard #461, Nu-Chek Prep, Inc., Elysian, Minn.).

The FAME profiles obtained from cells comprising the EgD9eS mutants were compared to that of the non-mutant EgD9eS control. The results of this primary screen served as the basis for the selection of mutants that would be subjected to the secondary confirmation assay. The criteria used to select mutants for the confirmation assay was based on the lipid profile, in particular the concentration of EDA as calculated from the GC peak area of the corresponding FAME as a percent relative to the sum of all integrated peaks ["EDA % TFAs"] and/or the conversion efficiency of LA to EDA. The conversion efficiency ["% Conv"] of LA to EDA was calculated for each transformant according to the following formula: ([product]/[substrate+product])*100, wherein the product was EDA % TFAs and the substrate was the concentration of LA as an area percent of TFAs ["LA % TFAs"].

"Confirmation" Assay

Mutants that demonstrated improvement in delta-9 elongation activity relative to the control via the quick screen "plate assay" were selected for subsequent confirmation assays.

*Yarrowia* transformed with mutants were first grown from fresh re-streaked MM plates and then each mutant was individually inoculated into triplicate cultures comprising 3 mL liquid MM at 30° C. and shaken at 250 rpm/min for 2 days. The cells were collected by centrifugation, lipids were extracted, and FAMEs were prepared by transesterification of the lipid extract with sodium methoxide (Roughan, G., and Nishida I., *Arch. Biochem. Biophys.*, 276(1):38-46 (1990)) and subsequently analyzed by GC, as described for the plate assay (supra).

Following confirmation of improved delta-9 elongation activity, each mutant pZUFmEgD9ES plasmid was recovered from the transformed *Y. lipolytica* strain Y2224 from which it was expressed, using the Zymoprep™ Yeast Plasmid Miniprep II kit (Cat. No. D2004, Zymo Research, Orange, Calif.), as recommended by the manufacturer.

The sequence of the rescued plasmid was characterized using standard DNA sequencing methods. In brief, DNA sequence was generated on an ABI Automatic sequencer using dye terminator technology (U.S. Pat. No. 5,366,860; EP 272,007) using a combination of vector and insert-specific primers. Comparisons of genetic sequences were accomplished using standard tools well known in the art.

Example 3

Construction of Two EgD9eS Error Prone PCR Libraries

The present Example describes the synthesis of two delta-9 elongase error prone polymerase chain reaction ["ePCR"] libraries. The two ePCR libraries were created in a two-step method that first required the generation of a suite of megaprimers comprising random mutations within the templates, followed by the use of these megaprimers to make point mutations into pZuFmEgD9ES. The construct pZuFmEgD9ES (SEQ ID NO:25) (Example 1) was used as the DNA template for the first ePCR library. The second ePCR library used hits from the first ePCR library as DNA templates.

Creation of Megaprimers Using a Random Mutagenesis Kit

The GeneMorph II Random Mutagenesis Kit (Cat. No. 200550, Stratagene, La Jolla, Calif.) was used to create random amino acid substitutions in the target protein. It functions by introducing mutations into the target gene during error-prone PCR using a novel error prone PCR enzyme blended formation comprising a combination of two different polymerases to produce a less biased mutational spectrum with equivalent mutation rates at A's and T's versus G's and C's. It is advertized that mutation rates of 1-16 mutations per kB can be achieved using a single set of buffer conditions optimized for high product yield. The desired mutation rate can be controlled simply by varying the initial amount of template DNA in the reaction and/or the number of amplification cycles performed.

The above kit was utilized to generate EgD9eS "megaprimers", using the protocol recommended by the manufacturer. These megaprimers were about 930 bp long and comprised the 777 bp encoding EgD9eS (SEQ ID NO:9). The reaction mixture contained either 16 ng of DNA template per μl for the first ePCR library or 2.0 ng of DNA template per μl for the second library. It also comprised reaction buffer, dNTPs (0.8 mM), primer pZUFm_6980_012208f (SEQ ID NO:26) (2 μM), primer pZUFm_210_012208r (SEQ ID NO:27) (2 μM) and Mutazyme® II DNA polymerase (0.25 U/μl). The PCR reaction was performed in a thin well 200 μl tube in Mastercycler gradient equipment (Brinkmann Instruments, Inc., Westbury, N.Y.). PCR amplification was performed using the following conditions: 95° C. for 2 min, followed by 30 cycles of denaturation at 95° C. for 30 sec, annealing at 55° C. for 30 sec, and elongation at 72° C. for 90 sec. A final elongation cycle at 72° C. for 4 min was carried out, followed by reaction termination at 4° C.

The PCR products were purified using a DNA Clean & Concentrator™-5 kit (Cat. No. D4003, Zymo Research, Orange, Calif.), as recommended by the manufacturer. The purified double-stranded PCR products were utilized as "megaprimers", each containing various mutations within EgD9eS.

Standard Cloning Methods to Create ePCR Mutant Genes of EgD9eS

For the first ePCR library, "megaprimers" were digested with NcoI and NotI restriction enzymes. The gel purified NcoI/NotI gene fragment was then directly ligated into gel purified NcoI/NotI pZUFmEgD9ES vector (SEQ ID NO:25) using T4 DNA ligase (Promega, Madison, Wis.), via a ligation reaction at room temperature for 5 hr.

Site-Directed Mutagenesis to Create ePCR Mutant Genes of EgD9eS

To create the second ePCR library, the "megaprimers" described above were utilized in reactions designed to introduce the EgD9eS mutations within the "megaprimers" into pZuFmEgD9ES (FIG. 2; SEQ ID NO:25), thereby replacing the non-mutant EgD9eS gene with various mutant EgD9eS genes. This was accomplished using the QuikChange® II XL site directed mutagenesis kit (Cat. No. 200524, Stratagene, La Jolla, Calif.).

The QuikChange® II site-directed mutagenesis kit is used to make point mutations, replace amino acids, and delete or insert single/multiple adjacent amino acids within an insert of interest in a double-stranded vector, using the high-fidelity PfuUltra DNA polymerase for mutagenic primer-directed replication of both plasmid strands. The kit requires no specialized vectors, unique restriction sites, or multiple transformations and allows site-specific mutation in virtually any double-stranded plasmid. The basic procedure utilizes two synthetic oligonucleotide primers, both containing the desired mutation and complementary to opposite strands of the vector, which are extended during temperature cycling by the high-fidelity DNA polymerase without primer displacement. Extension of the oligonucleotide primers generates a mutated plasmid containing staggered nicks, which is then treated with the Dpn I endonuclease. This restriction enzyme is specific for methylated and hemi-methylated DNA, thereby allowing digestion of the parental DNA template and selection for mutation-containing synthesized DNA. The nicked vector DNA containing the desired mutations is then transformed and propagated in an *Escherichia coli* host.

In the present methodology, however, the double-stranded megaprimers comprising various mutant EgD9eS genes were used in place of traditional synthetic oligonucleotide primers. Specifically, a 50 μl reaction was prepared comprising 5.0 μl of 10× kit-supplied reaction buffer, 1.0 μl of 50 ng/μl pZUFmEgD9ES template (SEQ ID NO:25), 42 μl megaprimer, 1.0 μl of 40 mM kit-supplied dNTP mix and 1.0 μl kit-supplied Pfu-Ultra DNA polymerase. This reaction mixture was placed in a thin well 200 μl-capacity PCR tube and subjected to PCR amplification, using the following conditions: 95° C. for 30 sec, followed by 25 cycles of denaturation at 95° C. for 30 sec, annealing at 55° C. for 1 min, and elongation at 68° C. for 6 min. A final elongation cycle at 68° C. for 8 min was carried out, followed by reaction termination at 4° C.

Kit-supplied DpnI restriction enzyme (1.0 μl) was directly added to the finished site-directed mutagenesis reaction mixture and enzymatic digestion was performed at 37° C. for 1 hr to remove the DNA template. The digested product was purified using a DNA cleaning kit (Zymo Research) and eluted to yield 10 μl of purified DNA, comprising various mutant EgD9eS genes contained within the pZUFmEgD9ES vector backbone.

Example 4

Identification of ePCR EgD9eS Library Mutants Having Improved Delta-9 Elongase Conversion Efficiency The present Example describes: 1) the identification of EgD9eS ePCR library mutants having improved delta-9 elongase conversion efficiency of LA to EDA, as compared to that of the wildtype protein EgD9eS (SEQ ID NO:10); and, 2) sequence analysis of these EgD9eS ePCR library mutants.

Identification of EgD9eS ePCR Mutants

The ePCR gene library mutants prepared in Example 3 were transformed into *E. coli* Top 10 electro-competent cells, purified and subsequently transformed into *Y. lipolytica* strain Y2224, as described in Example 2. The fatty acid profiles of 1,724 *Yarrowia* transformants were screened using the quick screen "plate assay" of Example 2. Most of these mutants exhibited reduced activity compared to the control. However, five transformants were confirmed to exhibit improved delta-9 elongation activity as compared to the control, based on confirmation assays of Example 2.

Data from two independent confirmation assays are presented in Table 5 and Table 6, and the FAME profiles of individual pZuFmEgD9ES control transformants are compared with those of ePCR mutants. More specifically, the concentration of each fatty acid as calculated from the GC peak area of the corresponding FAME as a percent relative to the sum of all integrated peaks ["% TFAs"] and % Conv. of LA to EDA (determined as described in Example 2) for each strain is shown below in Table 5 and Table 6, while averages are highlighted in gray and indicated with "Avg". Fatty acids are identified as 16:0 (palmitic acid), 16:1 (palmitoleic acid), 18:0 (stearic acid), 18:1 (oleic acid), LA and EDA. Comparison of each mutant's performance relative to the EgD9eS control should only be made within the particular confirmation assay in which each mutant was analyzed (i.e., comparisons can not be made between Assay #1 and Assay #2).

TABLE 5

Confirmation Assay #1: Lipid Composition In Transformant
*Y. lipolytica* Strain Y2224, Expressing EgD9eS
Or ePCR Library Mutant Variants Thereof

| Strain | Replicate No. | % TFAs |  |  |  |  |  | % Conv LA to EDA |
|---|---|---|---|---|---|---|---|---|
|  |  | 16:0 | 16:1 | 18:0 | 18:1 | LA | EDA |  |
| EgD9es Control-1 | 1 | 12.8 | 12.9 | 3.0 | 46.6 | 17.3 | 3.0 | 14.8 |
|  | 2 | 12.9 | 12.6 | 3.0 | 45.5 | 17.2 | 3.1 | 15.2 |
|  | 3 | 12.6 | 12.5 | 2.9 | 47.0 | 17.1 | 3.1 | 15.3 |
| EgD9eS Control-2 | 1 | 14.0 | 12.4 | 3.6 | 45.6 | 16.2 | 3.2 | 16.3 |
|  | 2 | 12.2 | 12.5 | 2.6 | 47.4 | 17.3 | 3.1 | 15.1 |
|  | 3 | 13.2 | 13.1 | 3.1 | 45.4 | 17.2 | 3.1 | 15.3 |
| EgD9eS Control-3 | 1 | 13.3 | 13.2 | 3.1 | 45.0 | 17.2 | 3.2 | 15.7 |
|  | 2 | 12.8 | 12.6 | 2.9 | 46.5 | 17.3 | 3.1 | 15.0 |
|  | 3 | 13.2 | 13.0 | 3.1 | 45.3 | 17.2 | 3.2 | 15.7 |
| EgD9eS Control-4 | 1 | 13.7 | 11.9 | 3.7 | 46.2 | 15.8 | 3.4 | 17.6 |
|  | 2 | 12.6 | 13.0 | 2.7 | 45.5 | 17.9 | 3.2 | 15.3 |
|  | 3 | 12.7 | 12.9 | 2.9 | 45.6 | 17.6 | 3.2 | 15.5 |
| EgD9eS Control-5 | 1 | 12.9 | 12.6 | 3.0 | 45.7 | 17.7 | 3.1 | 14.9 |
|  | 2 | 12.1 | 12.1 | 2.7 | 47.9 | 17.3 | 3.1 | 15.2 |
| Avg. Control | – | 12.9 | 12.7 | 3.0 | 46.1 | 17.2 | 3.1 | 15.5 |
| 1.2ep-8 | 1 | 11.8 | 12.6 | 2.4 | 47.7 | 17.1 | 3.6 | 17.3 |
|  | 2 | 12.1 | 12.9 | 2.5 | 47.0 | 16.9 | 3.7 | 17.9 |
|  | 3 | 12.7 | 12.8 | 2.9 | 45.9 | 16.9 | 3.7 | 18.0 |
| Avg | | 12.2 | 12.8 | 2.6 | 46.9 | 17.0 | 3.7 | 17.8 |
| 1.9ep-63 | 1 | 12.5 | 12.9 | 2.7 | 46.1 | 17.5 | 3.3 | 15.9 |
|  | 2 | 12.6 | 12.7 | 2.8 | 46.2 | 17.3 | 3.3 | 16.0 |
|  | 3 | 13.0 | 12.6 | 3.2 | 45.7 | 16.9 | 3.4 | 16.8 |
| Avg | | 12.7 | 12.7 | 2.9 | 46.0 | 17.2 | 3.3 | 16.3 |
| 1.4ep-161 | 1 | 13.7 | 12.3 | 3.5 | 45.8 | 16.2 | 3.3 | 17.0 |
|  | 2 | 12.4 | 12.7 | 2.9 | 46.9 | 16.8 | 3.2 | 16.0 |
|  | 3 | 12.5 | 12.4 | 3.0 | 46.8 | 16.9 | 3.3 | 16.3 |
| Avg | | 12.9 | 12.5 | 3.1 | 46.5 | 16.6 | 3.3 | 16.4 |

TABLE 6

Confirmation Assay #2: Lipid Composition In Transformant
*Y. lipolytica* Strain Y2224, Expressing EgD9eS
Or ePCR Library Mutant Variants Thereof

| Strain | Replicate No. | % TFAs |  |  |  |  |  | % Conv LA to EDA |
|---|---|---|---|---|---|---|---|---|
|  |  | 16:0 | 16:1 | 18:0 | 18:1 | LA | EDA |  |
| EgD9es Control-1 | 1 | 12.0 | 12.1 | 3.0 | 50.2 | 14.0 | 2.9 | 16.9 |
|  | 2 | 12.0 | 11.6 | 3.1 | 50.4 | 14.0 | 2.7 | 16.0 |
|  | 3 | 11.8 | 12.1 | 3.0 | 51.1 | 14.4 | 2.8 | 16.3 |
| EgD9eS Control-5 | 1 | 11.8 | 12.1 | 3.2 | 50.6 | 13.7 | 3.2 | 18.9 |
|  | 2 | 11.9 | 12.2 | 3.2 | 51.0 | 13.9 | 3.3 | 19.2 |
|  | 3 | 11.8 | 11.8 | 3.2 | 51.8 | 13.9 | 2.9 | 17.1 |
| EgD9eS Control-6 | 1 | 11.8 | 11.7 | 3.2 | 51.1 | 14.0 | 2.8 | 16.6 |
|  | 2 | 11.8 | 11.9 | 3.3 | 51.0 | 14.5 | 2.8 | 16.4 |
|  | 3 | 11.6 | 12.2 | 2.8 | 51.3 | 14.9 | 2.8 | 15.8 |
| EgD9eS Control-7 | 1 | 11.9 | 11.8 | 3.4 | 51.1 | 14.3 | 2.8 | 16.2 |
|  | 2 | 11.8 | 12.0 | 3.2 | 51.1 | 14.2 | 2.8 | 16.6 |
|  | 3 | 12.0 | 12.0 | 3.2 | 50.8 | 14.1 | 2.8 | 16.5 |
| EgD9eS Control-5 | 1 | 12.9 | 12.6 | 3.0 | 45.7 | 17.7 | 3.1 | 14.9 |
|  | 2 | 12.1 | 12.1 | 2.7 | 47.9 | 17.3 | 3.1 | 15.2 |

TABLE 6-continued

| | | | | | | | | |
|---|---|---|---|---|---|---|---|---|
| Avg. Control | – | 11.9 | 11.9 | 3.2 | 51.0 | 14.1 | 2.9 | 16.9 |
| 2.1ep-94 | 1 | 11.7 | 11.1 | 2.8 | 50.0 | 14.9 | 3.5 | 19.2 |
|  | 2 | 10.8 | 11.8 | 2.0 | 50.5 | 15.8 | 3.9 | 19.9 |
|  | 3 | 11.1 | 11.5 | 2.0 | 51.2 | 15.3 | 3.9 | 20.2 |
|  | Avg | 11.2 | 11.5 | 2.3 | 50.5 | 15.3 | 3.8 | 19.8 |
| 2.1ep-95 | 1 | 11.8 | 10.9 | 2.7 | 50.4 | 15.1 | 3.5 | 18.9 |
|  | 2 | 11.8 | 11.0 | 2.6 | 50.6 | 15.5 | 3.5 | 18.6 |
|  | 3 | 12.0 | 11.0 | 3.2 | 50.1 | 15.1 | 3.5 | 18.7 |
|  | Avg | 11.9 | 11.0 | 2.8 | 50.4 | 15.2 | 3.5 | 18.8 |

In summarizing the data shown above in confirmation assay #1, clones of *Y. lipolytica* strain Y2224 that were transformed with pZuFmEgD9ES, comprising the non-mutant codon-optimized EgD9eS gene, produced an average of 3.1 EDA % TFAs, wherein the average conversion efficiency ["% Conv"] of LA to EDA in these five clones was determined to be about 15.5%. In contrast, the average % Conv of LA to EDA for mutant strain 1.2ep-8 was 17.8% (or 115% relative to the control); the average % Conv for mutant strain 1.9ep-63 was 16.3% (or 105% relative to the control); and, the average Conv for mutant strain 1.4ep-161 was 16.4% (or 106% relative to the control).

In confirmation assay #2, clones of *Y. lipolytica* strain Y2224 that were transformed with pZuFmEgD9ES produced 2.9 EDA % TFAs, wherein the average % Conv of LA to EDA in these four strains was determined to be about 16.9%. The average % Conv of LA to EDA for mutant strain 2.1ep-94 was 19.8% (or 117% relative to the control); and, the average % Conv for mutant strain 2.1ep-95 was 18.8% (or 111% relative to the control).

Thus, these experiments confirmed the improved delta-9 elongase conversion efficiency exhibited by EgD9eS ePCR mutants 1.2ep-8, 1.9ep-63, 1.4ep-161, 2.1ep-94 and 2.1ep-95.

Sequence of EgD9eS ePCR Mutants

The plasmids rescued from mutants 1.2ep-8, 1.9ep-63, 1.4ep-161, 2.1ep-94 and 2.1ep-95 were characterized by DNA sequencing, and analysis revealed various nucleotide substitutions and expressed amino acid substitutions within the mutant EgD9eS genes, as shown in Table 7. A designation indicative of the amino acid substitution was given to each mutant EgD9eS gene and to each mutant pZuFmEgD9ES plasmid comprising the mutant EgD9eS gene. For each substitution listed (i.e. L35G), the first letter corresponds to the amino acid in the non-mutant EgD9eS (i.e., SEQ ID NO:10) and the second letter corresponds to the amino acid found in the same position in the mutant, i.e. L35G indicates a change from Leu in EgD9eS at position 35 to Gly in the EgD9eS mutant).

TABLE 7

Summary of Sequenced EgD9eS ePCR Library Mutants

| ePCR Mutant | Nucleotide Substitution | Resulting Amino Acid Substitution (Silent Mutation) | Designation For Mutant Gene | Designation For Mutant Plasmid |
|---|---|---|---|---|
| 1.2ep-8 | C103T and A654G | L35F and (G218G) | "EgD9eS-L35F" (SEQ ID NO: 28) | pZuFmEgD9ES-L35F (SEQ ID NO: 30) |
| 1.9ep-63 | A173G, T234G, | K58R, (S78S), | "EgD9eS-K58R/I257T" | pZuFmEgD9ES-K58R/I257T |

TABLE 7-continued

Summary of Sequenced EgD9eS ePCR Library Mutants

| ePCR Mutant | Nucleotide Substitution | Resulting Amino Acid Substitution (Silent Mutation) | Designation For Mutant Gene | Designation For Mutant Plasmid |
|---|---|---|---|---|
| | G402A and T770C | (Q134Q) and I257T | (SEQ ID NO: 31) | (SEQ ID NO: 33) |
| 1.4ep-161 | C388A, C450T and T728C | L130M, (N150N) and V243A | "EgD9eS-L130M/V243A$_1$" (SEQ ID NO: 34) | pZuFmEgD9ES-L130M/V243A$_1$ (SEQ ID NO: 36) |
| 2.1ep-95 | A293G | D98G | "EgD9eS-D98G" (SEQ ID NO: 37) | pZuFmEgD9ES-D98G (SEQ ID NO: 39) |
| 2.1ep-94 | C21T, C388A, C450T and T728C | (I7I), L130M, (N150N) and V243A | "EgD9eS-L130M/V243A$_2$" (SEQ ID NO: 40) | pZuFmEgD9ES-L130M/V243A$_2$ (SEQ ID NO: 42) |

Thus, for example, the plasmid rescued from mutant 1.2ep-8 comprised 2 nucleotide substitutions (i.e., C103T and A654G). These two nucleotide substitutions correspond to one expressed amino acid substitution (i.e., L35F), and one silent amino acid mutation (i.e., G218G; since both GGA and GGG code for Gly, this amino acid was unchanged in the mutant protein as a result of the A654G nucleotide substitution). The plasmid comprising the C103T and A654G mutations, resulting in the amino acid change L35F, was designated as pZuFmEgD9ES-L35F (SEQ ID NO:30), while the nucleotide sequence of the mutant delta-9 elongase therein is designated as "EgD9eS-L35F" (SEQ ID NO:28), having a protein sequence as set forth in SEQ ID NO:29.

Example 5

Construction of a Two-Site-Saturation EgD9eS Gene Library

The present example describes the synthesis of a site-saturation ["SS"] library, prepared by targeting amino acid positions 35 and 107 within EgD9eS (SEQ ID NO:10). The rationale for targeting position 35 was based on the results of Example 4, while the rationale for targeting position 107 is described below. The SS library was created in a two-step method that first required the generation of megaprimers comprising targeted mutations within the template, followed by use of these megaprimers to make point mutations into pZuFmEgD9ES.

Rationale For Targeting Position 107 of EgD9eS

First, the amino acid sequences of 17 fatty acid elongases, as described in Table 8 below, were aligned using the ClustalW method of alignment.

TABLE 8

Fatty Acid Elongases Subjected To Conservation Pattern Analysis

| Elongase Abbreviation | Organism | Reference | SEQ ID NO |
|---|---|---|---|
| Ci_elo | Ciona intestinalis | GenBank Accession No. AAV67802 | 43 |
| Om_elo | Oncorhynchus mykiss | GenBank Accession No. AAV67803 | 44 |
| Mp_elo1 | Marchantia polymorpha | GenBank Accession No. AAT85662 | 45 |
| Pp_elo1 | Physcomitrella patens | GenBank Accession No. AAL84174 | 46 |
| Mp_d5e | Marchantia polymorpha | GenBank Accession No. BAE71130 | 47 |
| Ot_elo1 | Ostreococcus tauri | GenBank Accession No. AAV67797 | 48 |
| Pav_elo2 | Pavlova sp. CCMP459 | GenBank Accession No. AAV33630 | 49 |
| Ps_elo2 | Pavlova salina | GenBank Accession No. AAY15135 | 50 |
| Ot_elo2 | Ostreococcus tauri | GenBank Accession No. AAV67798 | 51 |
| Ea_d9e | Euglena anabaena | U.S. Pat. 7,794,701 | 12 |
| Eg_d9e | Euglena gracilis | U.S. Pat. 7,645,604 | 8 |
| E398_d9e | Eutreptiella sp. CCMP389 | U.S. Pat. 7,645,604 | 4 |
| Ig_d9e | Isochrysis galbana | PCT Publications No. WO 2002/077213, No. WO 2005/083093, No. WO 2005/012316 and No. WO 2004/057001; GenBank Accession No. AAL37626 | 2 |
| Tp_elo2 | Thalassiosira pseudonana | GenBank Accession No. AAV67800 | 52 |
| Tp_elo1 | Thalassiosira pseudonana | GenBank Accession No. AAV67799 | 53 |
| Ma_d6e | Mortierella alpina | GenBank Accession No. AAF70417 | 54 |
| Th_elo2 | Thraustochytrium sp. FJN-10 | GenBank Accession No. ABC18314 | 55 |

Figure 3A:
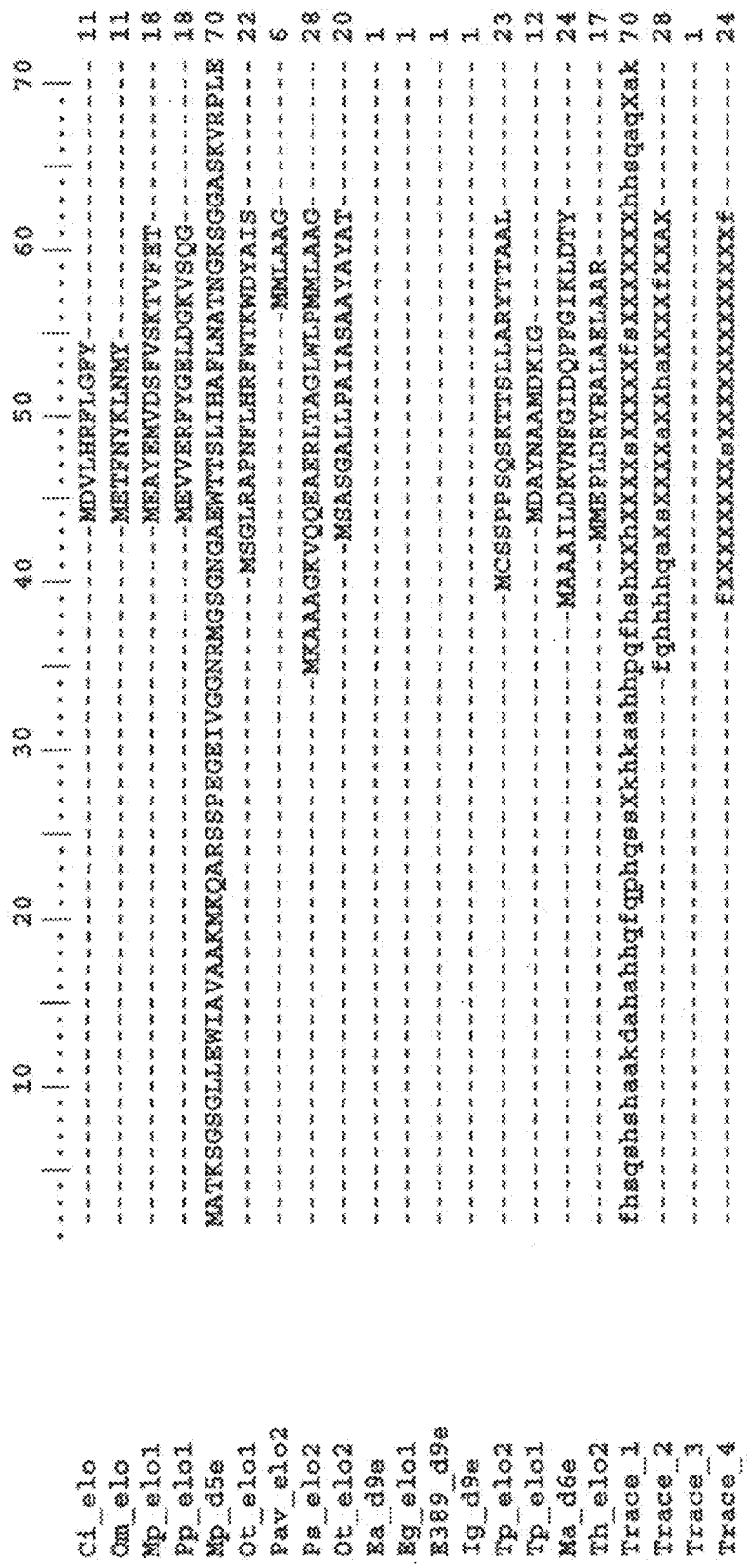
Figure 3B:
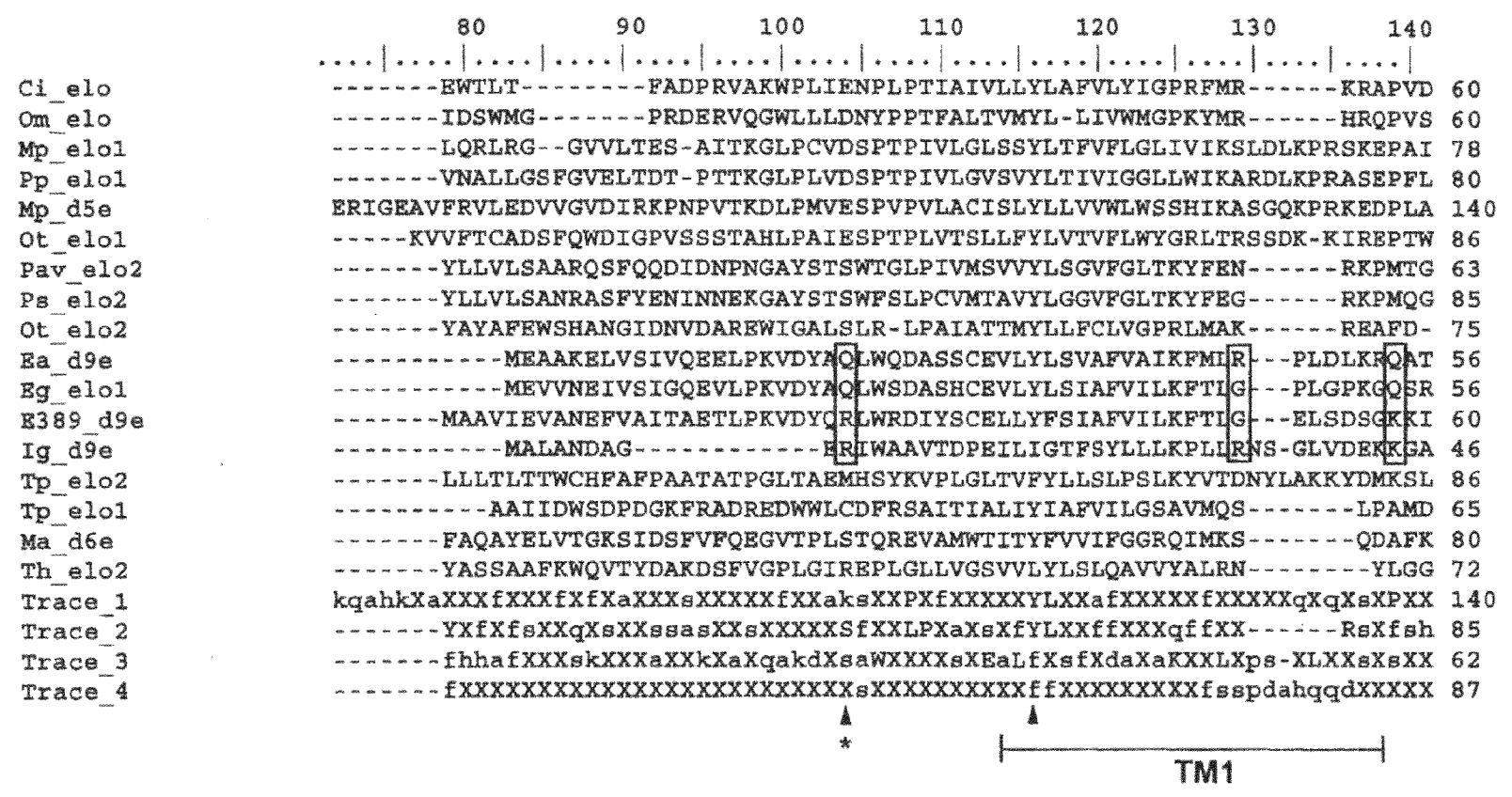
Figure 3C:
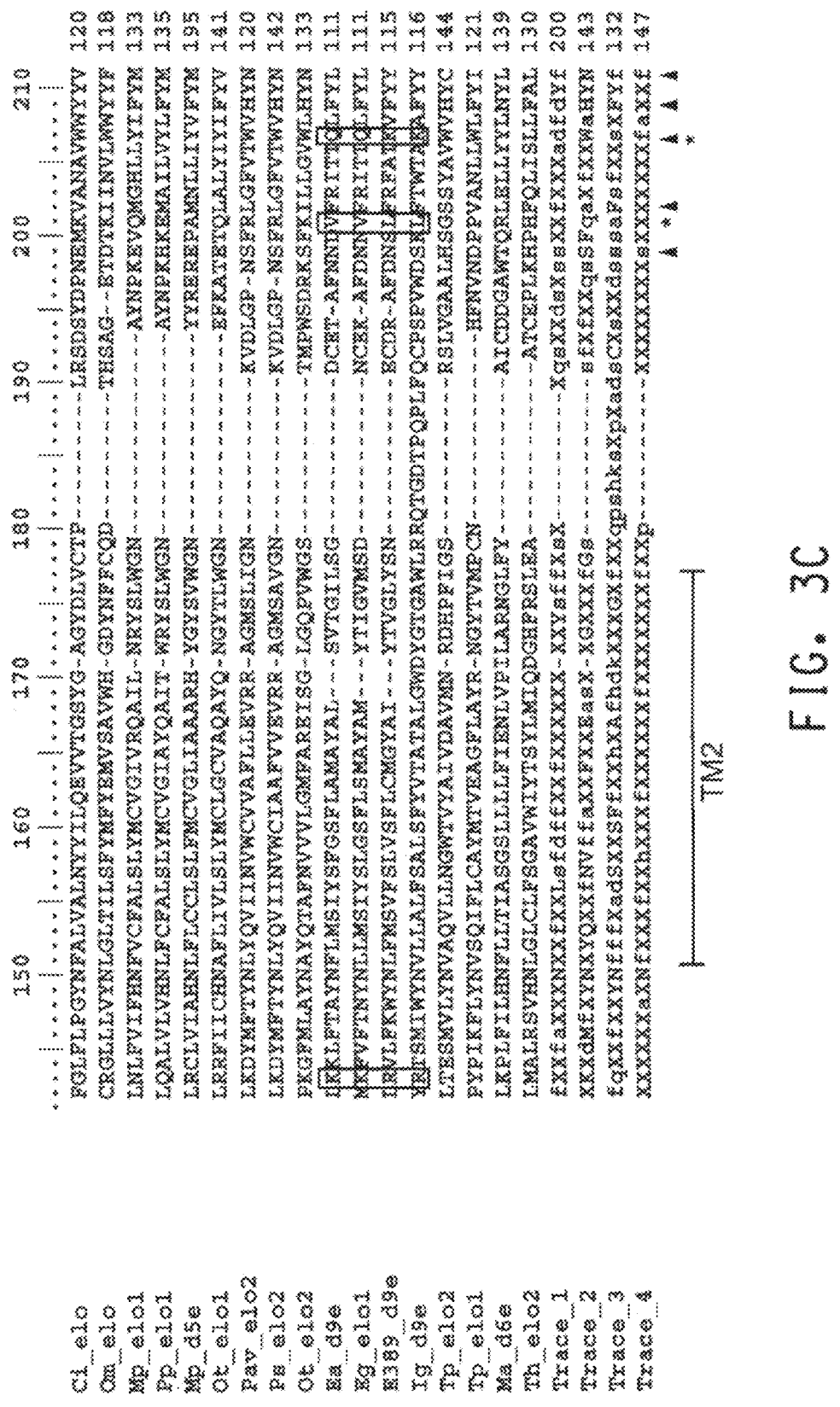
Figure 3D:
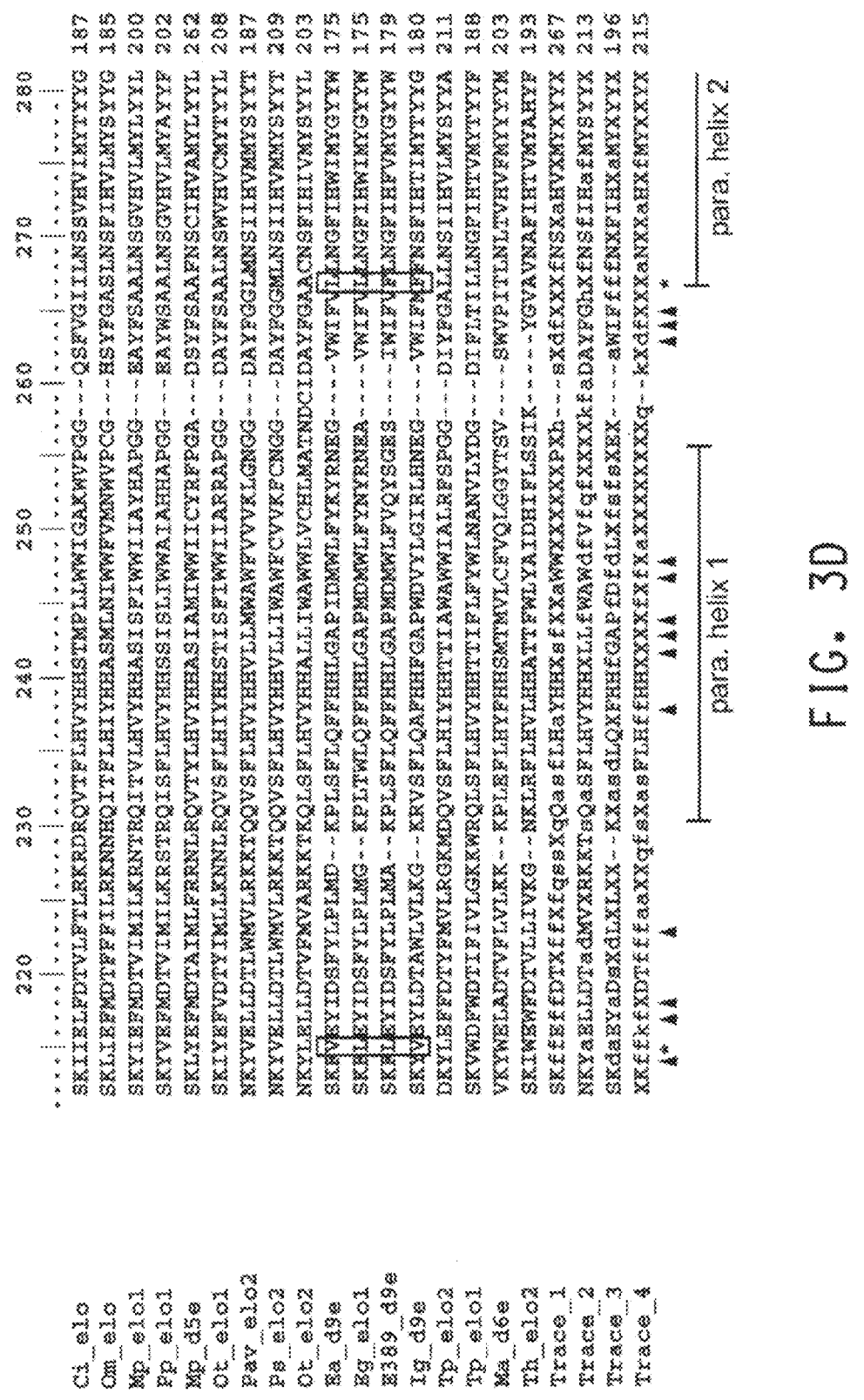

The Clustal W alignment method, described by Thompson et al. (*Nucleic Acids Res.* 22:4673-4680 (1994)), was performed using a ClustalW package (Version 1.83) with default parameters (i.e., protein weight matrix=Gonnet 250, gap opening penalty=10, gap extension penalty=0.2 and full alignment algorithm). Results of the alignment are shown in FIG. 3 (comprising FIGS. 3A, 3B, 3C, 3D, 3E, 3F, 3G and 3H). "Trace_1", "Trace_2", "Trace_3" and "Trace_4" represent the consensus of each column for functional Group I, Group II, Group III and Group IV, as defined infra, i.e., Trace 1 represents the consensus of the protein sequences in Group I, comprising Ci_elo, Om_elo, Mp_elo1, Pp_elo1, Mp_d5e and Ot_elo1. The consensus of each column was defined as follows. Specifically, if the column was completely conserved, then the consensus was represented as the conserved amino acid, shown as a capital letter. If the column was conserved in terms of physio-chemical properties, then the consensus was represented with a lower case letter, wherein "k" represents amino acids D and E (negatively-charged), "q" represents amino acids H, K and R (positively-charged), "p" represents amino acids N and Q (polar), "a" represents amino acids I, L and V (aliphatic), "d" represents amino acids F, W and Y (aromatic), "h" represents amino acids A and G (tiny), "s" represents amino acids D, E, N, Q, H, K, R, S and T (hydrophilic) and "f" represents amino acids I, L, V, F, W, Y, C and M (hydrophobic). If the column was not conserved, then the consensus was represented with a capital letter "X".

A neighbor-joining tree was generated from the Clustal W alignment. Based on the tree topology, the 17 sequences were partitioned into 4 groups, which are hypothesized to correspond to functional groups of different substrate specificity: Group I comprises Cl_elo, Om_elo, Mp_elo1, Pp_elo1, Mp_d5e and Ot_elo1; Group II comprises Pav_elo2, Ps_elo2 and Ot_elo2; Group III comprises Ea_d9e, Eg_d9e, E398_d9e and Ig_d9e; and, Group IV comprises Tp_elo2, Tp_elo1, Ma_d6e and Th_elo2.

Considering the alignment of FIG. 3 and the groupings of the neighbor-joining tree, the following conclusions were drawn. First, some positions are absolutely conserved across all 17 sequences within Group I, II, III and IV. These positions were considered to likely be essential for the catalytic activity of the elongase, and thus were eliminated as targets for mutation. Some positions were conserved in only some of the sequences within Group I, II, III and IV (i.e., not absolutely conserved). These positions were considered to likely be important for the substrate specificity exhibited by elongases within the functional groups of Group I, II, III or IV. Some positions were relatively conserved within Group III (comprising all four of the known delta-9 elongases), but variations were also exhibited; see, amino acid positions 22, 47, 54, 101, 107, 111, 115, 161, 182, 192 and 242, based on numbering of EgD9e. These positions were considered to likely be important for the activity of delta-9 elongases, and were hypothesized to modulate the differences in substrate specificity of Ea_d9e (SEQ ID NO:12), Eg_d9e (SEQ ID NO:8), E398_d9e (SEQ ID NO:4) and Ig_d9e (SEQ ID NO:2).

An analysis of the transmembrane ["TM"] domains within EgD9eS was performed using the TMHMM program ("Prediction of transmembrane helices in proteins"; TMHMM Server v. 2.0, Center for Biological Sequence Analysis, BioCentrum-DTU, Technical University of Denmark, DK-2800 Lyngby, Denmark). The prediction indicated six membrane-spanning helices (corresponding to amino acid residues 32-51, 66-88, 114-136, 156-175, 188-206, 221-243), with both N- and C-termini located on the cytoplasmic side. When Ot_elo2, Ig_elo1, Pav_elo2 and Tp_elo2 were similarly analyzed using the TMHMM program, the number of membrane-spanning helices varied from 4 to 8. Thus, in order to consolidate these varying predictions, the following pieces of functional information were used.

1. The highly conserved histidine-rich motif [Q/H]xxHH ("His-box") has been shown to be essential for optimum enzyme activity of Ig_d9e (SEQ ID NO:2), but is not directly responsible for substrate specificity (Qi et al., *FEBS Letters*, 547:137-139 (2003)). Thus, it strongly suggests that the His-box (corresponding to amino acid residues 134-138 in EgD9eS) is involved in the active site; and, it should be located in or near the cytosolic side of the folded protein such that substrate can access the active site.

2. Several highly conserved positions with charged residues are present at the C-terminal end of EgD9eS. They are likely relevant for the activity and thus the C-terminus is probably located in the cytosolic side of the folded protein.

In contrast to the TMHMM results which predicted a membrane-spanning helix between amino acid residues 114-136 and between amino acid residues 156-175, the above considerations indicate that the sequence region between residues 114-136 does not span the membrane since the His-box cannot be located in the external face of the membrane. If the C-terminus is located in the cytosolic side, then the predicted TM domain between 156-175 also does not span the membrane. Because the substrate for the elongase is highly hydrophobic, it will likely partition into the lipid bilayer. The active site (including the His-box) may occur at or very near the membrane surface.

Therefore, it is predicted herein that these two hydrophobic regions (i.e., corresponding to amino acid residues 114-136 and amino acid residues 156-175) lie in or near the inner membrane leaflet to ensure the active site sits close to the membrane. The final membrane topology model predicted for EgD9eS is shown in FIG. 4A. Specifically, each vertical cylinder indicates a membrane-spanning segment, while each horizontal cylinder indicates a hydrophobic stretch that lies in or near the inner membrane leaflet. The conserved glutamine [Q] and histidines [H] within the His-box (i.e., corresponding to amino acid residues 134-138) are indicated with small circles. Finally, "in" corresponds with the cytoplasmic space, while "out" corresponds with the periplasmic space.

While conservation pattern analysis identified 11 different amino acid residues within the Group III delta-9 fatty acid elongases (i.e., Ea_d9e [SEQ ID NO:12], Eg_d9e [SEQ ID NO:8], E398_d9e [SEQ ID NO:4] and Ig_d9e [SEQ ID NO:2]) that were predicted to affect enzyme activity, the results from the predicted topology model further limited candidate residues. Specifically, it was reasoned that positions that were important for enzymatic activity had to be on or near the cytosolic side, where the active site lies. Amino acid residues 47, 54 and 192 failed to meet this criterion and thus it was assumed that they could not be important for modulating the activity of the delta-9 elongases.

Based on the above rationale, the candidate residues that were likely to significantly impact delta-9 elongase activity of EgD9eS were reduced from 258 residues within the full-length protein of SEQ ID NO:10 to only 8 residues, corresponding to positions 22, 101, 107, 111, 115, 161, 182 and 242. These eight positions were recommended as targets for site-directed mutagenesis to improve the substrate conversion rate of EgD9eS. The experimental data below targeted position 107.

Creation of Megaprimers for Construction of the Site-Saturation Library

Oligonucleotides EgD9E_102_053008f (SEQ ID NO:56) and EgD9E_760_053008r (SEQ ID NO:57) were designed to target amino acid residues 35 and 107, respectively, of EgD9eS (SEQ ID NO:10). Following commercial synthesis of these oligonucleotides, they were utilized in a PCR reaction to create suitable megaprimers for use in the construction of the SS library. Specifically, a 50 µl reaction mixture was prepared to contain: 5.0 µl of 10× reaction buffer supplied with Pfu-Ultra polymerase (Stratagene), 1.0 µl of 50 ng/µl EgD9eS (SEQ ID NO:10), 1.0 µl of 10 pmol/µl primer EgD9E_102_053008f (SEQ ID NO:56), 1.0 µl of 10 pmol/µl primer EgD9E_760_053008r (SEQ ID NO:57), 1.0 µl of 40 mM dNTP mix (Promega, Madison, Wis.), 1.0 µl high fidelity Pfu-Ultra DNA polymerase (Stratagene) and 40 µl water. The mixture was placed in a thin well 200 µl tube for the PCR reaction in Mastercycler gradient equipment (Brinkmann Instruments, Inc. Westbury, N.Y.). PCR amplification was performed using the following conditions: 95° C. for 30 sec, followed by 30 cycles of denaturation at 95° C. for 30 sec, annealing at 54° C. for 1 min, and elongation at 72° C. for 2 min. A final elongation cycle at 72° C. for 4 min was carried out, followed by reaction termination at 4° C.

The PCR products were purified using a DNA Clean & Concentrator™-5 kit (Cat. No. D4003, Zymo Research, Orange, Calif.), as recommended by the manufacturer. The purified double-stranded PCR products were utilized as "megaprimers", each containing various mutations within EgD9eS.

Site-Directed Mutagenesis to Create Site-Saturation Mutant Genes of EgD9eS

The "megaprimers" described above were then utilized in reactions designed to introduce the EgD9eS mutations within the "megaprimers" into pZuFmEgD9ES (FIG. 2; SEQ ID NO:25), thereby replacing the non-mutant EgD9eS gene with various mutant EgD9eS genes. This was accomplished using the QuikChange® II XL site directed mutagenesis kit (Cat. No. 200524, Stratagene, La Jolla, Calif.), as described in Example 3. Specifically, the composition of the site directed mutagenesis reaction and amplification conditions were identical to that described in Example 3, as was the method of DpnI restriction and DNA clean-up.

Example 6

Identification of EgD9eS Site-Saturation Library Mutants Having Improved Delta-9 Elongase Conversion Efficiency The present Example describes: 1) the identification of EgD9eS mutants having improved delta-9 elongase conversion efficiency of LA to EDA, as compared to that of the wildtype protein EgD9eS (SEQ ID NO:10); and, 2) sequence analysis of these EgD9eS mutants.

Identification Of EgD9eS Site-Saturation Mutants

The SS library prepared in Example 5 was transformed into *E. coli* Top 10 electro-competent cells, purified and subsequently transformed into *Y. lipolytica* strain Y2224, as described in Example 2. The fatty acid profiles of 510 *Yarrowia* transformants with constructs from the SS library were analyzed using the quick screen "plate assay" of Example 2. Three transformants were confirmed to exhibit improved delta-9 elongation activity as compared to the control, based on the confirmation assay of Example 2.

Data from the confirmation assay is presented in Table 9, and the FAME profiles of individual pZuFmEgD9ES control transformants are compared with those of SS library mutants. More specifically, the concentration of each fatty acid as an area percent of TFAs ["% TFAs"] and % Conv. of LA to EDA (determined as described in Example 2) for each strain is shown below in Table 9, while averages are highlighted in gray and indicated with "Avg". Fatty acids are identified based on the abbreviations of Example 4.

TABLE 9

Confirmation Assay : Lipid Composition In Transformant
*Y. lipolytica* Strain Y2224, Expressing EgD9eS
Or SS Mutant Variants Thereof

| Strain | Replicate No. | % TFAs 16:0 | 16:1 | 18:0 | 18:1 | LA | EDA | % Conv LA to EDA |
|---|---|---|---|---|---|---|---|---|
| EgD9es | 1 | 12.6 | 11.5 | 5.2 | 47.0 | 15.0 | 3.4 | 18.3 |
| Control-1 | 2 | 12.5 | 11.8 | 4.9 | 47.1 | 15.1 | 3.4 | 18.4 |
| EgD9eS | 1 | 12.7 | 11.5 | 4.2 | 48.5 | 15.4 | 3.4 | 18.0 |
| Control-2 | 2 | 12.0 | 12.0 | 4.1 | 47.1 | 16.9 | 3.8 | 18.2 |
|  | 3 | 12.9 | 11.3 | 4.4 | 48.3 | 15.4 | 3.4 | 18.0 |
| EgD9eS | 1 | 12.5 | 11.7 | 3.7 | 49.4 | 15.5 | 3.5 | 18.6 |
| Control-3 | 2 | 12.4 | 11.6 | 5.1 | 47.8 | 15.0 | 3.4 | 18.6 |
|  | 3 | 12.1 | 11.8 | 5.0 | 48.3 | 15.4 | 3.5 | 18.6 |
| EgD9eS | 1 | 12.3 | 11.5 | 5.2 | 47.7 | 15.0 | 3.7 | 19.8 |
| Control-4 | 2 | 12.4 | 11.8 | 4.7 | 48.1 | 15.0 | 3.5 | 19.1 |
|  | 3 | 12.7 | 11.7 | 3.8 | 48.7 | 15.1 | 3.7 | 19.8 |
| Avg. Control | — | 12.5 | 11.6 | 4.6 | 48.0 | 15.3 | 3.5 | 18.7 |
| 2.4sd-24 | 1 | 12.6 | 11.8 | 4.0 | 48.6 | 13.3 | 4.9 | 27.0 |
|  | 2 | 12.6 | 11.6 | 4.6 | 48.6 | 13.0 | 4.9 | 27.5 |
|  | 3 | 12.5 | 11.8 | 3.9 | 49.6 | 13.2 | 4.9 | 27.0 |
|  | Avg | 12.6 | 11.7 | 4.1 | 48.9 | 13.2 | 4.9 | 27.2 |
| 2.4sd-52 | 1 | 12.6 | 11.5 | 3.8 | 50.3 | 13.2 | 4.7 | 26.4 |
|  | 2 | 12.5 | 11.2 | 4.3 | 49.4 | 13.2 | 4.7 | 26.2 |
|  | 3 | 12.6 | 11.2 | 5.0 | 48.7 | 12.8 | 4.8 | 27.2 |
|  | Avg | 12.6 | 11.3 | 4.4 | 49.4 | 13.1 | 4.7 | 26.6 |
| 2.4sd-53 | 1 | 12.6 | 12.0 | 3.6 | 50.1 | 13.8 | 4.5 | 24.8 |
|  | 2 | 12.3 | 12.0 | 3.8 | 49.1 | 14.4 | 4.6 | 24.3 |
|  | 3 | 12.5 | 12.4 | 3.6 | 49.2 | 13.6 | 4.4 | 24.6 |
|  | Avg | 12.5 | 12.1 | 3.7 | 49.5 | 13.9 | 4.5 | 24.6 |

In the confirmation assay, clones of *Y. lipolytica* strain Y2224 that were transformed with pZuFmEgD9ES, comprising the non-mutant codon-optimized EgD9eS gene, produced an average of 3.5 EDA % TFAs, wherein the average conversion efficiency ["% Conv"] of LA to EDA in these four strains was determined to be about 18.7%. By comparison, the average % Conv of LA to EDA for mutant strain 2.4sd2-24 was 27.2% (or 145% relative to the control); the average % Conv for mutant strain 2.4sd2-52 was 26.6% (or 142% relative to the control); and, the average % Conv for mutant strain 2.4sd2-53 was 24.6% (or 132% relative to the control). This assay therefore confirmed the improved delta-9 elongase conversion efficiency exhibited by site-saturation mutants 2.4sd2-24, 2.4sd2-52 and 22.4sd2-53.

Sequence of EgD9eS Site-Saturation Mutants

The plasmids rescued from mutants 2.4sd-24, 2.4sd-52 and 2.4sd-53 were characterized by DNA sequencing, and analysis revealed various nucleotide substitutions and expressed amino acid substitutions within the mutant EgD9eS genes, as shown in Table 10. A designation indicative of the amino acid substitution was given to each mutant EgD9eS gene and to each mutant pZuFmEgD9ES plasmid comprising the mutant EgD9eS gene.

TABLE 10

Summary of Sequenced EgD9eS SS Library Mutants

| Site-Saturation Mutant | Nucleotide Substitution | Resulting Amino Acid Substitution | Designation For Mutant Gene | Designation For Mutant Plasmid |
|---|---|---|---|---|
| 2.4sd-24 | C103G, T104G, C105G | L35G | "EgD9eS-L35G" (SEQ ID NO: 58) | pZuFmEgD9ES-L35G (SEQ ID NO: 60) |

TABLE 10-continued

Summary of Sequenced EgD9eS SS Library Mutants

| Site-Saturation Mutant | Nucleotide Substitution | Resulting Amino Acid Substitution | Designation For Mutant Gene | Designation For Mutant Plasmid |
|---|---|---|---|---|
| 2.4sd-52 | C103G, T104G, C105G | L35G | | |
| 2.4sd-53 | C103A, C105G, C319G | L35M and Q107E | "EgD9eS-L35M/Q107E" (SEQ ID NO: 61) | pZuFmEgD9ES-L35M/Q107E (SEQ ID NO: 63) |

As will be obvious to one of skill in the art, the Applicants appreciate that a variety of nucleotide sequences can encode, e.g., the protein set forth as EgD9eS-L35G, based on the degeneracy of the genetic code. Thus, for example, the Gly encoded in the mutant protein set forth as SEQ ID NO:59 at amino acid residue position 35 can be encoded by GGG (as in the delta-9 elongase open reading frame ["ORF"] set forth in SEQ ID NO:58), GGA (as in the delta-9 elongase ORF set forth in SEQ ID NO:95), GGC (as in the delta-9 elongase ORF set forth in SEQ ID NO:96) and GGT (as in the delta-9 elongase ORF set forth in SEQ ID NO:97). A variety of other nucleotide substitutions that result in silent mutations in the encoded protein are also contemplated, and thus the nucleotide sequences provided herein which encode EgD9eS-L35G (SEQ ID NO:59) should not be construed as a limitation to the present disclosure. Similar variation is contemplated within any of the nucleotide sequences described herein, encoding the mutant proteins of the invention and having delta-9 elongase activity.

Example 7

Creation of EgD9eS-L35G SlonoMax® Libraries

The present example describes the synthesis of SlonoMax® libraries, prepared by targeting 50 distinct amino acid positions within the EgD9eS-L35G mutant (SEQ ID NO:59; Example 6), which demonstrated a 42-45% improvement in LA to EDA conversion efficiency when compared to the parent enzyme. Thus, this Example sought to identify additional beneficial mutations that could be "stacked" into the EgD9eS mutant comprising the L35 mutation.

Slonomics®, an automated robotic platform described in additional detail infa, generates SlonoMax® libraries where the number of mutants per sequence position and their ratios can be very precisely controlled. Thus, the automated process offers advantages in that the number of candidate residues that could be experimentally examined to determine their impact on delta-9 elongase activity could be greatly increased, as opposed to the limited residues considered upon creation of the site-saturation library (Example 5).

Rationale for Targeting 50 Distinct Residues within EgD9eS for Functional Site Evaluation Delta-9 elongase enzymes have been identified and functionally characterized from Isochrysis galbana ["IgD9e"] (SEQ ID NO:2; PCT Publications No. WO 2002/077213, No. WO 2005/083093, No. WO 2005/012316 and No. WO 2004/057001; GenBank Accession No. AAL37626), Eutreptiella sp. CCMP389 ["E389D9e"] (SEQ ID NO:4; U.S. Pat. No. 7,645,604), Euglena gracilis ["EgD9e"] (SEQ ID NO:8; U.S. Pat. No. 7,645,604) and E. anabaena ["EaD9e"] (SEQ ID NO:12; U.S. Pat. No. 7,794,701). Each of these elongases has been shown to be capable of converting LA to EDA. EgD9e, EaD9e and E389D9e share more than 60% sequence similarity with one another, while IgD9E shares only about 35% sequence similarity to any one of EgD9e, EaD9e, and E389D9e (based on ClustalW (Version 1.83) analyses, using default parameters (i.e., protein weight matrix=Gonnet 250, gap opening penalty=10, gap extension penalty=0.2 and full alignment algorithm).

It was observed that positions leading to mutants with improved delta-9 elongase conversion efficiency (e.g., D98G [Example 4] and L35G [Example 6]) have moderate sequence conservativeness. An amino acid sequence alignment of IgD9e, EgD9e, EaD9e and E389D9e was created to identify other moderately conserved residues, using default parameters of Vector NTI®'s AlignX program (Invitrogen Corporation, Carlsbad, Calif.) (FIG. 1). It was hypothesized that these moderately conserved residues might be good candidates as targets for amino acid substitution to potentially yield a second generation of mutant enzymes having improved activity relative to the non-mutant EgD9eS control.

Comparing the sequence of these four homologous enzymes, 58 of the 258 amino acid positions were determined to be conserved among all four elongase enzymes; thus, these residues were eliminated from consideration. Additionally, 92 positions were determined to be conserved between EgD9e, EaD9e and E389D9e; these positions were also eliminated from consideration. Lastly, since positions having random amino acid changes among homologs normally do not play a significant role in protein function, an additional 22 positions determined to possess four different amino acid residues among all four elongase enzymes were thus eliminated from consideration as targeted positions for functional evaluation.

The remaining 86 positions within SEQ ID NO:8 (i.e., positions 1, 3, 4, 5, 9, 12, 21, 22, 27, 28, 29, 32, 35, 37, 41, 42, 45, 47, 48, 51, 52, 53, 54, 57, 58, 60, 62, 63, 66, 67, 70, 71, 73, 74, 80, 83, 84, 85, 89, 94, 98, 101, 104, 105, 107, 108, 111, 115, 127, 131, 132, 143, 149, 152, 153, 155, 156, 161, 168, 169, 179, 181, 182, 192, 196, 204, 207, 209, 210, 211, 216, 218, 222, 223, 225, 229, 236, 239, 242, 244, 245, 247, 250, 254, 257 and 258) were considered as potential targets for functional site evaluation. A comparison of the amino acid residue that is encoded at each one of these positions in EgD9e (SEQ ID NO:8), EaD9e (SEQ ID NO:12) and E389E9e (SEQ ID NO:4) is shown below in Table 11.

TABLE 11

Positions For Functional Site Evaluation

| Position* | EgD9e | EaD9e | 389D9e | Position* | EgD9e | EaD9e | 389D9e |
|---|---|---|---|---|---|---|---|
| 1 | M | M | I | 105 | T | T | A |
| 3 | V | A | V | 107 | Q | Q | K |
| 4 | V | A | A | 108 | L | L | V |
| 5 | N | K | N | 111 | L | L | Y |
| 9 | S | S | A | 115 | L | V | L |
| 12 | Q | Q | A | 127 | G | D | A |
| 21 | A | A | Q | 131 | T | S | S |
| 22 | Q | Q | R | 132 | W | F | F |
| 27 | A | A | I | 143 | M | I | M |
| 28 | S | S | Y | 149 | Y | Y | V |
| 29 | H | S | S | 152 | R | R | S |
| 32 | V | V | L | 153 | N | N | G |
| 35 | L | L | F | 155 | A | G | S |
| 37 | I | V | I | 156 | V | V | I |
| 41 | I | A | I | 161 | L | L | F |
| 42 | L | I | I | 168 | W | W | F |
| 45 | T | M | T | 169 | I | I | V |
| 47 | G | R | G | 179 | I | I | M |
| 48 | P | P | E | 181 | L | L | F |
| 51 | P | L | D | 182 | K | N | N |
| 52 | K | K | S | 192 | S | S | A |
| 53 | G | R | G | 196 | I | I | I |
| 54 | Q | Q | K | 204 | I | I | L |
| 57 | M | L | L | 207 | K | K | W |
| 58 | K | K | R | 209 | R | R | K |
| 60 | V | L | L | 210 | N | N | D |
| 62 | T | T | K | 211 | I | V | I |
| 63 | N | A | W | 216 | Q | Q | K |
| 66 | L | F | L | 218 | G | G | P |
| 67 | L | L | F | 222 | F | F | L |
| 70 | I | I | V | 223 | G | A | A |
| 71 | Y | Y | F | 225 | F | I | I |
| 73 | L | F | L | 229 | F | W | W |

TABLE 11-continued

Positions For Functional Site Evaluation

| 74 | G | G | V | 236 | C | L | L |
|---|---|---|---|---|---|---|---|
| 80 | A | A | G | 239 | L | L | I |
| 83 | M | L | I | 242 | V | V | F |
| 84 | Y | S | Y | 244 | Q | Q | K |
| 85 | T | V | T | 245 | T | T | S |
| 89 | M | L | Y | 247 | I | I | V |
| 94 | E | E | D | 250 | K | P | K |
| 98 | D | N | D | 254 | A | R | A |
| 101 | V | V | L | 257 | I | K | K |
| 104 | I | I | F | 258 | Q | E | V |

*Position is based on alignment EgD9e (SEQ ID NO: 8), which has an identical sequence to that of EgD9eS (SEQ ID NO: 10).

Of the 86 positions identified above in Table 11, those sites having greatest proximity to the periplasmic space, based on the membrane topology model of FIG. 4A, were eliminated from further consideration (i.e., positions 45, 47, 48, 51, 52, 53, 54, 57, 58, 60, 62, 63, 66, 67, 70, 71, 73, 74, 204, 207, 209, 210, 211, 216, 218, 222, 223, 225 and 229). Those sites highlighted in gray with bold text (i.e., positions 3, 5, 9, 12, 21, 22, 27, 28, 32, 37, 41, 42, 80, 84, 85, 94, 98, 101, 104, 105, 107, 108, 111, 115, 127, 131, 132, 143, 149, 152, 153, 156, 161, 168, 169, 179, 181, 182, 192, 196, 236, 239, 242, 244, 245, 247, 250, 254, 257 and 258 of EgD9eS) were selected for further experimental evaluation.

Slonomics® to Create SlonoMax® Mutant Genes of EgD9eS-L35G

Slonomics® (U.S. Pat. No. 7,695,906) uses a set of double stranded DNA triplets as universal building blocks for the synthesis of combinatorial libraries "one codon at a time" (Sloning BioTechnology, Puchheim, Germany). For library production, multiple codons can be introduced in parallel at any desired sequence position. The absence of functional bias and the ability to select and precisely control delivery of up to 20 codons at any ratio results in exceptionally high quality libraries containing the complete set of desired mutants.

SlonoMax® gene libraries (50 total) were thus created by Sloning BioTechnology, each gene library possessing at least 16 independent and unique sequence mutations at the targeted position (i.e., position 3, 5, 9, 12, 21, 22, 27, 28, 32, 37, 41, 42, 80, 84, 85, 94, 98, 101, 104, 105, 107, 108, 111, 115, 127, 131, 132, 143, 149, 152, 153, 156, 161, 168, 169, 179, 181, 182, 192, 196, 236, 239, 242, 244, 245, 247, 250, 254, 257 or 258 of EgD9eS), using pZuFmEgD9ES-L35G (SEQ ID NO:60) as the template.

All EgD9eS-L35G mutants were cloned into the vector backbone provided by pZuFmEgD9ES-L35G and subsequently transformed into *Y. lipolytica* strain Y2224 and cultured, as described in Example 2. The transformed cells (provided as frozen glycerol stocks) and DNA were obtained from Sloning BioTechnology. A small portion of transformed cells and DNA were sequenced and confirmed.

Example 8

Identification of EgD9eS-L35G SlonoMax® Library Mutants Having Improved Delta-9 Elongase Conversion Efficiency The present Example describes the identification of EgD9eS-L35G SlonoMax® mutants having improved delta-9 elongase conversion efficiency of LA to EDA, as compared to that of the variant protein EgD9eS-L35G identified in Example 6 (SEQ ID NO:59).

The fatty acid profiles of 807 *Yarrowia* transformants with constructs from the SlonoMax® library were screened using the "confirmation assay" methodology of Example 2, such that cells grown on fresh re-streaked MM plates were used to individually inoculate triplicate cultures comprising 3 mL liquid MM. In addition to the 807 mutants, *Yarrowia* strain Y2224 transformants, comprising pZuFmEgD9ES-L35G (SEQ ID NO:60) were inoculated in triplicate as experimental controls.

Data from selected mutants in the confirmation assay is presented in Table 12, and the FAME profiles of three representative EgD9eS-L35G controls are compared with those of the SlonoMax® library mutants demonstrating an increase in average % Conv. of LA to EDA. More specifically, the average (indicated with "Avg") concentration of each fatty acid as an area percent of TFAs ["% TFAs"] and the average % Conv. of LA to EDA (determined as described in Example 2) for each strain is shown below in Table 12. Fatty acids are identified based on the abbreviations of Example 4. Each strain description is indicative of the particular amino acid substitutions present in the respectively mutant EgD9eS gene. Thus, strain EgD9eS-L35G/S9A comprises a mutant pZuFmEgD9ES plasmid comprising a mutant EgD9eS gene, the gene having a L35G mutation and a S9A mutation when compared to the sequence of EgD9eS set forth as SEQ ID NO:10.

TABLE 12

Confirmation Assay: Lipid Composition In Transformant *Y. lipolytica* Strain Y2224, Expressing EgD9eS-L35G Or SlonoMax ® Mutant Variants Thereof

| Strain | Replicate No. | % TFAs | | | | | | % Conv LA to EDA |
|---|---|---|---|---|---|---|---|---|
| | | 16:0 | 16:1 | 18:0 | 18:1 | 18:2 | 20:2 | |
| EgD9eS-L35G | 1 | 13.7 | 12.0 | 2.9 | 40.4 | 19.0 | 4.8 | 20.2 |
| Control-1 | 2 | 14.2 | 12.7 | 2.9 | 41.7 | 19.5 | 4.4 | 18.5 |
| | 3 | 13.8 | 12.2 | 3.0 | 41.1 | 19.1 | 4.9 | 20.4 |
| EgD9eS-L35G | 1 | 13.8 | 12.5 | 2.8 | 40.7 | 19.8 | 4.5 | 18.4 |
| Control-2 | 2 | 14.0 | 12.5 | 2.8 | 41.1 | 19.8 | 3.7 | 15.6 |
| | 3 | 13.8 | 12.3 | 2.9 | 41.0 | 19.7 | 4.5 | 18.6 |
| EgD9eS-L35G | 1 | 13.9 | 12.8 | 2.7 | 41.7 | 18.5 | 3.9 | 17.5 |
| Control-3 | 2 | 13.7 | 12.7 | 2.7 | 42.6 | 19.0 | 3.7 | 16.2 |
| | 3 | 14.1 | 12.9 | 2.8 | 41.7 | 19.1 | 4.1 | 17.5 |
| Avg. Control | — | 13.9 | 12.5 | 2.8 | 41.3 | 19.3 | 4.3 | 18.1 |
| EgD9eS-L35G/S9A | Avg of 3 | 12.3 | 12.8 | 3.1 | 49.9 | 12.9 | 3.8 | 22.8 |
| EgD9eS-L35G/S9D | Avg of 3 | 12.3 | 12.3 | 3.2 | 48.6 | 12.2 | 4.3 | 25.6 |
| EgD9eS-L35G/S9G | Avg of 3 | 12.6 | 12.7 | 3.1 | 51.1 | 12.2 | 3.8 | 23.3 |
| EgD9eS-L35G/S9I | Avg of 3 | 13.0 | 12.2 | 2.9 | 52.5 | 12.2 | 3.1 | 20.4 |
| EgD9eS-L35G/S9K | Avg of 3 | 12.4 | 12.4 | 2.9 | 52.3 | 12.1 | 3.5 | 22.1 |
| EgD9eS-L35G/S9Q | Avg of 3 | 12.5 | 13.1 | 2.8 | 52.0 | 12.4 | 3.1 | 20.1 |
| EgD9eS-L35G/Q12K | Avg of 3 | 12.5 | 14.1 | 2.6 | 51.4 | 11.6 | 3.3 | 22.3 |
| EgD9eS-L35G/A21D | Avg of 3 | 12.4 | 14.2 | 2.7 | 49.7 | 12.1 | 3.3 | 21.4 |
| EgD9eS-L35G/A21T | Avg of 3 | 12.3 | 13.3 | 2.9 | 50.3 | 13.2 | 3.3 | 20.0 |
| EgD9eS-L35G/A21V | Avg of 3 | 12.7 | 15.1 | 2.3 | 49.1 | 13.4 | 3.6 | 21.3 |
| EgD9eS-L35G/V32F | Avg of 3 | 12.2 | 14.9 | 2.4 | 49.4 | 14.0 | 3.2 | 18.8 |
| EgD9eS-L35G/Y84C | Avg of 3 | 11.9 | 13.3 | 2.6 | 51.5 | 12.8 | 4.5 | 26.1 |
| EgD9eS-L35G/L108G | Avg of 3 | 13.0 | 13.4 | 3.0 | 48.4 | 14.8 | 3.4 | 18.8 |
| EgD9eS-L35G/G127L | Avg of 3 | 9.7 | 11.0 | 1.9 | 36.6 | 24.5 | 5.7 | 18.8 |
| EgD9eS-L35G/W132T | Avg of 3 | 13.8 | 12.8 | 3.0 | 43.7 | 18.2 | 4.0 | 18.1 |
| EgD9eS-L35G/M143N | Avg of 3 | 10.1 | 11.1 | 2.0 | 39.6 | 21.4 | 4.5 | 17.4 |
| EgD9eS-L35G/M143W | Avg of 3 | 11.4 | 12.2 | 2.3 | 43.8 | 18.4 | 4.4 | 19.1 |
| EgD9eS-L35G/L161T | Avg of 3 | 11.1 | 12.1 | 2.7 | 41.3 | 17.8 | 5.6 | 23.7 |
| EgD9eS-L35G/L161Y | Avg of 3 | 9.9 | 11.8 | 2.6 | 37.4 | 22.3 | 6.1 | 21.5 |
| EgD9eS-L35G/W168G | Avg of 3 | 11.5 | 12.3 | 2.5 | 44.0 | 17.6 | 4.7 | 20.8 |
| EgD9eS-L35G/I179M | Avg of 3 | 13.8 | 12.5 | 3.0 | 41.5 | 18.5 | 4.3 | 18.8 |
| EgD9eS-L35G/I179R | Avg of 3 | 10.2 | 11.9 | 2.2 | 40.5 | 18.4 | 6.3 | 25.5 |
| EgD9eS-L35G/C236N | Avg of 3 | 13.3 | 13.4 | 2.8 | 45.5 | 16.9 | 3.8 | 18.5 |
| EgD9eS-L35G/Q244N | Avg of 3 | 10.2 | 12.4 | 2.2 | 38.2 | 17.9 | 5.7 | 24.2 |
| EgD9eS-L35G/A254W | Avg of 3 | 11.7 | 16.8 | 2.0 | 48.8 | 14.8 | 3.7 | 20.2 |
| EgD9eS-L35G/A254Y | Avg of 3 | 13.1 | 16.2 | 2.5 | 48.4 | 12.9 | 3.4 | 21.0 |

It is noteworthy that the fatty acid profile and the % Conv. of LA to EDA of the replicate EgD9eS-L35G controls presented in Table 12 are somewhat different from the EgD9eS-L35G profiles previously presented. In the present set of experiments, the EgD9eS-L35G control "underperformed" in comparison to previous analyses (i.e., the average % Conv. of LA to EDA was determined to be about 18.1%, supra, while the average % Conv. of LA to EDA was determined to be about 26.6% and 27.2% in Example 6, Table 9). However, the transformants with EgD9eS-L35G produced 4.3 EDA % TFAs (average, supra), which was significantly greater than that produced in transformants with EgD9eS (i.e., 3.1 EDA % TFAs [Example 4, Table 5], 2.9 EDA % TFAs [Example 4, Table 6], and 3.5 EDA % TFAs [Example 6, Table 9]). For this reason, performance from previous experiments that repeated the functional analysis of EgD9eS-L35G (data not shown) was used in addition to EgD9eS-L35G performance in the present experiment as the basis for comparison of mutants from the EgD9eS site-evaluation library presented in Table 12.

Among the 26 selected elongase variants presented in Table 12, eleven were identified (highlighted in bold text) as demonstrating comparable or improved delta-9 elongase conversion activity relative to the control data of Table 12. These mutants included EgD9eS-L35G/S9D (141%), EgD9eS-L35G/A21V (118%), EgD9eS-L35G/V32F (104%), EgD9eS-L35G/Y84C (144%), EgD9eS-L35G/L108G (104%), EgD9eS-L35G/W132T (100%), EgD9eS-L35G/M143N (96%), EgD9eS-L35G/L161T (131%), EgD9eS-L35G/I179R (141%), EgD9eS-L35G/C236N (102%) and EgD9eS-L35G/Q244N (134%), wherein the delta-9 elongase conversion activity with respect to EgD9eS is shown in parentheses. Thus, up to a 44% improvement in LA to EDA conversion efficiency was demonstrated.

Example 9

Creation of a EgD9eS-L35G/S9D/A21V/V32F/ Y84C/L108G/W132T/M143N/L161T/I179R/ C236N/Q244N Combinatorial Library The present example describes the synthesis of a mutant EgD9eS combinatorial library, wherein various combinations of the beneficial mutations identified above in Example 8 (i.e., S9D, A21V, V32F, Y84C, L108G, W132T, M143N, L161T, I179R, C236N and Q244N) were "stacked" together into the EgD9eS mutant comprising the L35G mutation.

Creation of Synthetic Primers for Construction of the Combinatorial Library

Eleven pairs of primers were commercially synthesized, as described in SEQ ID NOs:64-85 (see Table 13, infra). Each primer pair was designed to introduce one of the following mutations into the EgD9eS-L35G gene: S9D, A21V, V32F, Y84C, L108G, W132T, M143N, L161T, I179R, C236N and Q244N.

The primers were phosphorylated at 37° C. for 60 min using T4 polynucleotide kinase ["PNK"] (Cat. No. 70031Z, USB Corp.) and then deactivated at 65° C. for 20 min. Each 20 µl phosphorylation reaction mixture contained: 2.0 µl of 10×T4 PNK buffer, 15.0 µl of primer DNA (about 7 µM), 0.6 µl of 100 mM ATP, 0.4 µl of T4 PNK and 2.0 µl of water.

Multiple Mutation Site Mutagenesis to Create Combinatorial Mutant Genes of EgD9eS-L35G The Change-IT™ Multiple Mutation Site Directed Mutagenesis Kit (Cat. No. 78480, USB Corporation, Cleveland, Ohio) was used to introduce the S9D, A21V, V32F, Y84C, L108G, W132T, M143N, L161T, I179R, C236N and Q244N mutations into EgD9eS-L35G in a series of 6 reactions, each reaction (with the exception of the final reaction) introducing two new mutations based on inclusion of a forward primer and reverse primer of Primer Set "A" and a forward primer and reverse primer of Primer Set "B" (Table 13). While the initial template in the series of reactions was EgD9eS-L35G, the product of Change-IT™ Rxn. 1 served as the template in Change-IT™ Rxn. 2, etc.

Following the sixth reaction, which introduced the last of the 11 mutations into the original EgD9eS-L35G template, DNA was purified from the transformant E. coli cells, as described above. The DNA was then transformed into Y. lipolytica strain Y2224 (supra, Example 2).

Example 10

Identification of EgD9eS-L35G/S9D/A21V/V32F/Y84C/L108G/W132T/M143N/L161T/I179R/C236N/Q244N Combinatorial Library Mutants Having Improved Delta-9 Elongase Conversion Efficiency The present Example describes: 1) the identification of EgD9eS-L35G/S9D/A21V/V32F/Y84C/L108G/W132T/M143N/L161T/I179R/C236N/Q244N combinatorial library mutants having improved delta-9 elongase conversion efficiency of LA to EDA, as compared to that of the wildtype protein EgD9eS (SEQ ID NO:10); 2) sequence analysis of

TABLE 13

Summary Of Change-IT ™ Multiple Mutation Site Directed Mutagenesis Reactions

| Change-IT ™ Rxn. No. | Template | Product | Primer Set "A" | | Primer Set "B" | |
|---|---|---|---|---|---|---|
| | | | Forward Primer | Reverse Primer | Forward Primer | Reverse Primer |
| #1 | EgD9eS-L35G | Change-IT ™ Rxn. #1 | Eg_9D_122709f (SEQ ID NO: 64) | Eg_84C_122709r (SEQ ID NO: 65) | Eg_84C_122709f (SEQ ID NO: 66) | Eg_9D_122709r (SEQ ID NO: 67) |
| #2 | Change-IT ™ Rxn. #1 | Change-IT ™ Rxn. #2 | Eg_161T_122709f (SEQ ID NO: 68) | Eg_179R_122709r (SEQ ID NO: 69) | Eg_179R_122709f (SEQ ID NO: 70) | Eg_161T_122709r (SEQ ID NO: 71) |
| #3 | Change-IT ™ Rxn. #2 | Change-IT ™ Rxn. #3 | Eg_244N_122709f (SEQ ID NO: 72) | Eg_21V_010710r (SEQ ID NO: 73) | Eg_21V_010710f (SEQ ID NO: 74) | Eg_244N_122709r (SEQ ID NO: 75) |
| #4 | Change-IT ™ Rxn. #3 | Change-IT ™ Rxn. #4 | Eg_32F_010710f (SEQ ID NO: 76) | Eg_108G_010710r (SEQ ID NO: 77) | Eg_108G_010710f (SEQ ID NO: 78) | Eg_32F_010710r (SEQ ID NO: 79) |
| #5 | Change-IT ™ Rxn. #4 | Change-IT ™ Rxn. #5 | Eg_132T_010710f (SEQ ID NO: 80) | Eg_143N_010710r (SEQ ID NO: 81) | Eg_143N_010710f (SEQ ID NO: 82) | Eg_132T_010710r (SEQ ID NO: 83) |
| #6 | Change-IT ™ Rxn. #5 | Change-IT ™ Rxn. #6 | Eg_236N_010710f (SEQ ID NO: 84) | Eg_236N_010710r (SEQ ID NO: 85) | — | — |

More specifically, two 25 µl PCR reaction mixtures were prepared, each one comprising 2.5 µl of 10× Change-IT™ buffer, 2.5 µl of phosphorylated forward primer, 2.5 µl of phosphorylated reverse primer, 1.0 µl of template (50 ng/µl), 15.5 µl Nuclease-free water and 1.0 µl Change-IT™ FideliTaq enzyme. The first reaction utilized primers from primer set "A", while the second utilized primer set "B" primers. PCR amplification was performed using the following conditions: 95° C. for 2 min, followed by 30 cycles of denaturation at 95° C. for 30 sec, annealing at 55° C. for 30 sec, and elongation/ligation at 68° C. for 25 min. A final elongation/ligation cycle at 68° C. for 30 min was carried out, followed by the reaction termination at 4° C.

Following amplification, the template was removed by adding DpnI enzyme and digestion was performed at 37° C. for 3 hr. The PCR DNA was used to transform E. coli Top 10 electro-competent cells (Cat. No. C404052, Invitrogen, Carlsbad, Calif.) by electroporation. The transformed cells were spread onto LB with 100 mg/L ampicillin agar plates and grown in a 37° C. incubator overnight. Plasmid DNA was extracted from the transformant E. coli cells using a QIAprep® Spin Miniprep kit (Qiagen Inc., Valencia, Calif.) following the manufacturer's protocol. The purified DNA was then used as template in the next Change-IT™ reaction.

these EgD9eS mutants; and, 3) re-creation of the sequenced EgD9eS mutants to confirm the improved delta-9 elongase conversion efficiency.

The fatty acid profiles of 2,388 Yarrowia transformants with constructs from the combinatorial library (Example 9) were screened using the quick screen "plate assay" of Example 2. Most of these mutants exhibited reduced conversion of LA to EDA compared to the wild type control, EgD9eS (SEQ ID NO:10). However, five transformants were confirmed to exhibit improved delta-9 elongation activity as compared to the control, based on confirmation assays of Example 2.

The DNA sequences of the mutant EgD9eS genes were determined using colony PCR. In brief, a small quantity of yeast cells was sampled from freshly streaked plates using a sterile pipette tip and the cells were suspended in 20 µl of molecular grade water. Cell suspension (2 µl) was transferred to TaKaRa Taq PCR mix prepared according to the manufacturer's recommendation (Takara Biotechnology Co., LTD.). The primers used for colony PCR were forward primer FBAIN-F (SEQ ID NO:98) and reverse primer Y1026 (SEQ ID NO:99). The thermal cycler program included an initial denaturation of template at 94° C. for 5 min, followed by 40 cycles of denaturation at 94° C. for 30 sec, annealing at 56° C.

for 30 sec and extension at 72° C. for 3 min. A final extension at 72° C. for 6 min was carried out.

The PCR products were sequenced with primers FBAIN-F (SEQ ID NO:98) and Y1026 (SEQ ID NO:99). Analysis of the DNA sequence data revealed the nucleotide substitutions and expressed amino acid substitutions within the mutant EgD9eS genes. A designation indicative of the amino acid substitution was given to the mutant EgD9eS gene and to the mutant pZuFmEgD9ES plasmid comprising the mutant EgD9eS gene, as shown in Table 14.

Top 10 electro-competent cells, purified, sequenced, and subsequently transformed into *Y. lipolytica* strain Y2224, as described in Example 2. In this way, the mutant EgD9eS genes shown in Table 14 were recreated on plasmids and re-introduced back into strain Y2224 to confirm that the improved delta-9 elongase conversion efficiency exhibited by the EgD9eS combinatorial mutants was attributed to the identified amino acid substitutions.

Data from these confirmation assays are presented in Table 15, and the FAME profiles of individual pZuFmEgD9ES

TABLE 14

Summary of Sequenced EgD9eS Combinatorial Library Mutants

| Combinatorial Mutant | Nucleotide Substitution | Resulting Amino Acid Substitution | Designation For Mutant Gene | Designation For Mutant Plasmid |
|---|---|---|---|---|
| EgD9EN-427 | C103G, T104G, and C105G | L35G | EgD9eS-L35G/W132T/I179R (SEQ ID NO: 100) | pZuFmEgD9ES-L35G/W132T/I179R (SEQ ID NO: 102) |
| | T394A, G395C, G396C | W132T | | |
| | A535C, T536G, C537A | I179R | | |
| EgD9EN-1043 | T25G, C26A | S9D | EgD9eS-S9D/L35G/Y84C/I179R (SEQ ID NO: 103) | pZuFmEgD9ES-S9D/L35G/Y84C/I179R (SEQ ID NO: 105) |
| | C103G, T104G, and C105G | L35G | | |
| | A251G, C252T | Y84C | | |
| | A535C, T536G, C537A | I179R | | |
| EgD9EN-1534 | C62T and T63G | A21V | EgD9eS-A21V/L35G/L108G/I179R (SEQ ID NO: 86) | pZuFmEgD9ES-A21V/L35G/L108G/I179R (SEQ ID NO: 88) |
| | C103G, T104G and C105G | L35G | | |
| | C322G, T323G and G324T | L108G | | |
| | A535C, T536G and C537A | I179R | | |
| EgD9EN-1635 | C103G, T104G, and C105G | L35G | EgD9eS-L35G/Y84C/I179R/Q244N (SEQ ID NO: 106) | pZuFmEgD9ES-L35G/Y84C/I179R/Q244N (SEQ ID NO: 108) |
| | A251G, C252T | Y84C | | |
| | A535C, T536G, C537A | I179R | | |
| | C730A, G732C | Q244N | | |
| EgD9EN-1734 | C62T, T63G | A21V | EgD9eS-A21V/L35G/W132T/I179R/Q244N (SEQ ID NO: 109) | pZuFmEgD9ES-A21V/L35G/W132T/I179R/Q244N (SEQ ID NO: 111) |
| | C103G, T104G, and C105G | L35G | | |
| | T394A, G395C, G396C | W132T | | |
| | A535C, T536G, C537A | I179R | | |
| | C730A, G732C | Q244N | | |

New primers for site-directed mutagenesis were designed, based on the amino acid substitutions of Table 14. These primers were then utilized in reactions designed to introduce the EgD9eS mutations within the "megaprimers" into pZuFmEgD9ES (FIG. 2; SEQ ID NO:25), thereby replacing the non-mutant EgD9eS gene with the various mutant EgD9eS genes listed in Table 14. This was accomplished using the QuikChange® II XL site directed mutagenesis kit (Cat. No. 200524, Stratagene, La Jolla, Calif.), as described in Example 3. These mutant genes were transformed into *E. coli* control transformants are compared with those mutants of the combinatorial library. For a conservative comparison, the data shown for each strain represents the FAME profiles for the 3 isolates with highest % Conv. of LA to EDA for each strain. More specifically, the concentration of each fatty acid as an area percent of TFAs ["% TFAs"] and Conv. of LA to EDA (determined as described in Example 2) for each strain is shown below, while averages are highlighted in gray and indicated with "Avg". Fatty acids are identified based on the abbreviations of Example 4.

TABLE 15

Confirmation Assay: Lipid Composition In Transformant *Y. lipolytica*
Strain Y2224, Expressing EgD9eS Or Combinatorial Mutant Variants Thereof

| Strain | Replicate No. | % TFAs | | | | | | %Conv LA to EDA |
|---|---|---|---|---|---|---|---|---|
| | | 16:0 | 16:1 | 18:0 | 18:1 | 18:2 | 20:2 | |
| EgD9eS-Control | 1 | 12.5 | 12.6 | 2.8 | 50.6 | 13.1 | 2.6 | 16.7 |
| | 2 | 12.1 | 13.1 | 2.5 | 52.1 | 13.4 | 2.5 | 15.8 |
| | 3 | 12.5 | 13.1 | 2.8 | 51.0 | 13.3 | 2.5 | 15.8 |
| | Avg | 12.4 | 12.9 | 2.7 | 51.2 | 13.2 | 2.5 | 16.1 |
| EgD9EN-427 | 1 | 11.6 | 13.2 | 2.6 | 49.7 | 14.2 | 3.2 | 18.1 |
| | 2 | 12.2 | 12.7 | 2.6 | 51.5 | 13.0 | 2.9 | 18.0 |
| | 3 | 11.8 | 12.7 | 2.5 | 52.4 | 13.0 | 2.7 | 17.2 |
| | Avg | 11.9 | 12.9 | 2.6 | 51.2 | 13.4 | 2.9 | 17.8 |
| EgD9EN-1043 | 1 | 11.7 | 13.3 | 2.4 | 52.2 | 13.3 | 2.8 | 17.7 |
| | 2 | 11.8 | 12.8 | 2.5 | 51.9 | 12.8 | 2.8 | 17.9 |
| | 3 | 11.8 | 12.6 | 2.5 | 51.6 | 12.8 | 2.6 | 16.9 |
| | Avg | 11.8 | 12.9 | 2.4 | 51.9 | 13.0 | 2.8 | 17.5 |
| EgD9EN-1534 | 1 | 11.4 | 11.8 | 2.4 | 48.4 | 12.5 | 2.6 | 17.2 |
| | 2 | 12.0 | 12.4 | 2.5 | 49.8 | 13.3 | 2.6 | 16.6 |
| | 3 | 12.2 | 12.4 | 2.6 | 50.8 | 13.1 | 2.6 | 16.6 |
| | Avg | 11.9 | 12.2 | 2.5 | 49.7 | 13.0 | 2.6 | 16.8 |
| EgD9EN-1635 | 1 | 11.1 | 12.9 | 2.4 | 51.2 | 13.1 | 3.0 | 18.8 |
| | 2 | 11.5 | 13.8 | 2.5 | 49.4 | 14.1 | 3.1 | 18.1 |
| | 3 | 11.9 | 13.5 | 2.6 | 50.1 | 14.1 | 2.9 | 17.1 |
| | Avg | 11.5 | 13.4 | 2.5 | 50.2 | 13.8 | 3.0 | 18.0 |
| EgD9EN-1734 | 1 | 11.5 | 12.7 | 2.4 | 51.7 | 12.4 | 3.3 | 21.2 |
| | 2 | 11.3 | 12.5 | 2.2 | 51.3 | 12.1 | 3.2 | 20.7 |
| | 3 | 11.8 | 12.8 | 2.4 | 52.8 | 13.0 | 2.8 | 18.0 |
| | Avg | 11.5 | 12.7 | 2.3 | 51.9 | 12.5 | 3.1 | 20.0 |

Clones of *Y. lipolytica* strain Y2224 that were transformed with pZuFmEgD9ES, comprising the codon-optimized EgD9eS gene of SEQ ID NO:10 (non-mutant), produced an average of 2.5 EDA % TFAs, wherein the average conversion efficiency ["% Conv"] of LA to EDA in these three clones was determined to be about 16.1%. In contrast, the average % Conv of LA to EDA for mutant strain EgD9EN-427 was 17.8% (or 110% relative to the control). Similarly, the average % Conv of LA to EDA for mutant strain EgD9EN-1043 was 17.5% (or 108% relative to the control). The average % Conv of LA to EDA for mutant strain EgD9EN-1534 was 16.8% (or 104% relative to the control); the average % Conv for mutant strain EgD9EN-1635 was 18.0% (or 111& relative to the control); and, the average % Conv for mutant strain EgD9EN-1734 was 20.0% (or 123% relative to the control).

Thus, these experiments thereby confirmed the improved delta-9 elongase conversion efficiency exhibited by EgD9eS combinatorial library mutants EgD9EN-427, EgD9EN-1043, EgD9EN-1534, EgD9EN-1635, and EgD9EN-1734, wherein the improvement ranged from 4-23%.

Example 11

Generation Of *Yarrowia lipolytica* Strain Z1978 to Produce About 58.7% EPA of Total Fatty Acids The present Example describes the construction of strain Z1978, derived from *Y. lipolytica* ATCC #20362, capable of producing about 58.7% EPA relative to the total lipids with 38.3% total lipid content ["TFAs % DCW"] via expression of a delta-9 elongase/delta-8 desaturase pathway. This strain includes the delta-9 elongase site-saturation mutant of Examples 5 and 6, comprising the L35G mutation (i.e., EgD9eS-L35G [SEQ ID NOs:58 and 59]).

The development of strain Z1978 (FIG. 6) required the construction of strains Y2224, Y4001, Y4001U, Y4036, Y4036U, L135, L135U9, Y8002, Y8006U6, Y8069, Y8069U, Y8154, Y8154U, Y8269, Y8269U, Y8412U6, Y8647, Y8467U, Y9028, Y9028U, Y9502 and strain Y9502U.

Fatty Acid Analysis of *Yarrowia lipolytica* During Strain Constructions

For fatty acid ["FA"] analysis, cells were collected by centrifugation and lipids were extracted as described in Bligh, E. G. & Dyer, W. J. (*Can. J. Biochem. Physiol.,* 37:911-917 (1959)). Fatty acid methyl esters ["FAMEs"] were prepared by transesterification of the lipid extract with sodium methoxide (Roughan, G., and Nishida I., *Arch Biochem Biophys.,* 276(1):38-46 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* cells (0.5 mL culture) were harvested, washed once in distilled water, and dried under vacuum in a Speed-Vac for 5-10 min. Sodium methoxide (100 µl of 1%) and a known amount of C15:0 triacylglycerol (C15:0 TAG; Cat. No. T-145, Nu-Check Prep, Elysian, Minn.) was added to the sample, and then the sample was vortexed and rocked for 30 min at 50° C. After adding 3 drops of 1 M NaCl and 400 µl hexane, the sample was vortexed and spun. The upper layer was removed and analyzed by GC.

Alternately, a modification of the base-catalysed transersterification method described in *Lipid Analysis*, William W. Christie, 2003 was used for routine analysis of the broth samples from either fermentation or flask samples. Specifically, broth samples were rapidly thawed in room temperature water, then weighed (to 0.1 mg) into a tarred 2 mL microcentrifuge tube with a 0.22 µm Corning® Costar® Spin-X® centrifuge tube filter (Cat. No. 8161). Sample (75-800 µl) was used, depending on the previously determined DCW. Using an Eppendorf 5430 centrifuge, samples are centrifuged for 5-7 min at 14,000 rpm or as long as necessary to remove the broth. The filter was removed, liquid was drained, and ~500 µl of deionized water was added to the filter to wash the sample. After centrifugation to remove the water, the filter was again removed, the liquid drained and the filter re-inserted. The tube was then re-inserted into the centrifuge, this time with the top open, for ~3-5 min to dry. The filter was then cut approximately ½ way up the tube and inserted into a fresh 2 mL round bottom Eppendorf tube (Cat. No. 22 36 335-2).

The filter was pressed to the bottom of the tube with an appropriate tool that only touches the rim of the cut filter container and not the sample or filter material. A known amount of C15:0 TAG (supra) in toluene was added and 500 µl of freshly made 1% sodium methoxide in methanol solution. The sample pellet was firmly broken up with the appropriate tool and the tubes were closed and placed in a 50° C. heat block (VWR Cat. No. 12621-088) for 30 min. The tubes were then allowed to cool for at least 5 min. Then, 400 µl of hexane and 500 µl of a 1 M NaCl in water solution were added, the tubes were vortexed for 2×6 sec and centrifuged for 1 min. Approximately 150 µl of the top (organic) layer was placed into a GC vial with an insert and analyzed by GC.

FAME peaks recorded via GC analysis were identified by their retention times, when compared to that of known fatty acids, and quantitated by comparing the FAME peak areas with that of the internal standard (C15:0 TAG) of known amount. Thus, the approximate amount (µg) of any fatty acid FAME ["µg FAME"] is calculated according to the formula: (area of the FAME peak for the specified fatty acid/area of the standard FAME peak)*(µg of the standard C15:0 TAG), while the amount (µg) of any fatty acid ["µg FA"] is calculated according to the formula: (area of the FAME peak for the specified fatty acid/area of the standard FAME peak)*(µg of the standard C15:0 TAG)*0.9503, since 1 µg of C15:0 TAG is equal to 0.9503 µg fatty acids. Note that the 0.9503 conversion factor is an approximation of the value determined for most fatty acids, which range between 0.95 and 0.96.

The lipid profile, summarizing the amount of each individual fatty acid as a weight percent of TFAs, was determined by dividing the individual FAME peak area by the sum of all FAME peak areas and multiplying by 100.

Analysis of Total Lipid Content and Composition in *Yarrowia lipolytica* During Strain Constructions by Flask Assay For a detailed analysis of the total lipid content and composition in a particular strain of *Y. lipolytica*, flask assays were conducted as followed. Specifically, one loop of freshly streaked cells was inoculated into 3 mL FM medium and grown overnight at 250 rpm and 30° C. The $OD_{600nm}$ was measured and an aliquot of the cells were added to a final $OD_{600nm}$ of 0.3 in 25 mL FM medium in a 125 mL flask. After 2 days in a shaker incubator at 250 rpm and at 30° C., 6 mL of the culture was harvested by centrifugation and resuspended in 25 mL HGM in a 125 mL flask. After 5 days in a shaker incubator at 250 rpm and at 30° C., a 1 mL aliquot was used for fatty acid analysis (supra) and 10 mL dried for dry cell weight ["DCW"] determination.

For DCW determination, 10 mL culture was harvested by centrifugation for 5 min at 4000 rpm in a Beckman GH-3.8 rotor in a Beckman GS-6R centrifuge. The pellet was resuspended in 25 mL of water and re-harvested as above. The washed pellet was re-suspended in 20 mL of water and transferred to a pre-weighed aluminum pan. The cell suspension was dried overnight in a vacuum oven at 80° C. The weight of the cells was determined.

Total lipid content of cells ["TFAs % DOW"] is calculated and considered in conjunction with data tabulating the concentration of each fatty acid as a weight percent of TFAs ["% TFAs"] and the EPA content as a percent of the dry cell weight ["EPA % DCW"]. Data from flask assays are presented as a table that summarizes the total dry cell weight of the cells ["DCW"], the total lipid content of cells ["TFAs % DCW"], the concentration of each fatty acid as a weight percent of TFAs ["% TFAs"] and the EPA content as a percent of the dry cell weight ["EPA % DCW"]. More specifically, fatty acids are identified as 16:0 (palmitate), 16:1 (palmitoleic acid), 18:0 (stearic acid), 18:1 (oleic acid), 18:2 (LA), ALA, EDA, DGLA, ARA, ETrA, ETA, EPA and other.

Genotype of *Yarrowia lipolytica* Strain Y9502

The generation of strain Y9502 is described in U.S. Pat. Pub. No. 2010-0317072-A1. Strain Y9502, derived from *Y. lipolytica* ATCC #20362, was capable of producing about 57.0% EPA relative to the total lipids via expression of a delta-9 elongase/delta-8 desaturase pathway (FIG. 6).

The final genotype of strain Y9502 with respect to wildtype *Yarrowia lipolytica* ATCC #20362 was Ura+, Pex3-, unknown 1-, unknown 2-, unknown 3-, unknown 4-, unknown 5-, unknown6-, unknown 7-, unknown 8-, unknown9-, unknown 10-, YAT1::ME3S::Pex16, GPD::ME3S::Pex20, YAT1::ME3S::Lip1, FBAINm::EgD9eS::Lip2, EXP1::EgD9eS::Lip1, GPAT::EgD9e::Lip2, YAT1::EgD9eS::Lip2, FBAINm::EgD8M::Pex20, EXP1::EgD8M::Pex16, FBAIN::EgD8M::Lip1, GPD::EaD8S::Pex16 (2 copies), YAT1::E389D9eS/EgD8M::Lip1, YAT1::EgD9eS/EgD8M::Aco, FBAINm::EaD9eS/EaD8S::Lip2, GPD::FmD12::Pex20, YAT1::FmD12::Oct, EXP1::FmD12S::Aco, GPDIN::FmD12::Pex16, EXP1::EgD5M::Pex16, FBAIN::EgD5SM::Pex20, GPDIN::EgD5SM::Aco, GPM::

EgD5SM::Oct, EXP1::EgD5SM::Lip1, YAT1::EaD5SM::Oct, FBAINm::PaD17::Aco, EXP1::PaD17::Pex16, YAT1::PaD17S::Lip1, YAT1::YICPT1::Aco, YAT1::MCS::Lip1, FBA::MCS::Lip1, YAT1::MaLPAAT1S::Pex16. Abbreviations are as follows: FmD12 is a *Fusarium moniliforme* delta-12 desaturase gene [U.S. Pat. No. 7,504,259]; FmD12S is a codon-optimized delta-12 desaturase gene, derived from *F. moniliforme* [U.S. Pat. No. 7,504,259]; ME3S is a codon-optimized $C_{16/18}$ elongase gene, derived from *Mortierella alpina* [U.S. Pat. No. 7,470,532]; EgD9e is a *Euglena gracilis* delta-9 elongase gene [U.S. Pat. No. 7,645,604]; EgD9eS is a codon-optimized delta-9 elongase gene, derived from *E. gracilis* [U.S. Pat. No. 7,645,604]; EgD8M is a synthetic mutant delta-8 desaturase gene [U.S. Pat. No. 7,709,239], derived from *E. gracilis* [U.S. Pat. No. 7,256,033]; EaD8S is a codon-optimized delta-8 desaturase gene, derived from *Euglena anabaena* [U.S. Pat. No. 7,790,156]; E389D9eS/EgD8M is a DGLA synthase created by linking a codon-optimized delta-9 elongase gene ("E389D9eS"), derived from *Eutreptiella* sp. CCMP389 delta-9 elongase (U.S. Pat. No. 7,645,604) to the delta-8 desaturase "EgD8M" (supra) [U.S. Pat. Pub. No. 2008-0254191-A1]; EgD9eS/EgD8M is a DGLA synthase created by linking the delta-9 elongase "EgD9eS" (supra) to the delta-8 desaturase "EgD8M" (supra) [U.S. Pat. Pub. No. 2008-0254191-A1]; EaD9eS/EgD8M is a DGLA synthase created by linking a codon-optimized delta-9 elongase gene ("EaD9eS"), derived from *E. anabaena* delta-9 elongase [U.S. Pat. No. 7,794,701] to the delta-8 desaturase "EgD8M" (supra) [U.S. Pat. Pub. No. 2008-0254191-A1]; EgDSM and EgDSSM are synthetic mutant delta-5 desaturase genes [U.S. Pat. Pub. No. 2010-0075386-A1], derived from *E. gracilis* [U.S. Pat. No. 7,678,560]; EaD5SM is a synthetic mutant delta-5 desaturase gene [U.S. Pat. Pub. No. 2010-0075386-A1], derived from *E. anabaena* [U.S. Pat. No. 7,943,365]; PaD17 is a *Pythium aphanidermatum* delta-17 desaturase gene [U.S. Pat. No. 7,556,949]; PaD17S is a codon-optimized delta-17 desaturase gene, derived from *P. aphanidermatum* [U.S. Pat. No. 7,556,949]; YICPT1 is a *Yarrowia lipolytica* diacylglycerol cholinephosphotransferase gene [U.S. Pat. No. 7,932,077]; MCS is a codon-optimized malonyl-CoA synthetase gene, derived from *Rhizobium leguminosarum* bv. viciae 3841 [U.S. Pat. Pub. No. 2010-0159558-A1], and, MaLPAAT1S is a codon-optimized lysophosphatidic acid acyltransferase gene, derived from *Mortierella alpina* [U.S. Pat. No. 7,879,591].

For a detailed analysis of the total lipid content and composition in strain Y9502, a flask assay was conducted wherein cells were grown in 2 stages for a total of 7 days. Based on analyses, strain Y9502 produced 3.8 g/L DCW, 37.1 TFAs % DCW, 21.3 EPA % DCW, and the lipid profile was as follows, wherein the concentration of each fatty acid is as a weight percent of TFAs ["% TFAs"]: 16:0 (palmitate)-2.5, 16:1 (palmitoleic acid)—0.5, 18:0 (stearic acid)—2.9, 18:1 (oleic acid)—5.0, 18:2 (LA)—12.7, ALA—0.9, EDA—3.5, DGLA—3.3, ARA—0.8, ETrA—0.7, ETA—2.4, EPA—57.0, other—7.5.

Generation of Strain Y9502U (Ura3-)

Figure 7A:
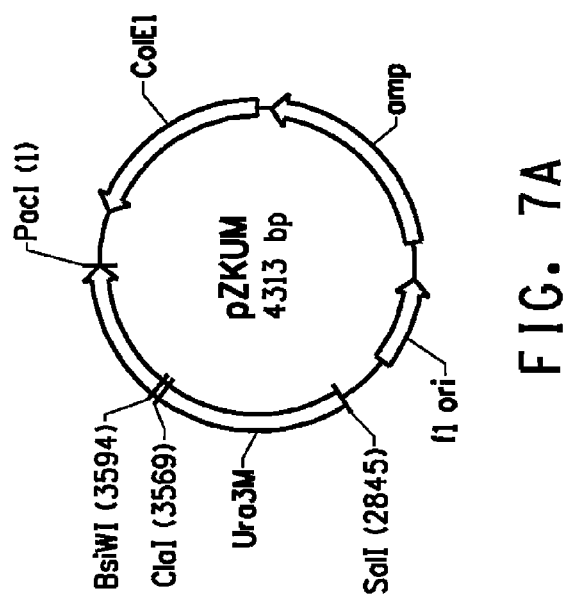

To disrupt the Ura3 gene in strain Y9502, SalI/PacI-digested construct pZKUM (FIG. 7A; SEQ ID NO:89; described in Table 15 of U.S. Pat. Pub. No. 2009-0093543-A1, hereby incorporated herein by reference) was used to integrate an Ura3 mutant gene into the Ura3 gene of strain Y9502, according to the General Methods. A total of 27 transformants (selected from a first group comprising 8 transformants, a second group comprising 8 transformants, and a third group comprising 11 transformants) were grown on Minimal Media+5-fluoroorotic acid ["MM+5-FOA"] selection plates and maintained at 30° C. for 2 to 5 days. Further experiments determined that only the third group of transformants possessed a real Ura-phenotype.

The Ura-cells were scraped from the MM+5-FOA plates and subjected to fatty acid analysis, according to the General Methods. In this way, GC analyses showed that there were 28.5%, 28.5%, 27.4%, 28.6%, 29.2%, 30.3% and 29.6% EPA of TFAs in pZKUM-transformants #1, #3, #6, #7, #8, #10 and #11 grown on MM+5-FOA plates of group 3, respectively. These seven strains were designated as strains Y9502U12, Y9502U14, Y9502U17, Y9502U18, Y9502U19, Y9502U21 and Y9502U22, respectively (collectively, Y9502U).

Generation of Strain Z1978

Figure 7B:
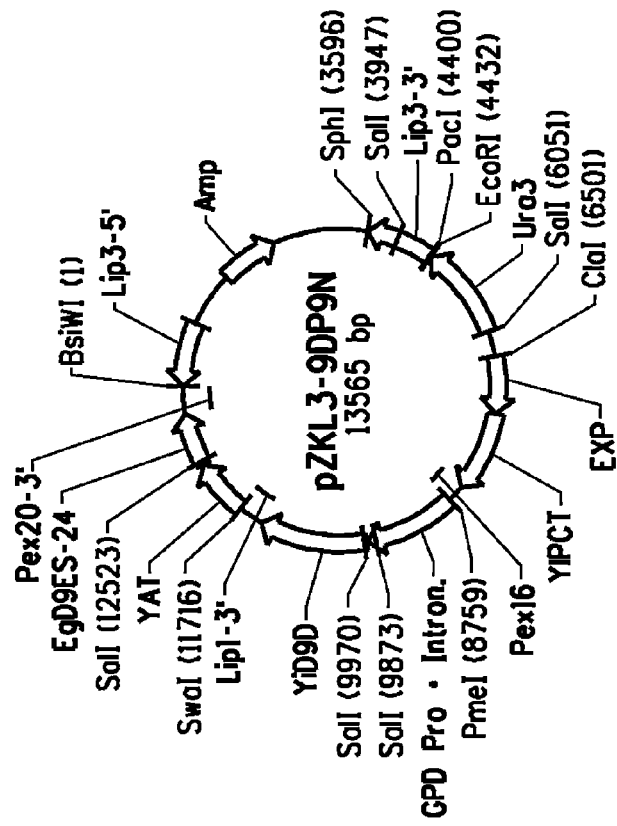

Construct pZKL3-9DP9N (FIG. 7B; SEQ ID NO:90) was then generated to integrate one delta-9 desaturase gene, one choline-phosphate cytidylyl-transferase gene, and one delta-9 elongase mutant gene into the *Yarrowia* YALI0F32131p locus (GenBank Accession No. XM_506121) of strain Y9502U. The pZKL3-9DP9N plasmid contained the following components:

TABLE 16

Description of Plasmid pZKL3-9DP9N (SEQ ID NO: 90)

| RE Sites And Nucleotides Within SEQ ID NO: 90 | Description Of Fragment And Chimeric Gene Components |
|---|---|
| AscI/BsiWI (887-4) | 884 bp 5' portion of YALI0F32131p locus (GenBank Accession No. XM_506121, labeled as "Lip3-5" in Figure) |
| PacI/SphI (4396-3596) | 801 bp 3' portion of YALI0F32131p locus (GenBank Accession No. XM_506121, labeled as "Lip3-3" in Figure) |
| SwaI/BsiWI (11716-1) | YAT1::EgD9eS-L35G::Pex20, comprising: YAT1: *Yarrowia lipolytica* YAT1 promoter (labeled as "YAT" in Figure; U.S. Pat. Pub. No. 2010-0068789-A1); EgD9eS-L35G: Synthetic mutant of delta-9 elongase gene (SEQ ID NO: 58), derived from *Euglena gracilis* ("EgD9eS"; U.S. Pat. No. 7,645,604) (labeled as "EgD9ES-24" in Figure); Pex20: Pex20 terminator sequence from *Yarrowia* Pex20 gene (GenBank Accession No. AF054613) |
| PmeI/SwaI (8759-11716) | GPDIN::YID9::Lip1, comprising: GPDIN: *Yarrowia lipolytica* GPDIN promoter (U.S. Pat. No. 7,459,546; labeled as "GPDPro + Intron" in Figure); YID9: *Yarrowia lipolytica* delta-9 desaturase gene (GenBank Accession No. XM_501496; SEQ ID NO: 91) (labeled as "YID9D" in Figure); Lip1: Lip1 terminator sequence from *Yarrowia* Lip1 gene (GenBank Accession No. Z50020) |
| ClaI/PmeI (6501-8759) | EXP1::YIPCT::Pex16, comprising: EXP1: *Yarrowia lipolytica* export protein (EXP1) promoter (labeled as "EXP" in Figure; U.S. Pat. No. 7,932,077); YIPCT: *Yarrowia lipolytica* choline-phosphate cytidylyl-transferase ["PCT"] gene (Gen Bank Accession No. XM_502978; SEQ ID NO: 93); Pex16: Pex16 terminator sequence from *Yarrowia* Pex16 gene (GenBank Accession No. U75433) |
| SalI/EcoRI (6501-4432) | *Yarrowia* Ura3 gene (GenBank Accession No. AJ306421) |

The pZKL3-9DP9N plasmid was digested with AscI/SphI, and then used for transformation of strain Y9502U17. The transformant cells were plated onto Minimal Media ["MM"] plates and maintained at 30° C. for 3 to 4 days. Single colonies were re-streaked onto MM plates, and then inoculated into liquid MM at 30° C. and shaken at 250 rpm/min for 2 days. The cells were collected by centrifugation, resuspended in High Glucose Media ["HGM"] and then shaken at 250 rpm/min for 5 days. The cells were subjected to fatty acid analysis, supra.

GC analyses showed that most of the selected 96 strains of Y9502U17 with pZKL3-9DP9N produced 50-56% EPA of TFAs. Five strains (i.e., #31, #32, #35, #70 and #80) that produced about 59.0%, 56.6%, 58.9%, 56.5%, and 57.6% EPA of TFAs were designated as strains Z1977, Z1978, Z1979, Z1980 and Z1981, respectively.

The final genotype of these pZKL3-9DP9N transformant strains with respect to wildtype Yarrowia lipolytica ATCC #20362 was Ura+, Pex3-, unknown 1-, unknown 2-, unknown 3-, unknown 4-, unknown 5-, unknown6-, unknown 7-, unknown 8-, unknown9-, unknown 10-, unknown 11-, YAT1:: ME3S::Pex16, GPD::ME3S::Pex20, YAT1::ME3S::Lip1, FBAINm::EgD9eS::Lip2, EXP1::EgD9eS::Lip1, GPAT:: EgD9e::Lip2, YAT1::EgD9eS::Lip2, YAT1::EgD9eS-L35G:: Pex20, FBAINm::EgD8M::Pex20, EXP1::EgD8M::Pex16, FBAIN::EgD8M::Lip1, GPD::EaD8S::Pex16 (2 copies), YAT1::E389D9eS/EgD8M::Lip1, YAT1::EgD9eS/EgD8M:: Aco, FBAINm::EaD9eS/EaD8S::Lip2, GPDIN::YID9:: Lip1, GPD::FmD12::Pex20, YAT1::FmD12::Oct, EXP1:: FmD12S::Aco, GPDIN::FmD12::Pex16, EXP1::EgD5M:: Pex16, FBAIN::EgD5SM::Pex20, GPDIN::EgD5SM::Aco, GPM::EgD5SM::Oct, EXP1::EgD5SM::Lip1, YAT1:: EaD5SM::Oct, FBAINm::PaD17::Aco, EXP1::PaD17:: Pex16, YAT1::PaD17S::Lip1, YAT1::YICPT1::Aco, YAT1:: MCS::Lip1, FBA::MCS::Lip1, YAT1::MaLPAAT1S::Pex16, EXP1::YIPCT::Pex16.

Knockout of the YALI0F32131p locus (GenBank Accession No. XM_50612) in strains Z1977, Z1978, Z1979, Z1980 and Z1981 was not confirmed in any of these EPA strains produced by transformation with pZKL3-9DP9N.

Cells from YPD plates of strains Z1977, Z1978, Z1979, Z1980 and Z1981 were grown and analyzed for total lipid content and composition by flask assays. Table 17 below summarizes total lipid content and composition in each of these strains. Specifically, the Table summarizes the total DCW, the TFAs % DCW, the concentration of each fatty acid as a weight percent of TFAs ["% TFAs"] and the EPA % DCW.

Strain Z1978 was subsequently subjected to partial genome sequencing. This work, as described in U.S. Provisional Application No. 61/428,277 (E.I. duPont de Nemours & Co., Inc., filed Dec. 30, 2010), determined that instead of six delta-5 desaturase genes integrated into the Yarrowia genome (i.e., chimeric genes EXP1::EgD5M::Pex16, FBAIN::EgD5SM::Pex20, GPDIN::EgD5SM::Aco, GPM:: EgD5SM::Oct, EXP1::EgD5SM::Lip1, YAT1::EaD5SM:: Oct), the engineered strain actually possessed only four delta-5 desaturase genes (i.e., EXP1::EgD5M::Pex16, FBAIN::EgD5SM::Pex20, EXP1::EgD5SM::Lip1, and YAT1::EaD5SM::Oct).

Comparison Of Yarrowia lipolytica Strain Y9502 and Strain Z1978

The heterologous genes expressed in strain Z1978 differ from those expressed in strain Y9502 only by the additional expression of one delta-9 desaturase gene, one cholinephosphate cytidylyltransferase gene, and one delta-9 elongase mutant (i.e., EgD9eS-L35G, as set forth in SEQ ID NOs:58 and 59). The total delta-9 elongase conversion efficiency ["% Conv"] of LA and ALA to EPA was calculated in Table 18 for Y9502 and Z1978 strains according to the following formula: ([product]/[substrate+product])*100, wherein the product was the sum of EDA % TFAs, ETrA % TFAs, DGLA % TFAs, ETA % TFAs, ARA % TFAs and EPA % TFAs and the substrate was the sum of LA % TFAs, ALA % TFAs, EDA % TFAs, ETrA % TFAs, DGLA % TFAs, ETA % TFAs, ARA % TFAs and EPA % TFAs.

TABLE 18

Comparison Of Total Lipid Content And Composition And Delta-9 Elongase Activity In Transformant Y. lipolytica Strains Y9502 And Z1978

|  |  | Yarrowia lipolytica strain Y9502 | Yarrowia lipolytica strain Z1978 |
|---|---|---|---|
| DCW (g/L) |  | 3.8 | 3.9 |
| TFAs % DCW |  | 37.1 | 38.3 |
| % TFAs | 16:0 | 2.5 | 2.4 |
|  | 16:1 | 0.5 | 0.4 |
|  | 18:0 | 2.9 | 2.4 |
|  | 18:1 | 5 | 4.8 |
|  | 18:2 | 12.7 | 11.1 |
|  | ALA | 0.9 | 0.7 |
|  | EDA | 3.5 | 3.2 |
|  | DGLA | 3.3 | 3.3 |
|  | ARA | 0.8 | 0.8 |
|  | ETrA | 0.7 | 0.6 |
|  | ETA | 2.4 | 2.1 |
|  | EPA | 57 | 58.7 |
|  | Other | 7.5 | 9.5 |

TABLE 17

Total Lipid Content And Composition In Yarrowia Strains Z1977, Z1978, Z1979, Z1980 and Z1981 By Flask Assay

| Strain | DCW (g/L) | TFAs % DCW | % TFAs | | | | | | | | | | | | | EPA % DCW |
|---|---|---|---|---|---|---|---|---|---|---|---|---|---|---|---|---|
|  |  |  | 16:0 | 16:1 | 18:0 | 18:1 | 18:2 | ALA | EDA | DGLA | ARA | EtrA | ETA | EPA | other |  |
| Z1977 | 3.8 | 34.3 | 2.0 | 0.5 | 1.9 | 4.6 | 11.2 | 0.7 | 3.1 | 3.3 | 0.9 | 0.7 | 2.2 | 59.1 | 9.9 | 20.3 |
| Z1978 | 3.9 | 38.3 | 2.4 | 0.4 | 2.4 | 4.8 | 11.1 | 0.7 | 3.2 | 3.3 | 0.8 | 0.6 | 2.1 | 58.7 | 9.5 | 22.5 |
| Z1979 | 3.7 | 33.7 | 2.3 | 0.4 | 2.4 | 4.1 | 10.5 | 0.6 | 3.2 | 3.6 | 0.9 | 0.6 | 2.2 | 59.4 | 9.8 | 20.0 |
| Z1980 | 3.6 | 32.7 | 2.1 | 0.4 | 2.2 | 4.0 | 10.8 | 0.6 | 3.1 | 3.5 | 0.9 | 0.7 | 2.2 | 59.5 | 10.0 | 19.5 |
| Z1981 | 3.5 | 34.3 | 2.2 | 0.4 | 2.1 | 4.2 | 10.6 | 0.6 | 3.3 | 3.4 | 1.0 | 0.8 | 2.2 | 58.5 | 10.7 | 20.1 |

TABLE 18-continued

Comparison Of Total Lipid Content And Composition And Delta-9 Elongase Activity In Transformant Y. lipolytica Strains Y9502 And Z1978

|  | Yarrowia lipolytica strain Y9502 | Yarrowia lipolytica strain Z1978 |
|---|---|---|
| EPA % DCW | 21.3 | 22.5 |
| Total % Conv LA to EPA | 83.3 | 85.3 |

As shown above, the total delta-9 elongase conversion efficiency was determined to be 83.3% in strain Y9502, while the efficiency was improved in strain Z1978 (i.e., 85.3%).

Based on this improvement in the delta-9 elongase activity, EgD9eS-L35G is considered a useful mutant gene to be used in a functional delta-9 elongase/delta-8 desaturase pathway for biosynthesis of PUFAs.

Any of the mutant delta-9 elongases of the invention herein could be similarly introduced into an appropriate vector for expression in a preferred strain of *Yarrowia lipolytica*, as demonstrated in this example.

---

What is claimed is:

1. An isolated polynucleotide comprising:
a nucleotide sequence encoding a mutant polypeptide having delta-9 elongase activity, wherein said mutant polypeptide comprises an amino acid sequence that (i) is at least 95% identical with the amino acid sequence of SEQ ID NO:10, and (ii) comprises an amino acid at position 35 selected from the group consisting of glycine, phenylalanine and methionine.

2. The isolated polynucleotide of claim 1, wherein the nucleotide sequence is selected from the group consisting of SEQ ID NO:28, SEQ ID NO:58, SEQ ID NO:61, SEQ ID NO:86, SEQ ID NO:95, SEQ ID NO:96, SEQ ID NO:97, SEQ ID NO:100, SEQ ID NO:103, SEQ ID NO:106 and SEQ ID NO:109.

3. The isolated polynucleotide of claim 1, wherein the mutant polypeptide comprises an amino acid sequence selected from the group consisting of: SEQ ID NO:29, SEQ ID NO:59, SEQ ID NO:62, SEQ ID NO:87, SEQ ID NO:101, SEQ ID NO:104, SEQ ID NO:107 and SEQ ID NO:110.

4. The isolated polynucleotide of claim 3, wherein the mutant polypeptide comprises the amino acid sequence set forth in SEQ ID NO:59.

5. A recombinant construct comprising the isolated polynucleotide of claim 1, wherein said nucleotide sequence is operably linked to at least one regulatory sequence.

6. A transformed cell comprising the recombinant construct of claim 5.

7. The transformed cell of claim 6, wherein said cell is selected from the group consisting of: plants, bacteria, yeast, algae, euglenoids, stramenopiles, oomycetes and fungi.

8. The transformed cell of claim 7, wherein the cell is an oleaginous yeast producing at least about 25% of its dry cell weight as oil.

9. The transformed cell of claim 8, wherein the oleaginous yeast further comprises at least one recombinant DNA construct comprising an isolated polynucleotide operably linked to at least one regulatory sequence, the recombinant DNA construct encoding a polypeptide selected from the group consisting of: delta-4 desaturase, delta-5 desaturase, delta-8 desaturase, delta-6 desaturase, delta-9 desaturase, delta-12 desaturase, delta-15 desaturase, delta-17 desaturase, $C_{14/16}$ elongase, $C_{16/18}$ elongase, $C_{18/20}$ elongase and $C_{20/22}$ elongase.

10. The transformed cell of claim 9, wherein oil produced by the oleaginous yeast comprises a long-chain polyunsaturated fatty acid selected from the group consisting of: arachidonic acid, eicosadienoic acid, eicosapentaenoic acid, eicosatetraenoic acid, eicosatrienoic acid, dihomo-gamma-linolenic acid, docosatetraenoic acid, docosapentaenoic acid and docosahexaenoic acid.

11. The transformed cell of claim 8, wherein the oleaginous yeast is selected from the group consisting of: *Yarrowia, Candida, Rhodotorula, Rhodosporidium, Cryptococcus, Trichosporon* and *Lipomyces*.

12. The transformed cell of claim 11, wherein the cell is a *Yarrowia lipolytica*.

13. A method for producing a polyunsaturated fatty acid comprising:
a) providing an oleaginous yeast comprising:
    i) the recombinant construct of claim 5, and
    ii) a source of substrate fatty acid selected from the group consisting of linoleic acid and alpha-linolenic acid;
b) growing the yeast of step (a) under conditions wherein the mutant polypeptide having delta-9 elongase activity is expressed and the substrate fatty acid is converted to product fatty acid, wherein linoleic acid is converted to eicosadienoic acid and alpha-linolenic acid is converted to eicosatrienoic acid, and
c) optionally recovering the product fatty acid of step (b).

14. A recombinant microbial host cell producing an oil comprising at least 22.5 weight percent of eicosapentaenoic acid measured as a weight percent of dry cell weight, said recombinant microbial host cell comprising at least one mutant delta-9 elongase polypeptide, wherein said mutant delta-9 elongase polypeptide comprises SEQ ID NO:59.

* * * * *

SEQUENCE LISTING

```
<160> NUMBER OF SEQ ID NOS: 111

<210> SEQ ID NO 1
<211> LENGTH: 1064
<212> TYPE: DNA
<213> ORGANISM: Isochrysis galbana (GenBank Accession No. AF390174)
<220> FEATURE:
<221> NAME/KEY: CDS
<222> LOCATION: (2)..(793)
<223> OTHER INFORMATION: delta-9 elongase (IgD9e)

<400> SEQUENCE: 1 g atg gcc ctc gca aac gac gcg gga gag cgc atc tgg gcg gct gtg acc      49
  Met Ala Leu Ala Asn Asp Ala Gly Glu Arg Ile Trp Ala Ala Val Thr
  1               5                  10                  15 gac ccg gaa atc ctc att ggc acc ttc tcg tac ttg cta ctc aaa ccg        97
Asp Pro Glu Ile Leu Ile Gly Thr Phe Ser Tyr Leu Leu Leu Lys Pro
             20                  25                  30 ctg ctc cgc aat tcc ggg ctg gtg gat gag aag aag ggc gca tac agg       145
Leu Leu Arg Asn Ser Gly Leu Val Asp Glu Lys Lys Gly Ala Tyr Arg
         35                  40                  45 acg tcc atg atc tgg tac aac gtt ctg ctg gcg ctc ttc tct gcg ctg       193
Thr Ser Met Ile Trp Tyr Asn Val Leu Leu Ala Leu Phe Ser Ala Leu
     50                  55                  60 agc ttc tac gtg acg gcg acc gcc ctc ggc tgg gac tat ggt acg ggc       241
Ser Phe Tyr Val Thr Ala Thr Ala Leu Gly Trp Asp Tyr Gly Thr Gly
 65                  70                  75                  80 gcg tgg ctg cgc agg caa acc ggc gac aca ccg cag ccg ctc ttc cag       289
Ala Trp Leu Arg Arg Gln Thr Gly Asp Thr Pro Gln Pro Leu Phe Gln
                 85                  90                  95 tgc ccg tcc ccg gtt tgg gac tcg aag ctc ttc aca tgg acc gcc aag       337
Cys Pro Ser Pro Val Trp Asp Ser Lys Leu Phe Thr Trp Thr Ala Lys
            100                 105                 110 gca ttc tat tac tcc aag tac gtg gag tac ctc gac acg gcc tgg ctg       385
Ala Phe Tyr Tyr Ser Lys Tyr Val Glu Tyr Leu Asp Thr Ala Trp Leu
        115                 120                 125 gtg ctc aag ggc aag agg gtc tcc ttt ctc cag gcc ttc cac cac ttt       433
Val Leu Lys Gly Lys Arg Val Ser Phe Leu Gln Ala Phe His His Phe
    130                 135                 140 ggc gcg ccg tgg gat gtg tac ctc ggc att cgg ctg cac aac gag ggc       481
Gly Ala Pro Trp Asp Val Tyr Leu Gly Ile Arg Leu His Asn Glu Gly
145                 150                 155                 160 gta tgg atc ttc atg ttt ttc aac tcg ttc att cac acc atc atg tac       529
Val Trp Ile Phe Met Phe Phe Asn Ser Phe Ile His Thr Ile Met Tyr
                165                 170                 175 acc tac tac ggc ctc acc gcc gcc ggg tat aag ttc aag gcc aag ccg       577
Thr Tyr Tyr Gly Leu Thr Ala Ala Gly Tyr Lys Phe Lys Ala Lys Pro
            180                 185                 190 ctc atc acc gcg atg cag atc tgc cag ttc gtg ggc ggc ttc ctg ttg       625
Leu Ile Thr Ala Met Gln Ile Cys Gln Phe Val Gly Gly Phe Leu Leu
        195                 200                 205 gtc tgg gac tac atc aac gtc ccc tgc ttc aac tcg gac aaa ggg aag       673
Val Trp Asp Tyr Ile Asn Val Pro Cys Phe Asn Ser Asp Lys Gly Lys
    210                 215                 220 ttg ttc agc tgg gct ttc aac tat gca tac gtc ggc tcg gtc ttc ttg       721
Leu Phe Ser Trp Ala Phe Asn Tyr Ala Tyr Val Gly Ser Val Phe Leu
225                 230                 235                 240
```

```
ctc ttc tgc cac ttt ttc tac cag gac aac ttg gca acg aag aaa tcg      769
Leu Phe Cys His Phe Phe Tyr Gln Asp Asn Leu Ala Thr Lys Lys Ser
                245                 250                 255 gcc aag gcg ggc aag cag ctc tag gcctcgagcc ggctcgcggg ttcaaggagg     823
Ala Lys Ala Gly Lys Gln Leu
            260 gcgacacggg ggtgggacgt ttgcatggag atggattgtg gatgtcctta cgccttactc    883 atcaatgtcc tcccatctct cccctctaga ccttctacta gccatctaga agggcagctc    943 agagacggat accgttcccc ctccccttcc ttttcgtctt tgctttgcca ttgtttgttt   1003 gtctctattt tttaaactat tgacgctaac gcgttacgct cgcaaaaaaa aaaaaaaaaa   1063 a                                                                  1064

<210> SEQ ID NO 2
<211> LENGTH: 263
<212> TYPE: PRT
<213> ORGANISM: Isochrysis galbana (GenBank Accession No. AF390174)

<400> SEQUENCE: 2
```

Met Ala Leu Ala Asn Asp Ala Gly Glu Arg Ile Trp Ala Ala Val Thr
1               5                   10                  15

Asp Pro Glu Ile Leu Ile Gly Thr Phe Ser Tyr Leu Leu Leu Lys Pro
                20                  25                  30

Leu Leu Arg Asn Ser Gly Leu Val Asp Glu Lys Lys Gly Ala Tyr Arg
            35                  40                  45

Thr Ser Met Ile Trp Tyr Asn Val Leu Leu Ala Leu Phe Ser Ala Leu
        50                  55                  60

Ser Phe Tyr Val Thr Ala Thr Ala Leu Gly Trp Asp Tyr Gly Thr Gly
65                  70                  75                  80

Ala Trp Leu Arg Arg Gln Thr Gly Asp Thr Pro Gln Pro Leu Phe Gln
                85                  90                  95

Cys Pro Ser Pro Val Trp Asp Ser Lys Leu Phe Thr Trp Thr Ala Lys
                100                 105                 110

Ala Phe Tyr Tyr Ser Lys Tyr Val Glu Tyr Leu Asp Thr Ala Trp Leu
            115                 120                 125

Val Leu Lys Gly Lys Arg Val Ser Phe Leu Gln Ala Phe His His Phe
130                 135                 140

Gly Ala Pro Trp Asp Val Tyr Leu Gly Ile Arg Leu His Asn Glu Gly
145                 150                 155                 160

Val Trp Ile Phe Met Phe Phe Asn Ser Phe Ile His Thr Ile Met Tyr
                165                 170                 175

Thr Tyr Tyr Gly Leu Thr Ala Ala Gly Tyr Lys Phe Lys Ala Lys Pro
            180                 185                 190

Leu Ile Thr Ala Met Gln Ile Cys Gln Phe Val Gly Gly Phe Leu Leu
        195                 200                 205

Val Trp Asp Tyr Ile Asn Val Pro Cys Phe Asn Ser Asp Lys Gly Lys
210                 215                 220

Leu Phe Ser Trp Ala Phe Asn Tyr Ala Tyr Val Gly Ser Val Phe Leu
225                 230                 235                 240

Leu Phe Cys His Phe Phe Tyr Gln Asp Asn Leu Ala Thr Lys Lys Ser
                245                 250                 255

Ala Lys Ala Gly Lys Gln Leu
            260

```
<210> SEQ ID NO 3
<211> LENGTH: 792
<212> TYPE: DNA
<213> ORGANISM: Eutreptiella sp. CCMP389
<220> FEATURE:
<221> NAME/KEY: CDS
<222> LOCATION: (1)..(792)
<223> OTHER INFORMATION: delta-9 elongase
<300> PUBLICATION INFORMATION:
<302> TITLE: DELTA-9 ELONGASES AND THEIR USE IN MAKING POLYUNSATURATED
       FATTY ACIDS
<310> PATENT DOCUMENT NUMBER: WO 2007/061742
<311> PATENT FILING DATE: 2006-11-16
<312> PUBLICATION DATE: 2007-05-31
<313> RELEVANT RESIDUES IN SEQ ID NO: (1)..(792)
<300> PUBLICATION INFORMATION:
<302> TITLE: DELTA-9 ELONGASES AND THEIR USE IN MAKING POLYUNSATURATED
       FATTY ACIDS
<310> PATENT DOCUMENT NUMBER: US 7,645,604
<311> PATENT FILING DATE: 2006-11-16
<312> PUBLICATION DATE: 2010-01-12
<313> RELEVANT RESIDUES IN SEQ ID NO: (1)..(792)

<400> SEQUENCE: 3
```

| | | | | | | | | | | | | | | | | |
|---|---|---|---|---|---|---|---|---|---|---|---|---|---|---|---|---|
| atg | gct | gcg | gtg | ata | gag | gtc | gcc | aac | gag | ttt | gta | gcc | atc | acg | gca | 48 |
| Met | Ala | Ala | Val | Ile | Glu | Val | Ala | Asn | Glu | Phe | Val | Ala | Ile | Thr | Ala | |
| 1 | | | | 5 | | | | | 10 | | | | | 15 | | |
| gaa | acg | ctc | ccc | aaa | gtt | gac | tat | caa | cga | cta | tgg | cga | gac | att | tac | 96 |
| Glu | Thr | Leu | Pro | Lys | Val | Asp | Tyr | Gln | Arg | Leu | Trp | Arg | Asp | Ile | Tyr | |
| | | | 20 | | | | | 25 | | | | | 30 | | | |
| agt | tgt | gag | cta | ctg | tat | ttc | tcc | att | gcc | ttc | gtg | atc | ttg | aag | ttt | 144 |
| Ser | Cys | Glu | Leu | Leu | Tyr | Phe | Ser | Ile | Ala | Phe | Val | Ile | Leu | Lys | Phe | |
| | | 35 | | | | | 40 | | | | | 45 | | | | |
| acg | ttg | ggc | gag | ttg | agc | gac | agc | gga | aaa | aag | att | ttg | aga | gtg | ttg | 192 |
| Thr | Leu | Gly | Glu | Leu | Ser | Asp | Ser | Gly | Lys | Lys | Ile | Leu | Arg | Val | Leu | |
| | 50 | | | | | 55 | | | | | 60 | | | | | |
| ttc | aag | tgg | tac | aat | ctc | ttc | atg | tcc | gtg | ttc | tcc | ttg | gtg | tct | ttc | 240 |
| Phe | Lys | Trp | Tyr | Asn | Leu | Phe | Met | Ser | Val | Phe | Ser | Leu | Val | Ser | Phe | |
| 65 | | | | | 70 | | | | | 75 | | | | | 80 | |
| ctt | tgc | atg | ggc | tat | gcc | att | tat | acc | gtg | ggc | cta | tac | tct | aac | gaa | 288 |
| Leu | Cys | Met | Gly | Tyr | Ala | Ile | Tyr | Thr | Val | Gly | Leu | Tyr | Ser | Asn | Glu | |
| | | | | 85 | | | | | 90 | | | | | 95 | | |
| tgc | gac | agg | gct | ttc | gac | aac | tcg | ttg | ttc | cgc | ttt | gca | aca | aag | gtg | 336 |
| Cys | Asp | Arg | Ala | Phe | Asp | Asn | Ser | Leu | Phe | Arg | Phe | Ala | Thr | Lys | Val | |
| | | | 100 | | | | | 105 | | | | | 110 | | | |
| ttc | tac | tac | agt | aag | ttt | ttg | gag | tac | atc | gac | tct | ttt | tat | ctt | ccg | 384 |
| Phe | Tyr | Tyr | Ser | Lys | Phe | Leu | Glu | Tyr | Ile | Asp | Ser | Phe | Tyr | Leu | Pro | |
| | | 115 | | | | | 120 | | | | | 125 | | | | |
| ctc | atg | gcc | aag | ccg | ctg | tct | ttc | ctg | caa | ttc | ttc | cat | cac | ttg | gga | 432 |
| Leu | Met | Ala | Lys | Pro | Leu | Ser | Phe | Leu | Gln | Phe | Phe | His | His | Leu | Gly | |
| | 130 | | | | | 135 | | | | | 140 | | | | | |
| gcc | ccc | atg | gac | atg | tgg | ctc | ttt | gtc | caa | tat | tct | ggg | gaa | tct | att | 480 |
| Ala | Pro | Met | Asp | Met | Trp | Leu | Phe | Val | Gln | Tyr | Ser | Gly | Glu | Ser | Ile | |
| 145 | | | | | 150 | | | | | 155 | | | | | 160 | |
| tgg | atc | ttt | gtg | ttt | ttg | aat | ggg | ttc | att | cac | ttt | gtt | atg | tac | ggg | 528 |
| Trp | Ile | Phe | Val | Phe | Leu | Asn | Gly | Phe | Ile | His | Phe | Val | Met | Tyr | Gly | |
| | | | | 165 | | | | | 170 | | | | | 175 | | |
| tac | tac | tgg | act | cgg | ctg | atg | aag | ttc | aat | ttc | cca | atg | ccc | aag | cag | 576 |
| Tyr | Tyr | Trp | Thr | Arg | Leu | Met | Lys | Phe | Asn | Phe | Pro | Met | Pro | Lys | Gln | |
| | | | 180 | | | | | 185 | | | | | 190 | | | |
| ttg | att | acc | gcg | atg | cag | atc | acg | cag | ttc | aac | gtt | ggt | ttc | tac | ctc | 624 |
| Leu | Ile | Thr | Ala | Met | Gln | Ile | Thr | Gln | Phe | Asn | Val | Gly | Phe | Tyr | Leu | |
| | | 195 | | | | | 200 | | | | | 205 | | | | |
| gtg | tgg | tgg | tac | aaa | gat | att | ccc | tgc | tac | cga | aag | gat | ccc | atg | cga | 672 |
| Val | Trp | Trp | Tyr | Lys | Asp | Ile | Pro | Cys | Tyr | Arg | Lys | Asp | Pro | Met | Arg | |

```
atg ttg gcc tgg atc ttc aat tac tgg tat gtt ggg act gtc ttg ctg    720
Met Leu Ala Trp Ile Phe Asn Tyr Trp Tyr Val Gly Thr Val Leu Leu
225                 230                 235                 240 ctg ttc att aat ttc ttc gtc aaa tcc tat gtg ttc cca aag ccg aag    768
Leu Phe Ile Asn Phe Phe Val Lys Ser Tyr Val Phe Pro Lys Pro Lys
            245                 250                 255 act gca gat aaa aag gtc caa tag                                    792
Thr Ala Asp Lys Lys Val Gln
            260
```

<210> SEQ ID NO 4
<211> LENGTH: 263
<212> TYPE: PRT
<213> ORGANISM: Eutreptiella sp. CCMP389

<400> SEQUENCE: 4

```
Met Ala Ala Val Ile Glu Val Ala Asn Glu Phe Val Ala Ile Thr Ala
1               5                   10                  15

Glu Thr Leu Pro Lys Val Asp Tyr Gln Arg Leu Trp Arg Asp Ile Tyr
            20                  25                  30

Ser Cys Glu Leu Leu Tyr Phe Ser Ile Ala Phe Val Ile Leu Lys Phe
        35                  40                  45

Thr Leu Gly Glu Leu Ser Asp Ser Gly Lys Lys Ile Leu Arg Val Leu
    50                  55                  60

Phe Lys Trp Tyr Asn Leu Phe Met Ser Val Phe Ser Leu Val Ser Phe
65              70                  75                  80

Leu Cys Met Gly Tyr Ala Ile Tyr Thr Val Gly Leu Tyr Ser Asn Glu
                85                  90                  95

Cys Asp Arg Ala Phe Asp Asn Ser Leu Phe Arg Phe Ala Thr Lys Val
            100                 105                 110

Phe Tyr Tyr Ser Lys Phe Leu Glu Tyr Ile Asp Ser Phe Tyr Leu Pro
        115                 120                 125

Leu Met Ala Lys Pro Leu Ser Phe Leu Gln Phe Phe His His Leu Gly
    130                 135                 140

Ala Pro Met Asp Met Trp Leu Phe Val Gln Tyr Ser Gly Glu Ser Ile
145                 150                 155                 160

Trp Ile Phe Val Phe Leu Asn Gly Phe Ile His Phe Met Tyr Gly
                165                 170                 175

Tyr Tyr Trp Thr Arg Leu Met Lys Phe Asn Phe Pro Met Pro Lys Gln
            180                 185                 190

Leu Ile Thr Ala Met Gln Ile Thr Gln Phe Asn Val Gly Phe Tyr Leu
        195                 200                 205

Val Trp Trp Tyr Lys Asp Ile Pro Cys Tyr Arg Lys Asp Pro Met Arg
    210                 215                 220

Met Leu Ala Trp Ile Phe Asn Tyr Trp Tyr Val Gly Thr Val Leu Leu
225                 230                 235                 240

Leu Phe Ile Asn Phe Phe Val Lys Ser Tyr Val Phe Pro Lys Pro Lys
                245                 250                 255

Thr Ala Asp Lys Lys Val Gln
            260
```

<210> SEQ ID NO 5
<211> LENGTH: 792
<212> TYPE: DNA
<213> ORGANISM: Eutreptiella sp. CCMP389
<220> FEATURE:

```
<221> NAME/KEY: CDS
<222> LOCATION: (1)..(792)
<223> OTHER INFORMATION: synthetic delta-9 elongase (codon-optimized for
      Yarrowia lipolytica)
<300> PUBLICATION INFORMATION:
<302> TITLE: DELTA-9 ELONGASES AND THEIR USE IN MAKING POLYUNSATURATED
      FATTY ACIDS
<310> PATENT DOCUMENT NUMBER: WO 2007/061742
<311> PATENT FILING DATE: 2006-11-16
<312> PUBLICATION DATE: 2007-05-31
<313> RELEVANT RESIDUES IN SEQ ID NO: (1)..(792)
<300> PUBLICATION INFORMATION:
<302> TITLE: DELTA-9 ELONGASES AND THEIR USE IN MAKING POLYUNSATURATED
      FATTY ACIDS
<310> PATENT DOCUMENT NUMBER: US 7,645,604
<311> PATENT FILING DATE: 2006-11-16
<312> PUBLICATION DATE: 2010-01-12
<313> RELEVANT RESIDUES IN SEQ ID NO: (1)..(792)

<400> SEQUENCE: 5 atg gct gcc gtc atc gag gtg gcc aac gag ttc gtc gct atc act gcc      48
Met Ala Ala Val Ile Glu Val Ala Asn Glu Phe Val Ala Ile Thr Ala
1               5                   10                  15 gag acc ctt ccc aag gtg gac tat cag cga ctc tgg cga gac atc tac      96
Glu Thr Leu Pro Lys Val Asp Tyr Gln Arg Leu Trp Arg Asp Ile Tyr
            20                  25                  30 tcc tgc gag ctc ctg tac ttc tcc att gct ttc gtc atc ctc aag ttt     144
Ser Cys Glu Leu Leu Tyr Phe Ser Ile Ala Phe Val Ile Leu Lys Phe
        35                  40                  45 acc ctt ggc gag ctc tcg gat tct ggc aaa aag att ctg cga gtg ctg     192
Thr Leu Gly Glu Leu Ser Asp Ser Gly Lys Lys Ile Leu Arg Val Leu
    50                  55                  60 ttc aag tgg tac aac ctc ttc atg tcc gtc ttt tcg ctg gtg tcc ttc     240
Phe Lys Trp Tyr Asn Leu Phe Met Ser Val Phe Ser Leu Val Ser Phe
65                  70                  75                  80 ctc tgt atg ggt tac gcc atc tac acc gtt gga ctg tac tcc aac gaa     288
Leu Cys Met Gly Tyr Ala Ile Tyr Thr Val Gly Leu Tyr Ser Asn Glu
                85                  90                  95 tgc gac aga gct ttc gac aac agc ttg ttc cga ttt gcc acc aag gtc     336
Cys Asp Arg Ala Phe Asp Asn Ser Leu Phe Arg Phe Ala Thr Lys Val
            100                 105                 110 ttc tac tat tcc aag ttt ctg gag tac atc gac tct ttc tac ctt ccc     384
Phe Tyr Tyr Ser Lys Phe Leu Glu Tyr Ile Asp Ser Phe Tyr Leu Pro
        115                 120                 125 ctc atg gcc aag cct ctg tcc ttt ctg cag ttc ttt cat cac ttg gga     432
Leu Met Ala Lys Pro Leu Ser Phe Leu Gln Phe Phe His His Leu Gly
    130                 135                 140 gct cct atg gac atg tgg ctc ttc gtg cag tac tct ggc gaa tcc att     480
Ala Pro Met Asp Met Trp Leu Phe Val Gln Tyr Ser Gly Glu Ser Ile
145                 150                 155                 160 tgg atc ttt gtg ttc ctg aac gga ttc att cac ttt gtc atg tac ggc     528
Trp Ile Phe Val Phe Leu Asn Gly Phe Ile His Phe Val Met Tyr Gly
                165                 170                 175 tac tat tgg aca cgg ctg atg aag ttc aac ttt ccc atg ccc aag cag     576
Tyr Tyr Trp Thr Arg Leu Met Lys Phe Asn Phe Pro Met Pro Lys Gln
            180                 185                 190 ctc att acc gca atg cag atc acc cag ttc aac gtt ggc ttc tac ctc     624
Leu Ile Thr Ala Met Gln Ile Thr Gln Phe Asn Val Gly Phe Tyr Leu
        195                 200                 205 gtg tgg tgg tac aag gac att ccc tgt tac cga aag gat ccc atg cga     672
Val Trp Trp Tyr Lys Asp Ile Pro Cys Tyr Arg Lys Asp Pro Met Arg
    210                 215                 220 atg ctg gcc tgg atc ttc aac tac tgg tac gtc ggt acc gtt ctt ctg     720
Met Leu Ala Trp Ile Phe Asn Tyr Trp Tyr Val Gly Thr Val Leu Leu
```

```
ctc ttc atc aac ttc ttt gtc aag tcc tac gtg ttt ccc aag cct aag    768
Leu Phe Ile Asn Phe Phe Val Lys Ser Tyr Val Phe Pro Lys Pro Lys
            245                 250                 255 act gcc gac aaa aag gtc cag tag                                    792
Thr Ala Asp Lys Lys Val Gln
            260

<210> SEQ ID NO 6
<211> LENGTH: 263
<212> TYPE: PRT
<213> ORGANISM: Eutreptiella sp. CCMP389

<400> SEQUENCE: 6
```

Met Ala Ala Val Ile Glu Val Ala Asn Glu Phe Val Ala Ile Thr Ala
1               5                   10                  15

Glu Thr Leu Pro Lys Val Asp Tyr Gln Arg Leu Trp Arg Asp Ile Tyr
            20                  25                  30

Ser Cys Glu Leu Leu Tyr Phe Ser Ile Ala Phe Val Ile Leu Lys Phe
        35                  40                  45

Thr Leu Gly Glu Leu Ser Asp Ser Gly Lys Lys Ile Leu Arg Val Leu
50                  55                  60

Phe Lys Trp Tyr Asn Leu Phe Met Ser Val Phe Ser Leu Val Ser Phe
65                  70                  75                  80

Leu Cys Met Gly Tyr Ala Ile Tyr Thr Val Gly Leu Tyr Ser Asn Glu
                85                  90                  95

Cys Asp Arg Ala Phe Asp Asn Ser Leu Phe Arg Phe Ala Thr Lys Val
            100                 105                 110

Phe Tyr Tyr Ser Lys Phe Leu Glu Tyr Ile Asp Ser Phe Tyr Leu Pro
        115                 120                 125

Leu Met Ala Lys Pro Leu Ser Phe Leu Gln Phe Phe His His Leu Gly
130                 135                 140

Ala Pro Met Asp Met Trp Leu Phe Val Gln Tyr Ser Gly Glu Ser Ile
145                 150                 155                 160

Trp Ile Phe Val Phe Leu Asn Gly Phe Ile His Phe Val Met Tyr Gly
                165                 170                 175

Tyr Tyr Trp Thr Arg Leu Met Lys Phe Asn Phe Pro Met Pro Lys Gln
            180                 185                 190

Leu Ile Thr Ala Met Gln Ile Thr Gln Phe Asn Val Gly Phe Tyr Leu
        195                 200                 205

Val Trp Trp Tyr Lys Asp Ile Pro Cys Tyr Arg Lys Asp Pro Met Arg
210                 215                 220

Met Leu Ala Trp Ile Phe Asn Tyr Trp Tyr Val Gly Thr Val Leu Leu
225                 230                 235                 240

Leu Phe Ile Asn Phe Phe Val Lys Ser Tyr Val Phe Pro Lys Pro Lys
                245                 250                 255

Thr Ala Asp Lys Lys Val Gln
            260

```
<210> SEQ ID NO 7
<211> LENGTH: 777
<212> TYPE: DNA
<213> ORGANISM: Euglena gracilis
<220> FEATURE:
<221> NAME/KEY: CDS
<222> LOCATION: (1)..(777)
<223> OTHER INFORMATION: delta-9 elongase
<300> PUBLICATION INFORMATION:
```

<302> TITLE: DELTA-9 ELONGASES AND THEIR USE IN MAKING POLYUNSATURATED
       FATTY ACIDS
<310> PATENT DOCUMENT NUMBER: WO 2007/061742
<311> PATENT FILING DATE: 2006-11-16
<312> PUBLICATION DATE: 2007-05-31
<313> RELEVANT RESIDUES IN SEQ ID NO: (1)..(777)
<300> PUBLICATION INFORMATION:
<302> TITLE: DELTA-9 ELONGASES AND THEIR USE IN MAKING POLYUNSATURATED
       FATTY ACIDS
<310> PATENT DOCUMENT NUMBER: US 7,645,604
<311> PATENT FILING DATE: 2006-11-16
<312> PUBLICATION DATE: 2010-01-12
<313> RELEVANT RESIDUES IN SEQ ID NO: (1)..(777)

<400> SEQUENCE: 7

```
atg gag gtg gtg aat gaa ata gtc tca att ggg cag gaa gtt tta ccc      48
Met Glu Val Val Asn Glu Ile Val Ser Ile Gly Gln Glu Val Leu Pro
1               5                   10                  15 aaa gtt gat tat gcc caa ctc tgg agt gat gcc agt cac tgt gag gtg      96
Lys Val Asp Tyr Ala Gln Leu Trp Ser Asp Ala Ser His Cys Glu Val
                20                  25                  30 ctt tac ttg tcc atc gca ttt gtc atc ttg aag ttc act ctt ggc ccc     144
Leu Tyr Leu Ser Ile Ala Phe Val Ile Leu Lys Phe Thr Leu Gly Pro
            35                  40                  45 ctt ggt cca aaa ggt cag tct cgt atg aag ttt gtt ttc acc aat tac     192
Leu Gly Pro Lys Gly Gln Ser Arg Met Lys Phe Val Phe Thr Asn Tyr
        50                  55                  60 aac ctt ctc atg tcc att tat tcg ttg gga tca ttc ctc tca atg gca     240
Asn Leu Leu Met Ser Ile Tyr Ser Leu Gly Ser Phe Leu Ser Met Ala
65                  70                  75                  80 tat gcc atg tac acc atc ggt gtt atg tct gac aac tgc gag aag gct     288
Tyr Ala Met Tyr Thr Ile Gly Val Met Ser Asp Asn Cys Glu Lys Ala
                85                  90                  95 ttt gac aac aac gtc ttc agg atc acc acg cag ttg ttc tat ttg agc     336
Phe Asp Asn Asn Val Phe Arg Ile Thr Thr Gln Leu Phe Tyr Leu Ser
                100                 105                 110 aag ttc ctg gag tat att gac tcc ttc tat ttg cca ctg atg ggc aag     384
Lys Phe Leu Glu Tyr Ile Asp Ser Phe Tyr Leu Pro Leu Met Gly Lys
            115                 120                 125 cct ctg acc tgg ttg caa ttc ttc cat cat ttg ggg gca ccg atg gat     432
Pro Leu Thr Trp Leu Gln Phe Phe His His Leu Gly Ala Pro Met Asp
        130                 135                 140 atg tgg ctg ttc tat aat tac cga aat gaa gct gtt tgg att ttt gtg     480
Met Trp Leu Phe Tyr Asn Tyr Arg Asn Glu Ala Val Trp Ile Phe Val
145                 150                 155                 160 ctg ttg aat ggt ttc atc cac tgg atc atg tac ggt tat tat tgg acc     528
Leu Leu Asn Gly Phe Ile His Trp Ile Met Tyr Gly Tyr Tyr Trp Thr
                165                 170                 175 aga ttg atc aag ctg aag ttc ccc atg cca aaa tcc ctg att aca tca     576
Arg Leu Ile Lys Leu Lys Phe Pro Met Pro Lys Ser Leu Ile Thr Ser
                180                 185                 190 atg cag atc att caa ttc aat gtt ggt ttc tac att gtc tgg aag tac     624
Met Gln Ile Ile Gln Phe Asn Val Gly Phe Tyr Ile Val Trp Lys Tyr
            195                 200                 205 agg aac att ccc tgt tat cgc caa gat ggg atg agg atg ttt ggc tgg     672
Arg Asn Ile Pro Cys Tyr Arg Gln Asp Gly Met Arg Met Phe Gly Trp
        210                 215                 220 ttc ttc aat tac ttt tat gtt ggc aca gtc ttg tgt ttg ttc ttg aat     720
Phe Phe Asn Tyr Phe Tyr Val Gly Thr Val Leu Cys Leu Phe Leu Asn
225                 230                 235                 240 ttc tat gtg caa acg tat atc gtc agg aag cac aag gga gcc aaa aag     768
Phe Tyr Val Gln Thr Tyr Ile Val Arg Lys His Lys Gly Ala Lys Lys
                245                 250                 255
```

```
att cag tga                                                          777
Ile Gln
```

<210> SEQ ID NO 8
<211> LENGTH: 258
<212> TYPE: PRT
<213> ORGANISM: Euglena gracilis

<400> SEQUENCE: 8

```
Met Glu Val Val Asn Glu Ile Val Ser Ile Gly Gln Glu Val Leu Pro
1               5                   10                  15

Lys Val Asp Tyr Ala Gln Leu Trp Ser Asp Ala Ser His Cys Glu Val
            20                  25                  30

Leu Tyr Leu Ser Ile Ala Phe Val Ile Leu Lys Phe Thr Leu Gly Pro
        35                  40                  45

Leu Gly Pro Lys Gly Gln Ser Arg Met Lys Phe Val Phe Thr Asn Tyr
    50                  55                  60

Asn Leu Leu Met Ser Ile Tyr Ser Leu Gly Ser Phe Leu Ser Met Ala
65                  70                  75                  80

Tyr Ala Met Tyr Thr Ile Gly Val Met Ser Asp Asn Cys Glu Lys Ala
                85                  90                  95

Phe Asp Asn Asn Val Phe Arg Ile Thr Thr Gln Leu Phe Tyr Leu Ser
            100                 105                 110

Lys Phe Leu Glu Tyr Ile Asp Ser Phe Tyr Leu Pro Leu Met Gly Lys
        115                 120                 125

Pro Leu Thr Trp Leu Gln Phe Phe His His Leu Gly Ala Pro Met Asp
    130                 135                 140

Met Trp Leu Phe Tyr Asn Tyr Arg Asn Glu Ala Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Lys Phe Pro Met Pro Lys Ser Leu Ile Thr Ser
            180                 185                 190

Met Gln Ile Ile Gln Phe Asn Val Gly Phe Tyr Ile Val Trp Lys Tyr
        195                 200                 205

Arg Asn Ile Pro Cys Tyr Arg Gln Asp Gly Met Arg Met Phe Gly Trp
    210                 215                 220

Phe Phe Asn Tyr Phe Tyr Val Gly Thr Val Leu Cys Leu Phe Leu Asn
225                 230                 235                 240

Phe Tyr Val Gln Thr Tyr Ile Val Arg Lys His Lys Gly Ala Lys Lys
                245                 250                 255

Ile Gln
```

<210> SEQ ID NO 9
<211> LENGTH: 777
<212> TYPE: DNA
<213> ORGANISM: Euglena gracilis
<220> FEATURE:
<221> NAME/KEY: CDS
<222> LOCATION: (1)..(777)
<223> OTHER INFORMATION: synthetic delta-9 elongase (codon-optimized for
      Yarrowia lipolytica)
<300> PUBLICATION INFORMATION:
<302> TITLE: DELTA-9 ELONGASES AND THEIR USE IN MAKING POLYUNSATURATED
      FATTY ACIDS
<310> PATENT DOCUMENT NUMBER: WO 2007/061742
<311> PATENT FILING DATE: 2006-11-16
<312> PUBLICATION DATE: 2007-05-31
<313> RELEVANT RESIDUES IN SEQ ID NO: (1)..(777)

```
<300> PUBLICATION INFORMATION:
<302> TITLE: DELTA-9 ELONGASES AND THEIR USE IN MAKING POLYUNSATURATED
      FATTY ACIDS
<310> PATENT DOCUMENT NUMBER: US 7,645,604
<311> PATENT FILING DATE: 2006-11-16
<312> PUBLICATION DATE: 2010-01-12
<313> RELEVANT RESIDUES IN SEQ ID NO: (1)..(777)

<400> SEQUENCE: 9 atg gag gtc gtg aac gaa atc gtc tcc att ggc cag gag gtt ctt ccc       48
Met Glu Val Val Asn Glu Ile Val Ser Ile Gly Gln Glu Val Leu Pro
1               5                   10                  15 aag gtc gac tat gct cag ctc tgg tct gat gcc tcg cac tgc gag gtg       96
Lys Val Asp Tyr Ala Gln Leu Trp Ser Asp Ala Ser His Cys Glu Val
            20                  25                  30 ctg tac ctc tcc atc gcc ttc gtc atc ctg aag ttc acc ctt ggt cct      144
Leu Tyr Leu Ser Ile Ala Phe Val Ile Leu Lys Phe Thr Leu Gly Pro
        35                  40                  45 ctc gga ccc aag ggt cag tct cga atg aag ttt gtg ttc acc aac tac      192
Leu Gly Pro Lys Gly Gln Ser Arg Met Lys Phe Val Phe Thr Asn Tyr
    50                  55                  60 aac ctg ctc atg tcc atc tac tcg ctg ggc tcc ttc ctc tct atg gcc      240
Asn Leu Leu Met Ser Ile Tyr Ser Leu Gly Ser Phe Leu Ser Met Ala
65                  70                  75                  80 tac gcc atg tac acc att ggt gtc atg tcc gac aac tgc gag aag gct      288
Tyr Ala Met Tyr Thr Ile Gly Val Met Ser Asp Asn Cys Glu Lys Ala
                85                  90                  95 ttc gac aac aat gtc ttc cga atc acc act cag ctg ttc tac ctc agc      336
Phe Asp Asn Asn Val Phe Arg Ile Thr Thr Gln Leu Phe Tyr Leu Ser
            100                 105                 110 aag ttc ctc gag tac att gac tcc ttc tat ctg ccc ctc atg ggc aag      384
Lys Phe Leu Glu Tyr Ile Asp Ser Phe Tyr Leu Pro Leu Met Gly Lys
        115                 120                 125 cct ctg acc tgg ttg cag ttc ttt cac cat ctc gga gct cct atg gac      432
Pro Leu Thr Trp Leu Gln Phe Phe His His Leu Gly Ala Pro Met Asp
    130                 135                 140 atg tgg ctg ttc tac aac tac cga aac gaa gcc gtt tgg atc ttt gtg      480
Met Trp Leu Phe Tyr Asn Tyr Arg Asn Glu Ala Val Trp Ile Phe Val
145                 150                 155                 160 ctg ctc aac ggc ttc att cac tgg atc atg tac ggc tac tat tgg acc      528
Leu Leu Asn Gly Phe Ile His Trp Ile Met Tyr Gly Tyr Tyr Trp Thr
                165                 170                 175 cga ctg atc aag ctc aag ttc cct atg ccc aag tcc ctg att act tct      576
Arg Leu Ile Lys Leu Lys Phe Pro Met Pro Lys Ser Leu Ile Thr Ser
            180                 185                 190 atg cag atc att cag ttc aac gtt ggc ttc tac atc gtc tgg aag tac      624
Met Gln Ile Ile Gln Phe Asn Val Gly Phe Tyr Ile Val Trp Lys Tyr
        195                 200                 205 cgg aac att ccc tgc tac cga caa gat gga atg aga atg ttt ggc tgg      672
Arg Asn Ile Pro Cys Tyr Arg Gln Asp Gly Met Arg Met Phe Gly Trp
    210                 215                 220 ttt ttc aac tac ttc tac gtt ggt act gtc ctg tgt ctg ttc ctc aac      720
Phe Phe Asn Tyr Phe Tyr Val Gly Thr Val Leu Cys Leu Phe Leu Asn
225                 230                 235                 240 ttc tac gtg cag acc tac atc gtc cga aag cac aag gga gcc aaa aag      768
Phe Tyr Val Gln Thr Tyr Ile Val Arg Lys His Lys Gly Ala Lys Lys
                245                 250                 255 att cag tga                                                          777
Ile Gln

<210> SEQ ID NO 10
```

```
<211> LENGTH: 258
<212> TYPE: PRT
<213> ORGANISM: Euglena gracilis

<400> SEQUENCE: 10

Met Glu Val Val Asn Glu Ile Val Ser Ile Gly Gln Glu Val Leu Pro
1               5                   10                  15

Lys Val Asp Tyr Ala Gln Leu Trp Ser Asp Ala Ser His Cys Glu Val
            20                  25                  30

Leu Tyr Leu Ser Ile Ala Phe Val Ile Leu Lys Phe Thr Leu Gly Pro
        35                  40                  45

Leu Gly Pro Lys Gly Gln Ser Arg Met Lys Phe Val Phe Thr Asn Tyr
    50                  55                  60

Asn Leu Leu Met Ser Ile Tyr Ser Leu Gly Ser Phe Leu Ser Met Ala
65                  70                  75                  80

Tyr Ala Met Tyr Thr Ile Gly Val Met Ser Asp Asn Cys Glu Lys Ala
                85                  90                  95

Phe Asp Asn Asn Val Phe Arg Ile Thr Thr Gln Leu Pro Tyr Leu Ser
            100                 105                 110

Lys Phe Leu Glu Tyr Ile Asp Ser Phe Tyr Leu Pro Leu Met Gly Lys
        115                 120                 125

Pro Leu Thr Trp Leu Gln Phe Phe His His Leu Gly Ala Pro Met Asp
    130                 135                 140

Met Trp Leu Phe Tyr Asn Tyr Arg Asn Glu Ala Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Lys Phe Pro Met Pro Lys Ser Leu Ile Thr Ser
            180                 185                 190

Met Gln Ile Ile Gln Phe Asn Val Gly Phe Tyr Ile Val Trp Lys Tyr
        195                 200                 205

Arg Asn Ile Pro Cys Tyr Arg Gln Asp Gly Met Arg Met Phe Gly Trp
    210                 215                 220

Phe Phe Asn Tyr Phe Tyr Val Gly Thr Val Leu Cys Leu Phe Leu Asn
225                 230                 235                 240

Phe Tyr Val Gln Thr Tyr Ile Val Arg Lys His Lys Gly Ala Lys Lys
                245                 250                 255

Ile Gln

<210> SEQ ID NO 11
<211> LENGTH: 774
<212> TYPE: DNA
<213> ORGANISM: Euglena anabaena UTEX 373
<220> FEATURE:
<221> NAME/KEY: CDS
<222> LOCATION: (1)..(774)
<223> OTHER INFORMATION: delta-9 elongase
<300> PUBLICATION INFORMATION:
<302> TITLE: DELTA-9 ELONGASES AND THEIR USE IN MAKING POLYUNSATURATED
      FATTY ACIDS
<310> PATENT DOCUMENT NUMBER: U.S. 7,794,701
<311> PATENT FILING DATE: 2008-04-15
<312> PUBLICATION DATE: 2010-09-14
<313> RELEVANT RESIDUES IN SEQ ID NO: (1)..(774)
<300> PUBLICATION INFORMATION:
<302> TITLE: DELTA-9 ELONGASES AND THEIR USE IN MAKING POLYUNSATURATED
      FATTY ACIDS
<310> PATENT DOCUMENT NUMBER: WO 2008/128241
<311> PATENT FILING DATE: 2008-04-16
<312> PUBLICATION DATE: 2008-10-23
<313> RELEVANT RESIDUES IN SEQ ID NO: (1)..(774)
```

<400> SEQUENCE: 11

```
atg gaa gca gcc aaa gaa ttg gtt tcc atc gtc caa gag gag ctc ccc    48
Met Glu Ala Ala Lys Glu Leu Val Ser Ile Val Gln Glu Glu Leu Pro
1               5                   10                  15 aag gtg gac tat gcc cag ctt tgg cag gat gcc agc agc tgt gag gtc    96
Lys Val Asp Tyr Ala Gln Leu Trp Gln Asp Ala Ser Ser Cys Glu Val
            20                  25                  30 ctt tac ctc tcg gtg gca ttc gtg gcg atc aag ttc atg ctg cgc cca   144
Leu Tyr Leu Ser Val Ala Phe Val Ala Ile Lys Phe Met Leu Arg Pro
        35                  40                  45 ctg gac ctg aag cgc cag gcc acc ttg aag aag ctg ttc aca gca tac   192
Leu Asp Leu Lys Arg Gln Ala Thr Leu Lys Lys Leu Phe Thr Ala Tyr
50                  55                  60 aac ttc ctc atg tcg atc tat tcc ttt ggc tcc ttc ctg gcc atg gcc   240
Asn Phe Leu Met Ser Ile Tyr Ser Phe Gly Ser Phe Leu Ala Met Ala
65                  70                  75                  80 tat gcc cta tca gta act ggc atc ctc tcc ggc gac tgt gag acg gcg   288
Tyr Ala Leu Ser Val Thr Gly Ile Leu Ser Gly Asp Cys Glu Thr Ala
                85                  90                  95 ttc aac aac gat gtg ttc agg atc aca act cag ctg ttc tac ctc agc   336
Phe Asn Asn Asp Val Phe Arg Ile Thr Thr Gln Leu Phe Tyr Leu Ser
            100                 105                 110 aag ttc gta gag tac atc gac tcc ttc tac ctt ccc ctt atg gac aag   384
Lys Phe Val Glu Tyr Ile Asp Ser Phe Tyr Leu Pro Leu Met Asp Lys
        115                 120                 125 cca ctg tcg ttc ctt cag ttc ttc cat cat ttg ggg gcc ccc att gac   432
Pro Leu Ser Phe Leu Gln Phe Phe His His Leu Gly Ala Pro Ile Asp
    130                 135                 140 atg tgg cta ttc tac aaa tac cgc aac gaa gga gtc tgg atc ttt gtc   480
Met Trp Leu Phe Tyr Lys Tyr Arg Asn Glu Gly Val Trp Ile Phe Val
145                 150                 155                 160 ctg ttg aat ggg ttc att cac tgg atc atg tac ggt tac tat tgg acg   528
Leu Leu Asn Gly Phe Ile His Trp Ile Met Tyr Gly Tyr Tyr Trp Thr
                165                 170                 175 cgg ctc atc aag ctg aac ttc ccc atg ccc aag aac ctg atc acc tcc   576
Arg Leu Ile Lys Leu Asn Phe Pro Met Pro Lys Asn Leu Ile Thr Ser
            180                 185                 190 atg cag atc atc cag ttc aat gtc ggg ttc tac atc gtc tgg aag tac   624
Met Gln Ile Ile Gln Phe Asn Val Gly Phe Tyr Ile Val Trp Lys Tyr
        195                 200                 205 cgc aat gtg cca tgc tac cgc cag gat ggg atg cgc atg ttt gcc tgg   672
Arg Asn Val Pro Cys Tyr Arg Gln Asp Gly Met Arg Met Phe Ala Trp
    210                 215                 220 atc ttc aac tac tgg tat gtc ggg acg gtc ttg ctg ctg ttc ctc aac   720
Ile Phe Asn Tyr Trp Tyr Val Gly Thr Val Leu Leu Leu Phe Leu Asn
225                 230                 235                 240 ttt tac gtg cag acg tac atc cgg aag ccg agg aag aac cga ggg aag   768
Phe Tyr Val Gln Thr Tyr Ile Arg Lys Pro Arg Lys Asn Arg Gly Lys
                245                 250                 255 aag gag                                                            774
Lys Glu
```

<210> SEQ ID NO 12
<211> LENGTH: 258
<212> TYPE: PRT
<213> ORGANISM: Euglena anabaena UTEX 373

<400> SEQUENCE: 12

Met Glu Ala Ala Lys Glu Leu Val Ser Ile Val Gln Glu Glu Leu Pro

```
                1               5                  10                    15
              Lys Val Asp Tyr Ala Gln Leu Trp Gln Asp Ala Ser Ser Cys Glu Val
                              20                  25                  30

Leu Tyr Leu Ser Val Ala Phe Val Ala Ile Lys Phe Met Leu Arg Pro
                          35                  40                  45

Leu Asp Leu Lys Arg Gln Ala Thr Leu Lys Lys Leu Phe Thr Ala Tyr
               50                  55                  60

Asn Phe Leu Met Ser Ile Tyr Ser Phe Gly Ser Phe Leu Ala Met Ala
               65                  70                  75                  80

Tyr Ala Leu Ser Val Thr Gly Ile Leu Ser Gly Asp Cys Glu Thr Ala
                              85                  90                  95

Phe Asn Asn Asp Val Phe Arg Ile Thr Thr Gln Leu Phe Tyr Leu Ser
                              100                 105                 110

Lys Phe Val Glu Tyr Ile Asp Ser Phe Tyr Leu Pro Leu Met Asp Lys
                              115                 120                 125

Pro Leu Ser Phe Leu Gln Phe Phe His His Leu Gly Ala Pro Ile Asp
                          130                 135                 140

Met Trp Leu Phe Tyr Lys Tyr Arg Asn Glu Gly Val Trp Ile Phe Val
               145                 150                 155                 160

Leu Leu Asn Gly Phe Ile His Trp Ile Met Tyr Gly Tyr Tyr Trp Thr
                                  165                 170                 175

Arg Leu Ile Lys Leu Asn Phe Pro Met Pro Lys Asn Leu Ile Thr Ser
                              180                 185                 190

Met Gln Ile Ile Gln Phe Asn Val Gly Phe Tyr Ile Val Trp Lys Tyr
                              195                 200                 205

Arg Asn Val Pro Cys Tyr Arg Gln Asp Gly Met Arg Met Phe Ala Trp
                          210                 215                 220

Ile Phe Asn Tyr Trp Tyr Val Gly Thr Val Leu Leu Leu Phe Leu Asn
               225                 230                 235                 240

Phe Tyr Val Gln Thr Tyr Ile Arg Lys Pro Arg Lys Asn Arg Gly Lys
                                  245                 250                 255

Lys Glu

<210> SEQ ID NO 13
<211> LENGTH: 774
<212> TYPE: DNA
<213> ORGANISM: Euglena anabaena UTEX 373
<220> FEATURE:
<221> NAME/KEY: CDS
<222> LOCATION: (1)..(774)
<223> OTHER INFORMATION: synthetic delta-9 elongase (codon-optimized for
      Yarrowia lipolytica)
<300> PUBLICATION INFORMATION:
<302> TITLE: DELTA-9 ELONGASES AND THEIR USE IN MAKING POLYUNSATURATED
      FATTY ACIDS
<310> PATENT DOCUMENT NUMBER: U.S. 7,794,701
<311> PATENT FILING DATE: 2008-04-15
<312> PUBLICATION DATE: 2010-09-14
<313> RELEVANT RESIDUES IN SEQ ID NO: (1)..(774)
<300> PUBLICATION INFORMATION:
<302> TITLE: DELTA-9 ELONGASES AND THEIR USE IN MAKING POLYUNSATURATED
      FATTY ACIDS
<310> PATENT DOCUMENT NUMBER: WO 2008/128241
<311> PATENT FILING DATE: 2008-04-16
<312> PUBLICATION DATE: 2008-10-23
<313> RELEVANT RESIDUES IN SEQ ID NO: (1)..(774)

<400> SEQUENCE: 13 atg gag gct gcc aag gag ctg gtc tcc atc gtc cag gag gaa ctt ccc      48
Met Glu Ala Ala Lys Glu Leu Val Ser Ile Val Gln Glu Glu Leu Pro
 1               5                  10                  15
```

| | | |
|---|---|---|
| aag gtg gac tac gcc cag ctc tgg cag gac gcc tcc tct tgc gag gtt<br>Lys Val Asp Tyr Ala Gln Leu Trp Gln Asp Ala Ser Ser Cys Glu Val<br>20　　　　　　　　25　　　　　　　　30 | | 96 |
| ctg tac ctc tcg gtc gct ttc gtg gcc atc aag ttc atg ctt cga cct<br>Leu Tyr Leu Ser Val Ala Phe Val Ala Ile Lys Phe Met Leu Arg Pro<br>35　　　　　　　　40　　　　　　　　45 | | 144 |
| ctg gac ctc aag cga caa gcc acc ctc aaa aag ctg ttc acc gca tac<br>Leu Asp Leu Lys Arg Gln Ala Thr Leu Lys Lys Leu Phe Thr Ala Tyr<br>50　　　　　　　　55　　　　　　　　60 | | 192 |
| aac ttt ctc atg tcc atc tac tcg ttc ggc tcc ttc ctg gcg atg gcc<br>Asn Phe Leu Met Ser Ile Tyr Ser Phe Gly Ser Phe Leu Ala Met Ala<br>65　　　　　　　　70　　　　　75　　　　　　　　80 | | 240 |
| tac gct ctc tct gtc act ggt att ctt tcc ggc gat tgt gag act gcc<br>Tyr Ala Leu Ser Val Thr Gly Ile Leu Ser Gly Asp Cys Glu Thr Ala<br>85　　　　　　　　90　　　　　　　　95 | | 288 |
| ttc aac aat gac gtg ttc cga atc acc act cag ctg ttc tac ctc agc<br>Phe Asn Asn Asp Val Phe Arg Ile Thr Thr Gln Leu Phe Tyr Leu Ser<br>100　　　　　　　　105　　　　　　　　110 | | 336 |
| aag ttc gtc gag tac atc gac tcc ttc tac ctt ccc ctc atg gac aag<br>Lys Phe Val Glu Tyr Ile Asp Ser Phe Tyr Leu Pro Leu Met Asp Lys<br>115　　　　　　　　120　　　　　　　　125 | | 384 |
| ccc ttg tcg ttt ctg cag ttc ttt cac cat ctc gga gct ccc atc gac<br>Pro Leu Ser Phe Leu Gln Phe Phe His His Leu Gly Ala Pro Ile Asp<br>130　　　　　　　　135　　　　　　　　140 | | 432 |
| atg tgg ctg ttc tac aag tat cga aac gaa ggc gtc tgg atc ttt gtt<br>Met Trp Leu Phe Tyr Lys Tyr Arg Asn Glu Gly Val Trp Ile Phe Val<br>145　　　　　　　150　　　　　　　155　　　　　　　　160 | | 480 |
| ctc ctc aac ggc ttc att cac tgg atc atg tac ggt tac tat tgg acg<br>Leu Leu Asn Gly Phe Ile His Trp Ile Met Tyr Gly Tyr Tyr Trp Thr<br>165　　　　　　　　170　　　　　　　　175 | | 528 |
| cga ctc atc aag ctg aac ttc cct atg ccc aag aac ctc att acc tcc<br>Arg Leu Ile Lys Leu Asn Phe Pro Met Pro Lys Asn Leu Ile Thr Ser<br>180　　　　　　　　185　　　　　　　　190 | | 576 |
| atg caa att atc cag ttc aac gtc gga ttc tac atc gtc tgg aag tac<br>Met Gln Ile Ile Gln Phe Asn Val Gly Phe Tyr Ile Val Trp Lys Tyr<br>195　　　　　　　　200　　　　　　　　205 | | 624 |
| cga aac gtg ccc tgc tac cgg cag gac ggt atg cga atg ttt gcc tgg<br>Arg Asn Val Pro Cys Tyr Arg Gln Asp Gly Met Arg Met Phe Ala Trp<br>210　　　　　　　　215　　　　　　　　220 | | 672 |
| atc ttc aac tac tgg tat gtc ggc acg gtg ctg ctt ctg ttc ctc aac<br>Ile Phe Asn Tyr Trp Tyr Val Gly Thr Val Leu Leu Leu Phe Leu Asn<br>225　　　　　　　230　　　　　　　235　　　　　　　　240 | | 720 |
| ttc tac gtc cag acc tac att cgg aag cct cga aag aac cga ggc aaa<br>Phe Tyr Val Gln Thr Tyr Ile Arg Lys Pro Arg Lys Asn Arg Gly Lys<br>245　　　　　　　　250　　　　　　　　255 | | 768 |
| aag gag<br>Lys Glu | | 774 |

<210> SEQ ID NO 14
<211> LENGTH: 258
<212> TYPE: PRT
<213> ORGANISM: Euglena anabaena UTEX 373

<400> SEQUENCE: 14

Met Glu Ala Ala Lys Glu Leu Val Ser Ile Val Gln Glu Glu Leu Pro
1               5                  10                  15

Lys Val Asp Tyr Ala Gln Leu Trp Gln Asp Ala Ser Ser Cys Glu Val
                20                  25                  30

Leu Tyr Leu Ser Val Ala Phe Val Ala Ile Lys Phe Met Leu Arg Pro

```
            35                  40                  45
Leu Asp Leu Lys Arg Gln Ala Thr Leu Lys Leu Phe Thr Ala Tyr
 50                  55                  60

Asn Phe Leu Met Ser Ile Tyr Ser Phe Gly Ser Phe Leu Ala Met Ala
 65                  70                  75                  80

Tyr Ala Leu Ser Val Thr Gly Ile Leu Ser Gly Asp Cys Glu Thr Ala
                 85                  90                  95

Phe Asn Asn Asp Val Phe Arg Ile Thr Thr Gln Leu Phe Tyr Leu Ser
                100                 105                 110

Lys Phe Val Glu Tyr Ile Asp Ser Phe Tyr Leu Pro Leu Met Asp Lys
                115                 120                 125

Pro Leu Ser Phe Leu Gln Phe Phe His His Leu Gly Ala Pro Ile Asp
130                 135                 140

Met Trp Leu Phe Tyr Lys Tyr Arg Asn Glu Gly Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Asn Phe Pro Met Pro Lys Asn Leu Ile Thr Ser
                180                 185                 190

Met Gln Ile Ile Gln Phe Asn Val Gly Phe Tyr Ile Val Trp Lys Tyr
                195                 200                 205

Arg Asn Val Pro Cys Tyr Arg Gln Asp Gly Met Arg Met Phe Ala Trp
210                 215                 220

Ile Phe Asn Tyr Trp Tyr Val Gly Thr Val Leu Leu Leu Phe Leu Asn
225                 230                 235                 240

Phe Tyr Val Gln Thr Tyr Ile Arg Lys Pro Arg Lys Asn Arg Gly Lys
                245                 250                 255

Lys Glu

<210> SEQ ID NO 15
<211> LENGTH: 13
<212> TYPE: PRT
<213> ORGANISM: Artificial Sequence
<220> FEATURE:
<223> OTHER INFORMATION: delta-9 elongase motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: X = L or F
<220> FEATURE:
<221> NAME/KEY: misc_feature
<222> LOCATION: (5)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<300> PUBLICATION INFORMATION:
<302> TITLE: DELTA-9 ELONGASES AND THEIR USE IN MAKING POLYUNSATURATED
      FATTY ACIDS
<310> PATENT DOCUMENT NUMBER: US 7,645,604
<311> PATENT FILING DATE: 2006-11-16
<312> PUBLICATION DATE: 2010-01-12
<313> RELEVANT RESIDUES IN SEQ ID NO: (1)..(13)

<400> SEQUENCE: 15

Tyr Asn Xaa Xaa Xaa Xaa Xaa Xaa Ser Xaa Xaa Ser Phe
 1               5                  10
```

```
<210> SEQ ID NO 16
<211> LENGTH: 15
<212> TYPE: PRT
<213> ORGANISM: Artificial Sequence
<220> FEATURE:
<223> OTHER INFORMATION: delta-9 elongase motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: X = E or D
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (12)..(12)
<223> OTHER INFORMATION: X = T or S
<220> FEATURE:
<221> NAME/KEY: misc_feature
<222> LOCATION: (13)..(14)
<223> OTHER INFORMATION: Xaa can be any naturally occurring amino acid
<300> PUBLICATION INFORMATION:
<302> TITLE: DELTA-9 ELONGASES AND THEIR USE IN MAKING POLYUNSATURATED
      FATTY ACIDS
<310> PATENT DOCUMENT NUMBER: U.S. 7,645,604
<311> PATENT FILING DATE: 2006-11-16
<312> PUBLICATION DATE: 2010-01-12
<313> RELEVANT RESIDUES IN SEQ ID NO: (1)..(15)

<400> SEQUENCE: 16

Phe Tyr Xaa Ser Lys Xaa Xaa Xaa Tyr Xaa Asp Xaa Xaa Xaa Leu
1               5                   10                  15

<210> SEQ ID NO 17
<211> LENGTH: 9
<212> TYPE: PRT
<213> ORGANISM: Artificial Sequence
<220> FEATURE:
<223> OTHER INFORMATION: delta-9 elongase motif
<220> FEATURE:
<221> NAME/KEY: MISC_FEATURE
<222> LOCATION: (2)..(2)
<223> OTHER INFORMATION: X = Q or H
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<300> PUBLICATION INFORMATION:
<302> TITLE: DELTA-9 ELONGASES AND THEIR USE IN MAKING POLYUNSATURATED
      FATTY ACIDS
<310> PATENT DOCUMENT NUMBER: U.S. 7,645,604
<311> PATENT FILING DATE: 2006-11-16
<312> PUBLICATION DATE: 2010-01-12
<313> RELEVANT RESIDUES IN SEQ ID NO: (1)..(9)

<400> SEQUENCE: 17

Leu Xaa Xaa Phe His His Xaa Gly Ala
1               5

<210> SEQ ID NO 18
<211> LENGTH: 14
```

```
<212> TYPE: PRT
<213> ORGANISM: Artificial Sequence
<220> FEATURE:
<223> OTHER INFORMATION: delta-9 elongase motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(12)
<223> OTHER INFORMATION: Xaa can be any naturally occurring amino acid
<220> FEATURE:
<221> NAME/KEY: MISC_FEATURE
<222> LOCATION: (13)..(13)
<223> OTHER INFORMATION: X = K or R or N
<300> PUBLICATION INFORMATION:
<302> TITLE: DELTA-9 ELONGASES AND THEIR USE IN MAKING POLYUNSATURATED
      FATTY ACIDS
<310> PATENT DOCUMENT NUMBER: U.S. 7,645,604
<311> PATENT FILING DATE: 2006-11-16
<312> PUBLICATION DATE: 2010-01-12
<313> RELEVANT RESIDUES IN SEQ ID NO: (1)..(14)

<400> SEQUENCE: 18

Met Tyr Xaa Tyr Tyr Xaa Xaa Xaa Xaa Xaa Xaa Xaa Phe
1               5                   10

<210> SEQ ID NO 19
<211> LENGTH: 8
<212> TYPE: PRT
<213> ORGANISM: Artificial Sequence
<220> FEATURE:
<223> OTHER INFORMATION: delta-9 elongase motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: X = I or L or M
<220> FEATURE:
<221> NAME/KEY: misc_feature
<222> LOCATION: (6)..(7)
<223> OTHER INFORMATION: Xaa can be any naturally occurring amino acid
<300> PUBLICATION INFORMATION:
<302> TITLE: DELTA-9 ELONGASES AND THEIR USE IN MAKING POLYUNSATURATED
      FATTY ACIDS
<310> PATENT DOCUMENT NUMBER: U.S. 7,645,604
<311> PATENT FILING DATE: 2006-11-16
<312> PUBLICATION DATE: 2010-01-12
<313> RELEVANT RESIDUES IN SEQ ID NO: (1)..(8)

<400> SEQUENCE: 19

Lys Xaa Leu Xaa Thr Xaa Xaa Gln
1               5

<210> SEQ ID NO 20
<211> LENGTH: 7
<212> TYPE: PRT
<213> ORGANISM: Artificial Sequence
<220> FEATURE:
<223> OTHER INFORMATION: delta-9 elongase motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<300> PUBLICATION INFORMATION:
<302> TITLE: DELTA-9 ELONGASES AND THEIR USE IN MAKING POLYUNSATURATED
      FATTY ACIDS
```

```
<310> PATENT DOCUMENT NUMBER: U.S. 7,645,604
<311> PATENT FILING DATE: 2006-11-16
<312> PUBLICATION DATE: 2010-01-12
<313> RELEVANT RESIDUES IN SEQ ID NO: (1)..(7)

<400> SEQUENCE: 20

Trp Xaa Phe Asn Tyr Xaa Tyr
1               5

<210> SEQ ID NO 21
<211> LENGTH: 9
<212> TYPE: PRT
<213> ORGANISM: Artificial Sequence
<220> FEATURE:
<223> OTHER INFORMATION: delta-9 elongase motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<300> PUBLICATION INFORMATION:
<302> TITLE: DELTA-9 ELONGASES AND THEIR USE IN MAKING POLYUNSATURATED
      FATTY ACIDS
<310> PATENT DOCUMENT NUMBER: U.S. 7,645,604
<311> PATENT FILING DATE: 2006-11-16
<312> PUBLICATION DATE: 2010-01-12
<313> RELEVANT RESIDUES IN SEQ ID NO: (1)..(9)

<400> SEQUENCE: 21

Tyr Xaa Gly Xaa Val Xaa Xaa Leu Phe
1               5

<210> SEQ ID NO 22
<211> LENGTH: 258
<212> TYPE: PRT
<213> ORGANISM: Euglena gracilis
<220> FEATURE:
<221> NAME/KEY: MISC_FEATURE
<222> LOCATION: (1)..(258)
<223> OTHER INFORMATION: mutant delta-9 elongase; EgD9eS-mutant
      consensus
<220> FEATURE:
<221> NAME/KEY: MISC_FEATURE
<222> LOCATION: (9)..(9)
<223> OTHER INFORMATION: Xaa = Ser [S] (synthetic codon-optimized) or
      (Ala [A] or Asp [D] or Gly [G] or Ile [I] or Lys [K] or Gln [Q])
      (mutant)
<220> FEATURE:
<221> NAME/KEY: MISC_FEATURE
<222> LOCATION: (12)..(12)
<223> OTHER INFORMATION: Xaa = Gln [Q] (synthetic codon-optimized) or
      Lys [K] (mutant)
<220> FEATURE:
<221> NAME/KEY: MISC_FEATURE
<222> LOCATION: (21)..(21)
<223> OTHER INFORMATION: Xaa = Ala [A] (synthetic codon-optimized) or
      (Asp [D] or Thr [T] or Val [V]) (mutant)
<220> FEATURE:
<221> NAME/KEY: MISC_FEATURE
<222> LOCATION: (32)..(32)
<223> OTHER INFORMATION: Xaa = Val [V] (synthetic codon-optimized) or
      Phe [F] (mutant)
<220> FEATURE:
<221> NAME/KEY: MISC_FEATURE
<222> LOCATION: (35)..(35)
<223> OTHER INFORMATION: Xaa = Leu [L] (synthetic codon-optimized) or
      (Phe [F] or Gly [G] or Met [M]) (mutant)
<220> FEATURE:
```

```
<221> NAME/KEY: MISC_FEATURE
<222> LOCATION: (58)..(58)
<223> OTHER INFORMATION: Xaa = Lys [K] (synthetic codon-optimized) or
      Arg [R] (mutant)
<220> FEATURE:
<221> NAME/KEY: MISC_FEATURE
<222> LOCATION: (84)..(84)
<223> OTHER INFORMATION: Xaa = Tyr [Y] (synthetic codon-optimized) or
      Cys [C] (mutant)
<220> FEATURE:
<221> NAME/KEY: MISC_FEATURE
<222> LOCATION: (98)..(98)
<223> OTHER INFORMATION: Xaa = Asp [D] (synthetic codon-optimized) or
      Gly [G] (mutant)
<220> FEATURE:
<221> NAME/KEY: MISC_FEATURE
<222> LOCATION: (107)..(107)
<223> OTHER INFORMATION: Xaa = Gln [Q] (synthetic codon-optimized) or
      Glu [E] (mutant)
<220> FEATURE:
<221> NAME/KEY: MISC_FEATURE
<222> LOCATION: (108)..(108)
<223> OTHER INFORMATION: Xaa = Leu [L] (synthetic codon-optimized) or
      Gly [G] (mutant)
<220> FEATURE:
<221> NAME/KEY: MISC_FEATURE
<222> LOCATION: (127)..(127)
<223> OTHER INFORMATION: Xaa = Gly [G] (synthetic codon-optimized) or
      Leu [L] (mutant)
<220> FEATURE:
<221> NAME/KEY: MISC_FEATURE
<222> LOCATION: (130)..(130)
<223> OTHER INFORMATION: Xaa = Leu [L] (synthetic codon-optimized) or
      Met [M] (mutant)
<220> FEATURE:
<221> NAME/KEY: MISC_FEATURE
<222> LOCATION: (132)..(132)
<223> OTHER INFORMATION: Xaa = Trp [W] (synthetic codon-optimized) or
      Thr [T] (mutant)
<220> FEATURE:
<221> NAME/KEY: MISC_FEATURE
<222> LOCATION: (143)..(143)
<223> OTHER INFORMATION: Xaa = Met [M] (synthetic codon-optimized) or
      (Asn [N] or Trp [W]) (mutant)
<220> FEATURE:
<221> NAME/KEY: MISC_FEATURE
<222> LOCATION: (161)..(161)
<223> OTHER INFORMATION: Xaa = Leu [L] (synthetic codon-optimized) or
      (Thr [T] or Tyr [Y]) (mutant)
<220> FEATURE:
<221> NAME/KEY: MISC_FEATURE
<222> LOCATION: (168)..(168)
<223> OTHER INFORMATION: Xaa = Trp [W] (synthetic codon-optimized) or
      Gly [G] (mutant)
<220> FEATURE:
<221> NAME/KEY: MISC_FEATURE
<222> LOCATION: (179)..(179)
<223> OTHER INFORMATION: Xaa = Ile [I] (synthetic codon-optimized) or
      (Met [M] or Arg [R]) (mutant)
<220> FEATURE:
<221> NAME/KEY: MISC_FEATURE
<222> LOCATION: (236)..(236)
<223> OTHER INFORMATION: Xaa = Cys [C] (synthetic codon-optimized) or
      Asn [N] (mutant)
<220> FEATURE:
<221> NAME/KEY: MISC_FEATURE
<222> LOCATION: (243)..(243)
<223> OTHER INFORMATION: Xaa = Val [V] (synthetic codon-optimized) or
      Ala [A] (mutant)
<220> FEATURE:
<221> NAME/KEY: MISC_FEATURE
<222> LOCATION: (244)..(244)
<223> OTHER INFORMATION: Xaa = Gln [Q] (synthetic codon-optimized) or
      Asn [N] (mutant)
<220> FEATURE:
<221> NAME/KEY: MISC_FEATURE
<222> LOCATION: (254)..(254)
<223> OTHER INFORMATION: Xaa = Ala [A] (synthetic codon-optimized) or
      (Trp [W] or Tyr [Y]) (mutant)
```

```
<220> FEATURE:
<221> NAME/KEY: MISC_FEATURE
<222> LOCATION: (257)..(257)
<223> OTHER INFORMATION: Xaa = Ile [I] (synthetic codon-optimized) or
      Thr [T] (mutant)

<400> SEQUENCE: 22

Met Glu Val Val Asn Glu Ile Val Xaa Ile Gly Xaa Glu Val Leu Pro
1               5                   10                  15

Lys Val Asp Tyr Xaa Gln Leu Trp Ser Asp Ala Ser His Cys Glu Xaa
                20                  25                  30

Leu Tyr Xaa Ser Ile Ala Phe Val Ile Leu Lys Phe Thr Leu Gly Pro
            35                  40                  45

Leu Gly Pro Lys Gly Gln Ser Arg Met Xaa Phe Val Phe Thr Asn Tyr
        50                  55                  60

Asn Leu Leu Met Ser Ile Tyr Ser Leu Gly Ser Phe Leu Ser Met Ala
65                  70                  75                  80

Tyr Ala Met Xaa Thr Ile Gly Val Met Ser Asp Asn Cys Glu Lys Ala
                85                  90                  95

Phe Xaa Asn Asn Val Phe Arg Ile Thr Thr Xaa Xaa Phe Tyr Leu Ser
    100                 105                 110

Lys Phe Leu Glu Tyr Ile Asp Ser Phe Tyr Leu Pro Leu Met Xaa Lys
        115                 120                 125

Pro Xaa Thr Xaa Leu Gln Phe Phe His His Leu Gly Ala Pro Xaa Asp
    130                 135                 140

Met Trp Leu Phe Tyr Asn Tyr Arg Asn Glu Ala Val Trp Ile Phe Val
145                 150                 155                 160

Xaa Leu Asn Gly Phe Ile His Xaa Ile Met Tyr Gly Tyr Tyr Trp Thr
                165                 170                 175

Arg Leu Xaa Lys Leu Lys Phe Pro Met Pro Lys Ser Leu Ile Thr Ser
            180                 185                 190

Met Gln Ile Ile Gln Phe Asn Val Gly Phe Tyr Ile Val Trp Lys Tyr
        195                 200                 205

Arg Asn Ile Pro Cys Tyr Arg Gln Asp Gly Met Arg Met Phe Gly Trp
    210                 215                 220

Phe Phe Asn Tyr Phe Tyr Val Gly Thr Val Leu Xaa Leu Phe Leu Asn
225                 230                 235                 240

Phe Tyr Xaa Xaa Thr Tyr Ile Val Arg Lys His Lys Gly Xaa Lys Lys
                245                 250                 255

Xaa Gln

<210> SEQ ID NO 23
<211> LENGTH: 5
<212> TYPE: PRT
<213> ORGANISM: Artificial Sequence
<220> FEATURE:
<223> OTHER INFORMATION: Variant His box
<220> FEATURE:
<221> NAME/KEY: misc_feature
<222> LOCATION: (2)..(3)
<223> OTHER INFORMATION: Xaa can be any naturally occurring amino acid

<400> SEQUENCE: 23

Gln Xaa Xaa His His
1               5

<210> SEQ ID NO 24
<211> LENGTH: 5
<212> TYPE: PRT
```

```
<213> ORGANISM: Artificial Sequence
<220> FEATURE:
<223> OTHER INFORMATION: His box
<220> FEATURE:
<221> NAME/KEY: misc_feature
<222> LOCATION: (2)..(3)
<223> OTHER INFORMATION: Xaa can be any naturally occurring amino acid

<400> SEQUENCE: 24

His Xaa Xaa His His
1               5

<210> SEQ ID NO 25
<211> LENGTH: 7769
<212> TYPE: DNA
<213> ORGANISM: Artificial Sequence
<220> FEATURE:
<223> OTHER INFORMATION: Plasmid pZUFmEgD9E

<400> SEQUENCE: 25
```

| | | | | | |
|---|---|---|---|---|---|
| ggccgcaagt | gtggatgggg | aagtgagtgc | ccggttctgt | gtgcacaatt | ggcaatccaa | 60 |
| gatggatgga | ttcaacacag | ggatatagcg | agctacgtgg | tggtgcgagg | atatagcaac | 120 |
| ggatatttat | gtttgacact | tgagaatgta | cgatacaagc | actgtccaag | tacaatacta | 180 |
| aacatactgt | acatactcat | actcgtaccc | gggcaacggt | ttcacttgag | tgcagtggct | 240 |
| agtgctctta | ctcgtacagt | gtgcaatact | gcgtatcata | gtctttgatg | tatatcgtat | 300 |
| tcattcatgt | tagttgcgta | cgagccggaa | gcataaagtg | taaagcctgg | ggtgcctaat | 360 |
| gagtgagcta | actcacatta | attgcgttgc | gctcactgcc | cgctttccag | tcgggaaacc | 420 |
| tgtcgtgcca | gctgcattaa | tgaatcggcc | aacgcgcggg | gagaggcggt | ttgcgtattg | 480 |
| ggcgctcttc | cgcttcctcg | ctcactgact | cgctgcgctc | ggtcgttcgg | ctgcggcgag | 540 |
| cggtatcagc | tcactcaaag | gcggtaatac | ggttatccac | agaatcaggg | gataacgcag | 600 |
| gaaagaacat | gtgagcaaaa | ggccagcaaa | aggccaggaa | ccgtaaaaag | gccgcgttgc | 660 |
| tggcgttttt | ccataggctc | cgcccccctg | acgagcatca | caaaaatcga | cgctcaagtc | 720 |
| agaggtggcg | aaacccgaca | ggactataaa | gataccaggc | gtttccccct | ggaagctccc | 780 |
| tcgtgcgctc | tcctgttccg | accctgccgc | ttaccggata | cctgtccgcc | tttctccctt | 840 |
| cgggaagcgt | ggcgctttct | catagctcac | gctgtaggta | tctcagttcg | gtgtaggtcg | 900 |
| ttcgctccaa | gctgggctgt | gtgcacgaac | cccccgttca | gcccgaccgc | tgcgccttat | 960 |
| ccggtaacta | tcgtcttgag | tccaacccgg | taagacacga | cttatcgcca | ctggcagcag | 1020 |
| ccactggtaa | caggattagc | agagcgaggt | atgtaggcgg | tgctacagag | ttcttgaagt | 1080 |
| ggtggcctaa | ctacggctac | actagaagga | cagtatttgg | tatctgcgct | ctgctgaagc | 1140 |
| cagttacctt | cggaaaaaga | gttggtagct | cttgatccgg | caaacaaacc | accgctggta | 1200 |
| gcggtggttt | ttttgtttgc | aagcagcaga | ttacgcgcag | aaaaaaagga | tctcaagaag | 1260 |
| atcctttgat | cttttctacg | gggtctgacg | ctcagtggaa | cgaaaactca | cgttaaggga | 1320 |
| ttttggtcat | gagattatca | aaaaggatct | tcacctagat | ccttttaaat | taaaaatgaa | 1380 |
| gttttaaatc | aatctaaagt | atatatgagt | aaacttggtc | tgacagttac | caatgcttaa | 1440 |
| tcagtgaggc | acctatctca | gcgatctgtc | tatttcgttc | atccatagtt | gcctgactcc | 1500 |
| ccgtcgtgta | gataactacg | atacgggagg | gcttaccatc | tggccccagt | gctgcaatga | 1560 |
| taccgcgaga | cccacgctca | ccggctccag | atttatcagc | aataaaccag | ccagccggaa | 1620 |
| gggccgagcg | cagaagtggt | cctgcaactt | tatccgcctc | catccagtct | attaattgtt | 1680 |

```
gccgggaagc tagagtaagt agttcgccag ttaatagttt gcgcaacgtt gttgccattg    1740
ctacaggcat cgtggtgtca cgctcgtcgt tggtatggc  ttcattcagc tccggttccc    1800
aacgatcaag gcgagttaca tgatccccca tgttgtgcaa aaaagcggtt agctccttcg    1860
gtcctccgat cgttgtcaga agtaagttgg ccgcagtgtt atcactcatg gttatggcag    1920
cactgcataa ttctcttact gtcatgccat ccgtaagatg ctttctgtg  actggtgagt    1980 actcaaccaa gtcattctga gaatagtgta tgcggcgacc gagttgctct tgccggcgt     2040 caatacggga taataccgcg ccacatagca gaactttaaa agtgctcatc attggaaaac    2100
gttcttcggg gcgaaaactc tcaaggatct taccgctgtt gagatccagt tcgatgtaac    2160
ccactcgtgc acccaactga tcttcagcat cttttacttt caccagcgtt tctgggtgag    2220
caaaaacagg aaggcaaaat gccgcaaaaa agggaataag ggcgacacgg aaatgttgaa    2280
tactcatact cttccttttt caatattatt gaagcattta tcagggttat tgtctcatga    2340
gcggatacat atttgaatgt atttagaaaa ataaacaaat aggggttccg cgcacatttc    2400
cccgaaaagt gccacctgac gcgccctgta gcggcgcatt aagcgcggcg ggtgtggtgg    2460
ttacgcgcag cgtgaccgct acacttgcca gcgccctagc gcccgctcct ttcgctttct    2520
tcccttcctt tctcgccacg ttcgccggct ttccccgtca gctctaaat  cggggggctcc   2580 ctttagggtt ccgatttagt gctttacggc acctcgaccc caaaaaactt gattagggtg    2640
atggttcacg tagtgggcca tcgccctgat agacggtttt tcgccctttg acgttggagt    2700
ccacgttctt aatagtgga  ctcttgttcc aaactggaac aacactcaac cctatctcgg    2760
tctattcttt tgatttataa gggattttgc cgatttcggc ctattggtta aaaaatgagc    2820
tgatttaaca aaaatttaac gcgaatttta acaaatatt  aacgcttaca atttccattc    2880
gccattcagg ctgcgcaact gttgggaagg gcgatcggtg cgggcctctt cgctattacg    2940
ccagctggcg aaagggggat gtgctgcaag gcgattaagt tgggtaacgc cagggttttc    3000
ccagtcacga cgttgtaaaa cgacggccag tgaattgtaa tacgactcac tatagggcga    3060
attgggtacc gggcccccc  tcgaggtcga tggtgtcgat aagcttgata tcgaattcat    3120
gtcacacaaa ccgatcttcg cctcaaggaa acctaattct acatccgaga gactgccgag    3180
atccagtcta cactgattaa ttttcgggcc aataattta  aaaaatcgtg ttatataata    3240
ttatatgtat tatatatata catcatgatg atactgacag tcatgtccca ttgctaaata    3300
gacagactcc atctgccgcc tccaactgat gttctcaata tttaaggggt catctcgcat    3360
tgtttaataa taaacagact ccatctaccg cctccaaatg atgttctcaa atatattgt     3420 atgaacttat ttttattact tagtattatt agacaactta cttgctttat gaaaaacact    3480
tcctatttag gaaacaattt ataatggcag ttcgttcatt taacaattta tgtagaataa    3540
atgttataaa tgcgtatggg aaatcttaaa tatggatagc ataaatgata tctgcattgc    3600
ctaattcgaa atcaacagca acgaaaaaaa tcccttgtac aacataaata gtcatcgaga    3660
aatatcaact atcaaagaac agctattcac acgttactat tgagattatt attggacgag    3720
aatcacacac tcaactgtct ttctctcttc tagaaataca ggtacaagta tgtactattc    3780
tcattgttca tacttctagt catttcatcc cacatattcc ttggatttct ctccaatgaa    3840
tgacattcta tcttgcaaat tcaacaatta taataagata taccaaagta gcggtatagt    3900
ggcaatcaaa aagcttctct ggtgtgcttc tcgtatttat ttttattcta atgatccatt    3960
aaaggtatat atttatttct tgttatataa tcctttgtt  tattacatgg gctggataca    4020
taaaggtatt ttgatttaat ttttgctta  aattcaatcc ccctcgttc  agtgtcaact    4080
```

```
gtaatggtag gaaattacca tacttttgaa gaagcaaaaa aaatgaaaga aaaaaaaaat      4140
cgtatttcca ggttagacgt tccgcagaat ctagaatgcg gtatgcggta cattgttctt      4200
cgaacgtaaa agttgcgctc cctgagatat tgtacatttt tgcttttaca agtacaagta      4260
catcgtacaa ctatgtacta ctgttgatgc atccacaaca gtttgttttg tttttttttg      4320
tttttttttt ttctaatgat tcattaccgc tatgtatacc tacttgtact tgtagtaagc      4380
cgggttattg gcgttcaatt aatcatagac ttatgaatct gcacggtgtg cgctgcgagt      4440
tacttttagc ttatgcatgc tacttgggtg taatattggg atctgttcgg aaatcaacgg      4500
atgctcaatc gatttcgaca gtaattaatt aagtcataca caagtcagct ttcttcgagc      4560
ctcatataag tataagtagt tcaacgtatt agcactgtac ccagcatctc cgtatcgaga      4620
aacacaacaa catgccccat tggacagatc atgcggatac acaggttgtg cagtatcata      4680
catactcgat cagacaggtc gtctgaccat catacaagct gaacaagcgc tccatacttg      4740
cacgctctct atatacacag ttaaattaca tatccatagt ctaacctcta acagttaatc      4800
ttctggtaag cctcccagcc agccttctgg tatcgcttgg cctcctcaat aggatctcgg      4860
ttctggccgt acagacctcg gccgacaatt atgatatccg ttccggtaga catgacatcc      4920
tcaacagttc ggtactgctg tccgagagcg tctcccttgt cgtcaagacc caccccgggg      4980
gtcagaataa gccagtcctc agagtcgccc ttaggtcggt tctgggcaat gaagccaacc      5040
acaaactcgg ggtcggatcg ggcaagctca atggtctgct tggagtactc gccagtggcc      5100
agagagccct tgcaagacag ctcggccagc atgagcagac ctctggccag cttctcgttg      5160
ggagagggga ctaggaactc cttgtactgg gagttctcgt agtcagagac gtcctccttc      5220
ttctgttcag agacagtttc ctcggcacca gctcgcaggc cagcaatgat tccggttccg      5280
ggtacaccgt gggcgttggt gatatcggac cactcggcga ttcggtgaca ccggtactgg      5340
tgcttgacag tgttgccaat atctgcgaac tttctgtcct cgaacaggaa gaaaccgtgc      5400
ttaagagcaa gttccttgag ggggagcaca gtgccggcgt aggtgaagtc gtcaatgatg      5460
tcgatatggg ttttgatcat gcacacataa ggtccgacct tatcggcaag ctcaatgagc      5520
tccttggtgg tggtaacatc cagagaagca cacaggttgg ttttcttggc tgccacgagc      5580
ttgagcactc gagcggcaaa ggcggacttg tggacgttag ctcgagcttc gtaggagggc      5640
attttggtgg tgaagaggag actgaaataa atttagtctg cagaactttt tatcggaacc      5700
ttatctgggg cagtgaagta tatgttatgg taatagttac gagttagttg aacttataga      5760
tagactggac tatacggcta tcggtccaaa ttagaaagaa cgtcaatggc tctctgggcg      5820
tcgcctttgc cgacaaaaat gtgatcatga tgaaagccag caatgacgtt gcagctgata      5880
ttgttgtcgc ccaaccgcgc cgaaaacgca gctgtcagac ccacagcctc caacgaagaa      5940
tgtatcgtca aagtgatcca agcacactca tagttggagt cgtactccaa aggcggcaat      6000
gacgagtcag acagatactc gtcgacgttt aaacagtgta cgcagatcta ctatagagga      6060
acatttaaat tgccccggag aagacggcca ggccgcctag atgacaaatt caacaactca      6120
cagctgactt tctgccattg ccactagggg ggggcctttt tatatggcca agccaagctc      6180
tccacgtcgg ttgggctgca cccaacaata aatgggtagg gttgcaccaa caagggatg      6240 ggatgggggg tagaagatac gaggataacg gggctcaatg gcacaaataa gaacgaatac      6300
tgccattaag actcgtgatc cagcgactga caccattgca tcatctaagg gcctcaaaac      6360
tacctcggaa ctgctgcgct gatctggaca ccacagaggt tccgagcact ttaggttgca      6420
```

-continued

| | |
|---|---|
| ccaaatgtcc caccaggtgc aggcagaaaa cgctggaaca gcgtgtacag tttgtcttaa | 6480 |
| caaaaagtga gggcgctgag gtcgagcagg gtggtgtgac ttgttatagc ctttagagct | 6540 |
| gcgaaagcgc gtatggattt ggctcatcag gccagattga gggtctgtgg acacatgtca | 6600 |
| tgttagtgta cttcaatcgc ccctggata tagccccgac aataggccgt ggcctcattt | 6660 |
| ttttgccttc cgcacattc cattgctcga tacccacacc ttgcttctcc tgcacttgcc | 6720 |
| aaccttaata ctggtttaca ttgaccaaca tcttacaagc gggggcttg tctagggtat | 6780 |
| atataaacag tggctctccc aatcggttgc cagtctcttt tttccttct ttccccacag | 6840 |
| attcgaaatc taaactacac atcacagaat tccgagccgt gagtatccac gacaagatca | 6900 |
| gtgtcgagac gacgcgtttt gtgtaatgac acaatccgaa agtcgctagc aacacacact | 6960 |
| ctctacacaa actaacccag ctctggtacc atggaggtcg tgaacgaaat cgtctccatt | 7020 |
| ggccaggagg ttcttcccaa ggtcgactat gctcagctct ggtctgatgc ctcgcactgc | 7080 |
| gaggtgctgt acctctccat cgccttcgtc atcctgaagt tcacccttgg tcctctcgga | 7140 |
| cccaagggtc agtctcgaat gaagtttgtg ttcaccaact acaacctgct catgtccatc | 7200 |
| tactcgctgg gctccttcct ctctatggcc tacgccatgt acaccattgg tgtcatgtcc | 7260 |
| gacaactgcg agaaggcttt cgacaacaat gtcttccgaa tcaccactca gctgttctac | 7320 |
| ctcagcaagt cctcgagta cattgactcc ttctatctgc ccctcatggg caagcctctg | 7380 |
| acctggttgc agttctttca ccatctcgga gctcctatgg acatgtggct gttctacaac | 7440 |
| taccgaaacg aagccgtttg gatctttgtg ctgctcaacg gcttcattca ctggatcatg | 7500 |
| tacggctact attggacccg actgatcaag ctcaagttcc ctatgcccaa gtccctgatt | 7560 |
| acttctatgc agatcattca gttcaacgtt ggcttctaca tcgtctggaa gtaccggaac | 7620 |
| attccctgct accgacaaga tggaatgaga atgtttggct ggtttttcaa ctacttctac | 7680 |
| gttggtactg tcctgtgtct gttcctcaac ttctacgtgc agacctacat cgtccgaaag | 7740 |
| cacaagggag ccaaaaagat tcagtgagc | 7769 |

<210> SEQ ID NO 26
<211> LENGTH: 20
<212> TYPE: DNA
<213> ORGANISM: Artificial Sequence
<220> FEATURE:
<223> OTHER INFORMATION: Primer pZUFm_6980_012208f

<400> SEQUENCE: 26
gctctggtac catggaggtc                                           20

<210> SEQ ID NO 27
<211> LENGTH: 20
<212> TYPE: DNA
<213> ORGANISM: Artificial Sequence
<220> FEATURE:
<223> OTHER INFORMATION: Primer pZUFm_40_012208r

<400> SEQUENCE: 27
acagaaccgg gcactcactt                                           20

<210> SEQ ID NO 28
<211> LENGTH: 777
<212> TYPE: DNA
<213> ORGANISM: Euglena gracilis
<220> FEATURE:
<221> NAME/KEY: CDS
<222> LOCATION: (1)..(777)
<223> OTHER INFORMATION: mutant delta-9 elongase "EgD9eS-L35F"

<400> SEQUENCE: 28

```
atg gag gtc gtg aac gaa atc gtc tcc att ggc cag gag gtt ctt ccc      48
Met Glu Val Val Asn Glu Ile Val Ser Ile Gly Gln Glu Val Leu Pro
1               5                   10                  15 aag gtc gac tat gct cag ctc tgg tct gat gcc tcg cac tgc gag gtg      96
Lys Val Asp Tyr Ala Gln Leu Trp Ser Asp Ala Ser His Cys Glu Val
            20                  25                  30 ctg tac ttc tcc atc gcc ttc gtc atc ctg aag ttc acc ctt ggt cct     144
Leu Tyr Phe Ser Ile Ala Phe Val Ile Leu Lys Phe Thr Leu Gly Pro
        35                  40                  45 ctc gga ccc aag ggt cag tct cga atg aag ttt gtg ttc acc aac tac     192
Leu Gly Pro Lys Gly Gln Ser Arg Met Lys Phe Val Phe Thr Asn Tyr
    50                  55                  60 aac ctg ctc atg tcc atc tac tcg ctg ggc tcc ttc ctc tct atg gcc     240
Asn Leu Leu Met Ser Ile Tyr Ser Leu Gly Ser Phe Leu Ser Met Ala
65                  70                  75                  80 tac gcc atg tac acc att ggt gtc atg tcc gac aac tgc gag aag gct     288
Tyr Ala Met Tyr Thr Ile Gly Val Met Ser Asp Asn Cys Glu Lys Ala
                85                  90                  95 ttc gac aac aat gtc ttc cga atc acc act cag ctg ttc tac ctc agc     336
Phe Asp Asn Asn Val Phe Arg Ile Thr Thr Gln Leu Phe Tyr Leu Ser
            100                 105                 110 aag ttc ctc gag tac att gac tcc ttc tat ctg ccc ctc atg ggc aag     384
Lys Phe Leu Glu Tyr Ile Asp Ser Phe Tyr Leu Pro Leu Met Gly Lys
        115                 120                 125 cct ctg acc tgg ttg cag ttc ttt cac cat ctc gga gct cct atg gac     432
Pro Leu Thr Trp Leu Gln Phe Phe His His Leu Gly Ala Pro Met Asp
    130                 135                 140 atg tgg ctg ttc tac aac tac cga aac gaa gcc gtt tgg atc ttt gtg     480
Met Trp Leu Phe Tyr Asn Tyr Arg Asn Glu Ala Val Trp Ile Phe Val
145                 150                 155                 160 ctg ctc aac ggc ttc att cac tgg atc atg tac ggc tac tat tgg acc     528
Leu Leu Asn Gly Phe Ile His Trp Ile Met Tyr Gly Tyr Tyr Trp Thr
                165                 170                 175 cga ctg atc aag ctc aag ttc cct atg ccc aag tcc ctg att act tct     576
Arg Leu Ile Lys Leu Lys Phe Pro Met Pro Lys Ser Leu Ile Thr Ser
            180                 185                 190 atg cag atc att cag ttc aac gtt ggc ttc tac atc gtc tgg aag tac     624
Met Gln Ile Ile Gln Phe Asn Val Gly Phe Tyr Ile Val Trp Lys Tyr
        195                 200                 205 cgg aac att ccc tgc tac cga caa gat ggg atg aga atg ttt ggc tgg     672
Arg Asn Ile Pro Cys Tyr Arg Gln Asp Gly Met Arg Met Phe Gly Trp
    210                 215                 220 ttt ttc aac tac ttc tac gtt ggt act gtc ctg tgt ctg ttc ctc aac     720
Phe Phe Asn Tyr Phe Tyr Val Gly Thr Val Leu Cys Leu Phe Leu Asn
225                 230                 235                 240 ttc tac gtg cag acc tac atc gtc cga aag cac aag gga gcc aaa aag     768
Phe Tyr Val Gln Thr Tyr Ile Val Arg Lys His Lys Gly Ala Lys Lys
                245                 250                 255 att cag tga                                                         777
Ile Gln
```

<210> SEQ ID NO 29
<211> LENGTH: 258
<212> TYPE: PRT
<213> ORGANISM: Euglena gracilis

<400> SEQUENCE: 29

Met Glu Val Val Asn Glu Ile Val Ser Ile Gly Gln Glu Val Leu Pro

```
            1               5                  10                 15
         Lys Val Asp Tyr Ala Gln Leu Trp Ser Asp Ala Ser His Cys Glu Val
                        20                 25                 30
         Leu Tyr Phe Ser Ile Ala Phe Val Ile Leu Lys Phe Thr Leu Gly Pro
                        35                 40                 45
         Leu Gly Pro Lys Gly Gln Ser Arg Met Lys Phe Val Phe Thr Asn Tyr
                        50                 55                 60
         Asn Leu Leu Met Ser Ile Tyr Ser Leu Gly Ser Phe Leu Ser Met Ala
          65                 70                 75                 80
         Tyr Ala Met Tyr Thr Ile Gly Val Met Ser Asp Asn Cys Glu Lys Ala
                        85                 90                 95
         Phe Asp Asn Asn Val Phe Arg Ile Thr Thr Gln Leu Phe Tyr Leu Ser
                        100                105                110
         Lys Phe Leu Glu Tyr Ile Asp Ser Phe Tyr Leu Pro Leu Met Gly Lys
                        115                120                125
         Pro Leu Thr Trp Leu Gln Phe Phe His His Leu Gly Ala Pro Met Asp
                        130                135                140
         Met Trp Leu Phe Tyr Asn Tyr Arg Asn Glu Ala Val Trp Ile Phe Val
         145                150                155                160
         Leu Leu Asn Gly Phe Ile His Trp Ile Met Tyr Gly Tyr Tyr Trp Thr
                        165                170                175
         Arg Leu Ile Lys Leu Lys Phe Pro Met Pro Lys Ser Leu Ile Thr Ser
                        180                185                190
         Met Gln Ile Ile Gln Phe Asn Val Gly Phe Tyr Ile Val Trp Lys Tyr
                        195                200                205
         Arg Asn Ile Pro Cys Tyr Arg Gln Asp Gly Met Arg Met Phe Gly Trp
                        210                215                220
         Phe Phe Asn Tyr Phe Tyr Val Gly Thr Val Leu Cys Leu Phe Leu Asn
         225                230                235                240
         Phe Tyr Val Gln Thr Tyr Ile Val Arg Lys His Lys Gly Ala Lys Lys
                        245                250                255
         Ile Gln
```

<210> SEQ ID NO 30
<211> LENGTH: 7769
<212> TYPE: DNA
<213> ORGANISM: Artificial Sequence
<220> FEATURE:
<223> OTHER INFORMATION: Plasmid pZUFmEgD9eS-L35F

<400> SEQUENCE: 30

```
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc gggcaacggt ttcacttgag tgcagtggct     240
agtgctctta ctcgtacagt gtgcaatact gcgtatcata gtctttgatg tatatcgtat     300
tcattcatgt tagttgcgta cgagccggaa gcataaagtg taaagcctgg ggtgcctaat     360
gagtgagcta actcacatta attgcgttgc gctcactgcc cgctttccag tcgggaaacc     420
tgtcgtgcca gctgcattaa tgaatcggcc aacgcgcggg gagaggcggt ttgcgtattg     480
ggcgctcttc cgcttcctcg ctcactgact cgctgcgctc ggtcgttcgg ctgcggcgag     540
cggtatcagc tcactcaaag gcggtaatac ggttatccac agaatcaggg gataacgcag     600
```

```
gaaagaacat gtgagcaaaa ggccagcaaa aggccaggaa ccgtaaaaag gccgcgttgc    660
tggcgttttt ccataggctc cgccccctg acgagcatca caaaaatcga cgctcaagtc     720
agaggtggcg aaacccgaca ggactataaa gataccaggc gtttccccct ggaagctccc    780
tcgtgcgctc tcctgttccg accctgccgc ttaccggata cctgtccgcc tttctccctt    840
cgggaagcgt ggcgctttct catagctcac gctgtaggta tctcagttcg gtgtaggtcg    900
ttcgctccaa gctgggctgt gtgcacgaac cccccgttca gcccgaccgc tgcgccttat    960
ccggtaacta tcgtcttgag tccaacccgg taagacacga cttatcgcca ctggcagcag   1020
ccactggtaa caggattagc agagcgaggt atgtaggcgg tgctacagag ttcttgaagt   1080
ggtggcctaa ctacggctac actagaagga cagtatttgg tatctgcgct ctgctgaagc   1140
cagttacctt cggaaaaaga gttggtagct cttgatccgg caaacaaacc accgctggta   1200
gcggtggttt ttttgtttgc aagcagcaga ttacgcgcag aaaaaaagga tctcaagaag   1260
atcctttgat cttttctacg gggtctgacg ctcagtggaa cgaaaactca cgttaaggga   1320
ttttggtcat gagattatca aaaaggatct tcacctagat ccttttaaat taaaaatgaa   1380
gttttaaatc aatctaaagt atatatgagt aaacttggtc tgacagttac caatgcttaa   1440
tcagtgaggc acctatctca gcgatctgtc tatttcgttc atccatagtt gcctgactcc   1500
ccgtcgtgta gataactacg atacgggagg gcttaccatc tggccccagt gctgcaatga   1560
taccgcgaga cccacgctca ccggctccag atttatcagc aataaaccag ccagccggaa   1620
gggccgagcg cagaagtggt cctgcaactt tatccgcctc catccagtct attaattgtt   1680
gccgggaagc tagagtaagt agttcgccag ttaatagttt cgcaacgtt gttgccattg    1740 ctacaggcat cgtggtgtca cgctcgtcgt ttggtatggc ttcattcagc tccggttccc   1800
aacgatcaag gcgagttaca tgatccccca tgttgtgcaa aaaagcggtt agctccttcg   1860
gtcctccgat cgttgtcaga agtaagttgg ccgcagtgtt atcactcatg gttatggcag   1920
cactgcataa ttctcttact gtcatgccat ccgtaagatg cttttctgtg actggtgagt   1980
actcaaccaa gtcattctga gaatagtgta tgcggcgacc gagttgctct tgcccggcgt   2040
caatacggga taataccgcg ccacatagca gaactttaaa agtgctcatc attggaaaac   2100
gttcttcggg gcgaaaactc tcaaggatct taccgctgtt gagatccagt tcgatgtaac   2160
ccactcgtgc acccaactga tcttcagcat cttttacttt caccagcgtt tctgggtgag   2220
caaaaacagg aaggcaaaat gccgcaaaaa agggaataag ggcgacacgg aaatgttgaa   2280
tactcatact cttccttttt caatattatt gaagcattta tcagggttat tgtctcatga   2340
gcggatacat atttgaatgt atttagaaaa ataaacaaat aggggttccg cgcacatttc   2400
cccgaaaagt gccacctgac gcgccctgta gcggcgcatt aagcgcggcg ggtgtggtgg   2460
ttacgcgcag cgtgaccgct acacttgcca gcgccctagc gcccgctcct ttcgctttct   2520
tcccttcctt tctcgccacg ttcgccggct ttccccgtca gctctaaat cggggggctcc    2580 ctttagggtt ccgatttagt gctttacggc acctcgaccc caaaaaactt gattagggtg   2640
atggttcacg tagtgggcca tcgccctgat agacggtttt tcgcccttg acgttggagt    2700 ccacgttctt taatagtgga ctcttgttcc aaactggaac aacactcaac cctatctcgg   2760
tctattcttt tgatttataa gggattttgc cgatttcggc ctattggtta aaaaatgagc   2820
tgatttaaca aaaatttaac gcgaattta acaaaatatt aacgcttaca atttccattc    2880
gccattcagg ctgcgcaact gttgggaagg gcgatcggtg cgggcctctt cgctattacg   2940
ccagctggcg aaaggggat gtgctgcaag gcgattaagt tgggtaacgc cagggttttc    3000
```

| | | | | | |
|---|---|---|---|---|---|
| ccagtcacga | cgttgtaaaa | cgacggccag | tgaattgtaa | tacgactcac | tatagggcga | 3060 |
| attgggtacc | gggccccccc | tcgaggtcga | tggtgtcgat | aagcttgata | tcgaattcat | 3120 |
| gtcacacaaa | ccgatcttcg | cctcaaggaa | acctaattct | acatccgaga | gactgccgag | 3180 |
| atccagtcta | cactgattaa | ttttcgggcc | aataatttaa | aaaaatcgtg | ttatataata | 3240 |
| ttatatgtat | tatatatata | catcatgatg | atactgacag | tcatgtccca | ttgctaaata | 3300 |
| gacagactcc | atctgccgcc | tccaactgat | gttctcaata | tttaagtggt | catctcgcat | 3360 |
| tgtttaataa | taaacagact | ccatctaccg | cctccaaatg | atgttctcaa | aatatattgt | 3420 |
| atgaacttat | ttttattact | tagtattatt | agacaactta | cttgctttat | gaaaaacact | 3480 |
| tcctatttag | gaaacaattt | ataatggcag | ttcgttcatt | taacaattta | tgtagaataa | 3540 |
| atgttataaa | tgcgtatggg | aaatcttaaa | tatggatagc | ataaatgata | tctgcattgc | 3600 |
| ctaattcgaa | atcaacagca | acgaaaaaaa | tcccttgtac | aacataaata | gtcatcgaga | 3660 |
| aatatcaact | atcaaagaac | agctattcac | acgttactat | tgagattatt | attggacgag | 3720 |
| aatcacacac | tcaactgtct | ttctctcttc | tagaaataca | ggtacaagta | tgtactattc | 3780 |
| tcattgttca | tacttctagt | catttcatcc | cacatattcc | ttggatttct | ctccaatgaa | 3840 |
| tgacattcta | tcttgcaaat | tcaacaatta | taataagata | taccaaagta | gcggtatagt | 3900 |
| ggcaatcaaa | aagcttctct | ggtgtgcttc | tcgtatttat | ttttattcta | atgatccatt | 3960 |
| aaaggtatat | atttatttct | tgttatataa | tcctttgtt | tattacatgg | gctggataca | 4020 |
| taaaggtatt | ttgatttaat | tttttgctta | aattcaatcc | ccctcgttc | agtgtcaact | 4080 |
| gtaatggtag | gaaattacca | tacttttgaa | gaagcaaaaa | aaatgaaaga | aaaaaaaat | 4140 |
| cgtatttcca | ggttagacgt | tccgcagaat | ctagaatgcg | gtatgcggta | cattgttctt | 4200 |
| cgaacgtaaa | agttgcgctc | cctgagatat | tgtacatttt | tgcttttaca | agtacaagta | 4260 |
| catcgtacaa | ctatgtacta | ctgttgatgc | atccacaaca | gtttgttttg | tttttttttg | 4320 |
| tttttttttt | ttctaatgat | tcattaccgc | tatgtatacc | tacttgtact | tgtagtaagc | 4380 |
| cgggttattg | gcgttcaatt | aatcatagac | ttatgaatct | gcacggtgtg | cgctgcgagt | 4440 |
| tactttagc | ttatgcatgc | tacttgggtg | taatattggg | atctgttcgg | aaatcaacgg | 4500 |
| atgctcaatc | gatttcgaca | gtaattaatt | aagtcataca | caagtcagct | ttcttcgagc | 4560 |
| ctcatataag | tataagtagt | tcaacgtatt | agcactgtac | ccagcatctc | cgtatcgaga | 4620 |
| aacacaacaa | catgccccat | tggacagatc | atgcggatac | acaggttgtg | cagtatcata | 4680 |
| catactcgat | cagacaggtc | gtctgaccat | catacaagct | gaacaagcgc | tccatacttg | 4740 |
| cacgctctct | atatacacag | ttaaattaca | tatccatagt | ctaacctcta | acagttaatc | 4800 |
| ttctggtaag | cctcccagcc | agccttctgg | tatcgcttgg | cctcctcaat | aggatctcgg | 4860 |
| ttctggccgt | acagacctcg | gccgacaatt | atgatatccg | ttccggtaga | catgacatcc | 4920 |
| tcaacagttc | ggtactgctg | tccgagacg | tctcccttgt | cgtcaagacc | caccccgggg | 4980 |
| gtcagaataa | gccagtcctc | agagtcgccc | ttaggtcggt | tctgggcaat | gaagccaacc | 5040 |
| acaaactcgg | ggtcggatcg | ggcaagctca | atggtctgct | tggagtactc | gccagtggcc | 5100 |
| agagagcct | tgcaagacag | ctcggccagc | atgagcagac | ctctggccag | cttctcgttg | 5160 |
| ggagagggga | ctaggaactc | cttgtactgg | gagttctcgt | agtcagagac | gtcctccttc | 5220 |
| ttctgttcag | agacagtttc | ctcggcacca | gctcgcaggc | cagcaatgat | tccggttccg | 5280 |
| ggtacaccgt | gggcgttggt | gatatcggac | cactcggcga | ttcggtgaca | ccggtactgg | 5340 |

```
tgcttgacag tgttgccaat atctgcgaac tttctgtcct cgaacaggaa gaaaccgtgc    5400
ttaagagcaa gttccttgag ggggagcaca gtgccggcgt aggtgaagtc gtcaatgatg    5460
tcgatatggg ttttgatcat gcacacataa ggtccgacct tatcggcaag ctcaatgagc    5520
tccttggtgg tggtaacatc cagagaagca cacaggttgg ttttcttggc tgccacgagc    5580
ttgagcactc gagcggcaaa ggcggacttg tggacgttag ctcgagcttc gtaggagggc    5640
attttggtgg tgaagaggag actgaaataa atttagtctg cagaactttt tatcggaacc    5700
ttatctgggg cagtgaagta tatgttatgg taatagttac gagttagttg aacttataga    5760
tagactggac tatacggcta tcggtccaaa ttagaaagaa cgtcaatggc tctctgggcg    5820
tcgcctttgc cgacaaaaat gtgatcatga tgaaagccag caatgacgtt gcagctgata    5880
ttgttgtcgg ccaaccgcgc cgaaaacgca gctgtcagac ccacagcctc caacgaagaa    5940
tgtatcgtca aagtgatcca agcacactca tagttggagt cgtactccaa aggcggcaat    6000
gacgagtcag acagatactc gtcgacgttt aaacagtgta cgcagatcta ctatagagga    6060
acatttaaat tgccccggag aagacggcca ggccgcctag atgacaaatt caacaactca    6120
cagctgactt tctgccattg ccactagggg ggggcctttt tatatggcca agccaagctc    6180
tccacgtcgg ttgggctgca cccaacaata aatgggtagg gttgcaccaa caaagggatg    6240
ggatgggggg tagaagatac gaggataacg gggctcaatg gcacaaataa gaacgaatac    6300
tgccattaag actcgtgatc cagcgactga caccattgca tcatctaagg gcctcaaaac    6360
tacctcggaa ctgctgcgct gatctggaca ccacagaggt tccgagcact ttaggttgca    6420
ccaaatgtcc caccaggtgc aggcagaaaa cgctggaaca gcgtgtacag tttgtcttaa    6480
caaaaagtga gggcgctgag gtcgagcagg gtggtgtgac ttgttatagc ctttagagct    6540
gcgaaagcgc gtatggattt ggctcatcag gccagattga gggtctgtgg acacatgtca    6600
tgttagtgta cttcaatcgc cccctggata tagccccgac aataggccgt ggcctcattt    6660
ttttgccttc cgcacatttc cattgctcga tacccacacc ttgcttctcc tgcacttgcc    6720
aaccttaata ctggtttaca ttgaccaaca tcttacaagc ggggggcttg tctagggtat    6780
atataaacag tggctctccc aatcggttgc cagtctcttt tttcctttct ttccccacag    6840
attcgaaatc taaactacac atcacagaat tccgagccgt gagtatccac gacaagatca    6900
gtgtcgagac gacgcgtttt gtgtaatgac acaatccgaa agtcgctagc aacacacact    6960
ctctacacaa actaacccag ctctggtacc atggaggtcg tgaacgaaat cgtctccatt    7020
ggccaggagg ttcttcccaa ggtcgactat gctcagctct ggtctgatgc ctcgcactgc    7080
gaggtgctgt acttctccat cgccttcgtc atcctgaagt tcaccttgg tcctctcgga    7140 cccaagggtc agtctcgaat gaagtttgtg ttcaccaact acaacctgct catgtccatc    7200
tactcgctgg gctccttcct ctctatggcc tacgccatgt acaccattgg tgtcatgtcc    7260
gacaactgcg agaaggcttt cgacaacaat gtcttccgaa tcaccactca gctgttctac    7320
ctcagcaagt tcctcgagta cattgactcc ttctatctgc ccctcatggg caagcctctg    7380
acctggttgc agttctttca ccatctcgga gctcctatgg acatgtggct gttctacaac    7440
taccgaaacg aagccgtttg gatctttgtg ctgctcaacg gcttcattca ctggatcatg    7500
tacggctact attggaccc actgatcaag ctcaagttcc ctatgcccaa gtccctgatt    7560
acttctatgc agatcattca gttcaacgtt ggcttctaca tcgtctggaa gtaccggaac    7620
attccctgct accgacaaga tgggatgaga atgtttggct ggtttttcaa ctacttctac    7680
gttggtactg tcctgtgtct gttcctcaac ttctacgtgc agacctacat cgtccgaaag    7740
```

```
cacaagggag ccaaaaagat tcagtgagc                                    7769
```

<210> SEQ ID NO 31
<211> LENGTH: 777
<212> TYPE: DNA
<213> ORGANISM: Euglena gracilis
<220> FEATURE:
<221> NAME/KEY: CDS
<222> LOCATION: (1)..(777)
<223> OTHER INFORMATION: mutant delta-9 elongase "EgD9eS-K58R/I257T"

<400> SEQUENCE: 31

```
atg gag gtc gtg aac gaa atc gtc tcc att ggc cag gag gtt ctt ccc      48
Met Glu Val Val Asn Glu Ile Val Ser Ile Gly Gln Glu Val Leu Pro
 1               5                  10                  15 aag gtc gac tat gct cag ctc tgg tct gat gcc tcg cac tgc gag gtg      96
Lys Val Asp Tyr Ala Gln Leu Trp Ser Asp Ala Ser His Cys Glu Val
             20                  25                  30 ctg tac ctc tcc atc gcc ttc gtc atc ctg aag ttc acc ctt ggt cct     144
Leu Tyr Leu Ser Ile Ala Phe Val Ile Leu Lys Phe Thr Leu Gly Pro
         35                  40                  45 ctc gga ccc aag ggt cag tct cga atg agg ttt gtg ttc acc aac tac     192
Leu Gly Pro Lys Gly Gln Ser Arg Met Arg Phe Val Phe Thr Asn Tyr
     50                  55                  60 aac ctg ctc atg tcc atc tac tcg ctg ggc tcc ttc ctc tcg atg gcc     240
Asn Leu Leu Met Ser Ile Tyr Ser Leu Gly Ser Phe Leu Ser Met Ala
 65                  70                  75                  80 tac gcc atg tac acc att ggt gtc atg tcc gac aac tgc gag aag gct     288
Tyr Ala Met Tyr Thr Ile Gly Val Met Ser Asp Asn Cys Glu Lys Ala
                 85                  90                  95 ttc gac aac aat gtc ttc cga atc acc act cag ctg ttc tac ctc agc     336
Phe Asp Asn Asn Val Phe Arg Ile Thr Thr Gln Leu Phe Tyr Leu Ser
            100                 105                 110 aag ttc ctc gag tac att gac tcc ttc tat ctg ccc ctc atg ggc aag     384
Lys Phe Leu Glu Tyr Ile Asp Ser Phe Tyr Leu Pro Leu Met Gly Lys
        115                 120                 125 cct ctg acc tgg ttg caa ttc ttt cac cat ctc gga gct cct atg gac     432
Pro Leu Thr Trp Leu Gln Phe Phe His His Leu Gly Ala Pro Met Asp
    130                 135                 140 atg tgg ctg ttc tac aac tac cga aac gaa gcc gtt tgg atc ttt gtg     480
Met Trp Leu Phe Tyr Asn Tyr Arg Asn Glu Ala Val Trp Ile Phe Val
145                 150                 155                 160 ctc ctc aac ggc ttc att cac tgg atc atg tac ggc tac tat tgg acc     528
Leu Leu Asn Gly Phe Ile His Trp Ile Met Tyr Gly Tyr Tyr Trp Thr
                165                 170                 175 cga ctg atc aag ctc aag ttc cct atg ccc aag tcc ctg att act tct     576
Arg Leu Ile Lys Leu Lys Phe Pro Met Pro Lys Ser Leu Ile Thr Ser
            180                 185                 190 atg cag atc att cag ttc aac gtt ggc ttc tac atc gtc tgg aag tac     624
Met Gln Ile Ile Gln Phe Asn Val Gly Phe Tyr Ile Val Trp Lys Tyr
        195                 200                 205 cgg aac att ccc tgc tac cga caa gat gga atg aga atg ttt ggc tgg     672
Arg Asn Ile Pro Cys Tyr Arg Gln Asp Gly Met Arg Met Phe Gly Trp
    210                 215                 220 ttt ttc aac tac ttc tac gtt ggt act gtc ctg tgt ctg ttc ctc aac     720
Phe Phe Asn Tyr Phe Tyr Val Gly Thr Val Leu Cys Leu Phe Leu Asn
225                 230                 235                 240 ttc tac gtg cag acc tac atc gtc cga aag cac aag gga gcc aaa aag     768
Phe Tyr Val Gln Thr Tyr Ile Val Arg Lys His Lys Gly Ala Lys Lys
                245                 250                 255
``` act cag tga                                                              777
Thr Gln <210> SEQ ID NO 32
<211> LENGTH: 258
<212> TYPE: PRT
<213> ORGANISM: Euglena gracilis

<400> SEQUENCE: 32

Met Glu Val Val Asn Glu Ile Val Ser Ile Gly Gln Glu Val Leu Pro
1               5                   10                  15

Lys Val Asp Tyr Ala Gln Leu Trp Ser Asp Ala Ser His Cys Glu Val
            20                  25                  30

Leu Tyr Leu Ser Ile Ala Phe Val Ile Leu Lys Phe Thr Leu Gly Pro
        35                  40                  45

Leu Gly Pro Lys Gly Gln Ser Arg Met Arg Phe Val Phe Thr Asn Tyr
    50                  55                  60

Asn Leu Leu Met Ser Ile Tyr Ser Leu Gly Ser Phe Leu Ser Met Ala
65                  70                  75                  80

Tyr Ala Met Tyr Thr Ile Gly Val Met Ser Asp Asn Cys Glu Lys Ala
                85                  90                  95

Phe Asp Asn Asn Val Phe Arg Ile Thr Thr Gln Leu Phe Tyr Leu Ser
            100                 105                 110

Lys Phe Leu Glu Tyr Ile Asp Ser Phe Tyr Leu Pro Leu Met Gly Lys
        115                 120                 125

Pro Leu Thr Trp Leu Gln Phe Phe His His Leu Gly Ala Pro Met Asp
    130                 135                 140

Met Trp Leu Phe Tyr Asn Tyr Arg Asn Glu Ala Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Lys Phe Pro Met Pro Lys Ser Leu Ile Thr Ser
            180                 185                 190

Met Gln Ile Ile Gln Phe Asn Val Gly Phe Tyr Ile Val Trp Lys Tyr
        195                 200                 205

Arg Asn Ile Pro Cys Tyr Arg Gln Asp Gly Met Arg Met Phe Gly Trp
    210                 215                 220

Phe Phe Asn Tyr Phe Tyr Val Gly Thr Val Leu Cys Leu Phe Leu Asn
225                 230                 235                 240

Phe Tyr Val Gln Thr Tyr Ile Val Arg Lys His Lys Gly Ala Lys Lys
                245                 250                 255

Thr Gln

<210> SEQ ID NO 33
<211> LENGTH: 7769
<212> TYPE: DNA
<213> ORGANISM: Artificial Sequence
<220> FEATURE:
<223> OTHER INFORMATION: Plasmid pZuFmEgD9eS-K58R/I257T

<400> SEQUENCE: 33
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc gggcaacggt tcacttgag tgcagtggct      240

-continued

```
agtgctctta ctcgtacagt gtgcaatact gcgtatcata gtctttgatg tatatcgtat      300
tcattcatgt tagttgcgta cgagccggaa gcataaagtg taaagcctgg ggtgcctaat      360
gagtgagcta actcacatta attgcgttgc gctcactgcc cgctttccag tcgggaaacc      420
tgtcgtgcca gctgcattaa tgaatcggcc aacgcgcggg gagaggcggt ttgcgtattg      480
ggcgctcttc cgcttcctcg ctcactgact cgctgcgctc ggtcgttcgg ctgcggcgag      540
cggtatcagc tcactcaaag gcggtaatac ggttatccac agaatcaggg gataacgcag      600
gaaagaacat gtgagcaaaa ggccagcaaa aggccaggaa ccgtaaaaag gccgcgttgc      660
tggcgttttt ccataggctc cgcccccctg acgagcatca caaaaatcga cgctcaagtc      720
agaggtggcg aaacccgaca ggactataaa gataccaggc gtttccccct ggaagctccc      780
tcgtgcgctc tcctgttccg accctgccgc ttaccggata cctgtccgcc tttctccctt      840
cgggaagcgt ggcgctttct catagctcac gctgtaggta tctcagttcg gtgtaggtcg      900
ttcgctccaa gctgggctgt gtgcacgaac cccccgttca gcccgaccgc tgcgccttat      960
ccggtaacta tcgtcttgag tccaacccgg taagacacga cttatcgcca ctggcagcag     1020
ccactggtaa caggattagc agagcgaggt atgtaggcgg tgctacagag ttcttgaagt     1080
ggtggcctaa ctacggctac actagaagga cagtatttgg tatctgcgct ctgctgaagc     1140
cagttacctt cggaaaaaga gttggtagct cttgatccgg caaacaaacc accgctggta     1200
gcggtggttt ttttgtttgc aagcagcaga ttacgcgcag aaaaaaagga tctcaagaag     1260
atcctttgat cttttctacg gggtctgacg ctcagtggaa cgaaaactca cgttaaggga     1320
ttttggtcat gagattatca aaaaggatct tcacctagat ccttttaaat taaaaatgaa     1380
gttttaaatc aatctaaagt atatatgagt aaacttggtc tgacagttac caatgcttaa     1440
tcagtgaggc acctatctca gcgatctgtc tatttcgttc atccatagtt gcctgactcc     1500
ccgtcgtgta gataactacg atacgggagg gcttaccatc tggccccagt gctgcaatga     1560
taccgcgaga cccacgctca ccggctccag atttatcagc aataaaccag ccagccggaa     1620
gggccgagcg cagaagtggt cctgcaactt tatccgcctc catccagtct attaattgtt     1680
gccgggaagc tagagtaagt agttcgccag ttaatagttt gcgcaacgtt gttgccattg     1740
ctacaggcat cgtggtgtca cgctcgtcgt ttggtatggc ttcattcagc tccggttccc     1800
aacgatcaag gcgagttaca tgatccccca tgttgtgcaa aaaagcggtt agctccttcg     1860
gtcctccgat cgttgtcaga agtaagttgg ccgcagtgtt atcactcatg gttatggcag     1920
cactgcataa ttctcttact gtcatgccat ccgtaagatg cttttctgtg actggtgagt     1980
actcaaccaa gtcattctga gaatagtgta tgcggcgacc gagttgctct tgcccggcgt     2040
caatacggga taataccgcg ccacatagca gaactttaaa agtgctcatc attggaaaac     2100
gttcttcggg gcgaaaactc tcaaggatct taccgctgtt gagatccagt tcgatgtaac     2160
ccactcgtgc acccaactga tcttcagcat cttttacttt caccagcgtt tctgggtgag     2220
caaaaacagg aaggcaaaat gccgcaaaaa agggaataag ggcgacacgg aaatgttgaa     2280
tactcatact cttcctttt caatattatt gaagcattta tcagggttat tgtctcatga     2340
gcggatacat atttgaatgt atttagaaaa ataaacaaat aggggttccg cgcacatttc     2400
cccgaaaagt gccacctgac gcgccctgta gcggcgcatt aagcgcggcg ggtgtggtgg     2460
ttacgcgcag cgtgaccgct acacttgcca gcgccctagc gcccgctcct ttcgctttct     2520
tcccttcctt tctcgccacg ttcgccggct ttccccgtca agctctaaat cggggggctcc     2580 ctttagggtt ccgatttagt gctttacggc acctcgaccc caaaaaactt gattagggtg     2640
```

```
atggttcacg tagtgggcca tcgccctgat agacggtttt tcgcccttg acgttggagt    2700 ccacgttctt taatagtgga ctcttgttcc aaactggaac aacactcaac cctatctcgg    2760
tctattcttt tgatttataa gggattttgc cgatttcggc ctattggtta aaaaatgagc    2820
tgatttaaca aaaattaac gcgaatttta acaaaatatt aacgcttaca atttccattc    2880
gccattcagg ctgcgcaact gttgggaagg gcgatcggtg cgggcctctt cgctattacg    2940
ccagctggcg aaagggggat gtgctgcaag gcgattaagt tgggtaacgc cagggttttc    3000
ccagtcacga cgttgtaaaa cgacggccag tgaattgtaa tacgactcac tatagggcga    3060
attgggtacc gggcccccc tcgaggtcga tggtgtcgat aagcttgata tcgaattcat    3120
gtcacacaaa ccgatcttcg cctcaaggaa acctaattct acatccgaga gactgccgag    3180
atccagtcta cactgattaa ttttcgggcc aataatttaa aaaaatcgtg ttatataata    3240
ttatatgtat tatatatata catcatgatg atactgacag tcatgtccca ttgctaaata    3300
gacagactcc atctgccgcc tccaactgat gttctcaata tttaaggggt catctcgcat    3360
tgtttaataa taaacagact ccatctaccg cctccaaatg atgttctcaa aatatattgt    3420
atgaacttat ttttattact tagtattatt agacaactta cttgctttat gaaaaacact    3480
tcctatttag gaaacaattt ataatggcag ttcgttcatt taacaattta tgtagaataa    3540
atgttataaa tgcgtatggg aaatcttaaa tatggatagc ataaatgata tctgcattgc    3600
ctaattcgaa atcaacagca acgaaaaaaa tcccttgtac aacataaata gtcatcgaga    3660
aatatcaact atcaaagaac agctattcac acgttactat tgagattatt attggacgag    3720
aatcacacac tcaactgtct ttctctcttc tagaaataca ggtacaagta tgtactattc    3780
tcattgttca tacttctagt catttcatcc cacatattcc ttggatttct ctccaatgaa    3840
tgacattcta tcttgcaaat tcaacaatta taataagata taccaaagta gcggtatagt    3900
ggcaatcaaa aagcttctct ggtgtgcttc tcgtatttat ttttattcta atgatccatt    3960
aaaggtatat atttatttct tgttatataa tccttttgtt tattacatgg gctggataca    4020
taaaggtatt ttgatttaat ttttttgctta aattcaatcc ccctcgttc agtgtcaact    4080 gtaatggtag gaaattacca tacttttgaa gaagcaaaaa aatgaaaga aaaaaaaaat    4140 cgtatttcca ggttagacgt tccgcagaat ctagaatgcg gtatgcggta cattgttctt    4200
cgaacgtaaa agttgcgctc cctgagatat tgtacatttt tgcttttaca agtacaagta    4260
catcgtacaa ctatgtacta ctgttgatgc atccacaaca gtttgttttg ttttttttg    4320 tttttttttt ttctaatgat tcattaccgc tatgtatacc tacttgtact tgtagtaagc    4380
cgggttattg gcgttcaatt aatcatagac ttatgaatct gcacggtgtg cgctgcgagt    4440
tacttttagc ttatgcatgc tacttgggtg taatattggg atctgttcgg aaatcaacgg    4500
atgctcaatc gatttcgaca gtaattaatt aagtcataca caagtcagct tcttcgagc    4560 ctcatataag tataagtagt tcaacgtatt agcactgtac ccagcatctc cgtatcgaga    4620
aacacaacaa catgccccat tggacagatc atgcggatac acaggttgtg cagtatcata    4680
catactcgat cagacaggtc gtctgaccat catacaagct gaacaagcgc tccatacttg    4740
cacgctctct atatacacag ttaaattaca tatccatagt ctaacctcta acagttaatc    4800
ttctggtaag cctcccagcc agccttctgg tatcgcttgg cctcctcaat aggatctcgg    4860
ttctggccgt acagacctcg gccgacaatt atgatatccg ttccggtaga catgacatcc    4920
tcaacagttc ggtactgctg tccgagagcg tctcccttgt cgtcaagacc caccccgggg    4980
```

```
gtcagaataa gccagtcctc agagtcgccc ttaggtcggt tctgggcaat gaagccaacc    5040
acaaactcgg ggtcggatcg ggcaagctca atggtctgct tggagtactc gccagtggcc    5100
agagagccct tgcaagacag ctcggccagc atgagcagac ctctggccag cttctcgttg    5160
ggagagggga ctaggaactc cttgtactgg gagttctcgt agtcagagac gtcctccttc    5220
ttctgttcag agacagtttc ctcggcacca gctcgcaggc cagcaatgat tccggttccg    5280
ggtacaccgt gggcgttggt gatatcggac cactcggcga ttcggtgaca ccggtactgg    5340
tgcttgacag tgttgccaat atctgcgaac tttctgtcct cgaacaggaa gaaaccgtgc    5400
ttaagagcaa gttccttgag ggggagcaca gtgccggcgt aggtgaagtc gtcaatgatg    5460
tcgatatggg ttttgatcat gcacacataa ggtccgacct tatcggcaag ctcaatgagc    5520
tccttggtgg tggtaacatc cagagaagca cacaggttgg ttttcttggc tgccacgagc    5580
ttgagcactc gagcggcaaa ggcggacttg tggacgttag ctcgagcttc gtaggagggc    5640
attttggtgg tgaagaggag actgaaataa atttagtctg cagaactttt tatcggaacc    5700
ttatctgggg cagtgaagta tatgttatgg taatagttac gagttagttg aacttataga    5760
tagactggac tatacggcta tcggtccaaa ttagaaagaa cgtcaatggc tctctgggcg    5820
tcgcctttgc cgacaaaaat gtgatcatga tgaaagccag caatgacgtt gcagctgata    5880
ttgttgtcgg ccaaccgcgc cgaaaacgca gctgtcagac ccacagcctc caacgaagaa    5940
tgtatcgtca aagtgatcca agcacactca tagttggagt cgtactccaa aggcggcaat    6000
gacgagtcag acagatactc gtcgacgttt aaacagtgta cgcagatcta ctatagagga    6060
acatttaaat tgccccggag aagacggcca ggccgcctag atgacaaatt caacaactca    6120
cagctgactt tctgccattg ccactagggg ggggcctttt tatatggcca agccaagctc    6180
tccacgtcgg ttgggctgca cccaacaata aatgggtagg gttgcaccaa caaagggatg    6240 ggatggggg tagaagatac gaggataacg gggctcaatg gcacaaataa gaacgaatac    6300
tgccattaag actcgtgatc cagcgactga caccattgca tcatctaagg gcctcaaaac    6360
tacctcggaa ctgctgcgct gatctggaca ccacagaggt tccgagcact ttaggttgca    6420
ccaaatgtcc caccaggtgc aggcagaaaa cgctggaaca gcgtgtacag tttgtcttaa    6480
caaaaagtga gggcgctgag gtcgagcagg gtggtgtgac ttgttatagc ctttagagct    6540
gcgaaagcgc gtatggattt ggctcatcag gccagattga gggtctgtgg acacatgtca    6600
tgttagtgta cttcaatcgc cccctggata tagccccgac aataggccgt ggcctcattt    6660
ttttgccttc cgcacatttc cattgctcga tacccacacc ttgcttctcc tgcacttgcc    6720
aaccttaata ctggtttaca ttgaccaaca tcttacaagc gggggcttg tctagggtat    6780 atataaacag tggctctccc aatcggttgc cagtctcttt tttcctttct ttccccacag    6840
attcgaaatc taaactacac atcacagaat tccgagccgt gagtatccac gacaagatca    6900
gtgtcgagac gacgcgtttt gtgtaatgac acaatccgaa agtcgctagc aacacacact    6960
ctctacacaa actaacccag ctctggtacc atggaggtcg tgaacgaaat cgtctccatt    7020
ggccaggagg ttcttcccaa ggtcgactat gctcagctct ggtctgatgc ctcgcactgc    7080
gaggtgctgt acctctccat cgccttcgtc atcctgaagt tcaccttgg tcctctcgga    7140 cccaagggtc agtctcgaat gaggtttgtg ttcaccaact acaacctgct catgtccatc    7200
tactcgctgg gctccttcct ctcgatggcc tacgccatgt acaccattgg tgtcatgtcc    7260
gacaactgcg agaaggcttt cgacaacaat gtcttccgaa tcaccactca gctgttctac    7320
ctcagcaagt tcctcgagta cattgactcc ttctatctgc ccctcatggg caagcctctg    7380
```

```
acctggttgc aattctttca ccatctcgga gctcctatgg acatgtggct gttctacaac    7440
taccgaaacg aagccgtttg atctttgtg ctgctcaacg gcttcattca ctggatcatg     7500
tacggctact attggacccg actgatcaag ctcaagttcc ctatgcccaa gtccctgatt    7560
acttctatgc agatcattca gttcaacgtt ggcttctaca tcgtctggaa gtaccggaac    7620
attccctgct accgacaaga tggaatgaga atgtttggct ggtttttcaa ctacttctac    7680
gttggtactg tcctgtgtct gttcctcaac ttctacgtgc agacctacat cgtccgaaag    7740
cacaagggag ccaaaaagac tcagtgagc                                      7769

<210> SEQ ID NO 34
<211> LENGTH: 777
<212> TYPE: DNA
<213> ORGANISM: Euglena gracilis
<220> FEATURE:
<221> NAME/KEY: CDS
<222> LOCATION: (1)..(777)
<223> OTHER INFORMATION: mutant delta-9 elongase "EgD9eS-L130M/V243A1"

<400> SEQUENCE: 34 atg gag gtc gtg aac gaa atc gtc tcc att ggc cag gag gtt ctt ccc     48
Met Glu Val Val Asn Glu Ile Val Ser Ile Gly Gln Glu Val Leu Pro
1               5                   10                  15 aag gtc gac tat gct cag ctc tgg tct gat gcc tcg cac tgc gag gtg     96
Lys Val Asp Tyr Ala Gln Leu Trp Ser Asp Ala Ser His Cys Glu Val
            20                  25                  30 ctg tac ctc tcc atc gcc ttc gtc atc ctg aag ttc acc ctt ggt cct    144
Leu Tyr Leu Ser Ile Ala Phe Val Ile Leu Lys Phe Thr Leu Gly Pro
        35                  40                  45 ctc gga ccc aag ggt cag tct cga atg aag ttt gtg ttc acc aac tac    192
Leu Gly Pro Lys Gly Gln Ser Arg Met Lys Phe Val Phe Thr Asn Tyr
    50                  55                  60 aac ctg ctc atg tcc atc tac tcg ctg ggc tcc ttc ctc tct atg gcc    240
Asn Leu Leu Met Ser Ile Tyr Ser Leu Gly Ser Phe Leu Ser Met Ala
65                  70                  75                  80 tac gcc atg tac acc att ggt gtc atg tcc gac aac tgc gag aag gct    288
Tyr Ala Met Tyr Thr Ile Gly Val Met Ser Asp Asn Cys Glu Lys Ala
                85                  90                  95 ttc gac aac aat gtc ttc cga atc acc act cag ctg ttc tac ctc agc    336
Phe Asp Asn Asn Val Phe Arg Ile Thr Thr Gln Leu Phe Tyr Leu Ser
            100                 105                 110 aag ttc ctc gag tac att gac tcc ttc tat ctg ccc ctc atg ggc aag    384
Lys Phe Leu Glu Tyr Ile Asp Ser Phe Tyr Leu Pro Leu Met Gly Lys
        115                 120                 125 cct atg acc tgg ttg cag ttc ttt cac cat ctc gga gct cct atg gac    432
Pro Met Thr Trp Leu Gln Phe Phe His His Leu Gly Ala Pro Met Asp
    130                 135                 140 atg tgg ctg ttc tac aat tac cga aac gaa gcc gtt tgg atc ttt gtg    480
Met Trp Leu Phe Tyr Asn Tyr Arg Asn Glu Ala Val Trp Ile Phe Val
145                 150                 155                 160 ctg ctc aac ggc ttc att cac tgg atc atg tac ggc tac tat tgg acc    528
Leu Leu Asn Gly Phe Ile His Trp Ile Met Tyr Gly Tyr Tyr Trp Thr
                165                 170                 175 cga ctg atc aag ctc aag ttc cct atg ccc aag tcc ctg att act tct    576
Arg Leu Ile Lys Leu Lys Phe Pro Met Pro Lys Ser Leu Ile Thr Ser
            180                 185                 190 atg cag atc att cag ttc aac gtt ggc ttc tac atc gtc tgg aag tac    624
Met Gln Ile Ile Gln Phe Asn Val Gly Phe Tyr Ile Val Trp Lys Tyr
        195                 200                 205
```

```
cgg aac att ccc tgc tac cga caa gat gga atg aga atg ttt ggc tgg    672
Arg Asn Ile Pro Cys Tyr Arg Gln Asp Gly Met Arg Met Phe Gly Trp
210                 215                 220 ttt ttc aac tac ttc tac gtt ggt act gtc ctg tgt ctg ttc ctc aac    720
Phe Phe Asn Tyr Phe Tyr Val Gly Thr Val Leu Cys Leu Phe Leu Asn
225                 230                 235                 240 ttc tac gcg cag acc tac atc gtc cga aag cac aag gga gcc aaa aag    768
Phe Tyr Ala Gln Thr Tyr Ile Val Arg Lys His Lys Gly Ala Lys Lys
            245                 250                 255 att cag tga                                                        777
Ile Gln

<210> SEQ ID NO 35
<211> LENGTH: 258
<212> TYPE: PRT
<213> ORGANISM: Euglena gracilis

<400> SEQUENCE: 35

Met Glu Val Val Asn Glu Ile Val Ser Ile Gly Gln Glu Val Leu Pro
1               5                   10                  15

Lys Val Asp Tyr Ala Gln Leu Trp Ser Asp Ala Ser His Cys Glu Val
            20                  25                  30

Leu Tyr Leu Ser Ile Ala Phe Val Ile Leu Lys Phe Thr Leu Gly Pro
        35                  40                  45

Leu Gly Pro Lys Gly Gln Ser Arg Met Lys Phe Val Phe Thr Asn Tyr
    50                  55                  60

Asn Leu Leu Met Ser Ile Tyr Ser Leu Gly Ser Phe Leu Ser Met Ala
65                  70                  75                  80

Tyr Ala Met Tyr Thr Ile Gly Val Met Ser Asp Asn Cys Glu Lys Ala
                85                  90                  95

Phe Asp Asn Asn Val Phe Arg Ile Thr Thr Gln Leu Phe Tyr Leu Ser
            100                 105                 110

Lys Phe Leu Glu Tyr Ile Asp Ser Phe Tyr Leu Pro Leu Met Gly Lys
        115                 120                 125

Pro Met Thr Trp Leu Gln Phe Phe His His Leu Gly Ala Pro Met Asp
    130                 135                 140

Met Trp Leu Phe Tyr Asn Tyr Arg Asn Glu Ala Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Lys Phe Pro Met Pro Lys Ser Leu Ile Thr Ser
            180                 185                 190

Met Gln Ile Ile Gln Phe Asn Val Gly Phe Tyr Ile Val Trp Lys Tyr
        195                 200                 205

Arg Asn Ile Pro Cys Tyr Arg Gln Asp Gly Met Arg Met Phe Gly Trp
    210                 215                 220

Phe Phe Asn Tyr Phe Tyr Val Gly Thr Val Leu Cys Leu Phe Leu Asn
225                 230                 235                 240

Phe Tyr Ala Gln Thr Tyr Ile Val Arg Lys His Lys Gly Ala Lys Lys
                245                 250                 255

Ile Gln

<210> SEQ ID NO 36
<211> LENGTH: 7769
<212> TYPE: DNA
<213> ORGANISM: Artificial Sequence
<220> FEATURE:
```

<223> OTHER INFORMATION: Plasmid pZuFmEgD9eS-L130M/V243A1

<400> SEQUENCE: 36

```
ggccgcaagt gtggatgggg aagtgagtgc ccggttctgt gtgcacaatt ggcaatccaa    60
gatggatgga ttcaacacag ggatatagcg agctacgtgg tggtgcgagg atatagcaac   120
ggatatttat gtttgacact tgagaatgta cgatacaagc actgtccaag tacaatacta   180
aacatactgt acatactcat actcgtaccc gggcaacggt ttcacttgag tgcagtggct   240
agtgctctta ctcgtacagt gtgcaatact gcgtatcata gtctttgatg tatatcgtat   300
tcattcatgt tagttgcgta cgagccggaa gcataaagtg taaagcctgg ggtgcctaat   360
gagtgagcta actcacatta attgcgttgc gctcactgcc cgctttccag tcgggaaacc   420
tgtcgtgcca gctgcattaa tgaatcggcc aacgcgcggg gagaggcggt ttgcgtattg   480
ggcgctcttc cgcttcctcg ctcactgact cgctgcgctc ggtcgttcgg ctgcggcgag   540
cggtatcagc tcactcaaag gcggtaatac ggttatccac agaatcaggg gataacgcag   600
gaaagaacat gtgagcaaaa ggccagcaaa aggccaggaa ccgtaaaaag gccgcgttgc   660
tggcgttttt ccataggctc cgcccccctg acgagcatca caaaaatcga cgctcaagtc   720
agaggtggcg aaacccgaca ggactataaa gataccaggc gtttccccct ggaagctccc   780
tcgtgcgctc tcctgttccg accctgccgc ttaccggata cctgtccgcc tttctccctt   840
cgggaagcgt ggcgctttct catagctcac gctgtaggta tctcagttcg gtgtaggtcg   900
ttcgctccaa gctgggctgt gtgcacgaac cccccgttca gcccgaccgc tgcgccttat   960
ccggtaacta tcgtcttgag tccaacccgg taagacacga cttatcgcca ctggcagcag  1020
ccactggtaa caggattagc agagcgaggt atgtaggcgg tgctacagag ttcttgaagt  1080
ggtggcctaa ctacggctac actagaagga cagtatttgg tatctgcgct ctgctgaagc  1140
cagttacctt cggaaaaaga gttggtagct cttgatccgg caaacaaacc accgctggta  1200
gcggtggttt ttttgtttgc aagcagcaga ttacgcgcag aaaaaaagga tctcaagaag  1260
atcctttgat cttttctacg gggtctgacg ctcagtggaa cgaaaactca cgttaaggga  1320
ttttggtcat gagattatca aaaaggatct cacctagatc cttttaaatt aaaaatgaa  1380
gttttaaatc aatctaaagt atatatgagt aaacttggtc tgacagttac caatgcttaa  1440
tcagtgaggc acctatctca gcgatctgtc tatttcgttc atccatagtt gcctgactcc  1500
ccgtcgtgta gataactacg atacgggagg gcttaccatc tggccccagt gctgcaatga  1560
taccgcgaga cccacgctca ccggctccag atttatcagc aataaaccag ccagccggaa  1620
gggccgagcg cagaagtggt cctgcaactt tatccgcctc catccagtct attaattgtt  1680
gccgggaagc tagagtaagt agttcgccag ttaatagttt gcgcaacgtt gttgccattg  1740
ctacaggcat cgtggtgtca cgctcgtcgt ttggtatggc ttcattcagc tccggttccc  1800
aacgatcaag gcgagttaca tgatccccca tgttgtgcaa aaaagcggtt agctccttcg  1860
gtcctccgat cgttgtcaga agtaagttgg ccgcagtgtt atcactcatg gttatggcag  1920
cactgcataa ttctcttact gtcatgccat ccgtaagatg cttttctgtg actggtgagt  1980
actcaaccaa gtcattctga gaatagtgta tgcggcgacc gagttgctct tgcccggcgt  2040
caatacggga taataccgcg ccacatagca gaactttaaa agtgctcatc attggaaaac  2100
gttcttcggg gcgaaaactc tcaaggatct taccgctgtt gagatccagt tcgatgtaac  2160
ccactcgtgc acccaactga tcttcagcat cttttacttt caccagcgtt tctgggtgag  2220
caaaaacagg aaggcaaaat gccgcaaaaa agggaataag ggcgacacgg aaatgttgaa  2280
```

| | |
|---|---|
| tactcatact cttcctttt caatattatt gaagcattta tcagggttat tgtctcatga | 2340 |
| gcggatacat atttgaatgt atttagaaaa ataaacaaat aggggttccg cgcacatttc | 2400 |
| cccgaaaagt gccacctgac gcgccctgta gcggcgcatt aagcgcggcg ggtgtggtgg | 2460 |
| ttacgcgcag cgtgaccgct acacttgcca gcgccctagc gcccgctcct ttcgctttct | 2520 |
| tcccttcctt tctcgccacg ttcgccggct ttccccgtca agctctaaat cgggggctcc | 2580 |
| ctttagggtt ccgatttagt gctttacggc acctcgaccc caaaaaactt gattagggtg | 2640 |
| atggttcacg tagtgggcca tcgccctgat agacggtttt tcgccctttg acgttggagt | 2700 |
| ccacgttctt taatagtgga ctcttgttcc aaactggaac aacactcaac cctatctcgg | 2760 |
| tctattcttt tgatttataa gggattttgc cgatttcggc ctattggtta aaaaatgagc | 2820 |
| tgatttaaca aaaatttaac gcgaatttta acaaaatatt aacgcttaca atttccattc | 2880 |
| gccattcagg ctgcgcaact gttgggaagg gcgatcggtg cgggcctctt cgctattacg | 2940 |
| ccagctggcg aaaggnggat gtgctgcaag gcgattaagt tgggtaacgc cagggttttc | 3000 |
| ccagtcacga cgttgtaaaa cgacggccag tgaattgtaa tacgactcac tatagggcga | 3060 |
| attgggtacc gggccccccc tcgaggtcga tggtgtcgat aagcttgata tcgaattcat | 3120 |
| gtcacacaaa ccgatcttcg cctcaaggaa acctaattct acatccgaga gactgccgag | 3180 |
| atccagtcta cactgattaa ttttcgggcc aataatttaa aaaaatcgtg ttatataata | 3240 |
| ttatatgtat tatatatata catcatgatg atactgacag tcatgtccca ttgctaaata | 3300 |
| gacagactcc atctgccgcc tccaactgat gttctcaata tttaaggggt catctcgcat | 3360 |
| tgtttaataa taaacagact ccatctaccg cctccaaatg atgttctcaa aatatattgt | 3420 |
| atgaacttat ttttattact tagtattatt agacaactta cttgctttat gaaaacact | 3480 |
| tcctatttag gaaacaattt ataatggcag ttcgttcatt taacaattta tgtagaataa | 3540 |
| atgttataaa tgcgtatggg aaatcttaaa tatggatagc ataaatgata tctgcattgc | 3600 |
| ctaattcgaa atcaacagca acgaaaaaaa tcccttgtac aacataaata gtcatcgaga | 3660 |
| aatatcaact atcaaagaac agctattcac acgttactat tgagattatt attggacgag | 3720 |
| aatcacacac tcaactgtct ttctctcttc tagaaataca ggtacaagta tgtactattc | 3780 |
| tcattgttca tacttctagt catttcatcc cacatattcc ttggatttct ctccaatgaa | 3840 |
| tgacattcta tcttgcaaat tcaacaatta taataagata taccaaagta gcggtatagt | 3900 |
| ggcaatcaaa aagcttctct ggtgtgcttc tcgtatttat ttttattcta atgatccatt | 3960 |
| aaaggtatat atttatttct tgttatataa tccttttgtt tattacatgg gctggataca | 4020 |
| taaaggtatt ttgatttaat ttttgctta aattcaatcc ccctcgttc agtgtcaact | 4080 |
| gtaatggtag gaaattacca tacttttgaa gaagcaaaaa aatgaaaga aaaaaaaat | 4140 |
| cgtatttcca ggttagacgt tccgcagaat ctagaatgcg gtatgcggta cattgttctt | 4200 |
| cgaacgtaaa agttgcgctc cctgagatat tgtacatttt tgcttttaca agtacaagta | 4260 |
| catcgtacaa ctatgtacta ctgttgatgc atccacaaca gtttgtttg tttttttttg | 4320 |
| tttttttttt ttctaatgat tcattaccgc tatgtatacc tacttgtact tgtagtaagc | 4380 |
| cgggttattg gcgttcaatt aatcatagac ttatgaatct gcacggtgtg cgctgcgagt | 4440 |
| tactttagc ttatgcatgc tacttgggtg taatattggg atctgttcgg aaatcaacgg | 4500 |
| atgctcaatc gatttcgaca gtaattaatt aagtcataca caagtcagct ttcttcgagc | 4560 |
| ctcatataag tataagtagt tcaacgtatt agcactgtac ccagcatctc cgtatcgaga | 4620 |

```
aacacaacaa catgccccat tggacagatc atgcggatac acaggttgtg cagtatcata    4680
catactcgat cagacaggtc gtctgaccat catacaagct gaacaagcgc tccatacttg    4740
cacgctctct atatacacag ttaaattaca tatccatagt ctaacctcta acagttaatc    4800
ttctggtaag cctcccagcc agccttctgg tatcgcttgg cctcctcaat aggatctcgg    4860
ttctggccgt acagacctcg gccgacaatt atgatatccg ttccggtaga catgacatcc    4920
tcaacagttc ggtactgctg tccgagagcg tctcccttgt cgtcaagacc caccccgggg    4980
gtcagaataa gccagtcctc agagtcgccc ttaggtcggt tctgggcaat gaagccaacc    5040
acaaactcgg ggtcggatcg ggcaagctca atggtctgct tggagtactc gccagtggcc    5100
agagagccct tgcaagacag ctcggccagc atgagcagac ctctggccag cttctcgttg    5160
ggagagggga ctaggaactc cttgtactgg gagttctcgt agtcagagac gtcctccttc    5220
ttctgttcag agacagtttc ctcggcacca gctcgcaggc cagcaatgat tccggttccg    5280
ggtacaccgt gggcgttggt gatatcggac cactcggcga ttcggtgaca ccggtactgg    5340
tgcttgacag tgttgccaat atctgcgaac tttctgtcct cgaacaggaa gaaaccgtgc    5400
ttaagagcaa gttccttgag ggggagcaca gtgccggcgt aggtgaagtc gtcaatgatg    5460
tcgatatggg ttttgatcat gcacacataa ggtccgacct tatcggcaag ctcaatgagc    5520
tccttggtgg tggtaacatc cagagaagca cacaggttgg ttttcttggc tgccacgagc    5580
ttgagcactc gagcggcaaa ggcggacttg tggacgttag ctcgagcttc gtaggagggc    5640
attttggtgg tgaagaggag actgaaataa atttagtctg cagaactttt tatcggaacc    5700
ttatctgggg cagtgaagta tatgttatgg taatagttac gagttagttg aacttataga    5760
tagactggac tatacggcta tcggtccaaa ttagaaagaa cgtcaatggc tctctgggcg    5820
tcgcctttgc cgacaaaaat gtgatcatga tgaaagccag caatgacgtt gcagctgata    5880
ttgttgtcgg ccaaccgcgc cgaaaacgca gctgtcagac ccacagcctc caacgaagaa    5940
tgtatcgtca aagtgatcca agcacactca tagttggagt cgtactccaa aggcggcaat    6000
gacgagtcag acagatactc gtcgacgttt aaacagtgta cgcagatcta ctatagagga    6060
acatttaaat tgccccggag aagacggcca ggccgcctag atgacaaatt caacaactca    6120
cagctgactt tctgccattg ccactagggg ggggccttt tatatggcca agccaagctc    6180
tccacgtcgg ttgggctgca cccaacaata aatgggtagg gttgcaccaa caaagggatg    6240
ggatgggggg tagaagatac gaggataacg gggctcaatg gcacaaataa gaacgaatac    6300
tgccattaag actcgtgatc cagcgactga caccattgca tcatctaagg gcctcaaaac    6360
tacctcggaa ctgctgcgct gatctggaca ccacagaggt tccgagcact ttaggttgca    6420
ccaaatgtcc caccaggtgc aggcagaaaa cgctggaaca gcgtgtacag tttgtcttaa    6480
caaaaagtga gggcgctgag gtcgagcagg gtggtgtgac ttgttatagc ctttagagct    6540
gcgaaagcgc gtatggattt ggctcatcag gccagattga gggtctgtgg acacatgtca    6600
tgttagtgta cttcaatcgc cccctggata tagccccgac aataggccgt ggcctcattt    6660
ttttgccttc cgcacatttc cattgctcga tacccacacc ttgcttctcc tgcacttgcc    6720
aaccttaata ctggtttaca ttgaccaaca tcttacaagc gggggcttg tctagggtat    6780
atataaacag tggctctccc aatcggttgc cagtctcttt tttcctttct ttccccacag    6840
attcgaaatc taaactacac atcacagaat tccgagccgt gagtatccac gacaagatca    6900
gtgtcgagac gacgcgtttt gtgtaatgac acaatccgaa agtcgctagc aacacacact    6960
ctctacacaa actaacccag ctctggtacc atggaggtcg tgaacgaaat cgtctccatt    7020
```

-continued

```
ggccaggagg ttcttcccaa ggtcgactat gctcagctct ggtctgatgc ctcgcactgc     7080
gaggtgctgt acctctccat cgccttcgtc atcctgaagt tcaccttgg tcctctcgga      7140 cccaagggtc agtctcgaat gaagtttgtg ttcaccaact acaacctgct catgtccatc    7200
tactcgctgg gctccttcct ctctatggcc tacgccatgt acaccattgg tgtcatgtcc    7260
gacaactgcg agaaggcttt cgacaacaat gtcttccgaa tcaccactca gctgttctac    7320
ctcagcaagt tcctcgagta cattgactcc ttctatctgc ccctcatggg caagcctatg    7380
acctggttgc agttctttca ccatctcgga gctcctatgg acatgtggct gttctacaat    7440
taccgaaacg aagccgtttg gatctttgtg ctgctcaacg gcttcattca ctggatcatg    7500
tacggctact attggacccg actgatcaag ctcaagttcc ctatgcccaa gtccctgatt    7560
acttctatgc agatcattca gttcaacgtt ggcttctaca tcgtctggaa gtaccggaac    7620
attccctgct accgacaaga tggaatgaga atgtttggct ggttttcaa ctacttctac      7680 gttggtactg tcctgtgtct gttcctcaac ttctacgcgc agacctacat cgtccgaaag    7740
cacaagggag ccaaaaagat tcagtgagc                                       7769

<210> SEQ ID NO 37
<211> LENGTH: 777
<212> TYPE: DNA
<213> ORGANISM: Euglena gracilis
<220> FEATURE:
<221> NAME/KEY: CDS
<222> LOCATION: (1)..(777)
<223> OTHER INFORMATION: mutant delta-9 elongase "EgD9eS-D98G"

<400> SEQUENCE: 37 atg gag gtc gtg aac gaa atc gtc tcc att ggc cag gag gtt ctt ccc      48
Met Glu Val Val Asn Glu Ile Val Ser Ile Gly Gln Glu Val Leu Pro
1               5                   10                  15 aag gtc gac tat gct cag ctc tgg tct gat gcc tcg cac tgc gag gtg       96
Lys Val Asp Tyr Ala Gln Leu Trp Ser Asp Ala Ser His Cys Glu Val
            20                  25                  30 ctg tac ctc tcc atc gcc ttc gtc atc ctg aag ttc acc ctt ggt cct      144
Leu Tyr Leu Ser Ile Ala Phe Val Ile Leu Lys Phe Thr Leu Gly Pro
        35                  40                  45 ctc gga ccc aag ggt cag tct cga atg aag ttt gtg ttc acc aac tac      192
Leu Gly Pro Lys Gly Gln Ser Arg Met Lys Phe Val Phe Thr Asn Tyr
    50                  55                  60 aac ctg ctc atg tcc atc tac tcg ctg ggc tcc ttc ctc tct atg gcc      240
Asn Leu Leu Met Ser Ile Tyr Ser Leu Gly Ser Phe Leu Ser Met Ala
65                  70                  75                  80 tac gcc atg tac acc att ggt gtc atg tcc gac aac tgc gag aag gct      288
Tyr Ala Met Tyr Thr Ile Gly Val Met Ser Asp Asn Cys Glu Lys Ala
                85                  90                  95 ttc ggc aac aat gtc ttc cga atc acc act cag ctg ttc tac ctc agc      336
Phe Gly Asn Asn Val Phe Arg Ile Thr Thr Gln Leu Phe Tyr Leu Ser
            100                 105                 110 aag ttc ctc gag tac att gac tcc ttc tat ctg ccc ctc atg ggc aag      384
Lys Phe Leu Glu Tyr Ile Asp Ser Phe Tyr Leu Pro Leu Met Gly Lys
        115                 120                 125 cct ctg acc tgg ttg cag ttc ttt cac cat ctc gga gct cct atg gac      432
Pro Leu Thr Trp Leu Gln Phe Phe His His Leu Gly Ala Pro Met Asp
    130                 135                 140 atg tgg ctg ttc tac aac tac cga aac gaa gcc gtt tgg atc ttt gtg      480
Met Trp Leu Phe Tyr Asn Tyr Arg Asn Glu Ala Val Trp Ile Phe Val
145                 150                 155                 160
```

```
ctg ctc aac ggc ttc att cac tgg atc atg tac ggc tac tat tgg acc       528
Leu Leu Asn Gly Phe Ile His Trp Ile Met Tyr Gly Tyr Tyr Trp Thr
            165                 170                 175 cga ctg atc aag ctc aag ttc cct atg ccc aag tcc ctg att act tct       576
Arg Leu Ile Lys Leu Lys Phe Pro Met Pro Lys Ser Leu Ile Thr Ser
            180                 185                 190 atg cag atc att cag ttc aac gtt ggc ttc tac atc gtc tgg aag tac       624
Met Gln Ile Ile Gln Phe Asn Val Gly Phe Tyr Ile Val Trp Lys Tyr
            195                 200                 205 cgg aac att ccc tgc tac cga caa gat gga atg aga atg ttt ggc tgg       672
Arg Asn Ile Pro Cys Tyr Arg Gln Asp Gly Met Arg Met Phe Gly Trp
            210                 215                 220 ttt ttc aac tac ttc tac gtt ggt act gtc ctg tgt ctg ttc ctc aac       720
Phe Phe Asn Tyr Phe Tyr Val Gly Thr Val Leu Cys Leu Phe Leu Asn
225                 230                 235                 240 ttc tac gtg cag acc tac atc gtc cga aag cac aag gga gcc aaa aag       768
Phe Tyr Val Gln Thr Tyr Ile Val Arg Lys His Lys Gly Ala Lys Lys
                245                 250                 255 att cag tga                                                            777
Ile Gln <210> SEQ ID NO 38
<211> LENGTH: 258
<212> TYPE: PRT
<213> ORGANISM: Euglena gracilis

<400> SEQUENCE: 38

Met Glu Val Val Asn Glu Ile Val Ser Ile Gly Gln Glu Val Leu Pro
1               5                   10                  15

Lys Val Asp Tyr Ala Gln Leu Trp Ser Asp Ala Ser His Cys Glu Val
            20                  25                  30

Leu Tyr Leu Ser Ile Ala Phe Val Ile Leu Lys Phe Thr Leu Gly Pro
        35                  40                  45

Leu Gly Pro Lys Gly Gln Ser Arg Met Lys Phe Val Phe Thr Asn Tyr
    50                  55                  60

Asn Leu Leu Met Ser Ile Tyr Ser Leu Gly Ser Phe Leu Ser Met Ala
65                  70                  75                  80

Tyr Ala Met Tyr Thr Ile Gly Val Met Ser Asp Asn Cys Glu Lys Ala
                85                  90                  95

Phe Gly Asn Asn Val Phe Arg Ile Thr Thr Gln Leu Pro Tyr Leu Ser
            100                 105                 110

Lys Phe Leu Glu Tyr Ile Asp Ser Phe Tyr Leu Pro Leu Met Gly Lys
        115                 120                 125

Pro Leu Thr Trp Leu Gln Phe His His Leu Gly Ala Pro Met Asp
    130                 135                 140

Met Trp Leu Phe Tyr Asn Tyr Arg Asn Glu Ala Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Lys Phe Pro Met Pro Lys Ser Leu Ile Thr Ser
            180                 185                 190

Met Gln Ile Ile Gln Phe Asn Val Gly Phe Tyr Ile Val Trp Lys Tyr
        195                 200                 205

Arg Asn Ile Pro Cys Tyr Arg Gln Asp Gly Met Arg Met Phe Gly Trp
    210                 215                 220

Phe Phe Asn Tyr Phe Tyr Val Gly Thr Val Leu Cys Leu Phe Leu Asn
225                 230                 235                 240
```

Phe Tyr Val Gln Thr Tyr Ile Val Arg Lys His Lys Gly Ala Lys Lys
            245                 250                 255

Ile Gln

<210> SEQ ID NO 39
<211> LENGTH: 7769
<212> TYPE: DNA
<213> ORGANISM: Artificial Sequence
<220> FEATURE:
<223> OTHER INFORMATION: Plasmid pZuFmEgD9eS-D98G

<400> SEQUENCE: 39

```
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc gggcaacggt ttcacttgag tgcagtggct     240
agtgctctta ctcgtacagt gtgcaatact gcgtatcata gtctttgatg tatatcgtat     300
tcattcatgt tagttgcgta cgagccggaa gcataaagtg taaagcctgg ggtgcctaat     360
gagtgagcta actcacatta attgcgttgc gctcactgcc cgctttccag tcgggaaacc     420
tgtcgtgcca gctgcattaa tgaatcggcc aacgcgcggg gagaggcggt ttgcgtattg     480
ggcgctcttc cgcttcctcg ctcactgact cgctgcgctc ggtcgttcgg ctgcggcgag     540
cggtatcagc tcactcaaag gcggtaatac ggttatccac agaatcaggg gataacgcag     600
gaaagaacat gtgagcaaaa ggccagcaaa aggccaggaa ccgtaaaaag gccgcgttgc     660
tggcgttttt ccataggctc cgcccccctg acgagcatca caaaaatcga cgctcaagtc     720
agaggtggcg aaacccgaca ggactataaa gataccaggc gtttccccct ggaagctccc     780
tcgtgcgctc tcctgttccg accctgccgc ttaccggata cctgtccgcc tttctccctt     840
cgggaagcgt ggcgctttct catagctcac gctgtaggta tctcagttcg gtgtaggtcg     900
ttcgctccaa gctgggctgt gtgcacgaac cccccgttca gcccgaccgc tgcgccttat     960
ccggtaacta tcgtcttgag tccaacccgg taagacacga cttatcgcca ctggcagcag    1020
ccactggtaa caggattagc agagcgaggt atgtaggcgg tgctacagag ttcttgaagt    1080
ggtggcctaa ctacggctac actagaagga cagtatttgg tatctgcgct ctgctgaagc    1140
cagttacctt cggaaaaaga gttggtagct cttgatccgg caaacaaacc accgctggta    1200
gcggtggttt ttttgtttgc aagcagcaga ttacgcgcag aaaaaaagga tctcaagaag    1260
atcctttgat cttttctacg gggtctgacg ctcagtggaa cgaaaactca cgttaaggga    1320
ttttggtcat gagattatca aaaaggatct cacctagat cctttttaaat taaaaatgaa    1380
gttttaaatc aatctaaagt atatatgagt aaacttggtc tgacagttac caatgcttaa    1440
tcagtgaggc acctatctca gcgatctgtc tatttcgttc atccatagtt gcctgactcc    1500
ccgtcgtgta gataactacg atacgggagg gcttaccatc tggccccagt gctgcaatga    1560
taccgcgaga cccacgctca ccggctccag atttatcagc aataaaccag ccagccggaa    1620
gggccgagcg cagaagtggt cctgcaactt tatccgcctc catccagtct attaattgtt    1680
gccgggaagc tagagtaagt agttcgccag ttaatagttt gcgcaacgtt gttgccattg    1740
ctacaggcat cgtggtgtca cgctcgtcgt ttggtatggc ttcattcagc tccggttccc    1800
aacgatcaag gcgagttaca tgatccccca tgttgtgcaa aaaagcggtt agctccttcg    1860
gtcctccgat cgttgtcaga agtaagttgg ccgcagtgtt atcactcatg gttatggcag    1920
```

```
cactgcataa ttctcttact gtcatgccat ccgtaagatg cttttctgtg actggtgagt    1980
actcaaccaa gtcattctga gaatagtgta tgcggcgacc gagttgctct tgcccggcgt    2040
caatacggga taataccgcg ccacatagca gaactttaaa agtgctcatc attggaaaac    2100
gttcttcggg gcgaaaactc tcaaggatct taccgctgtt gagatccagt tcgatgtaac    2160
ccactcgtgc acccaactga tcttcagcat cttttacttt caccagcgtt tctgggtgag    2220
caaaaacagg aaggcaaaat gccgcaaaaa agggaataag ggcgacacgg aaatgttgaa    2280
tactcatact cttcctttttt caatattatt gaagcattta tcagggttat tgtctcatga    2340
gcggatacat atttgaatgt atttagaaaa ataaacaaat aggggttccg cgcacatttc    2400
cccgaaaagt gccacctgac gcgcctgta gcggcgcatt aagcgcggcg ggtgtggtgg    2460
ttacgcgcag cgtgaccgct acacttgcca gcgccctagc gcccgctcct ttcgctttct    2520
tcccttcctt tctcgccacg ttcgccggct ttccccgtca gctctaaat cggggcctcc    2580 ctttagggtt ccgatttagt gctttacggc acctcgaccc caaaaaactt gattagggtg    2640
atggttcacg tagtgggcca tcgccctgat agacggtttt tcgccctttg acgttggagt    2700
ccacgttctt taatagtgga ctcttgttcc aaactggaac aacactcaac cctatctcgg    2760
tctattcttt tgatttataa gggattttgc cgatttcggc ctattggtta aaaaatgagc    2820
tgatttaaca aaaatttaac gcgaattta acaaaatatt aacgcttaca atttccattc    2880
gccattcagg ctgcgcaact gttgggaagg gcgatcggtg cgggcctctt cgctattacg    2940
ccagctggcg aaaggggat gtgctgcaag gcgattaagt tgggtaacgc cagggttttc    3000
ccagtcacga cgttgtaaaa cgacggccag tgaattgtaa tacgactcac tatagggcga    3060
attgggtacc gggcccccc tcgaggtcga tggtgtcgat aagcttgata tcgaattcat    3120
gtcacacaaa ccgatcttcg cctcaaggaa acctaattct acatccgaga gactgccgag    3180
atccagtcta cactgattaa ttttcgggcc aataatttaa aaaaatcgtg ttatataata    3240
ttatatgtat tatatatata catcatgatg atactgacag tcatgtccca ttgctaaata    3300
gacagactcc atctgccgcc tccaactgat gttctcaata tttaaggggt catctcgcat    3360
tgtttaataa taaacagact ccatctaccg cctccaaatg atgttctcaa atatatttgt    3420
atgaacttat ttttattact tagtattatt agacaactta cttgctttat gaaaacact    3480 tcctatttag gaaacaattt ataatggcag ttcgttcatt taacaattta tgtagaataa    3540
atgttataaa tgcgtatggg aaatcttaaa tatggatagc ataaatgata tctgcattgc    3600
ctaattcgaa atcaacagca acgaaaaaaa tcccttgtac aacataaata gtcatcgaga    3660
aatatcaact atcaaagaac agctattcac acgttactat tgagattatt attggacgag    3720
aatcacacac tcaactgtct ttctctcttc tagaaataca ggtacaagta tgtactattc    3780
tcattgttca tacttctagt catttcatcc cacatattcc ttggatttct ctccaatgaa    3840
tgacattcta tcttgcaaat tcaacaatta taataagata taccaaagta gcggtatagt    3900
ggcaatcaaa aagcttctct ggtgtgcttc tcgtatttat ttttattcta atgatccatt    3960
aaaggtatat atttatttct tgttatataa tccttttgtt tattacatgg gctggataca    4020
taaaggtatt ttgatttaat ttttttgctta aattcaatcc cccctcgttc agtgtcaact    4080
gtaatggtag gaaattacca tacttttgaa gaagcaaaaa aaatgaaaga aaaaaaaat    4140 cgtatttcca ggttagacgt tccgcagaat ctagaatgcg gtatgcggta cattgttctt    4200
cgaacgtaaa agttgcgctc cctgagatat tgtacatttt tgcttttaca agtacaagta    4260
```

```
catcgtacaa ctatgtacta ctgttgatgc atccacaaca gtttgttttg ttttttttttg    4320 ttttttttttt ttctaatgat tcattaccgc tatgtatacc tacttgtact tgtagtaagc    4380
cgggttattg gcgttcaatt aatcatagac ttatgaatct gcacggtgtg cgctgcgagt    4440
tacttttagc ttatgcatgc tacttgggtg taatattggg atctgttcgg aaatcaacgg    4500
atgctcaatc gatttcgaca gtaattaatt aagtcataca caagtcagct ttcttcgagc    4560
ctcatataag tataagtagt tcaacgtatt agcactgtac ccagcatctc cgtatcgaga    4620
aacacaacaa catgccccat tggacagatc atgcggatac acaggttgtg cagtatcata    4680
catactcgat cagacaggtc gtctgaccat catacaagct gaacaagcgc tccatacttg    4740
cacgctctct atatacacag ttaaattaca tatccatagt ctaacctcta acagttaatc    4800
ttctggtaag cctcccagcc agccttctgg tatcgcttgg cctcctcaat aggatctcgg    4860
ttctggccgt acagacctcg gccgacaatt atgatatccg ttccggtaga catgacatcc    4920
tcaacagttc ggtactgctg tccgagagcg tctcccttgt cgtcaagacc cacccgggg    4980 gtcagaataa gccagtcctc agagtcgccc ttaggtcggt tctgggcaat gaagccaacc    5040
acaaactcgg ggtcggatcg ggcaagctca atggtctgct ggagtactc gccagtggcc    5100 agagagccct tgcaagacag ctcggccagc atgagcagac ctctggccag cttctcgttg    5160
ggagagggga ctaggaactc cttgtactgg gagttctcgt agtcagagac gtcctccttc    5220
ttctgttcag agacagtttc ctcggcacca gctcgcaggc cagcaatgat tccggttccg    5280
ggtacaccgt gggcgttggt gatatcggac cactcggcga ttcggtgaca ccggtactgg    5340
tgcttgacag tgttgccaat atctgcgaac tttctgtcct cgaacaggaa gaaaccgtgc    5400
ttaagagcaa gttccttgag ggggagcaca gtgccggcgt aggtgaagtc gtcaatgatg    5460
tcgatatggg ttttgatcat gcacacataa ggtccgacct tatcggcaag ctcaatgagc    5520
tccttggtgg tggtaacatc cagagaagca cacaggttgg ttttcttggc tgccacgagc    5580
ttgagcactc gagcggcaaa gcggacttg tggacgttag ctcgagcttc gtaggagggc    5640
atttgggtgg tgaagaggag actgaaataa atttagtctg cagaactttt tatcggaacc    5700
ttatctgggg cagtgaagta tatgttatgg taatagttac gagttagttg aacttataga    5760
tagactggac tatacggcta tcggtccaaa ttagaaagaa cgtcaatggc tctctgggcg    5820
tcgcctttgc cgacaaaaat gtgatcatga tgaaagccag caatgacgtt gcagctgata    5880
ttgttgtcgg ccaaccgcgc cgaaaacgca gctgtcagac ccacagcctc caacgaagaa    5940
tgtatcgtca aagtgatcca agcacactca tagttggagt cgtactccaa aggcggcaat    6000
gacgagtcag acagatactc gtcgacgttt aaacagtgta cgcagatcta ctatagagga    6060
acatttaaat tgccccggag aagacggcca ggccgcctag atgacaaatt caacaactca    6120
cagctgactt tctgccattg ccactagggg ggggccttt tatatggcca agccaagctc    6180
tccacgtcgg ttgggctgca cccaacaata aatgggtagg gttgcaccaa caagggatg    6240 ggatgggggg tagaagatac gaggataacg gggctcaatg gcacaaataa gaacgaatac    6300
tgccattaag actcgtgatc cagcgactga caccattgca tcatctaagg gcctcaaaac    6360
tacctcggaa ctgctgcgct gatctggaca ccacagaggt tccgagcact ttaggttgca    6420
ccaaatgtcc caccaggtgc aggcagaaaa cgctggaaca gcgtgtacag tttgtcttaa    6480
caaaaagtga gggcgctgag gtcgagcagg gtggtgtgac ttgttatagc ctttagagct    6540
gcgaaagcgc gtatggattt ggctcatcag gccagattga gggtctgtgg acacatgtca    6600
tgttagtgta cttcaatcgc cccctggata tagccccgac aataggccgt ggcctcattt    6660
```

```
tttgccttc cgcacatttc cattgctcga tacccacacc ttgcttctcc tgcacttgcc    6720
aaccttaata ctggtttaca ttgaccaaca tcttacaagc gggggcttg tctagggtat    6780 atataaacag tggctctccc aatcggttgc cagtctcttt tttcctttct ttccccacag   6840
attcgaaatc taaactacac atcacagaat tccgagccgt gagtatccac gacaagatca   6900
gtgtcgagac gacgcgtttt gtgtaatgac acaatccgaa agtcgctagc aacacacact   6960
ctctacacaa actaacccag ctctggtacc atggaggtcg tgaacgaaat cgtctccatt   7020
ggccaggagg ttcttcccaa ggtcgactat gctcagctct ggtctgatgc ctcgcactgc   7080
gaggtgctgt acctctccat cgccttcgtc atcctgaagt tcacccttgg tcctctcgga   7140
cccaagggtc agtctcgaat gaagtttgtg ttcaccaact acaacctgct catgtccatc   7200
tactcgctgg gctccttcct ctctatggcc tacgccatgt acaccattgg tgtcatgtcc   7260
gacaactgcg agaaggcttt cggcaacaat gtcttccgaa tcaccactca gctgttctac   7320
ctcagcaagt cctcgagta cattgactcc ttctatctgc ccctcatggg caagcctctg    7380
acctggttgc agttctttca ccatctcgga gctcctatgg acatgtggct gttctacaac   7440
taccgaaacg aagccgtttg gatctttgtg ctgctcaacg gcttcattca ctggatcatg   7500
tacggctact attggacccg actgatcaag ctcaagttcc ctatgcccaa gtccctgatt   7560
acttctatgc agatcattca gttcaacgtt ggcttctaca tcgtctggaa gtaccggaac   7620
attccctgct accgacaaga tggaatgaga atgtttggct ggttttcaa ctacttctac    7680 gttggtactg tcctgtgtct gttcctcaac ttctacgtgc agacctacat cgtccgaaag   7740
cacaagggag ccaaaaagat tcagtgagc                                    7769

<210> SEQ ID NO 40
<211> LENGTH: 777
<212> TYPE: DNA
<213> ORGANISM: Euglena gracilis
<220> FEATURE:
<221> NAME/KEY: CDS
<222> LOCATION: (1)..(777)
<223> OTHER INFORMATION: mutant delta-9 elongase "EgD9eS-L130M/V243A2"

<400> SEQUENCE: 40 atg gag gtc gtg aac gaa att gtc tcc att ggc cag gag gtt ctt ccc     48
Met Glu Val Val Asn Glu Ile Val Ser Ile Gly Gln Glu Val Leu Pro
1               5                   10                  15 aag gtc gac tat gct cag ctc tgg tct gat gcc tcg cac tgc gag gtg    96
Lys Val Asp Tyr Ala Gln Leu Trp Ser Asp Ala Ser His Cys Glu Val
            20                  25                  30 ctg tac ctc tcc atc gcc ttc gtc atc ctg aag ttc acc ctt ggt cct   144
Leu Tyr Leu Ser Ile Ala Phe Val Ile Leu Lys Phe Thr Leu Gly Pro
        35                  40                  45 ctc gga ccc aag ggt cag tct cga atg aag ttt gtg ttc acc aac tac   192
Leu Gly Pro Lys Gly Gln Ser Arg Met Lys Phe Val Phe Thr Asn Tyr
    50                  55                  60 aac ctg ctc atg tcc atc tac tcg ctg ggc tcc ttc ctc tct atg gcc   240
Asn Leu Leu Met Ser Ile Tyr Ser Leu Gly Ser Phe Leu Ser Met Ala
65                  70                  75                  80 tac gcc atg tac acc att ggt gtc atg tcc gac aac tgc gag aag gct   288
Tyr Ala Met Tyr Thr Ile Gly Val Met Ser Asp Asn Cys Glu Lys Ala
                85                  90                  95 ttc gac aac aat gtc ttc cga atc acc act cag ctg ttc tac ctc agc   336
Phe Asp Asn Asn Val Phe Arg Ile Thr Thr Gln Leu Phe Tyr Leu Ser
            100                 105                 110
```

| | | |
|---|---|---|
| aag ttc ctc gag tac att gac tcc ttc tat ctg ccc ctc atg ggc aag<br>Lys Phe Leu Glu Tyr Ile Asp Ser Phe Tyr Leu Pro Leu Met Gly Lys<br>     115        120        125 | | 384 |
| cct atg acc tgg ttg cag ttc ttt cac cat ctc gga gct cct atg gac<br>Pro Met Thr Trp Leu Gln Phe Phe His His Leu Gly Ala Pro Met Asp<br>130         135        140 | | 432 |
| atg tgg ctg ttc tac aat tac cga aac gaa gcc gtt tgg atc ttt gtg<br>Met Trp Leu Phe Tyr Asn Tyr Arg Asn Glu Ala Val Trp Ile Phe Val<br>145         150        155        160 | | 480 |
| ctg ctc aac ggc ttc att cac tgg atc atg tac ggc tac tat tgg acc<br>Leu Leu Asn Gly Phe Ile His Trp Ile Met Tyr Gly Tyr Tyr Trp Thr<br>         165        170        175 | | 528 |
| cga ctg atc aag ctc aag ttc cct atg ccc aag tcc ctg att act tct<br>Arg Leu Ile Lys Leu Lys Phe Pro Met Pro Lys Ser Leu Ile Thr Ser<br>     180        185        190 | | 576 |
| atg cag atc att cag ttc aac gtt ggc ttc tac atc gtc tgg aag tac<br>Met Gln Ile Ile Gln Phe Asn Val Gly Phe Tyr Ile Val Trp Lys Tyr<br>        195        200        205 | | 624 |
| cgg aac att ccc tgc tac cga caa gat gga atg aga atg ttt ggc tgg<br>Arg Asn Ile Pro Cys Tyr Arg Gln Asp Gly Met Arg Met Phe Gly Trp<br>210         215        220 | | 672 |
| ttt ttc aac tac ttc tac gtt ggt act gtc ctg tgt ctg ttc ctc aac<br>Phe Phe Asn Tyr Phe Tyr Val Gly Thr Val Leu Cys Leu Phe Leu Asn<br>225         230        235        240 | | 720 |
| ttc tac gcg cag acc tac atc gtc cga aag cac aag gga gcc aaa aag<br>Phe Tyr Ala Gln Thr Tyr Ile Val Arg Lys His Lys Gly Ala Lys Lys<br>        245        250        255 | | 768 |
| att cag tga<br>Ile Gln | | 777 |

<210> SEQ ID NO 41
<211> LENGTH: 258
<212> TYPE: PRT
<213> ORGANISM: Euglena gracilis

<400> SEQUENCE: 41

Met Glu Val Val Asn Glu Ile Val Ser Ile Gly Gln Glu Val Leu Pro
1         5         10         15

Lys Val Asp Tyr Ala Gln Leu Trp Ser Asp Ala Ser His Cys Glu Val
        20         25         30

Leu Tyr Leu Ser Ile Ala Phe Val Ile Leu Lys Phe Thr Leu Gly Pro
     35         40         45

Leu Gly Pro Lys Gly Gln Ser Arg Met Lys Phe Val Phe Thr Asn Tyr
  50        55         60

Asn Leu Leu Met Ser Ile Tyr Ser Leu Gly Ser Phe Leu Ser Met Ala
65         70         75         80

Tyr Ala Met Tyr Thr Ile Gly Val Met Ser Asp Asn Cys Glu Lys Ala
        85         90         95

Phe Asp Asn Asn Val Phe Arg Ile Thr Thr Gln Leu Phe Tyr Leu Ser
         100        105        110

Lys Phe Leu Glu Tyr Ile Asp Ser Phe Tyr Leu Pro Leu Met Gly Lys
     115        120        125

Pro Met Thr Trp Leu Gln Phe Phe His His Leu Gly Ala Pro Met Asp
  130        135        140

Met Trp Leu Phe Tyr Asn Tyr Arg Asn Glu Ala Val Trp Ile Phe Val
145         150        155         160

Leu Leu Asn Gly Phe Ile His Trp Ile Met Tyr Gly Tyr Tyr Trp Thr
        165        170        175

```
Arg Leu Ile Lys Leu Lys Phe Pro Met Pro Lys Ser Leu Ile Thr Ser
            180                 185                 190
Met Gln Ile Ile Gln Phe Asn Val Gly Phe Tyr Ile Val Trp Lys Tyr
        195                 200                 205
Arg Asn Ile Pro Cys Tyr Arg Gln Asp Gly Met Arg Met Phe Gly Trp
210                 215                 220
Phe Phe Asn Tyr Phe Tyr Val Gly Thr Val Leu Cys Leu Phe Leu Asn
225                 230                 235                 240
Phe Tyr Ala Gln Thr Tyr Ile Val Arg Lys His Lys Gly Ala Lys Lys
                245                 250                 255
Ile Gln
```

<210> SEQ ID NO 42
<211> LENGTH: 7769
<212> TYPE: DNA
<213> ORGANISM: Artificial Sequence
<220> FEATURE:
<223> OTHER INFORMATION: Plasmid pZuFmEgD9eS-L130M/V243A2

<400> SEQUENCE: 42

```
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc gggcaacggt ttcacttgag tgcagtggct     240
agtgctctta ctcgtacagt gtgcaatact gcgtatcata gtctttgatg tatatcgtat     300
tcattcatgt tagttgcgta cgagccggaa gcataaagtg taaagcctgg ggtgcctaat     360
gagtgagcta actcacatta ttgcgttgc gctcactgcc cgctttccag tcgggaaacc      420
tgtcgtgcca gctgcattaa tgaatcggcc aacgcgcggg gagaggcggt ttgcgtattg     480
ggcgctcttc cgcttcctcg ctcactgact cgctgcgctc ggtcgttcgg ctgcggcgag     540
cggtatcagc tcactcaaag gcggtaatac ggttatccac agaatcaggg gataacgcag     600
gaaagaacat gtgagcaaaa ggccagcaaa aggccaggaa ccgtaaaaag gccgcgttgc     660
tggcgttttt ccataggctc cgcccccctg acgagcatca aaaaatcga cgctcaagtc      720
agaggtggcg aaacccgaca ggactataaa gataccaggc gtttccccct ggaagctccc     780
tcgtgcgctc tcctgttccg accctgccgc ttaccggata cctgtccgcc tttctccctt     840
cgggaagcgt ggcgctttct catagctcac gctgtaggta tctcagttcg gtgtaggtcg     900
ttcgctccaa gctgggctgt gtgcacgaac ccccgttca gcccgaccgc tgcgccttat      960
ccggtaacta tcgtcttgag tccaacccgg taagacacga cttatcgcca ctggcagcag    1020
ccactggtaa caggattagc agagcgaggt atgtaggcgg tgctacagag ttcttgaagt    1080
ggtggcctaa ctacggctac actagaagga cagtatttgg tatctgcgct ctgctgaagc    1140
cagttacctt cggaaaaaga gttggtagct cttgatccgg caaacaaacc accgctggta    1200
gcggtggttt ttttgtttgc aagcagcaga ttacgcgcag aaaaaaagga tctcaagaag    1260
atcctttgat cttttctacg ggtctgacgc tcagtggaa cgaaaactca cgttaaggga     1320
ttttggtcat gagattatca aaaaggatct tcacctagat cctttaaat taaaaatgaa     1380
gttttaaatc aatctaaagt atatatgagt aaacttggtc tgacagttac caatgcttaa    1440
tcagtgaggc acctatctca gcgatctgtc tatttcgttc atccatagtt gcctgactcc    1500
ccgtcgtgta gataactacg atacgggagg gcttaccatc tggccccagt gctgcaatga    1560
```

```
taccgcgaga cccacgctca ccggctccag atttatcagc aataaaccag ccagccggaa    1620
gggccgagcg cagaagtggt cctgcaactt tatccgcctc catccagtct attaattgtt    1680
gccgggaagc tagagtaagt agttcgccag ttaatagttt gcgcaacgtt gttgccattg    1740
ctacaggcat cgtggtgtca cgctcgtcgt ttggtatggc ttcattcagc tccggttccc    1800
aacgatcaag gcgagttaca tgatccccca tgttgtgcaa aaaagcggtt agctccttcg    1860
gtcctccgat cgttgtcaga agtaagttgg ccgcagtgtt atcactctg gttatggcag     1920
cactgcataa ttctcttact gtcatgccat ccgtaagatg cttttctgtg actggtgagt    1980
actcaaccaa gtcattctga gaatagtgta tgcggcgacc gagttgctct gcccggcgt     2040
caatacggga taataccgcg ccacatagca gaactttaaa agtgctcatc attggaaaac    2100
gttcttcggg gcgaaaactc tcaaggatct taccgctgtt gagatccagt tcgatgtaac    2160
ccactcgtgc acccaactga tcttcagcat cttttacttt caccagcgtt tctgggtgag    2220
caaaaacagg aaggcaaaat gccgcaaaaa agggaataag ggcgacacgg aaatgttgaa    2280
tactcatact cttcctttt caatattatt gaagcattta tcagggttat tgtctcatga     2340
gcggatacat atttgaatgt atttagaaaa ataaacaaat aggggttccg cgcacatttc    2400
cccgaaaagt gccacctgac gcgccctgta gcggcgcatt aagcgcggcg ggtgtggtgg    2460
ttacgcgcag cgtgaccgct acacttgcca gcgccctagc gcccgctcct ttcgctttct    2520
tcccttcctt tctcgccacg ttcgccggct ttccccgtca agctctaaat cggggggctcc   2580
ctttagggtt ccgatttagt gctttacggc acctcgaccc caaaaaactt gattagggtg    2640
atggttcacg tagtgggcca tcgccctgat agacggtttt tcgcccttg acgttggagt    2700
ccacgttctt taatagtgga ctcttgttcc aaactggaac aacactcaac cctatctcgg    2760
tctattcttt tgatttataa gggatttttgc cgatttcggc ctattggtta aaaatgagc    2820
tgatttaaca aaaatttaac gcgaattta acaaaatatt aacgcttaca atttccattc     2880
gccattcagg ctgcgcaact gttgggaagg gcgatcggtg cgggcctctt cgctattacg    2940
ccagctggcg aaaggggat gtgctgcaag gcgattaagt tgggtaacgc cagggttttc     3000
ccagtcacga cgttgtaaaa cgacggccag tgaattgtaa tacgactcac tatagggcga    3060
attgggtacc gggccccccc tcgaggtcga tggtgtcgat aagcttgata tcgaattcat    3120
gtcacacaaa ccgatcttcg cctcaaggaa acctaattct acatccgaga gactgccgag    3180
atccagtcta cactgattaa ttttcgggcc aataatttaa aaaatcgtg ttatataata     3240
ttatatgtat tatatatata catcatgatg atactgacag tcatgtccca ttgctaaata    3300
gacagactcc atctgccgcc tccaactgat gttctcaata tttaaggggt catctcgcat    3360
tgtttaataa taaacagact ccatctaccg cctccaaatg atgttctcaa aatatattgt    3420
atgaacttat ttttattact tagtattatt agacaactta cttgctttat gaaaaacact    3480
tcctatttag gaaacaattt ataatggcag ttcgttcatt taacaattta tgtagaataa    3540
atgttataaa tgcgtatggg aaatcttaaa tatggatagc ataaatgata tctgcattgc    3600
ctaattcgaa atcaacagca acgaaaaaaa tcccttgtac aacataaata gtcatcgaga    3660
aatatcaact atcaaagaac agctattcac acgttactat tgagattatt attggacgag    3720
aatcacacac tcaactgtct ttctctcttc tagaaataca ggtacaagta tgtactattc    3780
tcattgttca tacttctagt catttcatcc cacatattcc ttggatttct ctccaatgaa    3840
tgacattcta tcttgcaaat tcaacaatta taataagata taccaaagta gcggtatagt    3900
```

```
ggcaatcaaa aagcttctct ggtgtgcttc tcgtatttat ttttattcta atgatccatt    3960
aaaggtatat atttatttct tgttatataa tccttttgtt tattacatgg gctggataca    4020
taaaggtatt ttgatttaat tttttgctta aattcaatcc ccctcgttc agtgtcaact     4080 gtaatggtag gaaattacca tacttttgaa gaagcaaaaa aaatgaaaga aaaaaaaaat    4140
cgtatttcca ggttagacgt tccgcagaat ctagaatgcg gtatgcggta cattgttctt    4200
cgaacgtaaa agttgcgctc cctgagatat tgtacatttt tgcttttaca agtacaagta    4260
catcgtacaa ctatgtacta ctgttgatgc atccacaaca gtttgttttg ttttttttg    4320 ttttttttt ttctaatgat tcattaccgc tatgtatacc tacttgtact tgtagtaagc     4380
cgggttattg gcgttcaatt aatcatagac ttatgaatct gcacggtgtg cgctgcgagt    4440
tacttttagc ttatgcatgc tacttgggtg taatattggg atctgttcgg aaatcaacgg    4500
atgctcaatc gatttcgaca gtaattaatt aagtcataca caagtcagct ttcttcgagc    4560
ctcatataag tataagtagt tcaacgtatt agcactgtac ccagcatctc cgtatcgaga    4620
aacacaacaa catgccccat tggacagatc atgcggatac acaggttgtg cagtatcata    4680
catactcgat cagacaggtc gtctgaccat catacaagct gaacaagcgc tccatacttg    4740
cacgctctct atatacacag ttaaattaca tatccatagt ctaacctcta acagttaatc    4800
ttctggtaag cctcccagcc agccttctgg tatcgcttgg cctcctcaat aggatctcgg    4860
ttctggccgt acagacctcg gccgacaatt atgatatccg ttccggtaga catgacatcc    4920
tcaacagttc ggtactgctg tccgagagcg tctcccttgt cgtcaagacc cacccgggg    4980 gtcagaataa gccagtcctc agagtcgccc ttaggtcggt tctgggcaat gaagccaacc    5040
acaaactcgg ggtcggatcg ggcaagctca atggtctgct ggagtactc gccagtggcc    5100 agagagccct tgcaagacag ctcggccagc atgagcagac ctctggccag cttctcgttg    5160
ggagagggga ctaggaactc cttgtactgg gagttctcgt agtcagagac gtcctccttc    5220
ttctgttcag agacagtttc ctcggcacca gctcgcaggc cagcaatgat tccgttccg    5280 ggtacaccgt gggcgttggt gatatcggac cactcggcga ttcggtgaca ccggtactgg    5340
tgcttgacag tgttgccaat atctgcgaac tttctgtcct cgaacaggaa gaaaccgtgc    5400
ttaagagcaa gttccttgag ggggagcaca gtgccggcgt aggtgaagtc gtcaatgatg    5460
tcgatatggg ttttgatcat gcacacataa ggtccgacct tatcggcaag ctcaatgagc    5520
tccttggtgg tggtaacatc cagagaagca cacaggttgg ttttcttggc tgccacgagc    5580
ttgagcactc gagcggcaaa ggcggacttg tggacgttag ctcgagcttc gtaggagggc    5640
attttggtgg tgaagaggag actgaaataa atttagtctg cagaactttt tatcggaacc    5700
ttatctgggg cagtgaagta tatgttatgg taatagttac gagttagttg aacttataga    5760
tagactggac tatacggcta tcggtccaaa ttagaaagaa cgtcaatggc tctctgggcg    5820 tcgccttgc cgacaaaaat gtgatcatga tgaaagccag caatgacgtt gcagctgata    5880
ttgttgtcgg ccaaccgcgc cgaaaacgca gctgtcagac ccacagcctc caacgaagaa    5940
tgtatcgtca aagtgatcca agcacactca tagttggagt cgtactccaa aggcggcaat    6000
gacgagtcag acagatactc gtcgacgttt aaacagtgta cgcagatcta ctatagagga    6060
acatttaaat tgccccggag aagacggcca ggccgcctag atgacaaatt caacaactca    6120
cagctgactt tctgccattg ccactagggg ggggccttt tatatggcca agccaagctc     6180
tccacgtcgg ttgggctgca cccaacaata aatgggtagg gttgcaccaa caagggatg     6240 ggatggggg tagaagatac gaggataacg gggctcaatg gcacaaataa gaacgaatac     6300
```

```
tgccattaag actcgtgatc cagcgactga caccattgca tcatctaagg gcctcaaaac   6360
tacctcggaa ctgctgcgct gatctggaca ccacagaggt tccgagcact ttaggttgca   6420
ccaaatgtcc caccaggtgc aggcagaaaa cgctggaaca gcgtgtacag tttgtcttaa   6480
caaaaagtga gggcgctgag gtcgagcagg gtggtgtgac ttgttatagc ctttagagct   6540
gcgaaagcgc gtatggattt ggctcatcag gccagattga gggtctgtgg acacatgtca   6600
tgttagtgta cttcaatcgc ccctggata tagccccgac aataggccgt ggcctcattt   6660
ttttgccttc cgcacatttc cattgctcga tacccacacc ttgcttctcc tgcacttgcc   6720
aaccttaata ctggtttaca ttgaccaaca tcttacaagc gggggcttg tctagggtat   6780
atataaacag tggctctccc aatcggttgc cagtctcttt tttcctttct ttccccacag   6840
attcgaaatc taaactacac atcacagaat tccgagccgt gagtatccac gacaagatca   6900
gtgtcgagac gacgcgtttt gtgtaatgac acaatccgaa agtcgctagc aacacacact   6960
ctctacacaa actaacccag ctctggtacc atggaggtcg tgaacgaaat tgtctccatt   7020
ggccaggagg ttcttcccaa ggtcgactat gctcagctct ggtctgatgc ctcgcactgc   7080
gaggtgctgt acctctccat cgccttcgtc atcctgaagt tcacccttgg tcctctcgga   7140
cccaagggtc agtctcgaat gaagtttgtg ttcaccaact acaacctgct catgtccatc   7200
tactcgctgg gctccttcct ctctatggcc tacgccatgt acaccattgg tgtcatgtcc   7260
gacaactgcg agaaggcttt cgacaacaat gtcttccgaa tcaccactca gctgttctac   7320
ctcagcaagt cctcgagta cattgactcc ttctatctgc ccctcatggg caagcctatg   7380
acctggttgc agttctttca ccatctcgga gctcctatgg acatgtggct gttctacaat   7440
taccgaaacg aagccgtttg gatctttgtg ctgctcaacg gcttcattca ctggatcatg   7500
tacggctact attggacccg actgatcaag ctcaagttcc ctatgcccaa gtccctgatt   7560
acttctatgc agatcattca gttcaacgtt ggcttctaca tcgtctggaa gtaccggaac   7620
attccctgct accgacaaga tggaatgaga atgtttggct ggttttttcaa ctacttctac   7680
gttggtactg tcctgtgtct gttcctcaac ttctacgcgc agacctacat cgtccgaaag   7740
cacaagggag ccaaaaagat tcagtgagc                                     7769
```

<210> SEQ ID NO 43
<211> LENGTH: 289
<212> TYPE: PRT
<213> ORGANISM: Ciona intestinalis

<400> SEQUENCE: 43

```
Met Asp Val Leu His Arg Phe Leu Gly Phe Tyr Glu Trp Thr Leu Thr
1               5                   10                  15

Phe Ala Asp Pro Arg Val Ala Lys Trp Pro Leu Ile Glu Asn Pro Leu
            20                  25                  30

Pro Thr Ile Ala Ile Val Leu Leu Tyr Leu Ala Phe Val Leu Tyr Ile
        35                  40                  45

Gly Pro Arg Phe Met Arg Lys Arg Ala Pro Val Asp Phe Gly Leu Phe
    50                  55                  60

Leu Pro Gly Tyr Asn Phe Ala Leu Val Ala Leu Asn Tyr Tyr Ile Leu
65                  70                  75                  80

Gln Glu Val Val Thr Gly Ser Tyr Gly Ala Gly Tyr Asp Leu Val Cys
                85                  90                  95

Thr Pro Leu Arg Ser Asp Ser Tyr Asp Pro Asn Glu Met Lys Val Ala
            100                 105                 110
```

```
Asn Ala Val Trp Trp Tyr Tyr Val Ser Lys Ile Ile Glu Leu Phe Asp
            115                 120                 125

Thr Val Leu Phe Thr Leu Arg Lys Arg Asp Arg Gln Val Thr Phe Leu
130                 135                 140

His Val Tyr His His Ser Thr Met Pro Leu Leu Trp Trp Ile Gly Ala
145                 150                 155                 160

Lys Trp Val Pro Gly Gly Gln Ser Phe Val Gly Ile Ile Leu Asn Ser
                165                 170                 175

Ser Val His Val Ile Met Tyr Thr Tyr Tyr Gly Leu Ser Ala Leu Gly
            180                 185                 190

Pro His Met Gln Lys Phe Leu Trp Trp Lys Lys Tyr Ile Thr Met Leu
            195                 200                 205

Gln Leu Val Gln Phe Val Leu Ala Ile Tyr His Thr Ala Arg Ser Leu
210                 215                 220

Tyr Val Lys Cys Pro Ser Pro Val Trp Met His Trp Ala Leu Ile Leu
225                 230                 235                 240

Tyr Ala Phe Ser Phe Ile Leu Leu Phe Ser Asn Phe Tyr Met His Ala
                245                 250                 255

Tyr Ile Lys Lys Ser Arg Lys Gly Lys Glu Asn Gly Ser Arg Gly Lys
            260                 265                 270

Gly Gly Val Ser Asn Gly Lys Glu Lys Leu His Ala Asn Gly Lys Thr
            275                 280                 285

Asp

<210> SEQ ID NO 44
<211> LENGTH: 295
<212> TYPE: PRT
<213> ORGANISM: Oncorhynchus mykiss

<400> SEQUENCE: 44

Met Glu Thr Phe Asn Tyr Lys Leu Asn Met Tyr Ile Asp Ser Trp Met
1               5                   10                  15

Gly Pro Arg Asp Glu Arg Val Gln Gly Trp Leu Leu Leu Asp Asn Tyr
            20                  25                  30

Pro Pro Thr Phe Ala Leu Thr Val Met Tyr Leu Leu Ile Val Trp Met
        35                  40                  45

Gly Pro Lys Tyr Met Arg His Arg Gln Pro Val Ser Cys Arg Gly Leu
    50                  55                  60

Leu Leu Val Tyr Asn Leu Gly Leu Thr Ile Leu Ser Phe Tyr Met Phe
65                  70                  75                  80

Tyr Glu Met Val Ser Ala Val Trp His Gly Asp Tyr Asn Phe Phe Cys
                85                  90                  95

Gln Asp Thr His Ser Ala Gly Glu Thr Asp Thr Lys Ile Ile Asn Val
            100                 105                 110

Leu Trp Trp Tyr Tyr Phe Ser Lys Leu Ile Glu Phe Met Asp Thr Phe
        115                 120                 125

Phe Phe Ile Leu Arg Lys Asn Asn His Gln Ile Thr Phe Leu His Ile
130                 135                 140

Tyr His His Ala Ser Met Leu Asn Ile Trp Trp Phe Val Met Asn Trp
145                 150                 155                 160

Val Pro Cys Gly His Ser Tyr Phe Gly Ala Ser Leu Asn Ser Phe Ile
                165                 170                 175

His Val Leu Met Tyr Ser Tyr Tyr Gly Leu Ser Ala Val Pro Ala Leu
            180                 185                 190
```

```
Arg Pro Tyr Leu Trp Trp Lys Lys Tyr Ile Thr Gln Val Gln Leu Ile
            195                 200                 205

Gln Phe Phe Leu Thr Met Ser Gln Thr Ile Cys Ala Val Ile Trp Pro
        210                 215                 220

Cys Asp Phe Pro Arg Gly Trp Leu Tyr Phe Gln Ile Phe Tyr Val Ile
225                 230                 235                 240

Thr Leu Ile Ala Leu Phe Ser Asn Phe Tyr Ile Gln Thr Tyr Lys Lys
                245                 250                 255

His Leu Val Ser Gln Lys Lys Glu Tyr His Gln Asn Gly Ser Val Ala
            260                 265                 270

Ser Leu Asn Gly His Val Asn Gly Val Thr Pro Thr Glu Thr Ile Thr
        275                 280                 285

His Arg Lys Val Arg Gly Asp
    290                 295

<210> SEQ ID NO 45
<211> LENGTH: 290
<212> TYPE: PRT
<213> ORGANISM: Marchantia polymorpha

<400> SEQUENCE: 45

Met Glu Ala Tyr Glu Met Val Asp Ser Phe Val Ser Lys Thr Val Phe
1               5                   10                  15

Glu Thr Leu Gln Arg Leu Arg Gly Gly Val Val Leu Thr Glu Ser Ala
            20                  25                  30

Ile Thr Lys Gly Leu Pro Cys Val Asp Ser Pro Thr Pro Ile Val Leu
        35                  40                  45

Gly Leu Ser Ser Tyr Leu Thr Phe Val Phe Leu Gly Leu Ile Val Ile
    50                  55                  60

Lys Ser Leu Asp Leu Lys Pro Arg Ser Lys Glu Pro Ala Ile Leu Asn
65                  70                  75                  80

Leu Phe Val Ile Phe His Asn Phe Val Cys Phe Ala Leu Ser Leu Tyr
                85                  90                  95

Met Cys Val Gly Ile Val Arg Gln Ala Ile Leu Asn Arg Tyr Ser Leu
            100                 105                 110

Trp Gly Asn Ala Tyr Asn Pro Lys Glu Val Gln Met Gly His Leu Leu
        115                 120                 125

Tyr Ile Phe Tyr Met Ser Lys Tyr Ile Glu Phe Met Asp Thr Val Ile
    130                 135                 140

Met Ile Leu Lys Arg Asn Thr Arg Gln Ile Thr Val Leu His Val Tyr
145                 150                 155                 160

His His Ala Ser Ile Ser Phe Ile Trp Trp Ile Ile Ala Tyr His Ala
                165                 170                 175

Pro Gly Gly Glu Ala Tyr Phe Ser Ala Ala Leu Asn Ser Gly Val His
            180                 185                 190

Val Leu Met Tyr Leu Tyr Tyr Leu Leu Ala Ala Thr Leu Gly Lys Asn
        195                 200                 205

Glu Lys Ala Arg Arg Lys Tyr Leu Trp Trp Gly Lys Tyr Leu Thr Gln
    210                 215                 220

Leu Gln Met Phe Gln Phe Val Leu Asn Met Ile Gln Ala Tyr Tyr Asp
225                 230                 235                 240

Ile Lys Asn Asn Ser Pro Tyr Pro Gln Phe Leu Ile Gln Ile Leu Phe
                245                 250                 255

Tyr Tyr Met Ile Ser Leu Leu Ala Leu Phe Gly Asn Phe Tyr Val His
```

260                 265                 270
Lys Tyr Val Ser Ala Pro Ala Lys Pro Ala Lys Ile Lys Ser Lys Lys
            275                 280                 285

Ala Glu
    290

<210> SEQ ID NO 46
<211> LENGTH: 290
<212> TYPE: PRT
<213> ORGANISM: Physcomitrella patens

<400> SEQUENCE: 46

Met Glu Val Val Glu Arg Phe Tyr Gly Glu Leu Asp Gly Lys Val Ser
1               5                   10                  15

Gln Gly Val Asn Ala Leu Leu Gly Ser Phe Gly Val Glu Leu Thr Asp
            20                  25                  30

Thr Pro Thr Thr Lys Gly Leu Pro Leu Val Asp Ser Pro Thr Pro Ile
        35                  40                  45

Val Leu Gly Val Ser Val Tyr Leu Thr Ile Val Ile Gly Gly Leu Leu
    50                  55                  60

Trp Ile Lys Ala Arg Asp Leu Lys Pro Arg Ala Ser Glu Pro Phe Leu
65                  70                  75                  80

Leu Gln Ala Leu Val Leu Val His Asn Leu Phe Cys Phe Ala Leu Ser
                85                  90                  95

Leu Tyr Met Cys Val Gly Ile Ala Tyr Gln Ala Ile Thr Trp Arg Tyr
            100                 105                 110

Ser Leu Trp Gly Asn Ala Tyr Asn Pro Lys His Lys Glu Met Ala Ile
        115                 120                 125

Leu Val Tyr Leu Phe Tyr Met Ser Lys Tyr Val Glu Phe Met Asp Thr
    130                 135                 140

Val Ile Met Ile Leu Lys Arg Ser Thr Arg Gln Ile Ser Phe Leu His
145                 150                 155                 160

Val Tyr His His Ser Ser Ile Ser Leu Ile Trp Trp Ala Ile Ala His
                165                 170                 175

His Ala Pro Gly Gly Glu Ala Tyr Trp Ser Ala Ala Leu Asn Ser Gly
            180                 185                 190

Val His Val Leu Met Tyr Ala Tyr Tyr Phe Leu Ala Ala Cys Leu Arg
        195                 200                 205

Ser Ser Pro Lys Leu Lys Asn Lys Tyr Leu Phe Trp Gly Arg Tyr Leu
    210                 215                 220

Thr Gln Phe Gln Met Phe Gln Phe Met Leu Asn Leu Val Gln Ala Tyr
225                 230                 235                 240

Tyr Asp Met Lys Thr Asn Ala Pro Tyr Pro Gln Trp Leu Ile Lys Ile
                245                 250                 255

Leu Phe Tyr Tyr Met Ile Ser Leu Leu Phe Leu Phe Gly Asn Phe Tyr
            260                 265                 270

Val Gln Lys Tyr Ile Lys Pro Ser Asp Gly Lys Gln Lys Gly Ala Lys
        275                 280                 285

Thr Glu
    290

<210> SEQ ID NO 47
<211> LENGTH: 348
<212> TYPE: PRT
<213> ORGANISM: Marchantia polymorpha -continued

```
<400> SEQUENCE: 47

Met Ala Thr Lys Ser Gly Ser Gly Leu Leu Glu Trp Ile Ala Val Ala
1               5                   10                  15

Ala Lys Met Lys Gln Ala Arg Ser Ser Pro Glu Gly Glu Ile Val Gly
            20                  25                  30

Gly Asn Arg Met Gly Ser Gly Asn Gly Ala Glu Trp Thr Thr Ser Leu
        35                  40                  45

Ile His Ala Phe Leu Asn Ala Thr Asn Gly Lys Ser Gly Gly Ala Ser
50                  55                  60

Lys Val Arg Pro Leu Glu Glu Arg Ile Gly Glu Ala Val Phe Arg Val
65                  70                  75                  80

Leu Glu Asp Val Val Gly Val Asp Ile Arg Lys Pro Asn Pro Val Thr
                85                  90                  95

Lys Asp Leu Pro Met Val Glu Ser Pro Val Pro Val Leu Ala Cys Ile
            100                 105                 110

Ser Leu Tyr Leu Leu Val Val Trp Leu Trp Ser Ser His Ile Lys Ala
        115                 120                 125

Ser Gly Gln Lys Pro Arg Lys Glu Asp Pro Leu Ala Leu Arg Cys Leu
130                 135                 140

Val Ile Ala His Asn Leu Phe Leu Cys Cys Leu Ser Leu Phe Met Cys
145                 150                 155                 160

Val Gly Leu Ile Ala Ala Arg His Tyr Gly Tyr Ser Val Trp Gly
                165                 170                 175

Asn Tyr Tyr Arg Glu Arg Glu Pro Ala Met Asn Leu Leu Ile Tyr Val
            180                 185                 190

Phe Tyr Met Ser Lys Leu Tyr Glu Phe Met Asp Thr Ala Ile Met Leu
        195                 200                 205

Phe Arg Arg Asn Leu Arg Gln Val Thr Tyr Leu His Val Tyr His His
210                 215                 220

Ala Ser Ile Ala Met Ile Trp Trp Ile Ile Cys Tyr Arg Phe Pro Gly
225                 230                 235                 240

Ala Asp Ser Tyr Phe Ser Ala Ala Phe Asn Ser Cys Ile His Val Ala
                245                 250                 255

Met Tyr Leu Tyr Tyr Leu Leu Ala Ala Thr Val Ala Arg Asp Glu Lys
            260                 265                 270

Arg Arg Arg Lys Tyr Leu Phe Trp Gly Lys Tyr Leu Thr Ile Ile Gln
        275                 280                 285

Met Leu Gln Phe Leu Ser Phe Ile Gly Gln Ala Ile Tyr Ala Met Trp
290                 295                 300

Lys Phe Glu Tyr Tyr Pro Lys Gly Phe Gly Arg Met Leu Phe Phe Tyr
305                 310                 315                 320

Ser Val Ser Leu Leu Ala Phe Phe Gly Asn Phe Val Lys Lys Tyr
                325                 330                 335

Ser Asn Ala Ser Gln Pro Lys Thr Val Lys Val Glu
            340                 345

<210> SEQ ID NO 48
<211> LENGTH: 292
<212> TYPE: PRT
<213> ORGANISM: Ostreococcus tauri

<400> SEQUENCE: 48

Met Ser Gly Leu Arg Ala Pro Asn Phe Leu His Arg Phe Trp Thr Lys
1               5                   10                  15
```

```
Trp Asp Tyr Ala Ile Ser Lys Val Val Phe Thr Cys Ala Asp Ser Phe
             20                  25                  30

Gln Trp Asp Ile Gly Pro Val Ser Ser Thr Ala His Leu Pro Ala
         35                  40                  45

Ile Glu Ser Pro Thr Pro Leu Val Thr Ser Leu Leu Phe Tyr Leu Val
 50                  55                  60

Thr Val Phe Leu Trp Tyr Gly Arg Leu Thr Arg Ser Ser Asp Lys Lys
 65                  70                  75                  80

Ile Arg Glu Pro Thr Trp Leu Arg Arg Phe Ile Ile Cys His Asn Ala
                 85                  90                  95

Phe Leu Ile Val Leu Ser Leu Tyr Met Cys Leu Gly Cys Val Ala Gln
                100                 105                 110

Ala Tyr Gln Asn Gly Tyr Thr Leu Trp Gly Asn Glu Phe Lys Ala Thr
            115                 120                 125

Glu Thr Gln Leu Ala Leu Tyr Ile Tyr Ile Phe Tyr Val Ser Lys Ile
            130                 135                 140

Tyr Glu Phe Val Asp Thr Tyr Ile Met Leu Leu Lys Asn Asn Leu Arg
145                 150                 155                 160

Gln Val Ser Phe Leu His Ile Tyr His His Ser Thr Ile Ser Phe Ile
                165                 170                 175

Trp Trp Ile Ile Ala Arg Arg Ala Pro Gly Gly Asp Ala Tyr Phe Ser
            180                 185                 190

Ala Ala Leu Asn Ser Trp Val His Val Cys Met Tyr Thr Tyr Tyr Leu
            195                 200                 205

Leu Ser Thr Leu Ile Gly Lys Glu Asp Pro Lys Arg Ser Asn Tyr Leu
210                 215                 220

Trp Trp Gly Arg His Leu Thr Gln Met Gln Met Leu Gln Phe Phe Phe
225                 230                 235                 240

Asn Val Leu Gln Ala Leu Tyr Cys Ala Ser Phe Ser Thr Tyr Pro Lys
                245                 250                 255

Phe Leu Ser Lys Ile Leu Leu Val Tyr Met Met Ser Leu Leu Gly Leu
                260                 265                 270

Phe Gly His Phe Tyr Tyr Ser Lys His Ile Ala Ala Ala Lys Leu Gln
                275                 280                 285

Lys Lys Gln Gln
        290

<210> SEQ ID NO 49
<211> LENGTH: 277
<212> TYPE: PRT
<213> ORGANISM: Pavlova sp.

<400> SEQUENCE: 49

Met Met Leu Ala Ala Gly Tyr Leu Leu Val Leu Ser Ala Ala Arg Gln
 1               5                  10                  15

Ser Phe Gln Gln Asp Ile Asp Asn Pro Asn Gly Ala Tyr Ser Thr Ser
             20                  25                  30

Trp Thr Gly Leu Pro Ile Val Met Ser Val Val Tyr Leu Ser Gly Val
         35                  40                  45

Phe Gly Leu Thr Lys Tyr Phe Glu Asn Arg Lys Pro Met Thr Gly Leu
     50                  55                  60

Lys Asp Tyr Met Phe Thr Tyr Asn Leu Tyr Gln Val Ile Ile Asn Val
 65                  70                  75                  80

Trp Cys Val Val Ala Phe Leu Leu Glu Val Arg Arg Ala Gly Met Ser
                 85                  90                  95
```

-continued

```
Leu Ile Gly Asn Lys Val Asp Leu Gly Pro Asn Ser Phe Arg Leu Gly
            100                 105                 110

Phe Val Thr Trp Val His Tyr Asn Asn Lys Tyr Val Glu Leu Leu Asp
        115                 120                 125

Thr Leu Trp Met Val Leu Arg Lys Lys Thr Gln Gln Val Ser Phe Leu
    130                 135                 140

His Val Tyr His His Val Leu Leu Met Trp Ala Trp Phe Val Val
145                 150                 155                 160

Lys Leu Gly Asn Gly Gly Asp Ala Tyr Phe Gly Gly Leu Met Asn Ser
                165                 170                 175

Ile Ile His Val Met Met Tyr Ser Tyr Tyr Thr Met Ala Leu Leu Gly
            180                 185                 190

Trp Ser Cys Pro Trp Lys Arg Tyr Leu Thr Gln Ala Gln Leu Val Gln
        195                 200                 205

Phe Cys Ile Cys Leu Ala His Ser Thr Trp Ala Ala Val Thr Gly Ala
    210                 215                 220

Tyr Pro Trp Arg Ile Cys Leu Val Glu Val Trp Val Met Val Ser Met
225                 230                 235                 240

Leu Val Leu Phe Thr Arg Phe Tyr Arg Gln Ala Tyr Ala Lys Glu Ala
                245                 250                 255

Lys Ala Lys Glu Ala Lys Lys Leu Ala Gln Glu Ala Ser Gln Ala Lys
            260                 265                 270

Ala Val Lys Ala Glu
            275

<210> SEQ ID NO 50
<211> LENGTH: 302
<212> TYPE: PRT
<213> ORGANISM: Rebecca salina

<400> SEQUENCE: 50

Met Lys Ala Ala Ala Gly Lys Val Gln Gln Glu Ala Glu Arg Leu Thr
1               5                   10                  15

Ala Gly Leu Trp Leu Pro Met Met Leu Ala Ala Gly Tyr Leu Leu Val
            20                  25                  30

Leu Ser Ala Asn Arg Ala Ser Phe Tyr Glu Asn Ile Asn Asn Glu Lys
        35                  40                  45

Gly Ala Tyr Ser Thr Ser Trp Phe Ser Leu Pro Cys Val Met Thr Ala
    50                  55                  60

Val Tyr Leu Gly Gly Val Phe Gly Leu Thr Lys Tyr Phe Glu Gly Arg
65                  70                  75                  80

Lys Pro Met Gln Gly Leu Lys Asp Tyr Met Phe Thr Tyr Asn Leu Tyr
                85                  90                  95

Gln Val Ile Ile Asn Val Trp Cys Ile Ala Ala Phe Val Glu Val
            100                 105                 110

Arg Arg Ala Gly Met Ser Ala Val Gly Asn Lys Val Asp Leu Gly Pro
        115                 120                 125

Asn Ser Phe Arg Leu Gly Phe Val Thr Trp Val His Tyr Asn Asn Lys
    130                 135                 140

Tyr Val Glu Leu Leu Asp Thr Leu Trp Met Val Leu Arg Lys Lys Thr
145                 150                 155                 160

Gln Gln Val Ser Phe Leu His Val Tyr His His Val Leu Leu Ile Trp
                165                 170                 175

Ala Trp Phe Cys Val Val Lys Phe Cys Asn Gly Gly Asp Ala Tyr Phe
```

```
                180             185             190
Gly Gly Met Leu Asn Ser Ile Ile His Val Met Met Tyr Ser Tyr Tyr
            195             200             205
Thr Met Ala Leu Leu Gly Trp Ser Cys Pro Trp Lys Arg Tyr Leu Thr
        210             215             220
Gln Ala Gln Leu Val Gln Phe Cys Ile Cys Leu Ala His Ala Thr Trp
225             230             235             240
Ala Ala Ala Thr Gly Val Tyr Pro Phe His Ile Cys Leu Val Glu Ile
            245             250             255
Trp Val Met Val Ser Met Leu Tyr Leu Phe Thr Lys Phe Tyr Asn Ser
        260             265             270
Ala Tyr Lys Gly Ala Ala Lys Gly Ala Ala Ala Ser Ser Asn Gly Ala
            275             280             285
Ala Ala Pro Ser Gly Ala Lys Pro Lys Ser Ile Lys Ala Asn
        290             295             300

<210> SEQ ID NO 51
<211> LENGTH: 300
<212> TYPE: PRT
<213> ORGANISM: Ostreococcus tauri

<400> SEQUENCE: 51

Met Ser Ala Ser Gly Ala Leu Leu Pro Ala Ile Ala Ser Ala Ala Tyr
1               5                   10                  15
Ala Tyr Ala Thr Tyr Ala Tyr Ala Phe Glu Trp Ser His Ala Asn Gly
            20                  25                  30
Ile Asp Asn Val Asp Ala Arg Glu Trp Ile Gly Ala Leu Ser Leu Arg
        35                  40                  45
Leu Pro Ala Ile Ala Thr Thr Met Tyr Leu Leu Phe Cys Leu Val Gly
    50                  55                  60
Pro Arg Leu Met Ala Lys Arg Glu Ala Phe Asp Pro Lys Gly Phe Met
65                  70                  75                  80
Leu Ala Tyr Asn Ala Tyr Gln Thr Ala Phe Asn Val Val Leu Gly
            85                  90                  95
Met Phe Ala Arg Glu Ile Ser Gly Leu Gly Gln Pro Val Trp Gly Ser
            100             105             110
Thr Met Pro Trp Ser Asp Arg Lys Ser Phe Lys Ile Leu Leu Gly Val
        115             120             125
Trp Leu His Tyr Asn Asn Lys Tyr Leu Glu Leu Leu Asp Thr Val Phe
    130             135             140
Met Val Ala Arg Lys Lys Thr Lys Gln Leu Ser Phe Leu His Val Tyr
145             150             155             160
His His Ala Leu Leu Ile Trp Ala Trp Trp Leu Val Cys His Leu Met
            165             170             175
Ala Thr Asn Asp Cys Ile Asp Ala Tyr Phe Gly Ala Ala Cys Asn Ser
        180             185             190
Phe Ile His Ile Val Met Tyr Ser Tyr Tyr Leu Met Ser Ala Leu Gly
    195             200             205
Ile Arg Cys Pro Trp Lys Arg Tyr Ile Thr Gln Ala Gln Met Leu Gln
    210             215             220
Phe Val Ile Val Phe Ala His Ala Val Phe Val Leu Arg Gln Lys His
225             230             235             240
Cys Pro Val Thr Leu Pro Trp Ala Gln Met Phe Val Met Thr Asn Met
            245             250             255
```

```
Leu Val Leu Phe Gly Asn Phe Tyr Leu Lys Ala Tyr Ser Asn Lys Ser
                260                 265                 270

Arg Gly Asp Gly Ala Ser Ser Val Lys Pro Ala Glu Thr Thr Arg Ala
            275                 280                 285

Pro Ser Val Arg Arg Thr Arg Ser Arg Lys Ile Asp
        290                 295                 300

<210> SEQ ID NO 52
<211> LENGTH: 358
<212> TYPE: PRT
<213> ORGANISM: Thalassiosira pseudonana

<400> SEQUENCE: 52

Met Cys Ser Ser Pro Ser Gln Ser Lys Thr Thr Ser Leu Leu Ala
1               5                   10                  15

Arg Tyr Thr Thr Ala Ala Leu Leu Leu Thr Leu Thr Trp Cys
            20                  25                  30

His Phe Ala Phe Pro Ala Ala Thr Ala Thr Pro Gly Leu Thr Ala Glu
            35                  40                  45

Met His Ser Tyr Lys Val Pro Leu Gly Leu Thr Val Phe Tyr Leu Leu
    50                  55                  60

Ser Leu Pro Ser Leu Lys Tyr Val Thr Asp Asn Tyr Leu Ala Lys Lys
65                  70                  75                  80

Tyr Asp Met Lys Ser Leu Leu Thr Glu Ser Met Val Leu Tyr Asn Val
                85                  90                  95

Ala Gln Val Leu Leu Asn Gly Trp Thr Val Tyr Ala Ile Val Asp Ala
            100                 105                 110

Val Met Asn Arg Asp His Pro Phe Ile Gly Ser Arg Ser Leu Val Gly
        115                 120                 125

Ala Ala Leu His Ser Gly Ser Ser Tyr Ala Val Trp Val His Tyr Cys
    130                 135                 140

Asp Lys Tyr Leu Glu Phe Phe Asp Thr Tyr Phe Met Val Leu Arg Gly
145                 150                 155                 160

Lys Met Asp Gln Val Ser Phe Leu His Ile Tyr His His Thr Thr Ile
                165                 170                 175

Ala Trp Ala Trp Trp Ile Ala Leu Arg Phe Ser Pro Gly Gly Asp Ile
            180                 185                 190

Tyr Phe Gly Ala Leu Leu Asn Ser Ile Ile His Val Leu Met Tyr Ser
        195                 200                 205

Tyr Tyr Ala Leu Ala Leu Leu Lys Val Ser Cys Pro Trp Lys Arg Tyr
    210                 215                 220

Leu Thr Gln Ala Gln Leu Leu Gln Phe Thr Ser Val Val Tyr Thr
225                 230                 235                 240

Gly Cys Thr Gly Tyr Thr His Tyr Tyr His Thr Lys His Gly Ala Asp
                245                 250                 255

Glu Thr Gln Pro Ser Leu Gly Thr Tyr Tyr Phe Cys Cys Gly Val Gln
            260                 265                 270

Val Phe Glu Met Val Ser Leu Phe Val Leu Phe Ser Ile Phe Tyr Lys
        275                 280                 285

Arg Ser Tyr Ser Lys Lys Asn Lys Ser Gly Gly Lys Asp Ser Lys Lys
    290                 295                 300

Asn Asp Asp Gly Asn Asn Glu Asp Gln Cys His Lys Ala Met Lys Asp
305                 310                 315                 320

Ile Ser Glu Gly Ala Lys Glu Val Val Gly His Ala Ala Lys Asp Ala
                325                 330                 335
```

Gly Lys Leu Val Ala Thr Ala Ser Lys Ala Val Lys Arg Lys Gly Thr
                340                 345                 350

Arg Val Thr Gly Ala Met
        355

<210> SEQ ID NO 53
<211> LENGTH: 272
<212> TYPE: PRT
<213> ORGANISM: Thalassiosira pseudonana

<400> SEQUENCE: 53

Met Asp Ala Tyr Asn Ala Ala Met Asp Lys Ile Gly Ala Ala Ile Ile
1               5                   10                  15

Asp Trp Ser Asp Pro Asp Gly Lys Phe Arg Ala Asp Arg Glu Asp Trp
            20                  25                  30

Trp Leu Cys Asp Phe Arg Ser Ala Ile Thr Ile Ala Leu Ile Tyr Ile
        35                  40                  45

Ala Phe Val Ile Leu Gly Ser Ala Val Met Gln Ser Leu Pro Ala Met
    50                  55                  60

Asp Pro Tyr Pro Ile Lys Phe Leu Tyr Asn Val Ser Gln Ile Phe Leu
65                  70                  75                  80

Cys Ala Tyr Met Thr Val Glu Ala Gly Phe Leu Ala Tyr Arg Asn Gly
                85                  90                  95

Tyr Thr Val Met Pro Cys Asn His Phe Asn Val Asn Asp Pro Pro Val
            100                 105                 110

Ala Asn Leu Leu Trp Leu Phe Tyr Ile Ser Lys Val Trp Asp Phe Trp
        115                 120                 125

Asp Thr Ile Phe Ile Val Leu Gly Lys Lys Trp Arg Gln Leu Ser Phe
    130                 135                 140

Leu His Val Tyr His His Thr Thr Ile Phe Leu Phe Tyr Trp Leu Asn
145                 150                 155                 160

Ala Asn Val Leu Tyr Asp Gly Asp Ile Phe Leu Thr Ile Leu Leu Asn
                165                 170                 175

Gly Phe Ile His Thr Val Met Tyr Thr Tyr Tyr Phe Ile Cys Met His
            180                 185                 190

Thr Lys Asp Ser Lys Thr Gly Lys Ser Leu Pro Ile Trp Trp Lys Ser
        195                 200                 205

Ser Leu Thr Ala Phe Gln Leu Leu Gln Phe Thr Ile Met Met Ser Gln
    210                 215                 220

Ala Thr Tyr Leu Val Phe His Gly Cys Asp Lys Val Ser Leu Arg Ile
225                 230                 235                 240

Thr Ile Val Tyr Phe Val Ser Leu Leu Ser Leu Phe Phe Leu Phe Ala
                245                 250                 255

Gln Phe Phe Val Gln Ser Tyr Met Ala Pro Lys Lys Lys Ser Ala
            260                 265                 270

<210> SEQ ID NO 54
<211> LENGTH: 318
<212> TYPE: PRT
<213> ORGANISM: Mortierella alpina

<400> SEQUENCE: 54

Met Glu Ser Ile Ala Pro Phe Leu Pro Ser Lys Met Pro Gln Asp Leu
1               5                   10                  15

Phe Met Asp Leu Ala Thr Ala Ile Gly Val Arg Ala Ala Pro Tyr Val
            20                  25                  30

Asp Pro Leu Glu Ala Ala Leu Val Ala Gln Ala Glu Lys Tyr Ile Pro
        35                  40                  45

Thr Ile Val His His Thr Arg Gly Phe Leu Val Ala Val Glu Ser Pro
    50                  55                  60

Leu Ala Arg Glu Leu Pro Leu Met Asn Pro Phe His Val Leu Leu Ile
65                  70                  75                  80

Val Leu Ala Tyr Leu Val Thr Val Phe Val Gly Met Gln Ile Met Lys
                85                  90                  95

Asn Phe Glu Arg Phe Glu Val Lys Thr Phe Ser Leu Leu His Asn Phe
            100                 105                 110

Cys Leu Val Ser Ile Ser Ala Tyr Met Cys Gly Gly Ile Leu Tyr Glu
        115                 120                 125

Ala Tyr Gln Ala Asn Tyr Gly Leu Phe Glu Asn Ala Ala Asp His Thr
    130                 135                 140

Phe Lys Gly Leu Pro Met Ala Lys Met Ile Trp Leu Phe Tyr Phe Ser
145                 150                 155                 160

Lys Ile Met Glu Phe Val Asp Thr Met Ile Met Val Leu Lys Lys Asn
                165                 170                 175

Asn Arg Gln Ile Ser Phe Leu His Val Tyr His His Ser Ser Ile Phe
            180                 185                 190

Thr Ile Trp Trp Leu Val Thr Phe Val Ala Pro Asn Gly Glu Ala Tyr
        195                 200                 205

Phe Ser Ala Ala Leu Asn Ser Phe Ile His Val Ile Met Tyr Gly Tyr
    210                 215                 220

Tyr Phe Leu Ser Ala Leu Gly Phe Lys Gln Val Ser Phe Ile Lys Phe
225                 230                 235                 240

Tyr Ile Thr Arg Ser Gln Met Thr Gln Phe Cys Met Met Ser Val Gln
                245                 250                 255

Ser Ser Trp Asp Met Tyr Ala Met Lys Val Leu Gly Arg Pro Gly Tyr
            260                 265                 270

Pro Phe Phe Ile Thr Ala Leu Leu Trp Phe Tyr Met Trp Thr Met Leu
        275                 280                 285

Gly Leu Phe Tyr Asn Phe Tyr Arg Lys Asn Ala Lys Leu Ala Lys Gln
    290                 295                 300

Ala Lys Ala Asp Ala Ala Lys Glu Lys Ala Arg Lys Leu Gln
305                 310                 315

<210> SEQ ID NO 55
<211> LENGTH: 271
<212> TYPE: PRT
<213> ORGANISM: Thraustochytrium sp.

<400> SEQUENCE: 55

Met Met Glu Pro Leu Asp Arg Tyr Arg Ala Leu Ala Glu Leu Ala Ala
1               5                   10                  15

Arg Tyr Ala Ser Ser Ala Ala Phe Lys Trp Gln Val Tyr Asp Ala
            20                  25                  30

Lys Asp Ser Phe Val Gly Pro Leu Gly Ile Arg Glu Pro Leu Gly Leu
        35                  40                  45

Leu Val Gly Ser Val Val Leu Tyr Leu Ser Leu Gln Ala Val Val Tyr
    50                  55                  60

Ala Leu Arg Asn Tyr Leu Gly Gly Leu Met Ala Leu Arg Ser Val His
65                  70                  75                  80

Asn Leu Gly Leu Cys Leu Phe Ser Gly Ala Val Trp Ile Tyr Thr Ser

```
                      85                  90                  95
Tyr Leu Met Ile Gln Asp Gly His Phe Arg Ser Leu Glu Ala Ala Thr
                100                 105                 110

Cys Glu Pro Leu Lys His Pro His Phe Gln Leu Ile Ser Leu Leu Phe
            115                 120                 125

Ala Leu Ser Lys Ile Trp Glu Trp Phe Asp Thr Val Leu Leu Ile Val
        130                 135                 140

Lys Gly Asn Lys Leu Arg Phe Leu His Val Leu His His Ala Thr Thr
145                 150                 155                 160

Phe Trp Leu Tyr Ala Ile Asp His Ile Phe Leu Ser Ser Ile Lys Tyr
                165                 170                 175

Gly Val Ala Val Asn Ala Phe Ile His Thr Val Met Tyr Ala His Tyr
            180                 185                 190

Phe Arg Pro Phe Pro Lys Gly Leu Arg Pro Leu Ile Thr Gln Leu Gln
        195                 200                 205

Ile Val Gln Phe Ile Phe Ser Ile Gly Ile His Thr Ala Ile Tyr Trp
    210                 215                 220

His Tyr Asp Cys Glu Pro Leu Val His Thr His Phe Trp Glu Tyr Val
225                 230                 235                 240

Thr Pro Tyr Leu Phe Val Val Pro Phe Leu Ile Leu Phe Leu Asn Phe
                245                 250                 255

Tyr Leu Gln Gln Tyr Val Leu Ala Pro Ala Lys Thr Lys Lys Ala
            260                 265                 270

<210> SEQ ID NO 56
<211> LENGTH: 23
<212> TYPE: DNA
<213> ORGANISM: Artificial Sequence
<220> FEATURE:
<223> OTHER INFORMATION: Primer EgD9E_102_053008f
<220> FEATURE:
<221> NAME/KEY: misc_feature
<222> LOCATION: (10)..(11)
<223> OTHER INFORMATION: n is a, c, g, or t

<400> SEQUENCE: 56
gtgctgtacn nktccatcgc ctt                                          23

<210> SEQ ID NO 57
<211> LENGTH: 24
<212> TYPE: DNA
<213> ORGANISM: Artificial Sequence
<220> FEATURE:
<223> OTHER INFORMATION: Primer EgD9E_760_053008r

<400> SEQUENCE: 57
tcccttgtgc tttcggacga tgta                                         24

<210> SEQ ID NO 58
<211> LENGTH: 777
<212> TYPE: DNA
<213> ORGANISM: Euglena gracilis
<220> FEATURE:
<221> NAME/KEY: CDS
<222> LOCATION: (1)..(777)
<223> OTHER INFORMATION: mutant delta-9 elongase "EgD9eS-L35G"

<400> SEQUENCE: 58 atg gag gtc gtg aac gaa atc gtc tcc att ggc cag gag gtt ctt ccc     48
Met Glu Val Val Asn Glu Ile Val Ser Ile Gly Gln Glu Val Leu Pro
1               5                   10                  15
```

| | | |
|---|---|---|
| aag gtc gac tat gct cag ctc tgg tct gat gcc tcg cac tgc gag gtg<br>Lys Val Asp Tyr Ala Gln Leu Trp Ser Asp Ala Ser His Cys Glu Val<br>             20                 25              30 | 96 | |
| ctg tac ggg tcc atc gcc ttc gtc atc ctg aag ttc acc ctt ggt cct<br>Leu Tyr Gly Ser Ile Ala Phe Val Ile Leu Lys Phe Thr Leu Gly Pro<br>      35                 40                45 | 144 | |
| ctc gga ccc aag ggt cag tct cga atg aag ttt gtg ttc acc aac tac<br>Leu Gly Pro Lys Gly Gln Ser Arg Met Lys Phe Val Phe Thr Asn Tyr<br>50                   55               60 | 192 | |
| aac ctg ctc atg tcc atc tac tcg ctg ggc tcc ttc ctc tct atg gcc<br>Asn Leu Leu Met Ser Ile Tyr Ser Leu Gly Ser Phe Leu Ser Met Ala<br>65                   70               75              80 | 240 | |
| tac gcc atg tac acc att ggt gtc atg tcc gac aac tgc gag aag gct<br>Tyr Ala Met Tyr Thr Ile Gly Val Met Ser Asp Asn Cys Glu Lys Ala<br>                  85                90               95 | 288 | |
| ttc gac aac aat gtc ttc cga atc acc act cag ctg ttc tac ctc agc<br>Phe Asp Asn Asn Val Phe Arg Ile Thr Thr Gln Leu Phe Tyr Leu Ser<br>              100               105             110 | 336 | |
| aag ttc ctc gag tac att gac tcc ttc tat ctg ccc ctc atg ggc aag<br>Lys Phe Leu Glu Tyr Ile Asp Ser Phe Tyr Leu Pro Leu Met Gly Lys<br>        115               120             125 | 384 | |
| cct ctg acc tgg ttg cag ttc ttt cac cat ctc gga gct cct atg gac<br>Pro Leu Thr Trp Leu Gln Phe Phe His His Leu Gly Ala Pro Met Asp<br>130                 135              140 | 432 | |
| atg tgg ctg ttc tac aac tac cga aac gaa gcc gtt tgg atc ttt gtg<br>Met Trp Leu Phe Tyr Asn Tyr Arg Asn Glu Ala Val Trp Ile Phe Val<br>145                 150              155             160 | 480 | |
| ctg ctc aac ggc ttc att cac tgg atc atg tac ggc tac tat tgg acc<br>Leu Leu Asn Gly Phe Ile His Trp Ile Met Tyr Gly Tyr Tyr Trp Thr<br>              165               170             175 | 528 | |
| cga ctg atc aag ctc aag ttc cct atg ccc aag tcc ctg att act tct<br>Arg Leu Ile Lys Leu Lys Phe Pro Met Pro Lys Ser Leu Ile Thr Ser<br>        180               185             190 | 576 | |
| atg cag atc att cag ttc aac gtt ggc ttc tac atc gtc tgg aag tac<br>Met Gln Ile Ile Gln Phe Asn Val Gly Phe Tyr Ile Val Trp Lys Tyr<br>195                 200              205 | 624 | |
| cgg aac att ccc tgc tac cga caa gat gga atg aga atg ttt ggc tgg<br>Arg Asn Ile Pro Cys Tyr Arg Gln Asp Gly Met Arg Met Phe Gly Trp<br>210                 215              220 | 672 | |
| ttt ttc aac tac ttc tac gtt ggt act gtc ctg tgt ctg ttc ctc aac<br>Phe Phe Asn Tyr Phe Tyr Val Gly Thr Val Leu Cys Leu Phe Leu Asn<br>225                 230              235             240 | 720 | |
| ttc tac gtg cag acc tac atc gtc cga aag cac aag gga gcc aaa aag<br>Phe Tyr Val Gln Thr Tyr Ile Val Arg Lys His Lys Gly Ala Lys Lys<br>              245               250             255 | 768 | |
| att cag tga<br>Ile Gln | 777 | |

<210> SEQ ID NO 59
<211> LENGTH: 258
<212> TYPE: PRT
<213> ORGANISM: Euglena gracilis

<400> SEQUENCE: 59

Met Glu Val Val Asn Glu Ile Val Ser Ile Gly Gln Glu Val Leu Pro
1                 5                  10                15

Lys Val Asp Tyr Ala Gln Leu Trp Ser Asp Ala Ser His Cys Glu Val
             20                 25              30

Leu Tyr Gly Ser Ile Ala Phe Val Ile Leu Lys Phe Thr Leu Gly Pro
      35               40                45

Leu Gly Pro Lys Gly Gln Ser Arg Met Lys Phe Val Phe Thr Asn Tyr
      50                  55                  60

Asn Leu Leu Met Ser Ile Tyr Ser Leu Gly Ser Phe Leu Ser Met Ala
 65                  70                  75                  80

Tyr Ala Met Tyr Thr Ile Gly Val Met Ser Asp Asn Cys Glu Lys Ala
                 85                  90                  95

Phe Asp Asn Asn Val Phe Arg Ile Thr Thr Gln Leu Phe Tyr Leu Ser
                100                 105                 110

Lys Phe Leu Glu Tyr Ile Asp Ser Phe Tyr Leu Pro Leu Met Gly Lys
        115                 120                 125

Pro Leu Thr Trp Leu Gln Phe Phe His His Leu Gly Ala Pro Met Asp
        130                 135                 140

Met Trp Leu Phe Tyr Asn Tyr Arg Asn Glu Ala Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Lys Phe Pro Met Pro Lys Ser Leu Ile Thr Ser
                180                 185                 190

Met Gln Ile Ile Gln Phe Asn Val Gly Phe Tyr Ile Val Trp Lys Tyr
        195                 200                 205

Arg Asn Ile Pro Cys Tyr Arg Gln Asp Gly Met Arg Met Phe Gly Trp
        210                 215                 220

Phe Phe Asn Tyr Phe Tyr Val Gly Thr Val Leu Cys Leu Phe Leu Asn
225                 230                 235                 240

Phe Tyr Val Gln Thr Tyr Ile Val Arg Lys His Lys Gly Ala Lys Lys
                245                 250                 255

Ile Gln

<210> SEQ ID NO 60
<211> LENGTH: 7769
<212> TYPE: DNA
<213> ORGANISM: Artificial Sequence
<220> FEATURE:
<223> OTHER INFORMATION: Plasmid pZuFmEgD9ES-L35G

<400> SEQUENCE: 60

```
ggccgcaagt gtggatgggg aagtgagtgc ccggttctgt gtgcacaatt ggcaatccaa    60
gatggatgga ttcaacacag ggatatagcg agctacgtgg tggtgcgagg atatagcaac   120
ggatatttat gtttgacact tgagaatgta cgatacaagc actgtccaag tacaatacta   180
aacatactgt acatactcat actcgtaccc gggcaacggt ttcacttgag tgcagtggct   240
agtgctctta ctcgtacagt gtgcaatact gcgtatcata gtctttgatg tatatcgtat   300
tcattcatgt tagttgcgta cgagccggaa gcataaagtg taaagcctgg ggtgcctaat   360
gagtgagcta actcacatta attgcgttgc gctcactgcc cgctttccag tcgggaaacc   420
tgtcgtgcca gctgcattaa tgaatcggcc aacgcgcggg gagaggcggt ttgcgtattg   480
ggcgctcttc cgcttcctcg ctcactgact cgctgcgctc ggtcgttcgg ctgcggcgag   540
cggtatcagc tcactcaaag gcggtaatac ggttatccac agaatcaggg gataacgcag   600
gaaagaacat gtgagcaaaa ggccagcaaa aggccaggaa ccgtaaaaag gccgcgttgc   660
tggcgttttt ccataggctc cgcccccctg acgagcatca caaaaatcga cgctcaagtc   720
agaggtggcg aaacccgaca ggactataaa gataccaggc gtttccccct ggaagctccc   780
tcgtgcgctc tcctgttccg accctgccgc ttaccggata cctgtccgcc tttctccctt   840
```

```
cgggaagcgt ggcgctttct catagctcac gctgtaggta tctcagttcg gtgtaggtcg      900
ttcgctccaa gctgggctgt gtgcacgaac cccccgttca gcccgaccgc tgcgccttat      960
ccggtaacta tcgtcttgag tccaacccgg taagacacga cttatcgcca ctggcagcag     1020
ccactggtaa caggattagc agagcgaggt atgtaggcgg tgctacagag ttcttgaagt     1080
ggtggcctaa ctacggctac actagaagga cagtatttgg tatctgcgct ctgctgaagc     1140
cagttacctt cggaaaaaga gttggtagct cttgatccgg caaacaaacc accgctggta     1200
gcggtggttt ttttgtttgc aagcagcaga ttacgcgcag aaaaaaagga tctcaagaag     1260
atcctttgat cttttctacg gggtctgacg ctcagtggaa cgaaaactca cgttaaggga     1320
ttttggtcat gagattatca aaaggatctt cacctagat cctttttaaat taaaaatgaa     1380
gttttaaatc aatctaaagt atatatgagt aaacttggtc tgacagttac caatgcttaa     1440
tcagtgaggc acctatctca gcgatctgtc tatttcgttc atccatagtt gcctgactcc     1500
ccgtcgtgta gataactacg atacgggagg gcttaccatc tggccccagt gctgcaatga     1560
taccgcgaga cccacgctca ccggctccag atttatcagc aataaaccag ccagccggaa     1620
gggccgagcg cagaagtggt cctgcaactt tatccgcctc catccagtct attaattgtt     1680
gccgggaagc tagagtaagt agttcgccag ttaatagttt gcgcaacgtt gttgccattg     1740
ctacaggcat cgtggtgtca cgctcgtcgt ttggtatggc ttcattcagc tccggttccc     1800
aacgatcaag gcgagttaca tgatccccca tgttgtgcaa aaaagcggtt agctccttcg     1860
gtcctccgat cgttgtcaga agtaagttgg ccgcagtgtt atcactcatg gttatggcag     1920
cactgcataa ttctcttact gtcatgccat ccgtaagatg cttttctgtg actggtgagt     1980
actcaaccaa gtcattctga gaatagtgta tgcggcgacc gagttgctct tgcccggcgt     2040
caatacggga taataccgcg ccacatagca gaactttaaa agtgctcatc attggaaaac     2100
gttcttcggg gcgaaaactc tcaaggatct taccgctgtt gagatccagt tcgatgtaac     2160
ccactcgtgc acccaactga tcttcagcat cttttacttt caccagcgtt tctgggtgag     2220
caaaaacagg aaggcaaaat gccgcaaaaa agggaataag ggcgacacgg aaatgttgaa     2280
tactcatact cttccttttt caatattatt gaagcattta tcagggttat tgtctcatga     2340
gcggatacat atttgaatgt atttagaaaa ataaacaaat aggggttccg cgcacatttc     2400
cccgaaaagt gccacctgac gcgccctgta gcggcgcatt aagcgcggcg ggtgtggtgg     2460
ttacgcgcag cgtgaccgct acacttgcca gcgccctagc gcccgctcct ttcgctttct     2520
tcccttcctt tctcgccacg ttcgccggct ttccccgtca gctctaaat cggggggctcc     2580
ctttagggtt ccgatttagt gctttacggc acctcgaccc caaaaaactt gattagggtg     2640
atggttcacg tagtgggcca tcgccctgat agacggtttt tcgccctttg acgttggagt     2700
ccacgttctt taatagtgga ctcttgttcc aaactggaac aacactcaac cctatctcgg     2760
tctattcttt tgatttataa gggattttgc cgatttcggc ctattggtta aaaaatgagc     2820
tgatttaaca aaaatttaac gcgaatttta acaaaatatt aacgcttaca atttccattc     2880
gccattcagg ctgcgcaact gttgggaagg gcgatcggtg cgggcctctt cgctattacg     2940
ccagctggcg aaagggggat gtgctgcaag gcgattaagt tgggtaacgc cagggttttc     3000
ccagtcacga cgttgtaaaa cgacggccag tgaattgtaa tacgactcac tatagggcga     3060
attgggtacc gggccccccc tcgaggtcga tggtgtcgat aagcttgata tcgaattcat     3120
gtcacacaaa ccgatcttcg cctcaaggaa acctaattct acatccgaga gactgccgag     3180
```

-continued

```
atccagtcta cactgattaa ttttcgggcc aataatttaa aaaaatcgtg ttatataata    3240
ttatatgtat tatatatata catcatgatg atactgacag tcatgtccca ttgctaaata    3300
gacagactcc atctgccgcc tccaactgat gttctcaata tttaaggggt catctcgcat    3360
tgtttaataa taaacagact ccatctaccg cctccaaatg atgttctcaa aatatattgt    3420
atgaacttat ttttattact tagtattatt agacaactta cttgctttat gaaaaacact    3480
tcctatttag gaaacaattt ataatggcag ttcgttcatt taacaattta tgtagaataa    3540
atgttataaa tgcgtatggg aaatcttaaa tatggatagc ataaatgata tctgcattgc    3600
ctaattcgaa atcaacagca acgaaaaaaa tcccttgtac aacataaata gtcatcgaga    3660
aatatcaact atcaaagaac agctattcac acgttactat tgagattatt attggacgag    3720
aatcacacac tcaactgtct ttctctcttc tagaaataca ggtacaagta tgtactattc    3780
tcattgttca tacttctagt catttcatcc cacatattcc ttggatttct ctccaatgaa    3840
tgacattcta tcttgcaaat tcaacaatta taataagata taccaaagta gcggtatagt    3900
ggcaatcaaa aagcttctct ggtgtgcttc tcgtatttat ttttattcta atgatccatt    3960
aaaggtatat atttatttct tgttatataa tccttttgtt tattacatgg gctggataca    4020
taaaggtatt ttgatttaat ttttttgctta aattcaatcc cccctcgttc agtgtcaact    4080
gtaatggtag gaaattacca tacttttgaa gaagcaaaaa aaatgaaaga aaaaaaaat    4140
cgtatttcca ggttagacgt tccgcagaat ctagaatgcg gtatgcggta cattgttctt    4200
cgaacgtaaa agttgcgctc cctgagatat tgtacatttt tgcttttaca agtacaagta    4260
catcgtacaa ctatgtacta ctgttgatgc atccacaaca gtttgttttg tttttttttg    4320
tttttttttt ttctaatgat tcattaccgc tatgtatacc tacttgtact tgtagtaagc    4380
cgggttattg gcgttcaatt aatcatagac ttatgaatct gcacggtgtg cgctgcgagt    4440
tactttagc ttatgcatgc tacttgggtg taatattggg atctgttcgg aaatcaacgg    4500
atgctcaatc gatttcgaca gtaattaatt aagtcataca caagtcagct ttcttcgagc    4560
ctcatataag tataagtagt tcaacgtatt agcactgtac ccagcatctc cgtatcgaga    4620
aacacaacaa catgccccat tggacagatc atgcggatac acaggttgtg cagtatcata    4680
catactcgat cagacaggtc gtctgaccat catacaagct gaacaagcgc tccatacttg    4740
cacgctctct atatacacag ttaaattaca tatccatagt ctaacctcta acagttaatc    4800
ttctggtaag cctcccagcc agccttctgg tatcgcttgg cctcctcaat aggatctcgg    4860
ttctggccgt acagacctcg gccgacaatt atgatatccg ttccggtaga catgacatcc    4920
tcaacagttc ggtactgctg tccgagagcg tctcccttgt cgtcaagacc caccccgggg    4980
gtcagaataa gccagtcctc agagtcgccc ttaggtcggt tctgggcaat gaagccaacc    5040
acaaactcgg ggtcggatcg ggcaagctca atggtctgct tggagtactc gccagtggcc    5100
agagagccct tgcaagacag ctcggccagc atgagcagac ctctggccag cttctcgttg    5160
ggagagggga ctaggaactc cttgtactgg gagttctcgt agtcagagac gtcctccttc    5220
ttctgttcag agacagtttc ctcggcacca gctcgcaggc cagcaatgat tccggttccg    5280
ggtacaccgt gggcgttggt gatatcggac cactcggcga ttcggtgaca ccggtactgg    5340
tgcttgacag tgttgccaat atctgcgaac tttctgtcct cgaacaggaa gaaaccgtgc    5400
ttaagagcaa gttccttgag ggggagcaca gtgccggcgt aggtgaagtc gtcaatgatg    5460
tcgatatggg ttttgatcat gcacacataa ggtccgacct tatcggcaag ctcaatgagc    5520
tccttggtgg tggtaacatc cagagaagca cacaggttgg ttttcttggc tgccacgagc    5580
```

```
ttgagcactc gagcggcaaa ggcggacttg tggacgttag ctcgagcttc gtaggagggc   5640
attttggtgg tgaagaggag actgaaataa atttagtctg cagaactttt tatcggaacc   5700
ttatctgggg cagtgaagta tatgttatgg taatagttac gagttagttg aacttataga   5760
tagactggac tatacggcta tcggtccaaa ttagaaagaa cgtcaatggc tctctgggcg   5820
tcgcctttgc cgacaaaaat gtgatcatga tgaaagccag caatgacgtt gcagctgata   5880
ttgttgtcgg ccaaccgcgc cgaaaacgca gctgtcagac ccacagcctc caacgaagaa   5940
tgtatcgtca aagtgatcca agcacactca tagttggagt cgtactccaa aggcggcaat   6000
gacgagtcag acagatactc gtcgacgttt aaacagtgta cgcagatcta ctatagagga   6060
acatttaaat tgccccggag aagacggcca ggccgcctag atgacaaatt caacaactca   6120
cagctgactt tctgccattg ccactagggg ggggccttt tatatggcca agccaagctc   6180
tccacgtcgg ttgggctgca cccaacaata aatgggtagg gttgcaccaa caaagggatg   6240 ggatggggg tagaagatac gaggataacg gggctcaatg gcacaaataa gaacgaatac   6300
tgccattaag actcgtgatc cagcgactga caccattgca tcatctaagg gcctcaaaac   6360
tacctcggaa ctgctgcgct gatctggaca ccacagaggt tccgagcact ttaggttgca   6420
ccaaatgtcc caccaggtgc aggcagaaaa cgctggaaca gcgtgtacag tttgtcttaa   6480
caaaaagtga gggcgctgag gtcgagcagg gtggtgtgac ttgttatagc ctttagagct   6540
gcgaaagcgc gtatggattt ggctcatcag gccagattga gggtctgtgg acacatgtca   6600
tgttagtgta cttcaatcgc ccctggata taggcccgac aataggccgt ggcctcattt   6660
ttttgccttc cgcacatttc cattgctcga tacccacacc ttgcttctcc tgcacttgcc   6720
aaccttaata ctggtttaca ttgaccaaca tcttacaagc gggggcttg tctagggtat   6780 atataaacag tggctctccc aatcggttgc cagtctcttt tttcctttct ttccccacag   6840
attcgaaatc taaactacac atcacagaat tccgagccgt gagtatccac gacaagatca   6900
gtgtcgagac gacgcgtttt gtgtaatgac acaatccgaa agtcgctagc aacacacact   6960
ctctacacaa actaacccag ctctggtacc atggaggtcg tgaacgaaat cgtctccatt   7020
ggccaggagg ttcttcccaa ggtcgactat gctcagctct ggtctgatgc ctcgcactgc   7080
gaggtgctgt acgggtccat cgccttcgtc atcctgaagt tcaccccttgg tcctctcgga   7140 cccaagggtc agtctcgaat gaagtttgtg ttcaccaact acaacctgct catgtccatc   7200
tactcgctgg gctccttcct ctctatggcc tacgccatgt acaccattgg tgtcatgtcc   7260
gacaactgcg agaaggcttt cgacaacaat gtcttccgaa tcaccactca gctgttctac   7320
ctcagcaagt cctcgagtac cattgactcc ttctatctgc ccctcatggg caagcctctg   7380
acctggttgc agttctttca ccatctcgga gctcctatgg acatgtggct gttctacaac   7440
taccgaaacg aagccgtttg gatctttgtg ctgctcaacg gcttcattca ctggatcatg   7500
tacggctact attggaccccg actgatcaag ctcaagttcc ctatgcccaa gtccctgatt   7560
acttctatgc agatcattca gttcaacgtt ggcttctaca tcgtctggaa gtaccggaac   7620
attccctgct accgacaaga tggaatgaga atgtttggct ggtttttcaa ctacttctac   7680
gttggtactg tcctgtgtct gttcctcaac ttctacgtgc agacctacat cgtccgaaag   7740
cacaagggag ccaaaaagat tcagtgagc                                     7769
```

<210> SEQ ID NO 61
<211> LENGTH: 777
<212> TYPE: DNA

<213> ORGANISM: Euglena gracilis
<220> FEATURE:
<221> NAME/KEY: CDS
<222> LOCATION: (1)..(777)
<223> OTHER INFORMATION: mutant delta-9 elongase "EgD9eS-L35M/Q107E"

<400> SEQUENCE: 61

| | | | | | | | | | | | | | | | | |
|---|---|---|---|---|---|---|---|---|---|---|---|---|---|---|---|---|
| atg | gag | gtc | gtg | aac | gaa | atc | gtc | tcc | att | ggc | cag | gag | gtt | ctt | ccc | 48 |
| Met | Glu | Val | Val | Asn | Glu | Ile | Val | Ser | Ile | Gly | Gln | Glu | Val | Leu | Pro | |
| 1 | | | | 5 | | | | | 10 | | | | | 15 | | |

| aag | gtc | gac | tat | gct | cag | ctc | tgg | tct | gat | gcc | tcg | cac | tgc | gag | gtg | 96 |
|---|---|---|---|---|---|---|---|---|---|---|---|---|---|---|---|---|
| Lys | Val | Asp | Tyr | Ala | Gln | Leu | Trp | Ser | Asp | Ala | Ser | His | Cys | Glu | Val | |
| | | | 20 | | | | | 25 | | | | | 30 | | | |

| ctg | tac | atg | tcc | atc | gcc | ttc | gtc | atc | ctg | aag | ttc | acc | ctt | ggt | cct | 144 |
|---|---|---|---|---|---|---|---|---|---|---|---|---|---|---|---|---|
| Leu | Tyr | Met | Ser | Ile | Ala | Phe | Val | Ile | Leu | Lys | Phe | Thr | Leu | Gly | Pro | |
| | | | 35 | | | | | 40 | | | | | 45 | | | |

| ctc | gga | ccc | aag | ggt | cag | tct | cga | atg | aag | ttt | gtg | ttc | acc | aac | tac | 192 |
|---|---|---|---|---|---|---|---|---|---|---|---|---|---|---|---|---|
| Leu | Gly | Pro | Lys | Gly | Gln | Ser | Arg | Met | Lys | Phe | Val | Phe | Thr | Asn | Tyr | |
| | 50 | | | | | 55 | | | | | 60 | | | | | |

| aac | ctg | ctc | atg | tcc | atc | tac | tcg | ctg | ggc | tcc | ttc | ctc | tct | atg | gcc | 240 |
|---|---|---|---|---|---|---|---|---|---|---|---|---|---|---|---|---|
| Asn | Leu | Leu | Met | Ser | Ile | Tyr | Ser | Leu | Gly | Ser | Phe | Leu | Ser | Met | Ala | |
| 65 | | | | | 70 | | | | | 75 | | | | | 80 | |

| tac | gcc | atg | tac | acc | att | ggt | gtc | atg | tcc | gac | aac | tgc | gag | aag | gct | 288 |
|---|---|---|---|---|---|---|---|---|---|---|---|---|---|---|---|---|
| Tyr | Ala | Met | Tyr | Thr | Ile | Gly | Val | Met | Ser | Asp | Asn | Cys | Glu | Lys | Ala | |
| | | | | 85 | | | | | 90 | | | | | 95 | | |

| ttc | gac | aac | aat | gtc | ttc | cga | atc | acc | act | gag | ctg | ttc | tac | ctc | agc | 336 |
|---|---|---|---|---|---|---|---|---|---|---|---|---|---|---|---|---|
| Phe | Asp | Asn | Asn | Val | Phe | Arg | Ile | Thr | Thr | Glu | Leu | Phe | Tyr | Leu | Ser | |
| | | | 100 | | | | | 105 | | | | | 110 | | | |

| aag | ttc | ctc | gag | tac | att | gac | tcc | ttc | tat | ctg | ccc | ctc | atg | ggc | aag | 384 |
|---|---|---|---|---|---|---|---|---|---|---|---|---|---|---|---|---|
| Lys | Phe | Leu | Glu | Tyr | Ile | Asp | Ser | Phe | Tyr | Leu | Pro | Leu | Met | Gly | Lys | |
| | | 115 | | | | | 120 | | | | | 125 | | | | |

| cct | ctg | acc | tgg | ttg | cag | ttc | ttt | cac | cat | ctc | gga | gct | cct | atg | gac | 432 |
|---|---|---|---|---|---|---|---|---|---|---|---|---|---|---|---|---|
| Pro | Leu | Thr | Trp | Leu | Gln | Phe | Phe | His | His | Leu | Gly | Ala | Pro | Met | Asp | |
| | 130 | | | | | 135 | | | | | 140 | | | | | |

| atg | tgg | ctg | ttc | tac | aac | tac | cga | aac | gaa | gcc | gtt | tgg | atc | ttt | gtg | 480 |
|---|---|---|---|---|---|---|---|---|---|---|---|---|---|---|---|---|
| Met | Trp | Leu | Phe | Tyr | Asn | Tyr | Arg | Asn | Glu | Ala | Val | Trp | Ile | Phe | Val | |
| 145 | | | | | 150 | | | | | 155 | | | | | 160 | |

| ctg | ctc | aac | ggc | ttc | att | cac | tgg | atc | atg | tac | ggc | tac | tat | tgg | acc | 528 |
|---|---|---|---|---|---|---|---|---|---|---|---|---|---|---|---|---|
| Leu | Leu | Asn | Gly | Phe | Ile | His | Trp | Ile | Met | Tyr | Gly | Tyr | Tyr | Trp | Thr | |
| | | | | 165 | | | | | 170 | | | | | 175 | | |

| cga | ctg | atc | aag | ctc | aag | ttc | cct | atg | ccc | aag | tcc | ctg | att | act | tct | 576 |
|---|---|---|---|---|---|---|---|---|---|---|---|---|---|---|---|---|
| Arg | Leu | Ile | Lys | Leu | Lys | Phe | Pro | Met | Pro | Lys | Ser | Leu | Ile | Thr | Ser | |
| | | | 180 | | | | | 185 | | | | | 190 | | | |

| atg | cag | atc | att | cag | ttc | aac | gtt | ggc | ttc | tac | atc | gtc | tgg | aag | tac | 624 |
|---|---|---|---|---|---|---|---|---|---|---|---|---|---|---|---|---|
| Met | Gln | Ile | Ile | Gln | Phe | Asn | Val | Gly | Phe | Tyr | Ile | Val | Trp | Lys | Tyr | |
| | | 195 | | | | | 200 | | | | | 205 | | | | |

| cgg | aac | att | ccc | tgc | tac | cga | caa | gat | gga | atg | aga | atg | ttt | ggc | tgg | 672 |
|---|---|---|---|---|---|---|---|---|---|---|---|---|---|---|---|---|
| Arg | Asn | Ile | Pro | Cys | Tyr | Arg | Gln | Asp | Gly | Met | Arg | Met | Phe | Gly | Trp | |
| | 210 | | | | | 215 | | | | | 220 | | | | | |

| ttt | ttc | aac | tac | ttc | tac | gtt | ggt | act | gtc | ctg | tgt | ctg | ttc | ctc | aac | 720 |
|---|---|---|---|---|---|---|---|---|---|---|---|---|---|---|---|---|
| Phe | Phe | Asn | Tyr | Phe | Tyr | Val | Gly | Thr | Val | Leu | Cys | Leu | Phe | Leu | Asn | |
| 225 | | | | | 230 | | | | | 235 | | | | | 240 | |

| ttc | tac | gtg | cag | acc | tac | atc | gtc | cga | aag | cac | aag | gga | gcc | aaa | aag | 768 |
|---|---|---|---|---|---|---|---|---|---|---|---|---|---|---|---|---|
| Phe | Tyr | Val | Gln | Thr | Tyr | Ile | Val | Arg | Lys | His | Lys | Gly | Ala | Lys | Lys | |
| | | | | 245 | | | | | 250 | | | | | 255 | | |

| att | cag | tga | | | | | | | | | | | | | | 777 |
|---|---|---|---|---|---|---|---|---|---|---|---|---|---|---|---|---|
| Ile | Gln | | | | | | | | | | | | | | | |

<210> SEQ ID NO 62
<211> LENGTH: 258
<212> TYPE: PRT

<213> ORGANISM: Euglena gracilis

<400> SEQUENCE: 62

```
Met Glu Val Val Asn Glu Ile Val Ser Ile Gly Gln Glu Val Leu Pro
1               5                   10                  15

Lys Val Asp Tyr Ala Gln Leu Trp Ser Asp Ala Ser His Cys Glu Val
                20                  25                  30

Leu Tyr Met Ser Ile Ala Phe Val Ile Leu Lys Phe Thr Leu Gly Pro
            35                  40                  45

Leu Gly Pro Lys Gly Gln Ser Arg Met Lys Phe Val Phe Thr Asn Tyr
        50                  55                  60

Asn Leu Leu Met Ser Ile Tyr Ser Leu Gly Ser Phe Leu Ser Met Ala
65                  70                  75                  80

Tyr Ala Met Tyr Thr Ile Gly Val Met Ser Asp Asn Cys Glu Lys Ala
                85                  90                  95

Phe Asp Asn Asn Val Phe Arg Ile Thr Thr Glu Leu Phe Tyr Leu Ser
            100                 105                 110

Lys Phe Leu Glu Tyr Ile Asp Ser Phe Tyr Leu Pro Leu Met Gly Lys
        115                 120                 125

Pro Leu Thr Trp Leu Gln Phe Phe His His Leu Gly Ala Pro Met Asp
    130                 135                 140

Met Trp Leu Phe Tyr Asn Tyr Arg Asn Glu Ala Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Lys Phe Pro Met Pro Lys Ser Leu Ile Thr Ser
            180                 185                 190

Met Gln Ile Ile Gln Phe Asn Val Gly Phe Tyr Ile Val Trp Lys Tyr
        195                 200                 205

Arg Asn Ile Pro Cys Tyr Arg Gln Asp Gly Met Arg Met Phe Gly Trp
    210                 215                 220

Phe Phe Asn Tyr Phe Tyr Val Gly Thr Val Leu Cys Leu Phe Leu Asn
225                 230                 235                 240

Phe Tyr Val Gln Thr Tyr Ile Val Arg Lys His Lys Gly Ala Lys Lys
                245                 250                 255

Ile Gln
```

<210> SEQ ID NO 63
<211> LENGTH: 7769
<212> TYPE: DNA
<213> ORGANISM: Artificial Sequence
<220> FEATURE:
<223> OTHER INFORMATION: Plasmid pZuFmEgD9ES-L35M/Q107E

<400> SEQUENCE: 63

```
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc gggcaacggt ttcacttgag tgcagtggct     240
agtgctctta ctcgtacagt gtgcaatact gcgtatcata gtctttgatg tatatcgtat     300
tcattcatgt tagttgcgta cgagccggaa gcataaagtg taaagcctgg ggtgcctaat     360
gagtgagcta actcacatta attgcgttgc gctcactgcc cgctttccag tcgggaaacc     420
tgtcgtgcca gctgcattaa tgaatcggcc aacgcgcggg gagaggcggt ttgcgtattg     480
```

-continued

```
ggcgctcttc cgcttcctcg ctcactgact cgctgcgctc ggtcgttcgg ctgcggcgag      540
cggtatcagc tcactcaaag gcggtaatac ggttatccac agaatcaggg gataacgcag      600
gaaagaacat gtgagcaaaa ggccagcaaa aggccaggaa ccgtaaaaag gccgcgttgc      660
tggcgttttt ccataggctc cgcccccctg acgagcatca caaaaatcga cgctcaagtc      720
agaggtggcg aaacccgaca ggactataaa gataccaggc gtttccccct ggaagctccc      780
tcgtgcgctc tcctgttccg accctgccgc ttaccggata cctgtccgcc tttctccctt      840
cgggaagcgt ggcgctttct catagctcac gctgtaggta tctcagttcg gtgtaggtcg      900
ttcgctccaa gctgggctgt gtgcacgaac cccccgttca gcccgaccgc tgcgccttat      960
ccggtaacta tcgtcttgag tccaacccgg taagacacga cttatcgcca ctggcagcag     1020
ccactggtaa caggattagc agagcgaggt atgtaggcgg tgctacagag ttcttgaagt     1080
ggtggcctaa ctacggctac actagaagga cagtatttgg tatctgcgct ctgctgaagc     1140
cagttacctt cggaaaaaga gttggtagct cttgatccgg caaacaaacc accgctggta     1200
gcggtggttt ttttgtttgc aagcagcaga ttacgcgcag aaaaaaagga tctcaagaag     1260
atcctttgat cttttctacg gggtctgacg ctcagtggaa cgaaaactca cgttaaggga     1320
ttttggtcat gagattatca aaaaggatct tcacctagat ccttttaaat taaaaatgaa     1380
gttttaaatc aatctaaagt atatatgagt aaacttggtc tgacagttac caatgcttaa     1440
tcagtgaggc acctatctca gcgatctgtc tatttcgttc atccatagtt gcctgactcc     1500
ccgtcgtgta gataactacg atacgggagg gcttaccatc tggccccagt gctgcaatga     1560
taccgcgaga cccacgctca ccggctccag atttatcagc aataaaccag ccagccggaa     1620
gggccgagcg cagaagtggt cctgcaactt tatccgcctc catccagtct attaattgtt     1680
gccgggaagc tagagtaagt agttcgccag ttaatagttt gcgcaacgtt gttgccattg     1740
ctacaggcat cgtggtgtca cgctcgtcgt ttggtatggc ttcattcagc tccggttccc     1800
aacgatcaag gcgagttaca tgatccccca tgttgtgcaa aaaagcggtt agctccttcg     1860
gtcctccgat cgttgtcaga agtaagttgg ccgcagtgtt atcactcatg gttatggcag     1920
cactgcataa ttctcttact gtcatgccat ccgtaagatg cttttctgtg actggtgagt     1980
actcaaccaa gtcattctga aatagtgta tgcggcgacc gagttgctct tgcccggcgt     2040
caatacggga taataccgcg ccacatagca gaactttaaa agtgctcatc attggaaaac     2100
gttcttcggg gcgaaaactc tcaaggatct taccgctgtt gagatccagt tcgatgtaac     2160
ccactcgtgc acccaactga tcttcagcat cttttacttt caccagcgtt tctgggtgag     2220
caaaaacagg aaggcaaaat gccgcaaaaa agggaataag ggcgacacgg aaatgttgaa     2280
tactcatact cttccttttt caatattatt gaagcattta tcagggttat tgtctcatga     2340
gcggatacat atttgaatgt atttagaaaa ataaacaaat aggggttccg cgcacatttc     2400
cccgaaaagt gccacctgac gcgcctgta gcggcgcatt aagcgcggcg ggtgtggtgg     2460
ttacgcgcag cgtgaccgct acacttgcca gcgccctagc gcccgctcct ttcgctttct     2520
tcccttcctt tctcgccacg ttcgccggct ttccccgtca gctctaaat cgggggctcc     2580
ctttagggtt ccgatttagt gctttacggc acctcgaccc caaaaaactt gattagggtg     2640
atggttcacg tagtgggcca tcgccctgat agacggtttt tcgccctttg acgttggagt     2700
ccacgttctt taatagtgga ctcttgttcc aaactggaac aacactcaac cctatctcgg     2760
tctattcttt tgatttataa gggattttgc cgatttcggc ctattggtta aaaaatgagc     2820
```

```
tgatttaaca aaaatttaac gcgaatttta acaaaatatt aacgcttaca atttccattc    2880
gccattcagg ctgcgcaact gttgggaagg gcgatcggtg cgggcctctt cgctattacg    2940
ccagctggcg aaaggggat gtgctgcaag gcgattaagt tgggtaacgc cagggttttc     3000
ccagtcacga cgttgtaaaa cgacggccag tgaattgtaa tacgactcac tatagggcga    3060
attgggtacc gggcccccc tcgaggtcga tggtgtcgat aagcttgata tcgaattcat     3120
gtcacacaaa ccgatcttcg cctcaaggaa acctaattct acatccgaga gactgccgag    3180
atccagtcta cactgattaa ttttcgggcc aataatttaa aaaaatcgtg ttatataata    3240
ttatatgtat tatatatata catcatgatg atactgacag tcatgtccca ttgctaaata    3300
gacagactcc atctgccgcc tccaactgat gttctcaata tttaaggggt catctcgcat    3360
tgtttaataa taaacagact ccatctaccg cctccaaatg atgttctcaa atatattgt     3420 atgaacttat ttttattact tagtattatt agacaactta cttgctttat gaaaaacact    3480
tcctatttag gaaacaattt ataatggcag ttcgttcatt taacaattta tgtagaataa    3540
atgttataaa tgcgtatggg aaatcttaaa tatggatagc ataaatgata tctgcattgc    3600
ctaattcgaa atcaacagca acgaaaaaaa tcccttgtac aacataaata gtcatcgaga    3660
aatatcaact atcaaagaac agctattcac acgttactat tgagattatt attggacgag    3720
aatcacacac tcaactgtct ttctctcttc tagaaataca ggtacaagta tgtactattc    3780
tcattgttca tacttctagt catttcatcc cacatattcc ttggatttct ctccaatgaa    3840
tgacattcta tcttgcaaat tcaacaatta taataagata taccaaagta gcggtatagt    3900
ggcaatcaaa aagcttctct ggtgtgcttc tcgtatttat ttttattcta atgatccatt    3960
aaaggtatat atttatttct tgttatataa tccttttgtt tattacatgg gctggataca    4020
taaaggtatt ttgatttaat ttttgctta aattcaatcc cccctcgttc agtgtcaact     4080
gtaatggtag gaaattacca tacttttgaa gaagcaaaaa aaatgaaaga aaaaaaaaat    4140
cgtatttcca ggttagacgt tccgcagaat ctagaatgcg gtatgcggta cattgttctt    4200
cgaacgtaaa agttgcgctc cctgagatat tgtacatttt tgcttttaca agtacaagta    4260
catcgtacaa ctatgtacta ctgttgatgc atccacaaca gtttgttttg ttttttttg    4320 tttttttt  ttctaatgat tcattaccgc tatgtatacc tacttgtact tgtagtaagc    4380
cgggttattg gcgttcaatt aatcatagac ttatgaatct gcacggtgtg cgctgcgagt    4440 tactttagc ttatgcatgc tacttgggtg taatattggg atctgttcgg aaatcaacgg     4500
atgctcaatc gatttcgaca gtaattaatt aagtcataca caagtcagct ttcttcgagc    4560
ctcatataag tataagtagt tcaacgtatt agcactgtac ccagcatctc cgtatcgaga    4620
aacacaacaa catgccccat tggacagatc atgcggatac acaggttgtg cagtatcata    4680
catactcgat cagacaggtc gtctgaccat catacaagct gaacaagcgc tccatacttg    4740
cacgctctct atatacacag ttaaattaca tatccatagt ctaacctcta acagttaatc    4800
ttctggtaag cctcccagcc agccttctgg tatcgcttgg cctcctcaat aggatctcgg    4860
ttctggccgt acagacctcg gccgacaatt atgatatccg ttccggtaga catgacatcc    4920
tcaacagttc ggtactgctg tccgagagcg tctcccttgt cgtcaagacc cacccccggg    4980
gtcagaataa gccagtcctc agagtcgccc ttaggtcggt tctgggcaat gaagccaacc    5040
acaaactcgg ggtcggatcg ggcaagctca atggtctgct ggagtactc gccagtggcc     5100 agagagccct tgcaagacag ctcggccagc atgagcagac ctctggccag cttcgcgttg    5160 ggagaggga ctaggaactc cttgtactgg gagttctcgt agtcagagac gtcctccttc     5220
```

```
ttctgttcag agacagtttc ctcggcacca gctcgcaggc cagcaatgat tccggttccg    5280
ggtacaccgt gggcgttggt gatatcggac cactcggcga ttcggtgaca ccggtactgg    5340
tgcttgacag tgttgccaat atctgcgaac tttctgtcct cgaacaggaa gaaaccgtgc    5400
ttaagagcaa gttccttgag ggggagcaca gtgccgcgca ggtgaagtc gtcaatgatg     5460 tcgatatggg ttttgatcat gcacacataa ggtccgacct tatcggcaag ctcaatgagc    5520
tccttggtgg tggtaacatc cagagaagca cacaggttgg ttttcttggc tgccacgagc    5580
ttgagcactc gagcggcaaa ggcggacttg tggacgttag ctcgagcttc gtaggagggc    5640
attttggtgg tgaagaggag actgaaataa atttagtctg cagaactttt tatcggaacc    5700
ttatctgggg cagtgaagta tatgttatgg taatagttac gagttagttg aacttataga    5760
tagactggac tatacggcta tcggtccaaa ttagaaagaa cgtcaatggc tctctgggcg    5820
tcgcctttgc cgacaaaaat gtgatcatga tgaaagccag caatgacgtt gcagctgata    5880
ttgttgtcgg ccaaccgcgc cgaaaacgca gctgtcagac ccacagcctc caacgaagaa    5940
tgtatcgtca aagtgatcca agcacactca tagttggagt cgtactccaa aggcggcaat    6000
gacgagtcag acagatactc gtcgacgttt aaacagtgta cgcagatcta ctatagagga    6060
acatttaaat tgccccggag aagacggcca ggccgcctag atgacaaatt caacaactca    6120
cagctgactt tctgccattg ccactagggg ggggcctttt tatatggcca agccaagctc    6180
tccacgtcgg ttgggctgca cccaacaata aatgggtagg gttgcaccaa caaagggatg    6240
ggatgggggg tagaagatac gaggataacg gggctcaatg gcacaaataa gaacgaatac    6300
tgccattaag actcgtgatc cagcgactga caccattgca tcatctaagg gcctcaaaac    6360
tacctcggaa ctgctgcgct gatctggaca ccacagaggt tccgagcact ttaggttgca    6420
ccaaatgtcc caccaggtgc aggcagaaaa cgctggaaca gcgtgtacag tttgtcttaa    6480
caaaaagtga gggcgctgag gtcgagcagg gtggtgtgac ttgttatagc ctttagagct    6540
gcgaaagcgc gtatggattt ggctcatcag gccagattga gggtctgtgg acacatgtca    6600
tgttagtgta cttcaatcgc cccctggata tagccccgac aataggccgt ggcctcattt    6660
ttttgccttc cgcacatttc cattgctcga tacccacacc ttgcttctcc tgcacttgcc    6720
aaccttaata ctggtttaca ttgaccaaca tcttacaagc gggggcttg tctagggtat     6780 atataaacag tggctctccc aatcggttgc cagtctcttt tttcctttct ttccccacag    6840
attcgaaatc taaactacac atcacagaat tccgagccgt gagtatccac gacaagatca    6900
gtgtcgagac gacgcgtttt gtgtaatgac acaatccgaa agtcgctagc aacacacact    6960
ctctacacaa actaacccag ctctggtacc atggaggtcg tgaacgaaat cgtctccatt    7020
ggccaggagg ttcttcccaa ggtcgactat gctcagctct ggtctgatgc ctcgcactgc    7080
gaggtgctgt acatgtccat cgccttcgtc atcctgaagt tcaccccttgg tcctctcgga   7140 cccaagggtc agtctcgaat gaagtttgtg ttcaccaact acaacctgct catgtccatc    7200
tactcgctgg gctccttcct ctctatggcc tacgccatgt acaccattgg tgtcatgtcc    7260
gacaactgcg agaaggcttt cgacaacaat gtcttccgaa tcaccactga gctgttctac    7320
ctcagcaagt tcctcgagta cattgactcc ttctatctgc ccctcatggg caagcctctg    7380
acctggttgc agttctttca ccatctcgga gctcctatgg acatgtggct gttctacaac    7440
taccgaaacg aagccgtttg gatctttgtg ctgctcaacg gcttcattca ctggatcatg    7500
tacggctact attggacccg actgatcaag ctcaagttcc ctatgcccaa gtccctgatt    7560
```

```
acttctatgc agatcattca gttcaacgtt ggcttctaca tcgtctggaa gtaccggaac    7620
attccctgct accgacaaga tggaatgaga atgtttggct ggttttttcaa ctacttctac   7680 gttggtactg tcctgtgtct gttcctcaac ttctacgtgc agacctacat cgtccgaaag    7740
cacaagggag ccaaaaagat tcagtgagc                                      7769
```

<210> SEQ ID NO 64
<211> LENGTH: 22
<212> TYPE: DNA
<213> ORGANISM: Artificial Sequence
<220> FEATURE:
<223> OTHER INFORMATION: Primer Eg_9D_122709f

<400> SEQUENCE: 64

```
gaaatcgtcg acattggcca gg                                              22
```

<210> SEQ ID NO 65
<211> LENGTH: 27
<212> TYPE: DNA
<213> ORGANISM: Artificial Sequence
<220> FEATURE:
<223> OTHER INFORMATION: Primer Eg_84C_122709r

<400> SEQUENCE: 65

```
gacaccaatg gtacacatgg cgtaggc                                         27
```

<210> SEQ ID NO 66
<211> LENGTH: 27
<212> TYPE: DNA
<213> ORGANISM: Artificial Sequence
<220> FEATURE:
<223> OTHER INFORMATION: Primer Eg_84C_122709f

<400> SEQUENCE: 66

```
gcctacgcca tgtgtaccat tggtgtc                                         27
```

<210> SEQ ID NO 67
<211> LENGTH: 22
<212> TYPE: DNA
<213> ORGANISM: Artificial Sequence
<220> FEATURE:
<223> OTHER INFORMATION: Primer Eg_9D_122709r

<400> SEQUENCE: 67

```
cctggccaat gtcgacgatt tc                                              22
```

<210> SEQ ID NO 68
<211> LENGTH: 25
<212> TYPE: DNA
<213> ORGANISM: Artificial Sequence
<220> FEATURE:
<223> OTHER INFORMATION: Primer Eg_161T_122709f

<400> SEQUENCE: 68

```
gatctttgtg accctcaacg gcttc                                           25
```

<210> SEQ ID NO 69
<211> LENGTH: 25
<212> TYPE: DNA
<213> ORGANISM: Artificial Sequence
<220> FEATURE:
<223> OTHER INFORMATION: Primer Eg_179R_122709r

<400> SEQUENCE: 69

```
gaacttgagc tttcgcagtc gggtc                                           25
```

```
<210> SEQ ID NO 70
<211> LENGTH: 25
<212> TYPE: DNA
<213> ORGANISM: Artificial Sequence
<220> FEATURE:
<223> OTHER INFORMATION: Primer Eg_179R_122709f

<400> SEQUENCE: 70
gacccgactg cgaaagctca agttc                                         25

<210> SEQ ID NO 71
<211> LENGTH: 25
<212> TYPE: DNA
<213> ORGANISM: Artificial Sequence
<220> FEATURE:
<223> OTHER INFORMATION: Primer Eg_161T_122709r

<400> SEQUENCE: 71
gaagccgttg agggtcacaa agatc                                         25

<210> SEQ ID NO 72
<211> LENGTH: 22
<212> TYPE: DNA
<213> ORGANISM: Artificial Sequence
<220> FEATURE:
<223> OTHER INFORMATION: Primer Eg_244N_122709f

<400> SEQUENCE: 72
cttctacgtg aacacctaca tc                                            22

<210> SEQ ID NO 73
<211> LENGTH: 23
<212> TYPE: DNA
<213> ORGANISM: Artificial Sequence
<220> FEATURE:
<223> OTHER INFORMATION: Primer Eg_21V_010710r

<400> SEQUENCE: 73
gaccagagct gcacatagtc gac                                           23

<210> SEQ ID NO 74
<211> LENGTH: 23
<212> TYPE: DNA
<213> ORGANISM: Artificial Sequence
<220> FEATURE:
<223> OTHER INFORMATION: Primer Eg_21V_010710f

<400> SEQUENCE: 74
gtcgactatg tgcagctctg gtc                                           23

<210> SEQ ID NO 75
<211> LENGTH: 22
<212> TYPE: DNA
<213> ORGANISM: Artificial Sequence
<220> FEATURE:
<223> OTHER INFORMATION: Primer Eg_244N_122709r

<400> SEQUENCE: 75
gatgtaggtg ttcacgtaga ag                                            22

<210> SEQ ID NO 76
<211> LENGTH: 22
<212> TYPE: DNA
<213> ORGANISM: Artificial Sequence
<220> FEATURE:
```

```
<223> OTHER INFORMATION: Primer Eg_32F_010710f

<400> SEQUENCE: 76
gcactgcgag tttctgtacc tc                                              22

<210> SEQ ID NO 77
<211> LENGTH: 22
<212> TYPE: DNA
<213> ORGANISM: Artificial Sequence
<220> FEATURE:
<223> OTHER INFORMATION: Primer Eg_108G_010710r

<400> SEQUENCE: 77
gaggtagaaa ccctgagtgg tg                                              22

<210> SEQ ID NO 78
<211> LENGTH: 22
<212> TYPE: DNA
<213> ORGANISM: Artificial Sequence
<220> FEATURE:
<223> OTHER INFORMATION: Primer Eg_108G_010710f

<400> SEQUENCE: 78
caccactcag ggtttctacc tc                                              22

<210> SEQ ID NO 79
<211> LENGTH: 22
<212> TYPE: DNA
<213> ORGANISM: Artificial Sequence
<220> FEATURE:
<223> OTHER INFORMATION: Primer Eg_32F_010710r

<400> SEQUENCE: 79
gaggtacaga aactcgcagt gc                                              22

<210> SEQ ID NO 80
<211> LENGTH: 22
<212> TYPE: DNA
<213> ORGANISM: Artificial Sequence
<220> FEATURE:
<223> OTHER INFORMATION: Primer Eg_132T_010710f

<400> SEQUENCE: 80
gcctctgacc accttgcagt tc                                              22

<210> SEQ ID NO 81
<211> LENGTH: 22
<212> TYPE: DNA
<213> ORGANISM: Artificial Sequence
<220> FEATURE:
<223> OTHER INFORMATION: Primer Eg_143N_010710r

<400> SEQUENCE: 81
gccacatgtc gttaggagct cc                                              22

<210> SEQ ID NO 82
<211> LENGTH: 22
<212> TYPE: DNA
<213> ORGANISM: Artificial Sequence
<220> FEATURE:
<223> OTHER INFORMATION: Primer Eg_143N_010710f

<400> SEQUENCE: 82
ggagctccta acgacatgtg gc                                              22
```

-continued

```
<210> SEQ ID NO 83
<211> LENGTH: 22
<212> TYPE: DNA
<213> ORGANISM: Artificial Sequence
<220> FEATURE:
<223> OTHER INFORMATION: Primer Eg_132T_010710r

<400> SEQUENCE: 83
gaactgcaag gtggtcagag gc                                                22

<210> SEQ ID NO 84
<211> LENGTH: 23
<212> TYPE: DNA
<213> ORGANISM: Artificial Sequence
<220> FEATURE:
<223> OTHER INFORMATION: Primer Eg_236N_010710f

<400> SEQUENCE: 84
gtactgtcct gaacctgttc ctc                                               23

<210> SEQ ID NO 85
<211> LENGTH: 23
<212> TYPE: DNA
<213> ORGANISM: Artificial Sequence
<220> FEATURE:
<223> OTHER INFORMATION: Primer Eg_236N_010710r

<400> SEQUENCE: 85
gaggaacagg ttcaggacag tac                                               23

<210> SEQ ID NO 86
<211> LENGTH: 777
<212> TYPE: DNA
<213> ORGANISM: Euglena gracilis
<220> FEATURE:
<221> NAME/KEY: CDS
<222> LOCATION: (1)..(777)
<223> OTHER INFORMATION: mutant delta-9 elongase
      "EgD9eS-A21V/L35G/L108G/I179R"

<400> SEQUENCE: 86 atg gag gtc gtg aac gaa atc gtc tcc att ggc cag gag gtt ctt ccc        48
Met Glu Val Val Asn Glu Ile Val Ser Ile Gly Gln Glu Val Leu Pro
1               5                   10                  15 aag gtc gac tat gtg cag ctc tgg tct gat gcc tcg cac tgc gag gtg        96
Lys Val Asp Tyr Val Gln Leu Trp Ser Asp Ala Ser His Cys Glu Val
            20                  25                  30 ctg tac ggg tcc atc gcc ttc gtc atc ctg aag ttc acc ctt ggt cct       144
Leu Tyr Gly Ser Ile Ala Phe Val Ile Leu Lys Phe Thr Leu Gly Pro
        35                  40                  45 ctc gga ccc aag ggt cag tct cga atg aag ttt gtg ttc acc aac tac       192
Leu Gly Pro Lys Gly Gln Ser Arg Met Lys Phe Val Phe Thr Asn Tyr
    50                  55                  60 aac ctg ctc atg tcc atc tac tcg ctg ggc tcc ttc ctc tct atg gcc       240
Asn Leu Leu Met Ser Ile Tyr Ser Leu Gly Ser Phe Leu Ser Met Ala
65                  70                  75                  80 tac gcc atg tac acc att ggt gtc atg tcc gac aac tgc gag aag gct       288
Tyr Ala Met Tyr Thr Ile Gly Val Met Ser Asp Asn Cys Glu Lys Ala
                85                  90                  95 ttc gac aac aat gtc ttc cga atc acc act cag ggt ttc tac ctc agc       336
Phe Asp Asn Asn Val Phe Arg Ile Thr Thr Gln Gly Phe Tyr Leu Ser
            100                 105                 110 aag ttc ctc gag tac att gac tcc ttc tat ctg ccc ctc atg ggc aag       384
Lys Phe Leu Glu Tyr Ile Asp Ser Phe Tyr Leu Pro Leu Met Gly Lys
        115                 120                 125
```

```
cct ctg acc tgg ttg cag ttc ttt cac cat ctc gga gct cct atg gac     432
Pro Leu Thr Trp Leu Gln Phe Phe His His Leu Gly Ala Pro Met Asp
    130                 135                 140 atg tgg ctg ttc tac aac tac cga aac gaa gcc gtt tgg atc ttt gtg     480
Met Trp Leu Phe Tyr Asn Tyr Arg Asn Glu Ala Val Trp Ile Phe Val
145                 150                 155                 160 ctg ctc aac ggc ttc att cac tgg atc atg tac ggc tac tat tgg acc     528
Leu Leu Asn Gly Phe Ile His Trp Ile Met Tyr Gly Tyr Tyr Trp Thr
                165                 170                 175 cga ctg cga aag ctc aag ttc cct atg ccc aag tcc ctg att act tct     576
Arg Leu Arg Lys Leu Lys Phe Pro Met Pro Lys Ser Leu Ile Thr Ser
            180                 185                 190 atg cag atc att cag ttc aac gtt ggc ttc tac atc gtc tgg aag tac     624
Met Gln Ile Ile Gln Phe Asn Val Gly Phe Tyr Ile Val Trp Lys Tyr
        195                 200                 205 cgg aac att ccc tgc tac cga caa gat gga atg aga atg ttt ggc tgg     672
Arg Asn Ile Pro Cys Tyr Arg Gln Asp Gly Met Arg Met Phe Gly Trp
    210                 215                 220 ttt ttc aac tac ttc tac gtt ggt act gtc ctg tgt ctg ttc ctc aac     720
Phe Phe Asn Tyr Phe Tyr Val Gly Thr Val Leu Cys Leu Phe Leu Asn
225                 230                 235                 240 ttc tac gtg cag acc tac atc gtc cga aag cac aag gga gcc aaa aag     768
Phe Tyr Val Gln Thr Tyr Ile Val Arg Lys His Lys Gly Ala Lys Lys
                245                 250                 255 att cag tga                                                         777
Ile Gln

<210> SEQ ID NO 87
<211> LENGTH: 258
<212> TYPE: PRT
<213> ORGANISM: Euglena gracilis

<400> SEQUENCE: 87

Met Glu Val Val Asn Glu Ile Val Ser Ile Gly Gln Glu Val Leu Pro
1               5                   10                  15

Lys Val Asp Tyr Val Gln Leu Trp Ser Asp Ala Ser His Cys Glu Val
            20                  25                  30

Leu Tyr Gly Ser Ile Ala Phe Val Ile Leu Lys Phe Thr Leu Gly Pro
        35                  40                  45

Leu Gly Pro Lys Gly Gln Ser Arg Met Lys Phe Val Phe Thr Asn Tyr
    50                  55                  60

Asn Leu Leu Met Ser Ile Tyr Ser Leu Gly Ser Phe Leu Ser Met Ala
65                  70                  75                  80

Tyr Ala Met Tyr Thr Ile Gly Val Met Ser Asp Asn Cys Glu Lys Ala
                85                  90                  95

Phe Asp Asn Asn Val Phe Arg Ile Thr Thr Gln Gly Phe Tyr Leu Ser
            100                 105                 110

Lys Phe Leu Glu Tyr Ile Asp Ser Phe Tyr Leu Pro Leu Met Gly Lys
        115                 120                 125

Pro Leu Thr Trp Leu Gln Phe Phe His His Leu Gly Ala Pro Met Asp
    130                 135                 140

Met Trp Leu Phe Tyr Asn Tyr Arg Asn Glu Ala Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Arg Lys Leu Lys Phe Pro Met Pro Lys Ser Leu Ile Thr Ser
            180                 185                 190
```

```
Met Gln Ile Ile Gln Phe Asn Val Gly Phe Tyr Ile Val Trp Lys Tyr
        195                 200                 205

Arg Asn Ile Pro Cys Tyr Arg Gln Asp Gly Met Arg Met Phe Gly Trp
    210                 215                 220

Phe Phe Asn Tyr Phe Tyr Val Gly Thr Val Leu Cys Leu Phe Leu Asn
225                 230                 235                 240

Phe Tyr Val Gln Thr Tyr Ile Val Arg Lys His Lys Gly Ala Lys Lys
                245                 250                 255

Ile Gln

<210> SEQ ID NO 88
<211> LENGTH: 7769
<212> TYPE: DNA
<213> ORGANISM: Artificial Sequence
<220> FEATURE:
<223> OTHER INFORMATION: Plasmid pZuFmEgD9ES-A21V/L35G/L108G/I179R

<400> SEQUENCE: 88
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc gggcaacggt ttcacttgag tgcagtggct     240
agtgctctta ctcgtacagt gtgcaatact gcgtatcata gtctttgatg tatatcgtat     300
tcattcatgt tagttgcgta cgagccggaa gcataaagtg taaagcctgg ggtgcctaat     360
gagtgagcta actcacatta ttgcgttgc gctcactgcc cgctttccag tcgggaaacc      420
tgtcgtgcca gctgcattaa tgaatcggcc aacgcgcggg gagaggcggt ttgcgtattg     480
ggcgctcttc cgcttcctcg ctcactgact cgctgcgctc ggtcgttcgg ctgcggcgag     540
cggtatcagc tcactcaaag gcggtaatac ggttatccac agaatcaggg gataacgcag     600
gaaagaacat gtgagcaaaa ggccagcaaa aggccaggaa ccgtaaaaag gccgcgttgc     660
tggcgttttt ccataggctc cgcccccctg acgagcatca caaaaatcga cgctcaagtc     720
agaggtggcg aaacccgaca ggactataaa gataccaggc gtttccccct ggaagctccc     780
tcgtgcgctc tcctgttccg accctgccgc ttaccggata cctgtccgcc tttctccctt     840
cgggaagcgt ggcgctttct catagctcac gctgtaggta tctcagttcg gtgtaggtcg     900
ttcgctccaa gctgggctgt gtgcacgaac cccccgttca gcccgaccgc tgcgccttat     960
ccggtaacta tcgtcttgag tccaacccgg taagacacga cttatcgcca ctggcagcag    1020
ccactggtaa caggattagc agagcgaggt atgtaggcgg tgctacagag ttcttgaagt    1080
ggtggcctaa ctacggctac actagaagga cagtatttgg tatctgcgct ctgctgaagc    1140
cagttacctt cggaaaaaga gttggtagct cttgatccgg caaacaaacc accgctggta    1200
gcggtggttt ttttgtttgc aagcagcaga ttacgcgcag aaaaaaagga tctcaagaag    1260
atcctttgat cttttctacg gggtctgacg ctcagtggaa cgaaaactca cgttaaggga    1320
ttttggtcat gagattatca aaaggatct tcacctagat ccttttaaat taaaaatgaa    1380
gttttaaatc aatctaaagt atatatgagt aaacttggtc tgacagttac caatgcttaa    1440
tcagtgaggc acctatctca gcgatctgtc tatttcgttc atccatagtt gcctgactcc    1500
ccgtcgtgta gataactacg atacgggagg gcttaccatc tggccccagt gctgcaatga    1560
taccgcgaga cccacgctca ccggctccag atttatcagc aataaccagc cagccggaa     1620
```

```
gggccgagcg cagaagtggt cctgcaactt tatccgcctc catccagtct attaattgtt    1680
gccgggaagc tagagtaagt agttcgccag ttaatagttt gcgcaacgtt gttgccattg    1740
ctacaggcat cgtggtgtca cgctcgtcgt ttggtatggc ttcattcagc tccggttccc    1800
aacgatcaag gcgagttaca tgatccccca tgttgtgcaa aaaagcggtt agctccttcg    1860
gtcctccgat cgttgtcaga agtaagttgg ccgcagtgtt atcactcatg gttatggcag    1920
cactgcataa ttctcttact gtcatgccat ccgtaagatg cttttctgtg actggtgagt    1980
actcaaccaa gtcattctga aatagtgta tgcggcgacc gagttgctct tgcccggcgt     2040
caatacggga taataccgcg ccacatagca gaactttaaa agtgctcatc attggaaaac    2100
gttcttcggg gcgaaaactc tcaaggatct taccgctgtt gagatccagt tcgatgtaac    2160
ccactcgtgc acccaactga tcttcagcat cttttacttt caccagcgtt tctgggtgag    2220
caaaaacagg aaggcaaaat gccgcaaaaa agggaataag ggcgacacgg aaatgttgaa    2280
tactcatact cttccttttt caatattatt gaagcattta tcagggttat tgtctcatga    2340
gcggatacat atttgaatgt atttagaaaa ataaacaaat aggggttccg cgcacatttc    2400
cccgaaaagt gccacctgac gcgccctgta gcggcgcatt aagcgcggcg ggtgtggtgg    2460
ttacgcgcag cgtgaccgct acacttgcca gcgccctagc gcccgctcct ttcgctttct    2520
tcccttcctt tctcgccacg ttcgccggct ttccccgtca gctctaaat cggggctcc     2580
ctttagggtt ccgatttagt gctttacggc acctcgaccc caaaaaactt gattagggtg    2640
atggttcacg tagtgggcca tcgccctgat agacggtttt tcgccctttg acgttggagt    2700
ccacgttctt taatagtgga ctcttgttcc aaactggaac aacactcaac cctatctcgg    2760
tctattcttt tgatttataa gggattttgc cgatttcggc ctattggtta aaaaatgagc    2820
tgatttaaca aaaatttaac gcgaatttta acaaaatatt aacgcttaca atttccattc    2880
gccattcagg ctgcgcaact gttgggaagg gcgatcggtg cgggcctctt cgctattacg    2940
ccagctggcg aaaggggggat gtgctgcaag gcgattaagt tgggtaacgc cagggttttc    3000
ccagtcacga cgttgtaaaa cgacggccag tgaattgtaa tacgactcac tatagggcga    3060
attgggtacc gggccccccc tcgaggtcga tggtgtcgat aagcttgata tcgaattcat    3120
gtcacacaaa ccgatcttcg cctcaaggaa acctaattct acatccgaga gactgccgag    3180
atccagtcta cactgattaa ttttcgggcc aataatttaa aaaaatcgtg ttatataata    3240
ttatatgtat tatatatata catcatgatg atactgacag tcatgtccca ttgctaaata    3300
gacagactcc atctgccgcc tccaactgat gttctcaata tttaaggggt catctcgcat    3360
tgtttaataa taaacagact ccatctaccg cctccaaatg atgttctcaa aatatattgt    3420
atgaacttat ttttattact tagtattatt agacaactta cttgctttat gaaaaacact    3480
tcctatttag gaaacaattt ataatggcag ttcgttcatt taacaattta tgtagaataa    3540
atgttataaa tgcgtatggg aaatcttaaa tatggatagc ataaatgata tctgcattgc    3600
ctaattcgaa atcaacagca acgaaaaaaa tcccttgtac aacataaata gtcatcgaga    3660
aatatcaact atcaaagaac agctattcac acgttactat tgagattatt attggacgag    3720
aatcacacac tcaactgtct ttctctcttc tagaaataca ggtacaagta tgtactattc    3780
tcattgttca tacttctagt catttcatcc cacatattcc ttggatttct ctccaatgaa    3840
tgacattcta tcttgcaaat tcaacaatta taataagata taccaaagta gcggtatagt    3900
ggcaatcaaa aagcttctct ggtgtgcttc tcgtatttat ttttattcta atgatccatt    3960
aaaggtatat atttatttct tgttatataa tccttttgtt tattacatgg gctggataca    4020
```

```
taaaggtatt ttgatttaat tttttgctta aattcaatcc cccctcgttc agtgtcaact    4080
gtaatggtag gaaattacca tacttttgaa gaagcaaaaa aaatgaaaga aaaaaaaaat    4140
cgtatttcca ggttagacgt tccgcagaat ctagaatgcg gtatgcggta cattgttctt    4200
cgaacgtaaa agttgcgctc cctgagatat tgtacatttt tgcttttaca agtacaagta    4260
catcgtacaa ctatgtacta ctgttgatgc atccacaaca gtttgttttg ttttttttg     4320 ttttttttt ttctaatgat tcattaccgc tatgtatacc tacttgtact tgtagtaagc    4380
cgggttattg gcgttcaatt aatcatagac ttatgaatct gcacggtgtg cgctgcgagt    4440
tacttttagc ttatgcatgc tacttgggtg taatattggg atctgttcgg aaatcaacgg    4500
atgctcaatc gatttcgaca gtaattaatt aagtcataca caagtcagct ttcttcgagc    4560
ctcatataag tataagtagt tcaacgtatt agcactgtac ccagcatctc cgtatcgaga    4620
aacacaacaa catgccccat tggacagatc atgcggatac acaggttgtg cagtatcata    4680
catactcgat cagacaggtc gtctgaccat catacaagct gaacaagcgc tccatacttg    4740
cacgctctct atatacacag ttaaattaca tatccatagt ctaacctcta acagttaatc    4800
ttctggtaag cctcccagcc agccttctgg tatcgcttgg cctcctcaat aggatctcgg    4860
ttctggccgt acagacctcg gccgacaatt atgatatccg ttccggtaga catgacatcc    4920
tcaacagttc ggtactgctg tccgagagcg tctcccttgt cgtcaagacc caccccgggg    4980
gtcagaataa gccagtcctc agagtcgccc ttaggtcggt tctgggcaat gaagccaacc    5040
acaaactcgg ggtcggatcg ggcaagctca atggtctgct tggagtactc gccagtggcc    5100
agagagccct tgcaagacag ctcggccagc atgagcagac ctctggccag cttctcgttg    5160
ggagagggga ctaggaactc cttgtactgg gagttctcgt agtcagagac gtcctccttc    5220
ttctgttcag agacagtttc ctcggcacca gctcgcaggc cagcaatgat tccggttccg    5280
ggtacaccgt gggcgttggt gatatcggac cactcggcga ttcggtgaca ccggtactgg    5340
tgcttgacag tgttgccaat atctgcgaac tttctgtcct cgaacaggaa gaaaccgtgc    5400
ttaagagcaa gttccttgag ggggagcaca gtgccggcgt aggtgaagtc gtcaatgatg    5460
tcgatatggg ttttgatcat gcacacataa ggtccgacct tatcggcaag ctcaatgagc    5520
tccttggtgg tggtaacatc cagagaagca cacaggttgg ttttcttggc tgccacgagc    5580
ttgagcactc gagcggcaaa gcggacttg tggacgttag ctcgagcttc gtaggagggc     5640
attttggtgg tgaagaggag actgaaataa atttagtctg cagaactttt tatcggaacc    5700
ttatctgggg cagtgaagta tatgttatgg taatagttac gagttagttg aacttataga    5760
tagactggac tatacggcta tcggtccaaa ttagaaagaa cgtcaatggc tctctgggcg    5820
tcgcctttgc cgacaaaaat gtgatcatga tgaaagccag caatgacgtt gcagctgata    5880
ttgttgtcgg ccaaccgcgc cgaaaacgca gctgtcagac ccacagcctc caacgaagaa    5940
tgtatcgtca aagtgatcca agcacactca tagttggagt cgtactccaa aggcggcaat    6000
gacgagtcag acagatactc gtcgacgttt aaacagtgta cgcagatcta ctatagagga    6060
acatttaaat tgccccggag aagacggcca ggccgcctag atgacaaatt caacaactca    6120
cagctgactt tctgccattg ccactagggg ggggcctttt tatatggcca agccaagctc    6180
tccacgtcgg ttgggctgca cccaacaata aatgggtagg gttgcaccaa caaagggatg    6240 ggatggggg tagaagatac gaggataacg gggctcaatg gcacaaataa gaacgaatac     6300
tgccattaag actcgtgatc cagcgactga caccattgca tcatctaagg gcctcaaaac    6360
```

```
tacctcggaa ctgctgcgct gatctggaca ccacagaggt tccgagcact ttaggttgca      6420
ccaaatgtcc caccaggtgc aggcagaaaa cgctggaaca gcgtgtacag tttgtcttaa      6480
caaaaagtga gggcgctgag gtcgagcagg gtggtgtgac ttgttatagc ctttagagct      6540
gcgaaagcgc gtatggattt ggctcatcag gccagattga gggtctgtgg acacatgtca      6600
tgttagtgta cttcaatcgc ccctggata tagccccgac aataggccgt ggcctcattt       6660
ttttgccttc cgcacatttc cattgctcga tacccacacc ttgcttctcc tgcacttgcc      6720
aaccttaata ctggtttaca ttgaccaaca tcttacaagc gggggcttg tctagggtat       6780
atataaacag tggctctccc aatcggttgc cagtctcttt tttcctttct ttccccacag      6840
attcgaaatc taaactacac atcacagaat tccgagccgt gagtatccac gacaagatca      6900
gtgtcgagac gacgcgtttt gtgtaatgac acaatccgaa agtcgctagc aacacacact      6960
ctctacacaa actaacccag ctctggtacc atggaggtcg tgaacgaaat cgtctccatt      7020
ggccaggagg ttcttcccaa ggtcgactat gtgcagctct ggtctgatgc ctcgcactgc      7080
gaggtgctgt acgggtccat cgccttcgtc atcctgaagt tcaccettgg tcctctcgga     7140
cccaagggtc agtctcgaat gaagtttgtg ttcaccaact acaacctgct catgtccatc      7200
tactcgctgg gctccttcct ctctatggcc tacgccatgt acaccattgg tgtcatgtcc      7260
gacaactgcg agaaggcttt cgacaacaat gtcttccgaa tcaccactca gggtttctac      7320
ctcagcaagt cctcgagta cattgactcc ttctatctgc ccctcatggg caagcctctg      7380
acctggttgc agttctttca ccatctcgga gctcctatgg acatgtggct gttctacaac      7440
taccgaaacg aagccgtttg gatctttgtg ctgctcaacg gcttcattca ctggatcatg      7500
tacggctact attggacccg actgcgaaag ctcaagttcc ctatgcccaa gtccctgatt      7560
acttctatgc agatcattca gttcaacgtt ggcttctaca tcgtctggaa gtaccggaac      7620
attccctgct accgacaaga tggaatgaga atgtttggct ggttttttcaa ctacttctac      7680
gttggtactg tcctgtgtct gttcctcaac ttctacgtgc agacctacat cgtccgaaag      7740
cacaagggag ccaaaaagat tcagtgagc                                        7769
```

<210> SEQ ID NO 89
<211> LENGTH: 4313
<212> TYPE: DNA
<213> ORGANISM: Artificial Sequence
<220> FEATURE:
<223> OTHER INFORMATION: Plasmid pZKUM

<400> SEQUENCE: 89

```
taatcgagct tggcgtaatc atggtcatag ctgtttcctg tgtgaaattg ttatccgctc        60
acaattccac acaacatacg agccggaagc ataaagtgta aagcctgggg tgcctaatga       120
gtgagctaac tcacattaat tgcgttgcgc tcactgcccg ctttccagtc gggaaacctg       180
tcgtgccagc tgcattaatg aatcggccaa cgcgcgggga gaggcggttt gcgtattggg       240
cgctcttccg cttcctcgct cactgactcg ctgcgctcgg tcgttcggct gcggcgagcg       300
gtatcagctc actcaaaggc ggtaatacgg ttatccacag aatcagggga taacgcagga      360
aagaacatgt gagcaaaagg ccagcaaaag gccaggaacc gtaaaaaggc cgcgttgctg      420
gcgtttttcc ataggctccg ccccctgac gagcatcaca aaaatcgacg ctcaagtcag      480
aggtggcgaa acccgacagg actataaaga taccaggcgt ttccccctgg aagctccctc     540
gtgcgctctc ctgttccgac cctgccgctt accggatacc tgtccgcctt ctcccttcg      600
ggaagcgtgg cgctttctca tagctcacgc tgtaggtatc tcagttcggt gtaggtcgtt      660
```

```
cgctccaagc tgggctgtgt gcacgaaccc cccgttcagc ccgaccgctg cgccttatcc    720
ggtaactatc gtcttgagtc aacccggta agacacgact tatcgccact ggcagcagcc     780
actggtaaca ggattagcag agcgaggtat gtaggcggtg ctacagagtt cttgaagtgg    840
tggcctaact acggctacac tagaaggaca gtatttggta tctgcgctct gctgaagcca    900
gttaccttcg gaaaaagagt tggtagctct tgatccggca acaaaccac cgctggtagc     960 ggtggttttt ttgtttgcaa gcagcagatt acgcgcagaa aaaaggatc tcaagaagat     1020 cctttgatct tttctacggg gtctgacgct cagtggaacg aaaactcacg ttaagggatt    1080
ttggtcatga gattatcaaa aaggatcttc acctagatcc ttttaaatta aaaatgaagt    1140
tttaaatcaa tctaaagtat atatgagtaa acttggtctg acagttacca atgcttaatc    1200
agtgaggcac ctatctcagc gatctgtcta tttcgttcat ccatagttgc ctgactcccc    1260
gtcgtgtaga taactacgat acgggagggc ttaccatctg gccccagtgc tgcaatgata    1320
ccgcgagacc cacgctcacc ggctccagat ttatcagcaa taaaccagcc agccggaagg    1380
gccgagcgca gaagtggtcc tgcaacttta tccgcctcca tccagtctat taattgttgc    1440
cgggaagcta gagtaagtag ttcgccagtt aatagtttgc gcaacgttgt tgccattgct    1500
acaggcatcg tggtgtcacg ctcgtcgttt ggtatggctt cattcagctc cggttcccaa    1560
cgatcaaggc gagttacatg atcccccatg ttgtgcaaaa aagcggttag ctccttcggt    1620
cctccgatcg ttgtcagaag taagttggcc gcagtgttat cactcatggt tatggcagca    1680
ctgcataatt ctcttactgt catgccatcc gtaagatgct tttctgtgac tggtgagtac    1740
tcaaccaagt cattctgaga atagtgtatg cggcgaccga gttgctcttg cccggcgtca    1800
atacgggata taccgcgcc acatagcaga actttaaaag tgctcatcat tggaaaacgt     1860
tcttcggggc gaaaactctc aaggatctta ccgctgttga tccagttc gatgtaaccc      1920 actcgtgcac ccaactgatc ttcagcatct tttactttca ccagcgtttc tgggtgagca    1980
aaaacaggaa ggcaaaatgc cgcaaaaaag ggaataaggg cgacacggaa atgttgaata    2040
ctcatactct tcctttttca atattattga agcatttatc agggttattg tctcatgagc    2100
ggatacatat ttgaatgtat ttagaaaaat aaacaaatag gggttccgcg cacatttccc    2160
cgaaaagtgc cacctgacgc gccctgtagc ggcgcattaa gcgcggcggg tgtggtggtt    2220
acgcgcagcg tgaccgctac acttgccagc gccctagcgc ccgctccttt cgctttcttc    2280
ccttcctttc tcgccacgtt cgccggcttt ccccgtcaag ctctaaatcg ggggctccct    2340
ttagggttcc gatttagtgc tttacggcac ctcgaccca aaaaacttga ttagggtgat     2400
ggttcacgta gtgggccatc gccctgatag acggttttc gccctttgac gttggagtcc    2460
acgttcttta atagtggact cttgttccaa actggaacaa cactcaaccc tatctcggtc    2520
tattcttttg atttataagg gattttgccg atttcggcct attggttaaa aaatgagctg    2580
atttaacaaa aatttaacgc gaattttaac aaaatattaa cgcttacaat tccattcgc     2640 cattcaggct gcgcaactgt tgggaagggc gatcggtgcg ggcctcttcg ctattacgcc    2700
agctggcgaa agggggatgt gctgcaaggc gattaagttg ggtaacgcca ggttttccc     2760 agtcacgacg ttgtaaaacg acggccagtg aattgtaata cgactcacta tagggcgaat    2820
tgggtaccgg gccccccctc gaggtcgacg agtatctgtc tgactcgtca ttgccgcctt    2880
tggagtacga ctccaactat gagtgtgctt ggatcacttt gacgatacat tcttcgttgg    2940
aggctgtggg tctgacagct gcgttttcgg cgcggttggc cgacaacaat atcagctgca    3000
```

| | |
|---|---|
| acgtcattgc tggctttcat catgatcaca tttttgtcgg caaaggcgac gcccagagag | 3060 |
| ccattgacgt tctttctaat ttggaccgat agccgtatag tccagtctat ctataagttc | 3120 |
| aactaactcg taactattac cataacatat acttcactgc cccagataag gttccgataa | 3180 |
| aaagttctgc agactaaatt tatttcagtc tcctcttcac caccaaaatg ccctcctacg | 3240 |
| aagctcgagt gctcaagctc gtggcagcca agaaaaccaa cctgtgtgct tctctggatg | 3300 |
| ttaccaccac caaggagctc attgagcttg ccgataaggt cggacccttat gtgtgcatga | 3360 |
| tcaaaaccca tatcgacatc attgacgact tcacctacgc cggcactgtg ctccccctca | 3420 |
| aggaacttgc tcttaagcac ggtttcttcc tgttcgagga cagaaagttc gcagatattg | 3480 |
| gcaacactgt caagcaccag taccggtgtc accgaatcgc cgagtggtcc gatatcacca | 3540 |
| acgcccacgg tgtacccgga accggaatcg attgctggcc tgcgagctgg tgcgtacgag | 3600 |
| gaaactgtct ctgaacagaa gaaggaggac gtctctgact acgagaactc ccagtacaag | 3660 |
| gagttcctag tcccctctcc caacgagaag ctggccagag gtctgctcat gctggccgag | 3720 |
| ctgtcttgca agggctctct ggccactggc gagtactcca agcagaccat tgagcttgcc | 3780 |
| cgatccgacc ccgagtttgt ggttggcttc attgcccaga accgacctaa gggcgactct | 3840 |
| gaggactggc ttattctgac ccccggggtg ggtcttgacg acaagggaga cgctctcgga | 3900 |
| cagcagtacc gaactgttga ggatgtcatg tctaccggaa cggatatcat aattgtcggc | 3960 |
| cgaggtctgt acgccagaa ccgagatcct attgaggagg ccaagcgata ccagaaggct | 4020 |
| ggctgggagg cttaccagaa gattaactgt tagaggttag actatggata tgtaatttaa | 4080 |
| ctgtgtatat agagagcgtg caagtatgga gcgcttgttc agcttgtatg atggtcagac | 4140 |
| gacctgtctg atcgagtatg tatgatactg cacaacctgt gtatccgcat gatctgtcca | 4200 |
| atggggcatt tgttgtgtt tctcgatacg gagatgctgg gtacagtgct aatacgttga | 4260 |
| actacttata cttatatgag gctcgaagaa agctgacttg tgtatgactt aat | 4313 |

<210> SEQ ID NO 90
<211> LENGTH: 13565
<212> TYPE: DNA
<213> ORGANISM: Artificial Sequence
<220> FEATURE:
<223> OTHER INFORMATION: Plasmid pZKL3-9DP9N

<400> SEQUENCE: 90

| | |
|---|---|
| gtacggattg tgtatgtccc tgtacctgca tcttgatgga gagagctccg gaaagcggat | 60 |
| caggagctgt ccaattttaa ttttataaca tggaaacgag tccttggagc tagaagacca | 120 |
| ttttttcaac tgccctatcg actatattta tctactccaa aaccgactgc ttcccaagaa | 180 |
| tcttcagcca aggcttccaa agtaacccct cgcttcccga cacttaattg aaaccttaga | 240 |
| tgcagtcact gcgagtgaag tggactctaa catctccaac atagcgacga tattgcgagg | 300 |
| gtttgaatat aactaagatg catgatccat tacatttgta gaaatatcat aaacaacgaa | 360 |
| gcacatagac agaatgctgt tggttgttac atctgaagcc gaggtaccga tgtcatttttc | 420 |
| agctgtcact gcagagacag gggtatgtca catttgaaga tcatacaacc gacgtttatg | 480 |
| aaaaccagag atatagagaa tgtattgacg gttgtggcta tgtcataagt gcagtgaagt | 540 |
| gcagtgatta taggtatagt acacttactg tagctacaag tacatactgc tacagtaata | 600 |
| ctcatgtatg caaaccgtat tctgtgtcta cagaaggcga tacggaagag tcaatctctt | 660 |
| atgtagagcc atttctataa tcgaaggggc cttgtaattt ccaaacgagt aattgagtaa | 720 |
| ttgaagagca tcgtagacat tacttatcat gtattgtgag agggaggaga tgcagctgta | 780 |

```
gctactgcac atactgtact cgcccatgca gggataatgc atagcgagac ttggcagtag    840
gtgacagttg ctagctgcta cttgtagtcg ggtgggtgat agcatggcgc gccagctgca    900
ttaatgaatc ggccaacgcg cggggagagg cggtttgcgt attgggcgct cttccgcttc    960
ctcgctcact gactcgctgc gctcggtcgt tcggctgcgg cgagcggtat cagctcactc   1020
aaaggcggta atacggttat ccacagaatc aggggataac gcaggaaaga acatgtgagc   1080
aaaaggccag caaaaggcca ggaaccgtaa aaaggccgcg ttgctggcgt ttttccatag   1140
gctccgcccc cctgacgagc atcacaaaaa tcgacgctca agtcagaggt ggcgaaaccc   1200
gacaggacta taaagatacc aggcgttttc ccctggaagc tccctcgtgc gctctcctgt   1260
tccgaccctg ccgcttaccg gatacctgtc cgcctttctc ccttcgggaa gcgtggcgct   1320
ttctcatagc tcacgctgta ggtatctcag ttcggtgtag gtcgttcgct ccaagctggg   1380
ctgtgtgcac gaaccccccg ttcagcccga ccgctgcgcc ttatccggta actatcgtct   1440
tgagtccaac ccggtaagac acgacttatc gccactggca gcagccactg gtaacaggat   1500
tagcagagcg aggtatgtag gcggtgctac agagttcttg aagtggtggc ctaactacgg   1560
ctacactaga agaacagtat ttggtatctg cgctctgctg aagccagtta ccttcggaaa   1620
aagagttggt agctcttgat ccggcaaaca aaccaccgct ggtagcggtg gtttttttgt   1680
ttgcaagcag cagattacgc gcagaaaaaa aggatctcaa gaagatcctt tgatcttttc   1740 tacgggtct gacgctcagt ggaacgaaaa ctcacgttaa gggattttgg tcatgagatt   1800 atcaaaagg atcttcacct agatcctttt aaattaaaaa tgaagtttta atcaatcta   1860 aagtatatat gagtaaactt ggtctgacag ttaccaatgc ttaatcagtg aggcacctat   1920
ctcagcgatc tgtctatttc gttcatccat agttgcctga ctccccgtcg tgtagataac   1980
tacgatacgg gagggcttac catctggccc cagtgctgca atgataccgc gagacccacg   2040
ctcaccggct ccagatttat cagcaataaa ccagccagcc ggaagggccg agcgcagaag   2100
tggtcctgca actttatccg cctccatcca gtctattaat tgttgccggg aagctagagt   2160
aagtagttcg ccagttaata gtttgcgcaa cgttgttgcc attgctacag gcatcgtggt   2220
gtcacgctcg tcgtttggta tggcttcatt cagctccggt tcccaacgat caaggcgagt   2280
tacatgatcc cccatgttgt gcaaaaaagc ggttagctcc ttcggtcctc cgatcgttgt   2340
cagaagtaag ttggccgcag tgttatcact catggttatg gcagcactgc ataattctct   2400
tactgtcatg ccatccgtaa gatgcttttc tgtgactggt gagtactcaa ccaagtcatt   2460
ctgagaatag tgtatgcggc gaccgagttg ctcttgcccg gcgtcaatac gggataatac   2520
cgcgccacat agcagaactt taaaagtgct catcattgga aaacgttctt cggggcgaaa   2580
actctcaagg atcttaccgc tgttgagatc cagttcgatg taacccactc gtgcacccaa   2640
ctgatcttca gcatctttta ctttcaccag cgtttctggg tgagcaaaaa caggaaggca   2700
aaatgccgca aaaagggaa taagggcgac acggaaatgt tgaatactca tactcttcct   2760
ttttcaatat tattgaagca tttatcaggg ttattgtctc atgagcggat acatatttga   2820
atgtatttag aaaaataaac aaataggggt tccgcgcaca tttccccgaa aagtgccacc   2880
tgatgcggtg tgaaataccg cacagatgcg taaggagaaa ataccgcatc aggaaattgt   2940
aagcgttaat attttgttaa aattcgcgtt aaattttgt taaatcagct cattttttaa   3000
ccaataggcc gaaatcggca aaatccctta taaatcaaaa gaatagaccg agatagggtt   3060
gagtgttgtt ccagtttgga acaagagtcc actattaaag aacgtggact ccaacgtcaa   3120
```

```
agggcgaaaa accgtctatc agggcgatgg cccactacgt gaaccatcac cctaatcaag    3180
ttttttgggg tcgaggtgcc gtaaagcact aaatcggaac cctaaaggga gcccccgatt    3240
tagagcttga cggggaaagc cggcgaacgt ggcgagaaag gaagggaaga aagcgaaagg    3300
agcgggcgct agggcgctgg caagtgtagc ggtcacgctg cgcgtaacca ccacacccgc    3360
cgcgcttaat gcgccgctac agggcgcgtc cattcgccat tcaggctgcg caactgttgg    3420
gaagggcgat cggtgcgggc ctcttcgcta ttacgccagc tggcgaaagg gggatgtgct    3480
gcaaggcgat taagttgggt aacgccaggg ttttcccagt cacgacgttg taaaacgacg    3540
gccagtgaat tgtaatacga ctcactatag ggcgaattgg gcccgacgtc gcatgcagga    3600
atagacatct tcaataggag cattaatacc tgtgggatca ctgatgtaaa cttctcccag    3660
agtatgtgaa taaccagcgg gccatccaac aaagaagtcg ttccagtgag tgactcggta    3720
catccgtctt tcggggttga tggtaagtcc gtcgtctcct tgcttaaaga acagagcgtc    3780
cacgtagtct gcaaaagcct tgtttccaag tcgaggctgc ccatagttga ttagcgttgg    3840
atcatatcca agattcttca ggttgatgcc catgaataga gcagtgacag ctcctagaga    3900
gtggccagtt acgatcaatt tgtagtcagt gttgtttcca aggaagtcga ccagacgatc    3960
ctgtacgttc accatagtct ctctgtatgc cttctgaaag ccatcatgaa cttggcagcc    4020
aggacaattg atactggcag aagggtttgt ggagtttatg tcagtagtgt taagaggagg    4080
gatactggtc atgtagggtt gttggatcgt ttggatgtca gtaatagcgt ctgcaatgga    4140
gaaagtgcct cggaaaacaa tatactttc cttttggtg tgatcgtggg ccaaaaatcc    4200
agtaactgaa gtcgagaaga aatttcctcc aaactggtag tcaagagtca catcgggaaa    4260
atgagcgcaa gagtttccac aggtaaaatc gctctgcagg gcaaatgggc caggggctct    4320
gacacaatag gccacgttag atagccatcc gtacttgaga acaaagtcgt atgtctcctg    4380
ggtgatagga gccgttaatt aagttgcgac acatgtcttg atagtatctt gaattctctc    4440
tcttgagctt ttccataaca agttcttctg cctccaggaa gtccatgggt ggtttgatca    4500
tggttttggt gtagtggtag tgcagtggtg gtattgtgac tggggatgta gttgagaata    4560
agtcatacac aagtcagctt tcttcgagcc tcatataagt ataagtagtt caacgtatta    4620
gcactgtacc cagcatctcc gtatcgagaa acacaacaac atgccccatt ggacagatca    4680
tgcggataca caggttgtgc agtatcatac atactcgatc agacaggtcg tctgaccatc    4740
atacaagctg aacaagcgct ccatacttgc acgctctcta tatacacagt taaattacat    4800
atccatagtc taacctctaa cagttaatct tctggtaagc ctcccagcca gccttctggt    4860
atcgcttggc ctcctcaata ggatctcggt tctggccgta cagacctcgg ccgacaatta    4920
tgatatccgt tccggtagac atgacatcct caacagttcg gtactgctgt ccgagagcgt    4980
ctcccttgtc gtcaagaccc accccggggg tcagaataag ccagtcctca gagtcgccct    5040
taggtcggtt ctgggcaatg aagccaacca caaactcggg gtcggatcgg gcaagctcaa    5100
tggtctgctt ggagtactcg ccagtggcca gagagcccct gcaagacagc tcggccagca    5160
tgagcagacc tctggccagc ttctcgttgg gagagggac taggaactcc ttgtactggg    5220
agttctcgta gtcagagacg tcctccttct tctgttcaga gacagtttcc tcggcaccag    5280
ctcgcaggcc agcaatgatt ccggttccgg gtacaccgtg ggcgttggtg atatcggacc    5340
actcggcgat tcggtgacac cggtactggt gcttgacagt gttgccaata tctgcgaact    5400
ttctgtcctc gaacaggaag aaaccgtgct taagagcaag ttccttgagg gggagcacag    5460
tgccggcgta ggtgaagtcg tcaatgatgt cgatatgggt tttgatcatg cacacataag    5520
```

```
gtccgacctt atcggcaagc tcaatgagct ccttggtggt ggtaacatcc agagaagcac    5580
acaggttggt tttcttggct gccacgagct tgagcactcg agcggcaaag gcggacttgt    5640
ggacgttagc tcgagcttcg taggagggca ttttggtggt gaagaggaga ctgaaataaa    5700
tttagtctgc agaactttt atcggaacct tatctgggc agtgaagtat atgttatggt     5760
aatagttacg agttagttga acttatagat agactggact atacggctat cggtccaaat    5820
tagaaagaac gtcaatggct ctctgggcgt cgcctttgcc gacaaaaatg tgatcatgat    5880
gaaagccagc aatgacgttg cagctgatat tgttgtcggc caaccgcgcc gaaaacgcag    5940
ctgtcagacc cacagcctcc aacgaagaat gtatcgtcaa agtgatccaa gcacactcat    6000
agttggagtc gtactccaaa ggcggcaatg acgagtcaga cagatactcg tcgacctttt    6060
ccttgggaac caccaccgtc agcccttctg actcacgtat tgtagccacc gacacaggca    6120
acagtccgtg gatagcagaa tatgtcttgt cggtccattt ctcaccaact ttaggcgtca    6180
agtgaatgtt gcagaagaag tatgtgcctt cattgagaat cggtgttgct gatttcaata    6240
aagtcttgag atcagtttgg ccagtcatgt tgtgggggt aattggattg agttatcgcc      6300
tacagtctgt acaggtatac tcgctgccca ctttatactt tttgattccg ctgcacttga    6360
agcaatgtcg tttaccaaaa gtgagaatgc tccacagaac acaccccagg gtatggttga    6420 gcaaaaata aacactccga tacggggaat cgaaccccgg tctccacggt tctcaagaag      6480
tattcttgat gagagcgtat cgatggttaa tgctgctgtg tgctgtgtgt gtgtgttgtt    6540
tggcgctcat tgttgcgtta tgcagcgtac accacaatat tggaagctta ttagcctttc    6600 tatttttcg tttgcaaggc ttaacaacat tgctgtggag agggatgggg atatggaggc     6660
cgctggaggg agtcggagag gcgttttgga gcggcttggc ctggcgccca gctcgcgaaa    6720
cgcacctagg acccttggc acgccgaaat gtgccacttt tcagtctagt aacgccttac      6780
ctacgtcatt ccatgcgtgc atgttttcgc ctttttccc ttgcccttga tcgccacaca     6840
gtacagtgca ctgtacagtg gaggttttgg ggggtctta gatgggagct aaaagcggcc      6900
tagcggtaca ctagtgggat tgtatggagt ggcatggagc ctaggtggag cctgacagga    6960
cgcacgaccg gctagcccgt gacagacgat gggtggctcc tgttgtccac cgcgtacaaa    7020
tgtttgggcc aaagtcttgt cagccttgct tgcgaaccta attcccaatt ttgtcacttc    7080 gcaccccat tgatcgagcc ctaaccctg cccatcaggc aatccaatta agctcgcatt       7140
gtctgccttg tttagtttgg ctcctgcccg tttcggcgtc cacttgcaca aacacaaaca    7200
agcattatat ataaggctcg tctctccctc ccaaccacac tcactttttt gcccgtcttc    7260
ccttgctaac acaaagtca agaacacaaa caaccacccc aaccccctta cacacaagac      7320
atatctacag caatggccat ggccaaaagc aaacgacggt cggaggctgt ggaagagcac    7380
gtgaccggct cggacgaggg cttgaccgat acttcgggtc acgtgagccc tgccgccaag    7440
aagcagaaga actcggagat tcatttcacc acccaggctg cccagcagtt ggatcgggag    7500
cgcaaggagg agtatctgga ctcgctgatc gacaacaagg actatctcaa gtaccgtcct    7560
cgaggctgga agctcaacaa cccgcctacc gaccgacctg tgcgaatcta cgccgatgga    7620
gtgtttgatt tgttccatct gggacacatg cgtcagctgg agcagtccaa gaaggccttc    7680
cccaacgcag tgttgattgt gggcattccc agcgacaagg agacccacaa gcggaaggga    7740
ttgaccgtgc tgagtgacgt ccagcggtac gagacggtgc gacactgcaa gtgggtggac    7800
gaggtggtgg aggatgctcc ctggtgtgtc accatggact ttctggaaaa acacaaaatc    7860
```

```
gactacgtgg cccatgacga tctgccctac gcttccggca acgacgatga tatctacaag    7920
cccatcaagg agaagggcat gtttctggcc acccagcgaa ccgagggcat ttccacctcg    7980
gacatcatca ccaagattat ccgagactac gacaagtatt taatgcgaaa ctttgcccgg    8040
ggtgctaacc gaaaggatct caacgtctcg tggctcaaga agaacgagct ggacttcaag    8100
cgtcatgtgg ccgagttccg aaactcgttc aagcgaaaga aggtcggtaa ggatctctac    8160
ggcgagattc gcggtctgct gcagaatgtg ctcatttgga acggcgacaa ctccggcact    8220
tccactcccc agcgaaagac gctgcagacc aacgccaaga agatgtacat gaacgtgctc    8280
aagactctgc aggctcctga cgctgttgac gtggactcct cggagaacgt gtctgagaac    8340
gtcactgatg aggaggagga agacgacgac gaggttgatg aggacgaaga agccgacgac    8400
gacgacgaag acgacgaaga cgaggaagac gacgagtagg cggccgcatt gatgattgga    8460
aacacacaca tgggttatat ctaggtgaga gttagttgga cagttatata ttaaatcagc    8520
tatgccaacg gtaacttcat tcatgtcaac gaggaaccag tgactgcaag taatatagaa    8580
tttgaccacc ttgccattct cttgcactcc tttactatat ctcatttatt tcttatatac    8640
aaatcacttc ttcttcccag catcgagctc ggaaacctca tgagcaataa catcgtggat    8700
ctcgtcaata gagggctttt tggactcctt gctgttggcc accttgtcct tgctgtttaa    8760
acacgcagta ggatgtcctg cacgggtctt tttgtggggt gtggagaaag gggtgcttgg    8820
agatggaagc cggtagaacc gggctgcttg tgcttggaga tggaagccgg tagaaccggg    8880
ctgcttgggg ggatttgggg ccgctgggct ccaaagaggg gtaggcattt cgttggggtt    8940
acgtaattgc ggcatttggg tcctgcgcgc atgtcccatt ggtcagaatt agtccggata    9000
ggagacttat cagccaatca cagcgccgga tccacctgta ggttgggttg ggtgggagca    9060
cccctccaca gagtagagtc aaacagcagc agcaacatga tagttggggg tgtgcgtgtt    9120
aaaggaaaaa aaagaagctt gggttatatt cccgctctat ttagaggttg cgggatagac    9180
gccgacggag ggcaatggcg ctatggaacc ttgcggatat ccatacgccg cggcggactg    9240
cgtccgaacc agctccagca gcgttttttc cgggccattg agccgactgc gaccccgcca    9300
acgtgtcttg gccacgcac tcatgtcatg ttggtgttgg gaggccactt tttaagtagc    9360
acaaggcacc tagctcgcag caaggtgtcc gaaccaaaga agcggctgca gtggtgcaaa    9420
cggggcggaa acgcgggaa aaagccacgg gggcacgaat tgaggcacgc cctcgaattt    9480
gagacgagtc acggcccat tcgcccgcgc aatggctcgc caacgcccgg tcttttgcac    9540
cacatcaggt taccccaagc caaaccttg tgttaaaaag cttaacatat tataccgaac    9600
gtaggtttgg gcgggcttgc tccgtctgtc caaggcaaca tttatataag ggtctgcatc    9660
gccggctcaa ttgaatcttt tttcttcttc tcttctctat attcattctt gaattaaaca    9720
cacatcaaca tggccatcaa agtcggtatt aacggattcg gcgaatcgg acgaattgtg    9780
agtaccatag aaggtgatgg aaacatgacc aacagaaac agatgacaag tgtcatcgac    9840
ccaccagagc ccaattgagc tcatactaac agtcgacaac ctgtcgaacc aattgatgac    9900
tcccgacaa tgtactaaca caggtcctgc ccatggtgaa aaacgtggac caagtggatc    9960
tctcgcaggt cgacaccatt gcctccgcc gagatgtcaa ctacaaggtc aagtacacct   10020
ccggcgttaa gatgagccag ggcgcctacg acgacaaggg ccgccacatt tccgagcagc   10080
ccttcacctg ggccaactgg caccagcaca tcaactggct caacttcatt ctggtgattg   10140
cgctgcctct gtcgtccttt gctgccgctc ccttcgtctc cttcaactgg aagaccgccg   10200
cgtttgctgt cggctattac atgtgcaccg gtctcggtat caccgccggc taccaccgaa   10260
```

```
tgtgggccca tcgagcctac aaggccgctc tgcccgttcg aatcatcctt gctctgtttg   10320
gaggaggagc tgtcgagggc tccatccgat ggtgggcctc gtctcaccga gtccaccacc   10380
gatggaccga ctccaacaag gacccttacg acgcccgaaa gggattctgg ttctcccact   10440
ttggctggat gctgcttgtg cccaaccccc agaacaaggg ccgaactgac atttctgacc   10500
tcaacaacga ctgggttgtc cgactccagc acaagtacta cgtttacgtt ctcgtcttca   10560
tggccattgt tctgcccacc ctcgtctgtg ctttggctg gggcgactgg aagggaggtc    10620
ttgtctacgc cggtatcatg cgatacacct ttgtgcagca ggtgactttc tgtgtcaact   10680
cccttgccca ctggattgga gagcagccct tcgacgaccg acgaactccc cgagaccacg   10740
ctcttaccgc cctggtcacc tttggagagg ctaccacaa cttccaccac gagttcccct    10800
cggactaccg aaacgccctc atctggtacc agtacgaccc caccaagtgg ctcatctgga   10860
ccctcaagca ggttggtctc gcctgggacc tccagacctt ctcccagaac gccatcgagc   10920
agggtctcgt gcagcagcga cagaagaagc tggacaagtg gcgaaacaac ctcaactggg   10980
gtatccccat tgagcagctg cctgtcattg agtttgagga gttccaagag caggccaaga   11040
cccgagatct ggttctcatt tctggcattg tccacgacgt gtctgccttt gtcgagcacc   11100
accctggtgg aaaggccctc attatgagcg ccgtcggcaa ggacggtacc gctgtcttca   11160
acggaggtgt ctaccgacac tccaacgctg ccacaacct gcttgccacc atgcgagttt    11220
cggtcattcg aggcggcatg gaggttgagg tgtggaagac tgcccagaac gaaaagaagg   11280
accagaacat tgtctccgat gagagtggaa accgaatcca ccgagctggt ctccaggcca   11340
cccgggtcga gaaccccggt atgtctggca tggctgctta ggcggccgca tgagaagata   11400
aatatataaa tacattgaga tattaaatgc gctagattag agagcctcat actgctcgga   11460
gagaagccaa gacgagtact caaaggggat tacaccatcc atatccacag acacaagctg   11520
gggaaaggtt ctatatacac tttccggaat accgtagttt ccgatgttat caatgggggc   11580
agccaggatt tcaggcactt cggtgtctcg gggtgaaatg gcgttcttgg cctccatcaa   11640
gtcgtaccat gtcttcattt gcctgtcaaa gtaaaacaga agcagatgaa gaatgaactt   11700
gaagtgaagg aatttaaata gttggagcaa gggagaaatg tagagtgtga aagactcact   11760
atggtccggg cttatctcga ccaatagcca aagtctggag tttctgagag aaaaaggcaa   11820
gatacgtatg taacaaagcg acgcatggta caataatacc ggaggcatgt atcatagaga   11880
gttagtggtt cgatgatggc actggtgcct ggtatgactt tatacggctg actacatatt   11940
tgtcctcaga catacaatta cagtcaagca cttacccttg acatctgta ggtacccccc     12000 ggccaagacg atctcagcgt gtcgtatgtc ggattggcgt agctccctcg ctcgtcaatt   12060
ggctcccatc tactttcttc tgcttggcta cacccagcat gtctgctatg gctcgttttc   12120
gtgccttatc tatcctccca gtattaccaa ctctaaatga catgatgtga ttgggtctac   12180
actttcatat cagagataag gagtagcaca gttgcataaa aagcccaact ctaatcagct   12240
tcttcctttc ttgtaattag tacaaaggtg attagcgaaa tctggaagct tagttggccc   12300
taaaaaaatc aaaaaaagca aaaacgaaa acgaaaaac cacagttttg agaacaggga     12360
ggtaacgaag gatcgtatat atatatatat atatatatac ccacggatcc cgagaccggc   12420
ctttgattct tccctacaac caaccattct caccacccta attcacaacc atggaggtcg   12480
tgaacgaaat cgtctccatt ggccaggagg ttcttcccaa ggtcgactat gctcagctct   12540
ggtctgatgc ctcgcactgc gaggtgctgt acctctccat cgccttcgtc atcctgaagt   12600
```

-continued

```
tcacccttgg tcctctcgga cccaagggtc agtctcgaat gaagtttgtg ttcaccaact    12660
acaacctgct catgtccatc tactcgctgg gctccttcct ctctatggcc tacgccatgt    12720
acaccattgg tgtcatgtcc gacaactgcg agaaggcttt cgacaacaat gtcttccgaa    12780
tcaccactca gctgttctac ctcagcaagt tcctcgagta cattgactcc ttctatctgc    12840
ccctcatggg caagcctctg acctggttgc agttctttca ccatctcgga gctcctatgg    12900
acatgtggct gttctacaac taccgaaacg aagccgtttg gatctttgtg ctgctcaacg    12960
gcttcattca ctggatcatg tacggctact attggacccg actgatcaag ctcaagttcc    13020
ctatgcccaa gtccctgatt acttctatgc agatcattca gttcaacgtt ggcttctaca    13080
tcgtctggaa gtaccggaac attccctgct accgacaaga tggaatgaga atgtttggct    13140 ggttttcaa ctacttctac gttggtactg tcctgtgtct gttcctcaac ttctacgtgc    13200
agacctacat cgtccgaaag cacaagggag ccaaaaagat tcagtgagcg gccgcaagtg    13260
tggatgggga agtgagtgcc cggttctgtg tgcacaattg gcaatccaag atggatggat    13320
tcaacacagg gatatagcga gctacgtggt ggtgcgagga tatagcaacg gatatttatg    13380
tttgacactt gagaatgtac gatacaagca ctgtccaagt acaatactaa acatactgta    13440
catactcata ctcgtacccg gcaacggttt cacttgagtg cagtggctag tgctcttact    13500
cgtacagtgt gcaatactgc gtatcatagt ctttgatgta tatcgtattc attcatgtta    13560
gttgc                                                                13565
```

<210> SEQ ID NO 91
<211> LENGTH: 1449
<212> TYPE: DNA
<213> ORGANISM: Yarrowia lipolytica
<220> FEATURE:
<221> NAME/KEY: CDS
<222> LOCATION: (1)..(1449)
<223> OTHER INFORMATION: delta-9 desaturase; GenBank Accession No.
   XM_501496

<400> SEQUENCE: 91

```
atg gtg aaa aac gtg gac caa gtg gat ctc tcg cag gtc gac acc att        48
Met Val Lys Asn Val Asp Gln Val Asp Leu Ser Gln Val Asp Thr Ile
1               5                   10                  15 gcc tcc ggc cga gat gtc aac tac aag gtc aag tac acc tcc ggc gtt        96
Ala Ser Gly Arg Asp Val Asn Tyr Lys Val Lys Tyr Thr Ser Gly Val
            20                  25                  30 aag atg agc cag ggc gcc tac gac gac aag ggc cgc cac att tcc gag       144
Lys Met Ser Gln Gly Ala Tyr Asp Asp Lys Gly Arg His Ile Ser Glu
        35                  40                  45 cag ccc ttc acc tgg gcc aac tgg cac cag cac atc aac tgg ctc aac       192
Gln Pro Phe Thr Trp Ala Asn Trp His Gln His Ile Asn Trp Leu Asn
    50                  55                  60 ttc att ctg gtg att gcg ctg cct ctg tcg tcc ttt gct gcc gct ccc       240
Phe Ile Leu Val Ile Ala Leu Pro Leu Ser Ser Phe Ala Ala Ala Pro
65                  70                  75                  80 ttc gtc tcc ttc aac tgg aag acc gcc gcg ttt gct gtc ggc tat tac       288
Phe Val Ser Phe Asn Trp Lys Thr Ala Ala Phe Ala Val Gly Tyr Tyr
                85                  90                  95 atg tgc acc ggt ctc ggt atc acc gcc ggc tac cac cga atg tgg gcc       336
Met Cys Thr Gly Leu Gly Ile Thr Ala Gly Tyr His Arg Met Trp Ala
            100                 105                 110 cat cga gcc tac aag gcc gct ctg ccc gtt cga atc atc ctt gct ctg       384
His Arg Ala Tyr Lys Ala Ala Leu Pro Val Arg Ile Ile Leu Ala Leu
        115                 120                 125
```

-continued

| | |
|---|---|
| ttt gga gga gga gct gtc gag ggc tcc atc cga tgg tgg gcc tcg tct<br>Phe Gly Gly Gly Ala Val Glu Gly Ser Ile Arg Trp Trp Ala Ser Ser<br>130                    135                    140 | 432 |
| cac cga gtc cac cac cga tgg acc gac tcc aac aag gac cct tac gac<br>His Arg Val His His Arg Trp Thr Asp Ser Asn Lys Asp Pro Tyr Asp<br>145                    150                    155                    160 | 480 |
| gcc cga aag gga ttc tgg ttc tcc cac ttt ggc tgg atg ctg ctt gtg<br>Ala Arg Lys Gly Phe Trp Phe Ser His Phe Gly Trp Met Leu Leu Val<br>                    165                    170                    175 | 528 |
| ccc aac ccc aag aac aag ggc cga act gac att tct gac ctc aac aac<br>Pro Asn Pro Lys Asn Lys Gly Arg Thr Asp Ile Ser Asp Leu Asn Asn<br>                180                    185                    190 | 576 |
| gac tgg gtt gtc cga ctc cag cac aag tac tac gtt tac gtt ctc gtc<br>Asp Trp Val Val Arg Leu Gln His Lys Tyr Tyr Val Tyr Val Leu Val<br>          195                    200                    205 | 624 |
| ttc atg gcc att gtt ctg ccc acc ctc gtc tgt ggc ttt ggc tgg ggc<br>Phe Met Ala Ile Val Leu Pro Thr Leu Val Cys Gly Phe Gly Trp Gly<br>210                    215                    220 | 672 |
| gac tgg aag gga ggt ctt gtc tac gcc ggt atc atg cga tac acc ttt<br>Asp Trp Lys Gly Gly Leu Val Tyr Ala Gly Ile Met Arg Tyr Thr Phe<br>225                    230                    235                    240 | 720 |
| gtg cag cag gtg act ttc tgt gtc aac tcc ctt gcc cac tgg att gga<br>Val Gln Gln Val Thr Phe Cys Val Asn Ser Leu Ala His Trp Ile Gly<br>                    245                    250                    255 | 768 |
| gag cag ccc ttc gac gac cga cga act ccc cga gac cac gct ctt acc<br>Glu Gln Pro Phe Asp Asp Arg Arg Thr Pro Arg Asp His Ala Leu Thr<br>                260                    265                    270 | 816 |
| gcc ctg gtc acc ttt gga gag ggc tac cac aac ttc cac cac gag ttc<br>Ala Leu Val Thr Phe Gly Glu Gly Tyr His Asn Phe His His Glu Phe<br>          275                    280                    285 | 864 |
| ccc tcg gac tac cga aac gcc ctc atc tgg tac cag tac gac ccc acc<br>Pro Ser Asp Tyr Arg Asn Ala Leu Ile Trp Tyr Gln Tyr Asp Pro Thr<br>290                    295                    300 | 912 |
| aag tgg ctc atc tgg acc ctc aag cag gtt ggt ctc gcc tgg gac ctc<br>Lys Trp Leu Ile Trp Thr Leu Lys Gln Val Gly Leu Ala Trp Asp Leu<br>305                    310                    315                    320 | 960 |
| cag acc ttc tcc cag aac gcc atc gag cag ggt ctc gtg cag cag cga<br>Gln Thr Phe Ser Gln Asn Ala Ile Glu Gln Gly Leu Val Gln Gln Arg<br>                    325                    330                    335 | 1008 |
| cag aag aag ctg gac aag tgg cga aac aac ctc aac tgg ggt atc ccc<br>Gln Lys Lys Leu Asp Lys Trp Arg Asn Asn Leu Asn Trp Gly Ile Pro<br>                340                    345                    350 | 1056 |
| att gag cag ctg cct gtc att gag ttt gag gag ttc caa gag cag gcc<br>Ile Glu Gln Leu Pro Val Ile Glu Phe Glu Glu Phe Gln Glu Gln Ala<br>          355                    360                    365 | 1104 |
| aag acc cga gat ctg gtt ctc att tct ggc att gtc cac gac gtg tct<br>Lys Thr Arg Asp Leu Val Leu Ile Ser Gly Ile Val His Asp Val Ser<br>370                    375                    380 | 1152 |
| gcc ttt gtc gag cac cac cct ggt gga aag gcc ctc att atg agc gcc<br>Ala Phe Val Glu His His Pro Gly Gly Lys Ala Leu Ile Met Ser Ala<br>385                    390                    395                    400 | 1200 |
| gtc ggc aag gac ggt acc gct gtc ttc aac gga ggt gtc tac cga cac<br>Val Gly Lys Asp Gly Thr Ala Val Phe Asn Gly Gly Val Tyr Arg His<br>                    405                    410                    415 | 1248 |
| tcc aac gct ggc cac aac ctg ctt gcc acc atg cga gtt tcg gtc att<br>Ser Asn Ala Gly His Asn Leu Leu Ala Thr Met Arg Val Ser Val Ile<br>                420                    425                    430 | 1296 |
| cga ggc ggc atg gag gtt gag gtg tgg aag act gcc cag aac gaa aag<br>Arg Gly Gly Met Glu Val Glu Val Trp Lys Thr Ala Gln Asn Glu Lys<br>          435                    440                    445 | 1344 |

```
aag gac cag aac att gtc tcc gat gag agt gga aac cga atc cac cga   1392
Lys Asp Gln Asn Ile Val Ser Asp Glu Ser Gly Asn Arg Ile His Arg
    450                 455                 460 gct ggt ctc cag gcc acc cgg gtc gag aac ccc ggt atg tct ggc atg   1440
Ala Gly Leu Gln Ala Thr Arg Val Glu Asn Pro Gly Met Ser Gly Met
465                 470                 475                 480 gct gct tag                                                       1449
Ala Ala
```

<210> SEQ ID NO 92
<211> LENGTH: 482
<212> TYPE: PRT
<213> ORGANISM: Yarrowia lipolytica

<400> SEQUENCE: 92

```
Met Val Lys Asn Val Asp Gln Val Asp Leu Ser Gln Val Asp Thr Ile
1               5                   10                  15

Ala Ser Gly Arg Asp Val Asn Tyr Lys Val Lys Tyr Thr Ser Gly Val
            20                  25                  30

Lys Met Ser Gln Gly Ala Tyr Asp Asp Lys Gly Arg His Ile Ser Glu
        35                  40                  45

Gln Pro Phe Thr Trp Ala Asn Trp His Gln His Ile Asn Trp Leu Asn
    50                  55                  60

Phe Ile Leu Val Ile Ala Leu Pro Leu Ser Ser Phe Ala Ala Ala Pro
65                  70                  75                  80

Phe Val Ser Phe Asn Trp Lys Thr Ala Ala Phe Ala Val Gly Tyr Tyr
                85                  90                  95

Met Cys Thr Gly Leu Gly Ile Thr Ala Gly Tyr His Arg Met Trp Ala
            100                 105                 110

His Arg Ala Tyr Lys Ala Ala Leu Pro Val Arg Ile Ile Leu Ala Leu
        115                 120                 125

Phe Gly Gly Gly Ala Val Glu Gly Ser Ile Arg Trp Trp Ala Ser Ser
    130                 135                 140

His Arg Val His His Arg Trp Thr Asp Ser Asn Lys Asp Pro Tyr Asp
145                 150                 155                 160

Ala Arg Lys Gly Phe Trp Phe Ser His Phe Gly Trp Met Leu Leu Val
                165                 170                 175

Pro Asn Pro Lys Asn Lys Gly Arg Thr Asp Ile Ser Asp Leu Asn Asn
            180                 185                 190

Asp Trp Val Val Arg Leu Gln His Lys Tyr Tyr Val Tyr Val Leu Val
        195                 200                 205

Phe Met Ala Ile Val Leu Pro Thr Leu Val Cys Gly Phe Gly Trp Gly
    210                 215                 220

Asp Trp Lys Gly Gly Leu Val Tyr Ala Gly Ile Met Arg Tyr Thr Phe
225                 230                 235                 240

Val Gln Gln Val Thr Phe Cys Val Asn Ser Leu Ala His Trp Ile Gly
                245                 250                 255

Glu Gln Pro Phe Asp Asp Arg Arg Thr Pro Arg Asp His Ala Leu Thr
            260                 265                 270

Ala Leu Val Thr Phe Gly Glu Gly Tyr His Asn Phe His His Glu Phe
        275                 280                 285

Pro Ser Asp Tyr Arg Asn Ala Leu Ile Trp Tyr Gln Tyr Asp Pro Thr
    290                 295                 300

Lys Trp Leu Ile Trp Thr Leu Lys Gln Val Gly Leu Ala Trp Asp Leu
305                 310                 315                 320
```

```
Gln Thr Phe Ser Gln Asn Ala Ile Glu Gln Gly Leu Val Gln Arg
                325                 330                 335

Gln Lys Lys Leu Asp Lys Trp Arg Asn Asn Leu Asn Trp Gly Ile Pro
            340                 345                 350

Ile Glu Gln Leu Pro Val Ile Glu Phe Glu Glu Phe Gln Glu Gln Ala
                355                 360                 365

Lys Thr Arg Asp Leu Val Leu Ile Ser Gly Ile Val His Asp Val Ser
            370                 375                 380

Ala Phe Val Glu His His Pro Gly Gly Lys Ala Leu Ile Met Ser Ala
385                 390                 395                 400

Val Gly Lys Asp Gly Thr Ala Val Phe Asn Gly Gly Val Tyr Arg His
                405                 410                 415

Ser Asn Ala Gly His Asn Leu Leu Ala Thr Met Arg Val Ser Val Ile
            420                 425                 430

Arg Gly Gly Met Glu Val Glu Val Trp Lys Thr Ala Gln Asn Glu Lys
        435                 440                 445

Lys Asp Gln Asn Ile Val Ser Asp Glu Ser Gly Asn Arg Ile His Arg
            450                 455                 460

Ala Gly Leu Gln Ala Thr Arg Val Glu Asn Pro Gly Met Ser Gly Met
465                 470                 475                 480

Ala Ala

<210> SEQ ID NO 93
<211> LENGTH: 1101
<212> TYPE: DNA
<213> ORGANISM: Yarrowia lipolytica
<220> FEATURE:
<221> NAME/KEY: CDS
<222> LOCATION: (1)..(1101)
<223> OTHER INFORMATION: choline-phosphate cytidylyl-transferase;
      GenBank Accession No. XM_502978

<400> SEQUENCE: 93 atg gcc aaa agc aaa cga cgg tcg gag gct gtg gaa gag cac gtg acc        48
Met Ala Lys Ser Lys Arg Arg Ser Glu Ala Val Glu Glu His Val Thr
1               5                   10                  15 ggc tcg gac gag ggc ttg acc gat act tcg ggt cac gtg agc cct gcc        96
Gly Ser Asp Glu Gly Leu Thr Asp Thr Ser Gly His Val Ser Pro Ala
            20                  25                  30 gcc aag aag cag aag aac tcg gag att cat ttc acc acc cag gct gcc       144
Ala Lys Lys Gln Lys Asn Ser Glu Ile His Phe Thr Thr Gln Ala Ala
        35                  40                  45 cag cag ttg gat cgg gag cgc aag gag gag tat ctg gac tcg ctg atc       192
Gln Gln Leu Asp Arg Glu Arg Lys Glu Glu Tyr Leu Asp Ser Leu Ile
    50                  55                  60 gac aac aag gac tat ctc aag tac cgt cct cga ggc tgg aag ctc aac       240
Asp Asn Lys Asp Tyr Leu Lys Tyr Arg Pro Arg Gly Trp Lys Leu Asn
65                  70                  75                  80 aac ccg cct acc gac cga cct gtg cga atc tac gcc gat gga gtg ttt       288
Asn Pro Pro Thr Asp Arg Pro Val Arg Ile Tyr Ala Asp Gly Val Phe
                85                  90                  95 gat ttg ttc cat ctg gga cac atg cgt cag ctg gag cag tcc aag aag       336
Asp Leu Phe His Leu Gly His Met Arg Gln Leu Glu Gln Ser Lys Lys
            100                 105                 110 gcc ttc ccc aac gca gtg ttg att gtg ggc att ccc agc gac aag gag       384
Ala Phe Pro Asn Ala Val Leu Ile Val Gly Ile Pro Ser Asp Lys Glu
        115                 120                 125 acc cac aag cgg aag gga ttg acc gtg ctg agt gac gtc cag cgg tac       432
```

-continued

```
                Thr His Lys Arg Lys Gly Leu Thr Val Leu Ser Asp Val Gln Arg Tyr
                130                 135                 140 gag acg gtg cga cac tgc aag tgg gtg gac gag gtg gtg gag gat gct       480
Glu Thr Val Arg His Cys Lys Trp Val Asp Glu Val Val Glu Asp Ala
145                 150                 155                 160 ccc tgg tgt gtc acc atg gac ttt ctg gaa aaa cac aaa atc gac tac       528
Pro Trp Cys Val Thr Met Asp Phe Leu Glu Lys His Lys Ile Asp Tyr
                165                 170                 175 gtg gcc cat gac gat ctg ccc tac gct tcc ggc aac gac gat gat atc       576
Val Ala His Asp Asp Leu Pro Tyr Ala Ser Gly Asn Asp Asp Asp Ile
            180                 185                 190 tac aag ccc atc aag gag aag ggc atg ttt ctg gcc acc cag cga acc       624
Tyr Lys Pro Ile Lys Glu Lys Gly Met Phe Leu Ala Thr Gln Arg Thr
        195                 200                 205 gag ggc att tcc acc tcg gac atc atc acc aag att atc cga gac tac       672
Glu Gly Ile Ser Thr Ser Asp Ile Ile Thr Lys Ile Ile Arg Asp Tyr
    210                 215                 220 gac aag tat tta atg cga aac ttt gcc cgg ggt gct aac cga aag gat       720
Asp Lys Tyr Leu Met Arg Asn Phe Ala Arg Gly Ala Asn Arg Lys Asp
225                 230                 235                 240 ctc aac gtc tcg tgg ctc aag aag aac gag ctg gac ttc aag cgt cat       768
Leu Asn Val Ser Trp Leu Lys Lys Asn Glu Leu Asp Phe Lys Arg His
                245                 250                 255 gtg gcc gag ttc cga aac tcg ttc aag cga aag aag gtc ggt aag gat       816
Val Ala Glu Phe Arg Asn Ser Phe Lys Arg Lys Lys Val Gly Lys Asp
                260                 265                 270 ctc tac ggc gag att cgc ggt ctg ctg cag aat gtg ctc att tgg aac       864
Leu Tyr Gly Glu Ile Arg Gly Leu Leu Gln Asn Val Leu Ile Trp Asn
            275                 280                 285 ggc gac aac tcc ggc act tcc act ccc cag cga aag acg ctg cag acc       912
Gly Asp Asn Ser Gly Thr Ser Thr Pro Gln Arg Lys Thr Leu Gln Thr
        290                 295                 300 aac gcc aag aag atg tac atg aac gtg ctc aag act ctg cag gct cct       960
Asn Ala Lys Lys Met Tyr Met Asn Val Leu Lys Thr Leu Gln Ala Pro
305                 310                 315                 320 gac gct gtt gac gtg gac tcc tcg gag aac gtg tct gag aac gtc act      1008
Asp Ala Val Asp Val Asp Ser Ser Glu Asn Val Ser Glu Asn Val Thr
                325                 330                 335 gat gag gag gag gaa gac gac gac gag gtt gat gag gac gaa gaa gcc      1056
Asp Glu Glu Glu Glu Asp Asp Asp Glu Val Asp Glu Asp Glu Glu Ala
                340                 345                 350 gac gac gac gac gaa gac gac gaa gac gag gaa gac gac gag tag          1101
Asp Asp Asp Asp Glu Asp Asp Glu Asp Glu Glu Asp Asp Glu
                355                 360                 365

<210> SEQ ID NO 94
<211> LENGTH: 366
<212> TYPE: PRT
<213> ORGANISM: Yarrowia lipolytica

<400> SEQUENCE: 94

Met Ala Lys Ser Lys Arg Arg Ser Glu Ala Val Glu Glu His Val Thr
1               5                   10                  15

Gly Ser Asp Glu Gly Leu Thr Asp Thr Ser Gly His Val Ser Pro Ala
            20                  25                  30

Ala Lys Lys Gln Lys Asn Ser Glu Ile His Phe Thr Thr Gln Ala Ala
        35                  40                  45

Gln Gln Leu Asp Arg Glu Arg Lys Glu Glu Tyr Leu Asp Ser Leu Ile
    50                  55                  60
```

Asp Asn Lys Asp Tyr Leu Lys Tyr Arg Pro Arg Gly Trp Lys Leu Asn
 65                  70                  75                  80

Asn Pro Pro Thr Asp Arg Pro Val Arg Ile Tyr Ala Asp Gly Val Phe
             85                  90                  95

Asp Leu Phe His Leu Gly His Met Arg Gln Leu Glu Gln Ser Lys Lys
        100                 105                 110

Ala Phe Pro Asn Ala Val Leu Ile Val Gly Ile Pro Ser Asp Lys Glu
    115                 120                 125

Thr His Lys Arg Lys Gly Leu Thr Val Leu Ser Asp Val Gln Arg Tyr
130                 135                 140

Glu Thr Val Arg His Cys Lys Trp Val Asp Glu Val Val Glu Asp Ala
145                 150                 155                 160

Pro Trp Cys Val Thr Met Asp Phe Leu Glu Lys His Lys Ile Asp Tyr
                165                 170                 175

Val Ala His Asp Asp Leu Pro Tyr Ala Ser Gly Asn Asp Asp Asp Ile
            180                 185                 190

Tyr Lys Pro Ile Lys Glu Lys Gly Met Phe Leu Ala Thr Gln Arg Thr
        195                 200                 205

Glu Gly Ile Ser Thr Ser Asp Ile Ile Thr Lys Ile Ile Arg Asp Tyr
210                 215                 220

Asp Lys Tyr Leu Met Arg Asn Phe Ala Arg Gly Ala Asn Arg Lys Asp
225                 230                 235                 240

Leu Asn Val Ser Trp Leu Lys Lys Asn Glu Leu Asp Phe Lys Arg His
                245                 250                 255

Val Ala Glu Phe Arg Asn Ser Phe Lys Arg Lys Val Gly Lys Asp
            260                 265                 270

Leu Tyr Gly Glu Ile Arg Gly Leu Leu Gln Asn Val Leu Ile Trp Asn
        275                 280                 285

Gly Asp Asn Ser Gly Thr Ser Thr Pro Gln Arg Lys Thr Leu Gln Thr
290                 295                 300

Asn Ala Lys Lys Met Tyr Met Asn Val Leu Lys Thr Leu Gln Ala Pro
305                 310                 315                 320

Asp Ala Val Asp Val Asp Ser Ser Glu Asn Val Ser Glu Asn Val Thr
                325                 330                 335

Asp Glu Glu Glu Glu Asp Asp Asp Val Asp Glu Asp Glu Ala
            340                 345                 350

Asp Asp Asp Asp Glu Asp Glu Asp Glu Asp Glu
        355                 360                 365

<210> SEQ ID NO 95
<211> LENGTH: 777
<212> TYPE: DNA
<213> ORGANISM: Euglena gracilis
<220> FEATURE:
<221> NAME/KEY: misc_feature
<222> LOCATION: (1)..(777)
<223> OTHER INFORMATION: mutant delta-9 elongase "EgD9eS-L35G"

<400> SEQUENCE: 95
atggaggtcg tgaacgaaat cgtctccatt ggccaggagg ttcttcccaa ggtcgactat      60
gctcagctct ggtctgatgc ctcgcactgc gaggtgctgt acggatccat cgccttcgtc     120
atcctgaagt tcacccttgg tcctctcgga cccaagggtc agtctcgaat gaagtttgtg     180
ttcaccaact acaacctgct catgtccatc tactcgctgg gctccttcct ctctatggcc     240
tacgccatgt acaccattgg tgtcatgtcc gacaactgcg agaaggcttt cgacaacaat     300

| | |
|---|---|
| gtcttccgaa tcaccactca gctgttctac ctcagcaagt tcctcgagta cattgactcc | 360 |
| ttctatctgc ccctcatggg caagcctctg acctggttgc agttctttca ccatctcgga | 420 |
| gctcctatgg acatgtggct gttctacaac taccgaaacg aagccgtttg gatctttgtg | 480 |
| ctgctcaacg gcttcattca ctggatcatg tacggctact attggacccg actgatcaag | 540 |
| ctcaagttcc ctatgcccaa gtccctgatt acttctatgc agatcattca gttcaacgtt | 600 |
| ggcttctaca tcgtctggaa gtaccggaac attccctgct accgacaaga tggaatgaga | 660 |
| atgtttggct ggttttttcaa ctacttctac gttggtactg tcctgtgtct gttcctcaac | 720 |
| ttctacgtgc agacctacat cgtccgaaag cacaagggag ccaaaaagat tcagtga | 777 |

<210> SEQ ID NO 96
<211> LENGTH: 777
<212> TYPE: DNA
<213> ORGANISM: Euglena gracilis
<220> FEATURE:
<221> NAME/KEY: misc_feature
<222> LOCATION: (1)..(777)
<223> OTHER INFORMATION: mutant delta-9 elongase "EgD9eS-L35G"

<400> SEQUENCE: 96

| | |
|---|---|
| atggaggtcg tgaacgaaat cgtctccatt ggccaggagg ttcttcccaa ggtcgactat | 60 |
| gctcagctct ggtctgatgc ctcgcactgc gaggtgctgt acggctccat cgccttcgtc | 120 |
| atcctgaagt tcacccttgg tcctctcgga cccaagggtc agtctcgaat gaagtttgtg | 180 |
| ttcaccaact acaacctgct catgtccatc tactcgctgg gctccttcct ctctatggcc | 240 |
| tacgccatgt acaccattgg tgtcatgtcc gacaactgcg agaaggcttt cgacaacaat | 300 |
| gtcttccgaa tcaccactca gctgttctac ctcagcaagt tcctcgagta cattgactcc | 360 |
| ttctatctgc ccctcatggg caagcctctg acctggttgc agttctttca ccatctcgga | 420 |
| gctcctatgg acatgtggct gttctacaac taccgaaacg aagccgtttg gatctttgtg | 480 |
| ctgctcaacg gcttcattca ctggatcatg tacggctact attggacccg actgatcaag | 540 |
| ctcaagttcc ctatgcccaa gtccctgatt acttctatgc agatcattca gttcaacgtt | 600 |
| ggcttctaca tcgtctggaa gtaccggaac attccctgct accgacaaga tggaatgaga | 660 |
| atgtttggct ggttttttcaa ctacttctac gttggtactg tcctgtgtct gttcctcaac | 720 |
| ttctacgtgc agacctacat cgtccgaaag cacaagggag ccaaaaagat tcagtga | 777 |

<210> SEQ ID NO 97
<211> LENGTH: 777
<212> TYPE: DNA
<213> ORGANISM: Euglena gracilis
<220> FEATURE:
<221> NAME/KEY: misc_feature
<222> LOCATION: (1)..(777)
<223> OTHER INFORMATION: mutant delta-9 elongase "EgD9eS-L35G"

<400> SEQUENCE: 97

| | |
|---|---|
| atggaggtcg tgaacgaaat cgtctccatt ggccaggagg ttcttcccaa ggtcgactat | 60 |
| gctcagctct ggtctgatgc ctcgcactgc gaggtgctgt acggttccat cgccttcgtc | 120 |
| atcctgaagt tcacccttgg tcctctcgga cccaagggtc agtctcgaat gaagtttgtg | 180 |
| ttcaccaact acaacctgct catgtccatc tactcgctgg gctccttcct ctctatggcc | 240 |
| tacgccatgt acaccattgg tgtcatgtcc gacaactgcg agaaggcttt cgacaacaat | 300 |
| gtcttccgaa tcaccactca gctgttctac ctcagcaagt tcctcgagta cattgactcc | 360 |
| ttctatctgc ccctcatggg caagcctctg acctggttgc agttctttca ccatctcgga | 420 |

```
gctcctatgg acatgtggct gttctacaac taccgaaacg aagccgtttg gatctttgtg      480
ctgctcaacg gcttcattca ctggatcatg tacggctact attggacccg actgatcaag      540
ctcaagttcc ctatgcccaa gtccctgatt acttctatgc agatcattca gttcaacgtt      600
ggcttctaca tcgtctggaa gtaccggaac attcccgctc accgacaaga tggaatgaga      660
atgtttggct ggttttcaa ctacttctac gttggtactg tcctgtgtct gttcctcaac       720
ttctacgtgc agacctacat cgtccgaaag cacaagggag ccaaaaagat tcagtga         777
```

<210> SEQ ID NO 98
<211> LENGTH: 25
<212> TYPE: DNA
<213> ORGANISM: Artificial Sequence
<220> FEATURE:
<223> OTHER INFORMATION: Primer FBAIN-F

<400> SEQUENCE: 98

```
caagcggggg gcttgtctag ggtat                                              25
```

<210> SEQ ID NO 99
<211> LENGTH: 40
<212> TYPE: DNA
<213> ORGANISM: Artificial Sequence
<220> FEATURE:
<223> OTHER INFORMATION: Primer Y1026

<400> SEQUENCE: 99

```
tttgcggccg ctcactgaat cttttggct cccttgtgct                               40
```

<210> SEQ ID NO 100
<211> LENGTH: 777
<212> TYPE: DNA
<213> ORGANISM: Euglena gracilis
<220> FEATURE:
<221> NAME/KEY: CDS
<222> LOCATION: (1)..(777)
<223> OTHER INFORMATION: mutant delta-9 elongase
    "EgD9eS-L35G/W132T/I179R"

<400> SEQUENCE: 100

```
atg gag gtc gtg aac gaa atc gtc tcc att ggc cag gag gtt ctt ccc          48
Met Glu Val Val Asn Glu Ile Val Ser Ile Gly Gln Glu Val Leu Pro
1               5                   10                  15 aag gtc gac tat gct cag ctc tgg tct gat gcc tcg cac tgc gag gtg          96
Lys Val Asp Tyr Ala Gln Leu Trp Ser Asp Ala Ser His Cys Glu Val
                20                  25                  30 ctg tac ggg tcc atc gcc ttc gtc atc ctg aag ttc acc ctt ggt cct         144
Leu Tyr Gly Ser Ile Ala Phe Val Ile Leu Lys Phe Thr Leu Gly Pro
            35                  40                  45 ctc gga ccc aag ggt cag tct cga atg aag ttt gtg ttc acc aac tac         192
Leu Gly Pro Lys Gly Gln Ser Arg Met Lys Phe Val Phe Thr Asn Tyr
        50                  55                  60 aac ctg ctc atg tcc atc tac tcg ctg ggc tcc ttc ctc tct atg gcc         240
Asn Leu Leu Met Ser Ile Tyr Ser Leu Gly Ser Phe Leu Ser Met Ala
65                  70                  75                  80 tac gcc atg tac acc att ggt gtc atg tcc gac aac tgc gag aag gct         288
Tyr Ala Met Tyr Thr Ile Gly Val Met Ser Asp Asn Cys Glu Lys Ala
                85                  90                  95 ttc gac aac aat gtc ttc cga atc acc act cag ctg ttc tac ctc agc         336
Phe Asp Asn Asn Val Phe Arg Ile Thr Thr Gln Leu Phe Tyr Leu Ser
                100                 105                 110 aag ttc ctc gag tac att gac tcc ttc tat ctg ccc ctc atg ggc aag         384
```

```
Lys Phe Leu Glu Tyr Ile Asp Ser Phe Tyr Leu Pro Leu Met Gly Lys
            115                 120                 125 cct ctg acc acc ttg cag ttc ttt cac cat ctc gga gct cct atg gac     432
Pro Leu Thr Thr Leu Gln Phe Phe His His Leu Gly Ala Pro Met Asp
        130                 135                 140 atg tgg ctg ttc tac aac tac cga aac gaa gcc gtt tgg atc ttt gtg     480
Met Trp Leu Phe Tyr Asn Tyr Arg Asn Glu Ala Val Trp Ile Phe Val
145                 150                 155                 160 ctg ctc aac ggc ttc att cac tgg atc atg tac ggc tac tat tgg acc     528
Leu Leu Asn Gly Phe Ile His Trp Ile Met Tyr Gly Tyr Tyr Trp Thr
                165                 170                 175 cga ctg cga aag ctc aag ttc cct atg ccc aag tcc ctg att act tct     576
Arg Leu Arg Lys Leu Lys Phe Pro Met Pro Lys Ser Leu Ile Thr Ser
            180                 185                 190 atg cag atc att cag ttc aac gtt ggc ttc tac atc gtc tgg aag tac     624
Met Gln Ile Ile Gln Phe Asn Val Gly Phe Tyr Ile Val Trp Lys Tyr
        195                 200                 205 cgg aac att ccc tgc tac cga caa gat gga atg aga atg ttt ggc tgg     672
Arg Asn Ile Pro Cys Tyr Arg Gln Asp Gly Met Arg Met Phe Gly Trp
    210                 215                 220 ttt ttc aac tac ttc tac gtt ggt act gtc ctg tgt ctg ttc ctc aac     720
Phe Phe Asn Tyr Phe Tyr Val Gly Thr Val Leu Cys Leu Phe Leu Asn
225                 230                 235                 240 ttc tac gtg cag acc tac atc gtc cga aag cac aag gga gcc aaa aag     768
Phe Tyr Val Gln Thr Tyr Ile Val Arg Lys His Lys Gly Ala Lys Lys
                245                 250                 255 att cag tga                                                         777
Ile Gln

<210> SEQ ID NO 101
<211> LENGTH: 258
<212> TYPE: PRT
<213> ORGANISM: Euglena gracilis

<400> SEQUENCE: 101

Met Glu Val Val Asn Glu Ile Val Ser Ile Gly Gln Glu Val Leu Pro
1               5                   10                  15

Lys Val Asp Tyr Ala Gln Leu Trp Ser Asp Ala Ser His Cys Glu Val
            20                  25                  30

Leu Tyr Gly Ser Ile Ala Phe Val Ile Leu Lys Phe Thr Leu Gly Pro
        35                  40                  45

Leu Gly Pro Lys Gly Gln Ser Arg Met Lys Phe Val Phe Thr Asn Tyr
    50                  55                  60

Asn Leu Leu Met Ser Ile Tyr Ser Leu Gly Ser Phe Leu Ser Met Ala
65                  70                  75                  80

Tyr Ala Met Tyr Thr Ile Gly Val Met Ser Asp Asn Cys Glu Lys Ala
                85                  90                  95

Phe Asp Asn Asn Val Phe Arg Ile Thr Thr Gln Leu Phe Tyr Leu Ser
            100                 105                 110

Lys Phe Leu Glu Tyr Ile Asp Ser Phe Tyr Leu Pro Leu Met Gly Lys
        115                 120                 125

Pro Leu Thr Thr Leu Gln Phe Phe His His Leu Gly Ala Pro Met Asp
    130                 135                 140

Met Trp Leu Phe Tyr Asn Tyr Arg Asn Glu Ala Val Trp Ile Phe Val
145                 150                 155                 160

Leu Leu Asn Gly Phe Ile His Trp Ile Met Tyr Gly Tyr Tyr Trp Thr
                165                 170                 175
```

Arg Leu Arg Lys Leu Lys Phe Pro Met Pro Lys Ser Leu Ile Thr Ser
             180                 185                 190

Met Gln Ile Ile Gln Phe Asn Val Gly Phe Tyr Ile Val Trp Lys Tyr
         195                 200                 205

Arg Asn Ile Pro Cys Tyr Arg Gln Asp Gly Met Arg Met Phe Gly Trp
     210                 215                 220

Phe Phe Asn Tyr Phe Tyr Val Gly Thr Val Leu Cys Leu Phe Leu Asn
225                 230                 235                 240

Phe Tyr Val Gln Thr Tyr Ile Val Arg Lys His Lys Gly Ala Lys Lys
                 245                 250                 255

Ile Gln

<210> SEQ ID NO 102
<211> LENGTH: 7769
<212> TYPE: DNA
<213> ORGANISM: Artificial Sequence
<220> FEATURE:
<223> OTHER INFORMATION: Plasmid EgD9eS-L35G/W132T/I179R

<400> SEQUENCE: 102

| | | | | | |
|---|---|---|---|---|---|
| ggccgcaagt | gtggatgggg | aagtgagtgc | ccggttctgt | gtgcacaatt | ggcaatccaa | 60 |
| gatggatgga | ttcaacacag | ggatatagcg | agctacgtgg | tggtgcgagg | atatagcaac | 120 |
| ggatatttat | gtttgacact | tgagaatgta | cgatacaagc | actgtccaag | tacaatacta | 180 |
| aacatactgt | acatactcat | actcgtaccc | gggcaacggt | ttcacttgag | tgcagtggct | 240 |
| agtgctctta | ctcgtacagt | gtgcaatact | gcgtatcata | gtctttgatg | tatatcgtat | 300 |
| tcattcatgt | tagttgcgta | cgagccggaa | gcataaagtg | taaagcctgg | ggtgcctaat | 360 |
| gagtgagcta | actcacatta | attgcgttgc | gctcactgcc | cgctttccag | tcgggaaacc | 420 |
| tgtcgtgcca | gctgcattaa | tgaatcggcc | aacgcgcggg | gagaggcggt | ttgcgtattg | 480 |
| ggcgctcttc | cgcttcctcg | ctcactgact | cgctgcgctc | ggtcgttcgg | ctgcggcgag | 540 |
| cggtatcagc | tcactcaaag | gcggtaatac | ggttatccac | agaatcaggg | gataacgcag | 600 |
| gaaagaacat | gtgagcaaaa | ggccagcaaa | aggccaggaa | ccgtaaaaag | gccgcgttgc | 660 |
| tggcgttttt | ccataggctc | cgcccccctg | acgagcatca | caaaaatcga | cgctcaagtc | 720 |
| agaggtggcg | aaacccgaca | ggactataaa | gataccaggc | gtttccccct | ggaagctccc | 780 |
| tcgtgcgctc | tcctgttccg | accctgccgc | ttaccggata | cctgtccgcc | tttctccctt | 840 |
| cgggaagcgt | ggcgctttct | catagctcac | gctgtaggta | tctcagttcg | gtgtaggtcg | 900 |
| ttcgctccaa | gctgggctgt | gtgcacgaac | cccccgttca | gcccgaccgc | tgcgccttat | 960 |
| ccggtaacta | tcgtcttgag | tccaacccgg | taagacacga | cttatcgcca | ctggcagcag | 1020 |
| ccactggtaa | caggattagc | agagcgaggt | atgtaggcgg | tgctacagag | ttcttgaagt | 1080 |
| ggtggcctaa | ctacggctac | actagaagga | cagtatttgg | tatctgcgct | ctgctgaagc | 1140 |
| cagttacctt | cggaaaaaga | gttggtagct | cttgatccgg | caaacaaacc | accgctggta | 1200 |
| gcggtggttt | ttttgtttgc | aagcagcaga | ttacgcgcag | aaaaaaagga | tctcaagaag | 1260 |
| atcctttgat | cttttctacg | ggtctgacg | ctcagtggaa | cgaaaactca | cgttaaggga | 1320 |
| ttttggtcat | gagattatca | aaaaggatct | tcacctagat | ccttttaaat | taaaaatgaa | 1380 |
| gttttaaatc | aatctaaagt | atatatgagt | aaacttggtc | tgacagttac | caatgcttaa | 1440 |
| tcagtgaggc | acctatctca | gcgatctgtc | tatttcgttc | atccatagtt | gcctgactcc | 1500 |
| ccgtcgtgta | gataactacg | atacgggagg | gcttaccatc | tggccccagt | gctgcaatga | 1560 |

```
taccgcgaga cccacgctca ccggctccag atttatcagc aataaaccag ccagccggaa    1620
gggccgagcg cagaagtggt cctgcaactt tatccgcctc catccagtct attaattgtt    1680
gccgggaagc tagagtaagt agttcgccag ttaatagttt gcgcaacgtt gttgccattg    1740
ctacaggcat cgtggtgtca cgctcgtcgt ttggtatggc ttcattcagc tccggttccc    1800
aacgatcaag gcgagttaca tgatccccca tgttgtgcaa aaagcggtt agctccttcg     1860 gtcctccgat cgttgtcaga agtaagttgg ccgcagtgtt atcactcatg gttatggcag    1920
cactgcataa ttctcttact gtcatgccat ccgtaagatg cttttctgtg actggtgagt    1980
actcaaccaa gtcattctga gaatagtgta tgcggcgacc gagttgctct tgcccggcgt    2040
caatacggga taataccgcg ccacatagca gaactttaaa agtgctcatc attggaaaac    2100
gttcttcggg gcgaaaactc tcaaggatct taccgctgtt gagatccagt tcgatgtaac    2160
ccactcgtgc acccaactga tcttcagcat cttttacttt caccagcgtt tctgggtgag    2220
caaaaacagg aaggcaaaat gccgcaaaaa agggaataag ggcgacacgg aaatgttgaa    2280
tactcatact cttccttttt caatattatt gaagcattta tcagggttat tgtctcatga    2340
gcggatacat atttgaatgt atttagaaaa ataaacaaat aggggttccg cgcacatttc    2400
cccgaaaagt gccacctgac gcgccctgta gcggcgcatt aagcgcggcg ggtgtggtgg    2460
ttacgcgcag cgtgaccgct acacttgcca gcgccctagc gcccgctcct ttcgctttct    2520
tcccttcctt tctcgccacg ttcgccggct ttccccgtca gctctaaat cggggggctcc     2580 ctttagggtt ccgatttagt gctttacggc acctcgaccc caaaaaactt gattagggtg    2640
atggttcacg tagtgggcca tcgccctgat agacggtttt tcgccctttg acgttggagt    2700
ccacgttctt taatagtgga ctcttgttcc aaactggaac aacactcaac cctatctcgg    2760
tctattcttt tgatttataa gggattttgc cgatttcggc ctattggtta aaaaatgagc    2820
tgatttaaca aaaatttaac gcgaatttta acaaaatatt aacgcttaca atttccattc    2880
gccattcagg ctgcgcaact gttgggaagg gcgatcggtg cgggcctctt cgctattacg    2940
ccagctggcg aaagggggat gtgctgcaag gcgattaagt tgggtaacgc cagggttttc    3000
ccagtcacga cgttgtaaaa cgacggccag tgaattgtaa tacgactcac tatagggcga    3060
attgggtacc gggccccccc tcgaggtcga tggtgtcgat aagcttgata tcgaattcat    3120
gtcacacaaa ccgatcttcg cctcaaggaa acctaattct acatccgaga gactgccgag    3180
atccagtcta cactgattaa ttttcgggcc aataatttaa aaaaatcgtg ttatataata    3240
ttatatgtat tatatatata catcatgatg atactgacag tcatgtccca ttgctaaata    3300
gacagactcc atctgccgcc tccaactgat gttctcaata tttaaggggt catctcgcat    3360
tgtttaataa taaacagact ccatctaccg cctccaaatg atgttctcaa aatatattgt    3420
atgaacttat ttttattact tagtattatt agacaactta cttgctttat gaaaaacact    3480
tcctatttag gaaacaattt ataatggcag ttcgttcatt taacaattta tgtagaataa    3540
atgttataaa tgcgtatggg aaatcttaaa tatggatagc ataaatgata tctgcattgc    3600
ctaattcgaa atcaacagca acgaaaaaaa tcccttgtac aacataaata gtcatcgaga    3660
aatatcaact atcaaagaac agctattcac acgttactat tgagattatt attggacgag    3720
aatcacacac tcaactgtct ttctctcttc tagaaataca ggtacaagta tgtactattc    3780
tcattgttca tacttctagt catttcatcc cacatattcc ttggatttct ctccaatgaa    3840
tgacattcta tcttgcaaat tcaacaatta taataagata taccaaagta gcggtatagt    3900
ggcaatcaaa aagcttctct ggtgtgcttc tcgtatttat ttttattcta atgatccatt    3960
```

```
aaaggtatat atttatttct tgttatataa tccttttgtt tattacatgg gctggataca    4020
taaaggtatt ttgatttaat ttttttgctta aattcaatcc ccctcgttc agtgtcaact    4080
gtaatggtag gaaattacca tactttgaa gaagcaaaaa aaatgaaaga aaaaaaaat    4140
cgtatttcca ggttagacgt tccgcagaat ctagaatgcg gtatgcggta cattgttctt    4200
cgaacgtaaa agttgcgctc cctgagatat tgtacatttt tgcttttaca agtacaagta    4260
catcgtacaa ctatgtacta ctgttgatgc atccacaaca gtttgttttg tttttttttg    4320
tttttttttt ttctaatgat tcattaccgc tatgtatacc tacttgtact tgtagtaagc    4380
cgggttattg gcgttcaatt aatcatagac ttatgaatct gcacggtgtg cgctgcgagt    4440
tactttagc ttatgcatgc tacttgggtg taatattggg atctgttcgg aaatcaacgg    4500
atgctcaatc gatttcgaca gtaattaatt aagtcataca caagtcagct ttcttcgagc    4560
ctcatataag tataagtagt tcaacgtatt agcactgtac ccagcatctc cgtatcgaga    4620
aacacaacaa catgccccat tggacagatc atgcggatac acaggttgtg cagtatcata    4680
catactcgat cagacaggtc gtctgaccat catacaagct gaacaagcgc tccatacttg    4740
cacgctctct atatacacag ttaaattaca tatccatagt ctaacctcta acagttaatc    4800
ttctggtaag cctcccagcc agccttctgg tatcgcttgg cctcctcaat aggatctcgg    4860
ttctggccgt acagacctcg gccgacaatt atgatatccg ttccggtaga catgacatcc    4920
tcaacagttc ggtactgctg tccgagagcg tctcccttgt cgtcaagacc caccccgggg    4980
gtcagaataa gccagtcctc agagtcgccc ttaggtcggt tctgggcaat gaagccaacc    5040
acaaactcgg ggtcggatcg ggcaagctca atggtctgct tggagtactc gccagtggcc    5100
agagagccct tgcaagacag ctcggccagc atgagcagac ctctggccag cttctcgttg    5160
ggagagggga ctaggaactc cttgtactgg gagttctcgt agtcagagac gtcctccttc    5220
ttctgttcag agacagtttc ctcggcacca gctcgcaggc cagcaatgat tccggttccg    5280
ggtacaccgt gggcgttggt gatatcggac cactcggcga ttcggtgaca ccggtactgg    5340
tgcttgacag tgttgccaat atctgcgaac tttctgtcct cgaacaggaa gaaaccgtgc    5400
ttaagagcaa gttccttgag ggggagcaca gtgccggcgt aggtgaagtc gtcaatgatg    5460
tcgatatggg ttttgatcat gcacacataa ggtccgacct tatcggcaag ctcaatgagc    5520
tccttggtgg tggtaacatc cagagaagca cacaggttgg ttttcttggc tgccacgagc    5580
ttgagcactc gagcggcaaa ggcggacttg tggacgttag ctcgagcttc gtaggagggc    5640
attttggtgg tgaagaggag actgaaataa atttagtctg cagaactttt tatcggaacc    5700
ttatctgggg cagtgaagta tatgttatgg taatagttac gagttagttg aacttataga    5760
tagactggac tatacggcta tcggtccaaa ttagaaagaa cgtcaatggc tctctgggcg    5820
tcgcctttgc cgacaaaaat gtgatcatga tgaaagccag caatgacgtt gcagctgata    5880
ttgttgtcgg ccaaccgcgc cgaaaacgca gctgtcagac ccacagcctc caacgaagaa    5940
tgtatcgtca aagtgatcca agcacactca tagttggagt cgtactccaa aggcggcaat    6000
gacgagtcag acagatactc gtcgacgttt aaacagtgta cgcagatcta ctatagagga    6060
acatttaaat tgccccggag aagacggcca ggccgcctag atgacaaatt caacaactca    6120
cagctgactt tctgccattg ccactagggg ggggcctttt tatatggcca agccaagctc    6180
tccacgtcgg ttgggctgca cccaacaata aatgggtagg gttgcaccaa caaagggatg    6240
ggatggggggg tagaagatac gaggataacg gggctcaatg gcacaaataa gaacgaatac    6300
```

```
tgccattaag actcgtgatc cagcgactga caccattgca tcatctaagg gcctcaaaac   6360
tacctcggaa ctgctgcgct gatctggaca ccacagaggt tccgagcact ttaggttgca   6420
ccaaatgtcc caccaggtgc aggcagaaaa cgctggaaca gcgtgtacag tttgtcttaa   6480
caaaaagtga gggcgctgag gtcgagcagg gtggtgtgac ttgttatagc ctttagagct   6540
gcgaaagcgc gtatggattt ggctcatcag gccagattga gggtctgtgg acacatgtca   6600
tgttagtgta cttcaatcgc ccctggata taggcccgac aataggccgt ggcctcattt    6660
ttttgccttc cgcacatttc cattgctcga tacccacacc ttgcttctcc tgcacttgcc   6720
aaccttaata ctggtttaca ttgaccaaca tcttacaagc gggggcttg tctagggtat    6780 atataaacag tggctctccc aatcggttgc cagtctcttt tttcctttct ttccccacag   6840
attcgaaatc taaactacac atcacagaat tccgagccgt gagtatccac gacaagatca   6900
gtgtcgagac gacgcgtttt gtgtaatgac acaatccgaa agtcgctagc aacacacact   6960
ctctacacaa actaacccag ctctggtacc atggaggtcg tgaacgaaat cgtctccatt   7020
ggccaggagg ttcttcccaa ggtcgactat gctcagctct ggtctgatgc ctcgcactgc   7080
gaggtgctgt acgggtccat cgccttcgtc atcctgaagt tcacccttgg tcctctcgga   7140
cccaagggtc agtctcgaat gaagtttgtg ttcaccaact acaacctgct catgtccatc   7200
tactcgctgg gctccttcct ctctatggcc tacgccatgt acaccattgg tgtcatgtcc   7260
gacaactgcg agaaggcttt cgacaacaat gtcttccgaa tcaccactca gctgttctac   7320
ctcagcaagt cctcgagta cattgactcc ttctatctgc ccctcatggg caagcctctg   7380
accaccttgc agttctttca ccatctcgga gctcctatgg acatgtggct gttctacaac   7440
taccgaaacg aagccgtttg gatctttgtg ctgctcaacg gcttcattca ctggatcatg   7500
tacggctact attggacccg actgcgaaag ctcaagttcc ctatgcccaa gtccctgatt   7560
acttctatgc agatcattca gttcaacgtt ggcttctaca tcgtctggaa gtaccggaac   7620
attccctgct accgacaaga tggaatgaga atgtttggct ggttttcaa ctacttctac    7680 gttggtactg tcctgtgtct gttcctcaac ttctacgtgc agacctacat cgtccgaaag   7740
cacaagggag ccaaaaagat tcagtgagc                                     7769
```

<210> SEQ ID NO 103
<211> LENGTH: 777
<212> TYPE: DNA
<213> ORGANISM: Euglena gracilis
<220> FEATURE:
<221> NAME/KEY: CDS
<222> LOCATION: (1)..(777)
<223> OTHER INFORMATION: mutant delta-9 elongase
    "EgD9eS-S9D/L35G/Y84C/I179R"

<400> SEQUENCE: 103

```
atg gag gtc gtg aac gaa atc gtc gac att ggc cag gag gtt ctt ccc    48
Met Glu Val Val Asn Glu Ile Val Asp Ile Gly Gln Glu Val Leu Pro
1               5                   10                  15 aag gtc gac tat gct cag ctc tgg tct gat gcc tcg cac tgc gag gtg    96
Lys Val Asp Tyr Ala Gln Leu Trp Ser Asp Ala Ser His Cys Glu Val
            20                  25                  30 ctg tac ggg tcc atc gcc ttc gtc atc ctg aag ttc acc ctt ggt cct    144
Leu Tyr Gly Ser Ile Ala Phe Val Ile Leu Lys Phe Thr Leu Gly Pro
        35                  40                  45 ctc gga ccc aag ggt cag tct cga atg aag ttt gtg ttc acc aac tac    192
Leu Gly Pro Lys Gly Gln Ser Arg Met Lys Phe Val Phe Thr Asn Tyr
    50                  55                  60
```

```
aac ctg ctc atg tcc atc tac tcg ctg ggc tcc ttc ctc tct atg gcc    240
Asn Leu Leu Met Ser Ile Tyr Ser Leu Gly Ser Phe Leu Ser Met Ala
 65                  70                  75                  80 tac gcc atg tgt acc att ggt gtc atg tcc gac aac tgc gag aag gct    288
Tyr Ala Met Cys Thr Ile Gly Val Met Ser Asp Asn Cys Glu Lys Ala
                 85                  90                  95 ttc gac aac aat gtc ttc cga atc acc act cag ctg ttc tac ctc agc    336
Phe Asp Asn Asn Val Phe Arg Ile Thr Thr Gln Leu Phe Tyr Leu Ser
            100                 105                 110 aag ttc ctc gag tac att gac tcc ttc tat ctg ccc ctc atg ggc aag    384
Lys Phe Leu Glu Tyr Ile Asp Ser Phe Tyr Leu Pro Leu Met Gly Lys
        115                 120                 125 cct ctg acc tgg ttg cag ttc ttt cac cat ctc gga gct cct atg gac    432
Pro Leu Thr Trp Leu Gln Phe Phe His His Leu Gly Ala Pro Met Asp
    130                 135                 140 atg tgg ctg ttc tac aac tac cga aac gaa gcc gtt tgg atc ttt gtg    480
Met Trp Leu Phe Tyr Asn Tyr Arg Asn Glu Ala Val Trp Ile Phe Val
145                 150                 155                 160 ctg ctc aac ggc ttc att cac tgg atc atg tac ggc tac tat tgg acc    528
Leu Leu Asn Gly Phe Ile His Trp Ile Met Tyr Gly Tyr Tyr Trp Thr
                165                 170                 175 cga ctg cga aag ctc aag ttc cct atg ccc aag tcc ctg att act tct    576
Arg Leu Arg Lys Leu Lys Phe Pro Met Pro Lys Ser Leu Ile Thr Ser
            180                 185                 190 atg cag atc att cag ttc aac gtt ggc ttc tac atc gtc tgg aag tac    624
Met Gln Ile Ile Gln Phe Asn Val Gly Phe Tyr Ile Val Trp Lys Tyr
        195                 200                 205 cgg aac att ccc tgc tac cga caa gat gga atg aga atg ttt ggc tgg    672
Arg Asn Ile Pro Cys Tyr Arg Gln Asp Gly Met Arg Met Phe Gly Trp
    210                 215                 220 ttt ttc aac tac ttc tac gtt ggt act gtc ctg tgt ctg ttc ctc aac    720
Phe Phe Asn Tyr Phe Tyr Val Gly Thr Val Leu Cys Leu Phe Leu Asn
225                 230                 235                 240 ttc tac gtg cag acc tac atc gtc cga aag cac aag gga gcc aaa aag    768
Phe Tyr Val Gln Thr Tyr Ile Val Arg Lys His Lys Gly Ala Lys Lys
                245                 250                 255 att cag tga                                                        777
Ile Gln

<210> SEQ ID NO 104
<211> LENGTH: 258
<212> TYPE: PRT
<213> ORGANISM: Euglena gracilis

<400> SEQUENCE: 104

Met Glu Val Val Asn Glu Ile Val Asp Ile Gly Gln Glu Val Leu Pro
  1               5                  10                  15

Lys Val Asp Tyr Ala Gln Leu Trp Ser Asp Ala Ser His Cys Glu Val
                 20                  25                  30

Leu Tyr Gly Ser Ile Ala Phe Val Ile Leu Lys Phe Thr Leu Gly Pro
             35                  40                  45

Leu Gly Pro Lys Gly Gln Ser Arg Met Lys Phe Val Phe Thr Asn Tyr
         50                  55                  60

Asn Leu Leu Met Ser Ile Tyr Ser Leu Gly Ser Phe Leu Ser Met Ala
 65                  70                  75                  80

Tyr Ala Met Cys Thr Ile Gly Val Met Ser Asp Asn Cys Glu Lys Ala
                 85                  90                  95

Phe Asp Asn Asn Val Phe Arg Ile Thr Thr Gln Leu Phe Tyr Leu Ser
            100                 105                 110
```

Lys Phe Leu Glu Tyr Ile Asp Ser Phe Tyr Leu Pro Leu Met Gly Lys
            115                 120                 125

Pro Leu Thr Trp Leu Gln Phe Phe His His Leu Gly Ala Pro Met Asp
        130                 135                 140

Met Trp Leu Phe Tyr Asn Tyr Arg Asn Glu Ala Val Trp Ile Phe Val
145                 150                 155                 160

Leu Leu Asn Gly Phe Ile His Trp Ile Met Gly Tyr Tyr Trp Thr
                165                 170                 175

Arg Leu Arg Lys Leu Lys Phe Pro Met Pro Lys Ser Leu Ile Thr Ser
            180                 185                 190

Met Gln Ile Ile Gln Phe Asn Val Gly Phe Tyr Ile Val Trp Lys Tyr
            195                 200                 205

Arg Asn Ile Pro Cys Tyr Arg Gln Asp Gly Met Arg Met Phe Gly Trp
        210                 215                 220

Phe Phe Asn Tyr Phe Tyr Val Gly Thr Val Leu Cys Leu Phe Leu Asn
225                 230                 235                 240

Phe Tyr Val Gln Thr Tyr Ile Val Arg Lys His Lys Gly Ala Lys Lys
                245                 250                 255

Ile Gln

<210> SEQ ID NO 105
<211> LENGTH: 7769
<212> TYPE: DNA
<213> ORGANISM: Artificial Sequence
<220> FEATURE:
<223> OTHER INFORMATION: Plasmid EgD9eS-S9D/L35G/Y84C/I179R

<400> SEQUENCE: 105

| | | | | | |
|---|---|---|---|---|---|
| ggccgcaagt | gtggatgggg | aagtgagtgc | ccggttctgt | gtgcacaatt | ggcaatccaa | 60 |
| gatggatgga | ttcaacacag | ggatatagcg | agctacgtgg | tggtgcgagg | atatagcaac | 120 |
| ggatatttat | gtttgacact | tgagaatgta | cgatacaagc | actgtccaag | tacaatacta | 180 |
| aacatactgt | acatactcat | actcgtaccc | gggcaacggt | ttcacttgag | tgcagtggct | 240 |
| agtgctctta | ctcgtacagt | gtgcaatact | gcgtatcata | gtctttgatg | tatatcgtat | 300 |
| tcattcatgt | tagttgcgta | cgagccggaa | gcataaagtg | taaagcctgg | ggtgcctaat | 360 |
| gagtgagcta | actcacatta | attgcgttgc | gctcactgcc | cgctttccag | tcgggaaacc | 420 |
| tgtcgtgcca | gctgcattaa | tgaatcggcc | aacgcgcggg | gagaggcggt | ttgcgtattg | 480 |
| ggcgctcttc | cgcttcctcg | ctcactgact | cgctgcgctc | ggtcgttcgg | ctgcggcgag | 540 |
| cggtatcagc | tcactcaaag | gcggtaatac | ggttatccac | agaatcaggg | gataacgcag | 600 |
| gaaagaacat | gtgagcaaaa | ggccagcaaa | aggccaggaa | ccgtaaaaag | gccgcgttgc | 660 |
| tggcgttttt | ccataggctc | cgcccccctg | acgagcatca | caaaaatcga | cgctcaagtc | 720 |
| agaggtggcg | aaacccgaca | ggactataaa | gataccaggc | gtttccccct | ggaagctccc | 780 |
| tcgtgcgctc | tcctgttccg | accctgccgc | ttaccggata | cctgtccgcc | tttctccctt | 840 |
| cgggaagcgt | ggcgctttct | catagctcac | gctgtaggta | tctcagttcg | gtgtaggtcg | 900 |
| ttcgctccaa | gctgggctgt | gtgcacgaac | cccccgttca | gcccgaccgc | tgcgccttat | 960 |
| ccggtaacta | tcgtcttgag | tccaacccgg | taagacacga | cttatcgcca | ctggcagcag | 1020 |
| ccactggtaa | caggattagc | agagcgaggt | atgtaggcgg | tgctacagag | ttcttgaagt | 1080 |
| ggtggcctaa | ctacggctac | actagaagga | cagtatttgg | tatctgcgct | ctgctgaagc | 1140 |
| cagttacctt | cggaaaaaga | gttggtagct | cttgatccgg | caaacaaacc | accgctggta | 1200 |

```
gcggtggttt ttttgtttgc aagcagcaga ttacgcgcag aaaaaaagga tctcaagaag    1260
atcctttgat cttttctacg gggtctgacg ctcagtggaa cgaaaactca cgttaaggga    1320
ttttggtcat gagattatca aaaggatct tcacctagat ccttttaaat taaaaatgaa     1380
gttttaaatc aatctaaagt atatatgagt aaacttggtc tgacagttac caatgcttaa    1440
tcagtgaggc acctatctca gcgatctgtc tatttcgttc atccatagtt gcctgactcc    1500
ccgtcgtgta gataactacg atacgggagg gcttaccatc tggccccagt gctgcaatga    1560
taccgcgaga cccacgctca ccggctccag atttatcagc aataaaccag ccagccggaa    1620
gggccgagcg cagaagtggt cctgcaactt tatccgcctc catccagtct attaattgtt    1680
gccgggaagc tagagtaagt agttcgccag ttaatagttt gcgcaacgtt gttgccattg    1740
ctacaggcat cgtggtgtca cgctcgtcgt ttggtatggc ttcattcagc tccgttccc     1800 aacgatcaag gcgagttaca tgatccccca tgttgtgcaa aaaagcggtt agctccttcg    1860
gtcctccgat cgttgtcaga agtaagttgg ccgcagtgtt atcactcatg gttatggcag    1920
cactgcataa ttctcttact gtcatgccat ccgtaagatg cttttctgtg actggtgagt    1980
actcaaccaa gtcattctga gaatagtgta tgcggcgacc gagttgctct tgcccggcgt    2040
caatacggga taataccgcg ccacatagca gaactttaaa agtgctcatc attggaaaac    2100
gttcttcggg gcgaaaactc tcaaggatct taccgctgtt gagatccagt tcgatgtaac    2160
ccactcgtgc acccaactga tcttcagcat cttttacttt caccagcgtt tctgggtgag    2220
caaaaacagg aaggcaaaat gccgcaaaaa agggaataag ggcgacacgg aaatgttgaa    2280
tactcatact cttccttttt caatattatt gaagcattta tcagggttat tgtctcatga    2340
gcggatacat atttgaatgt atttagaaaa ataaacaaat aggggttccg cgcacatttc    2400
cccgaaaagt gccacctgac gcgccctgta gcggcgcatt aagcgcggcg ggtgtggtgg    2460
ttacgcgcag cgtgaccgct acacttgcca gcgccctagc gcccgctcct ttcgctttct    2520
tcccttcctt tctcgccacg ttcgccggct ttccccgtca gctctaaat cggggggctcc    2580 ctttagggtt ccgatttagt gctttacggc acctcgaccc caaaaaactt gattagggtg    2640
atggttcacg tagtgggcca tcgccctgat agacggtttt tcgccctttg acgttggagt    2700
ccacgttctt taatagtgga ctcttgttcc aaactggaac aacactcaac cctatctcgg    2760
tctattcttt tgatttataa gggattttgc cgatttcggc ctattggtta aaaaatgagc    2820
tgatttaaca aaaatttaac gcgaattttta caaaatatt aacgcttaca atttccattc    2880
gccattcagg ctgcgcaact gttgggaagg gcgatcggtg cgggcctctt cgctattacg    2940
ccagctggcg aaagggggat gtgctgcaag gcgattaagt tgggtaacgc cagggttttc    3000
ccagtcacga cgttgtaaaa cgacggccag tgaattgtaa tacgactcac tatagggcga    3060
attgggtacc gggccccccc tcgaggtcga tggtgtcgat aagcttgata tcgaattcat    3120
gtcacacaaa ccgatcttcg cctcaaggaa acctaattct acatccgaga gactgccgag    3180
atccagtcta cactgattaa ttttcgggcc aataatttaa aaaaatcgtg ttatataata    3240
ttatatgtat tatatatata catcatgatg atactgacag tcatgtccca ttgctaaata    3300
gacagactcc atctgccgcc tccaactgat gttctcaata tttaaggggt catctcgcat    3360
tgtttaataa taaacagact ccatctaccg cctccaaatg atgttctcaa aatatattgt    3420
atgaacttat ttttattact tagtattatt agacaactta cttgctttat gaaaaacact    3480
tcctatttag gaaacaattt ataatggcag ttcgttcatt taacaattta tgtagaataa    3540
```

```
atgttataaa tgcgtatggg aaatcttaaa tatggatagc ataaatgata tctgcattgc   3600
ctaattcgaa atcaacagca acgaaaaaaa tcccttgtac aacataaata gtcatcgaga   3660
aatatcaact atcaaagaac agctattcac acgttactat tgagattatt attggacgag   3720
aatcacacac tcaactgtct ttctctcttc tagaaataca ggtacaagta tgtactattc   3780
tcattgttca tacttctagt catttcatcc cacatattcc ttggatttct ctccaatgaa   3840
tgacattcta tcttgcaaat tcaacaatta taataagata taccaaagta gcggtatagt   3900
ggcaatcaaa aagcttctct ggtgtgcttc tcgtatttat ttttattcta atgatccatt   3960
aaaggtatat atttatttct tgttatataa tcctttttgtt tattacatgg gctggataca   4020
taaaggtatt ttgatttaat tttttgctta aattcaatcc cccctcgttc agtgtcaact   4080
gtaatggtag gaaattacca tactttgaa gaagcaaaaa aaatgaaaga aaaaaaaaat    4140
cgtatttcca ggttagacgt tccgcagaat ctagaatgcg gtatgcggta cattgttctt   4200
cgaacgtaaa agttgcgctc cctgagatat tgtacatttt tgcttttaca agtacaagta   4260
catcgtacaa ctatgtacta ctgttgatgc atccacaaca gtttgttttg tttttttttg   4320
tttttttttt ttctaatgat tcattaccgc tatgtatacc tacttgtact tgtagtaagc   4380
cgggttattg gcgttcaatt aatcatagac ttatgaatct gcacggtgtg cgctgcgagt   4440
tacttttagc ttatgcatgc tacttggtg taatattggg atctgttcgg aaatcaacgg   4500
atgctcaatc gatttcgaca gtaattaatt aagtcataca caagtcagct ttcttcgagc   4560
ctcatataag tataagtagt tcaacgtatt agcactgtac ccagcatctc cgtatcgaga   4620
aacacaacaa catgccccat tggacagatc atgcggatac acaggttgtg cagtatcata   4680
catactcgat cagacaggtc gtctgaccat catacaagct gaacaagcgc tccatacttg   4740
cacgctctct atatacacag ttaaattaca tatccatagt ctaacctcta acagttaatc   4800
ttctggtaag cctcccagcc agccttctgg tatcgcttgg cctcctcaat aggatctcgg   4860
ttctggccgt acagacctcg gccgacaatt atgatatccg ttccggtaga catgacatcc   4920
tcaacagttc ggtactgctg tccgagagcg tctcccttgt cgtcaagacc caccccgggg   4980
gtcagaataa gccagtcctc agagtcgccc ttaggtcggt tctgggcaat gaagccaacc   5040
acaaactcgg ggtcggatcg ggcaagctca atggtctgct tggagtactc gccagtggcc   5100
agagagccct tgcaagacag ctcggccagc atgagcagac ctctggccag cttctcgttg   5160
ggagagggga ctaggaactc cttgtactgg gagttctcgt agtcagagac gtcctccttc   5220
ttctgttcag agacagtttc ctcggcacca gctcgcaggc cagcaatgat tccggttccg   5280
ggtacaccgt gggcgttggt gatatcggac cactcggcga ttcggtgaca ccggtactgg   5340
tgcttgacag tgttgccaat atctgcgaac tttctgtcct cgaacaggaa gaaaccgtgc   5400
ttaagagcaa gttccttgag ggggagcaca gtgccggcgt aggtgaagtc gtcaatgatg   5460
tcgtatgggg ttttgatcat gcacacataa ggtccgacct tatcggcaag ctcaatgagc   5520
tccttggtgg tggtaacatc cagagaagca cacaggttgg ttttcttggc tgccacgagc   5580
ttgagcactc gagcggcaaa ggcggacttg tggacgttag ctcgagcttc gtaggagggc   5640
attttggtgt tgaagaggag actgaaataa atttagtctg cagaacttttt tatcggaacc   5700 ttatctgggg cagtgaagta tatgttatgg taatagttac gagttagttg aacttataga   5760
tagactggac tatacggcta tcggtccaaa ttagaaagaa cgtcaatggc tctctgggcg   5820
tcgcctttgc cgacaaaaat gtgatcatga tgaaagccag caatgacgtt gcagctgata   5880
ttgttgtcgg ccaaccgcgc cgaaaacgca gctgtcagac ccacagcctc caacgaagaa   5940
```

```
tgtatcgtca aagtgatcca agcacactca tagttggagt cgtactccaa aggcggcaat    6000
gacgagtcag acagatactc gtcgacgttt aaacagtgta cgcagatcta ctatagagga    6060
acatttaaat tgccccggag aagacggcca ggccgcctag atgacaaatt caacaactca    6120
cagctgactt tctgccattg ccactagggg ggggcctttt tatatggcca agccaagctc    6180
tccacgtcgg ttgggctgca cccaacaata aatgggtagg gttgcaccaa caaagggatg    6240
ggatgggggg tagaagatac gaggataacg gggctcaatg gcacaaataa gaacgaatac    6300
tgccattaag actcgtgatc cagcgactga caccattgca tcatctaagg gcctcaaaac    6360
tacctcggaa ctgctgcgct gatctggaca ccacagaggt tccgagcact ttaggttgca    6420
ccaaatgtcc caccaggtgc aggcagaaaa cgctggaaca gcgtgtacag tttgtcttaa    6480
caaaaagtga gggcgctgag gtcgagcagg gtggtgtgac ttgttatagc ctttagagct    6540
gcgaaagcgc gtatggattt ggctcatcag gccagattga gggtctgtgg acacatgtca    6600
tgttagtgta cttcaatcgc ccctggata tagccccgac aataggccgt ggcctcattt    6660
ttttgccttc cgcacatttc cattgctcga tacccacacc ttgcttctcc tgcacttgcc    6720
aaccttaata ctggtttaca ttgaccaaca tcttacaagc gggggcttg tctagggtat    6780
atataaacag tggctctccc aatcggttgc cagtctcttt tttcctttct ttccccacag    6840
attcgaaatc taaactacac atcacagaat tccgagccgt gagtatccac gacaagatca    6900
gtgtcgagac gacgcgtttt gtgtaatgac acaatccgaa agtcgctagc aacacacact    6960
ctctacacaa actaacccag ctctggtacc atggaggtcg tgaacgaaat cgtcgacatt    7020
ggccaggagg ttcttcccaa ggtcgactat gctcagctct ggtctgatgc ctcgcactgc    7080
gaggtgctgt acgggtccat cgccttcgtc atcctgaagt tcacccttgg tcctctcgga    7140
cccaagggtc agtctcgaat gaagtttgtg ttcaccaact acaacctgct catgtccatc    7200
tactcgctgg gctccttcct ctctatggcc tacgccatgt gtaccattgg tgtcatgtcc    7260
gacaactgcg agaaggcttt cgacaacaat gtcttccgaa tcaccactca gctgttctac    7320
ctcagcaagt cctcgagta cattgactcc ttctatctgc ccctcatggg caagcctctg    7380
acctggttgc agttctttca ccatctcgga gctcctatgg acatgtggct gttctacaac    7440
taccgaaacg aagccgtttg gatctttgtg ctgctcaacg gcttcattca ctggatcatg    7500
tacggctact attggacccg actgcgaaag ctcaagttcc ctatgcccaa gtccctgatt    7560
acttctatgc agatcattca gttcaacgtt ggcttctaca tcgtctggaa gtaccggaac    7620
attccctgct accgacaaga tggaatgaga atgtttggct ggttttttcaa ctacttctac    7680
gttggtactg tcctgtgtct gttcctcaac ttctacgtgc agacctacat cgtccgaaag    7740
cacaagggag ccaaaaagat tcagtgagc                                      7769
```

<210> SEQ ID NO 106
<211> LENGTH: 777
<212> TYPE: DNA
<213> ORGANISM: Euglena gracilis
<220> FEATURE:
<221> NAME/KEY: CDS
<222> LOCATION: (1)..(777)
<223> OTHER INFORMATION: mutant delta-9 elongase
    "EgD9eS-L35G/Y84C/I179R/Q244N"

<400> SEQUENCE: 106

```
atg gag gtc gtg aac gaa atc gtc tcc att ggc cag gag gtt ctt ccc      48
Met Glu Val Val Asn Glu Ile Val Ser Ile Gly Gln Glu Val Leu Pro
1               5                   10                  15
```

```
aag gtc gac tat gct cag ctc tgg tct gat gcc tcg cac tgc gag gtg        96
Lys Val Asp Tyr Ala Gln Leu Trp Ser Asp Ala Ser His Cys Glu Val
         20                  25                  30 ctg tac ggg tcc atc gcc ttc gtc atc ctg aag ttc acc ctt ggt cct       144
Leu Tyr Gly Ser Ile Ala Phe Val Ile Leu Lys Phe Thr Leu Gly Pro
     35                  40                  45 ctc gga ccc aag ggt cag tct cga atg aag ttt gtg ttc acc aac tac       192
Leu Gly Pro Lys Gly Gln Ser Arg Met Lys Phe Val Phe Thr Asn Tyr
 50                  55                  60 aac ctg ctc atg tcc atc tac tcg ctg ggc tcc ttc ctc tct atg gcc       240
Asn Leu Leu Met Ser Ile Tyr Ser Leu Gly Ser Phe Leu Ser Met Ala
 65                  70                  75                  80 tac gcc atg tgt acc att ggt gtc atg tcc gac aac tgc gag aag gct       288
Tyr Ala Met Cys Thr Ile Gly Val Met Ser Asp Asn Cys Glu Lys Ala
                 85                  90                  95 ttc gac aac aat gtc ttc cga atc acc act cag ctg ttc tac ctc agc       336
Phe Asp Asn Asn Val Phe Arg Ile Thr Thr Gln Leu Phe Tyr Leu Ser
            100                 105                 110 aag ttc ctc gag tac att gac tcc ttc tat ctg ccc ctc atg ggc aag       384
Lys Phe Leu Glu Tyr Ile Asp Ser Phe Tyr Leu Pro Leu Met Gly Lys
        115                 120                 125 cct ctg acc tgg ttg cag ttc ttt cac cat ctc gga gct cct atg gac       432
Pro Leu Thr Trp Leu Gln Phe Phe His His Leu Gly Ala Pro Met Asp
    130                 135                 140 atg tgg ctg ttc tac aac tac cga aac gaa gcc gtt tgg atc ttt gtg       480
Met Trp Leu Phe Tyr Asn Tyr Arg Asn Glu Ala Val Trp Ile Phe Val
145                 150                 155                 160 ctc ctc aac ggc ttc att cac tgg atc atg tac ggc tac tat tgg acc       528
Leu Leu Asn Gly Phe Ile His Trp Ile Met Tyr Gly Tyr Tyr Trp Thr
                165                 170                 175 cga ctg cga aag ctc aag ttc cct atg ccc aag tcc ctg att act tct       576
Arg Leu Arg Lys Leu Lys Phe Pro Met Pro Lys Ser Leu Ile Thr Ser
            180                 185                 190 atg cag atc att cag ttc aac gtt ggc ttc tac atc gtc tgg aag tac       624
Met Gln Ile Ile Gln Phe Asn Val Gly Phe Tyr Ile Val Trp Lys Tyr
        195                 200                 205 cgg aac att ccc tgc tac cga caa gat gga atg aga atg ttt ggc tgg       672
Arg Asn Ile Pro Cys Tyr Arg Gln Asp Gly Met Arg Met Phe Gly Trp
    210                 215                 220 ttt ttc aac tac ttc tac gtt ggt act gtc ctg tgt ctg ttc ctc aac       720
Phe Phe Asn Tyr Phe Tyr Val Gly Thr Val Leu Cys Leu Phe Leu Asn
225                 230                 235                 240 ttc tac gtg aac acc tac atc gtc cga aag cac aag gga gcc aaa aag       768
Phe Tyr Val Asn Thr Tyr Ile Val Arg Lys His Lys Gly Ala Lys Lys
                245                 250                 255 att cag tga                                                            777
Ile Gln <210> SEQ ID NO 107
<211> LENGTH: 258
<212> TYPE: PRT
<213> ORGANISM: Euglena gracilis

<400> SEQUENCE: 107

Met Glu Val Val Asn Glu Ile Val Ser Ile Gly Gln Glu Val Leu Pro
 1               5                  10                  15

Lys Val Asp Tyr Ala Gln Leu Trp Ser Asp Ala Ser His Cys Glu Val
             20                  25                  30

Leu Tyr Gly Ser Ile Ala Phe Val Ile Leu Lys Phe Thr Leu Gly Pro
```

```
                    35                  40                  45
Leu Gly Pro Lys Gly Gln Ser Arg Met Lys Phe Val Phe Thr Asn Tyr
 50                  55                  60

Asn Leu Leu Met Ser Ile Tyr Ser Leu Gly Ser Phe Leu Ser Met Ala
 65                  70                  75                  80

Tyr Ala Met Cys Thr Ile Gly Val Met Ser Asp Asn Cys Glu Lys Ala
                 85                  90                  95

Phe Asp Asn Asn Val Phe Arg Ile Thr Thr Gln Leu Phe Tyr Leu Ser
                100                 105                 110

Lys Phe Leu Glu Tyr Ile Asp Ser Phe Tyr Leu Pro Leu Met Gly Lys
            115                 120                 125

Pro Leu Thr Trp Leu Gln Phe Phe His His Leu Gly Ala Pro Met Asp
130                 135                 140

Met Trp Leu Phe Tyr Asn Tyr Arg Asn Glu Ala Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Arg Lys Leu Lys Phe Pro Met Pro Lys Ser Leu Ile Thr Ser
            180                 185                 190

Met Gln Ile Ile Gln Phe Asn Val Gly Phe Tyr Ile Val Trp Lys Tyr
        195                 200                 205

Arg Asn Ile Pro Cys Tyr Arg Gln Asp Gly Met Arg Met Phe Gly Trp
210                 215                 220

Phe Phe Asn Tyr Phe Tyr Val Gly Thr Val Leu Cys Leu Phe Leu Asn
225                 230                 235                 240

Phe Tyr Val Asn Thr Tyr Ile Val Arg Lys His Lys Gly Ala Lys Lys
                245                 250                 255

Ile Gln

<210> SEQ ID NO 108
<211> LENGTH: 7769
<212> TYPE: DNA
<213> ORGANISM: Artificial Sequence
<220> FEATURE:
<223> OTHER INFORMATION: Plasmid EgD9eS-L35G/Y84C/I179R/Q244N

<400> SEQUENCE: 108
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc gggcaacggt ttcacttgag tgcagtggct     240
agtgctctta ctcgtacagt gtgcaatact gcgtatcata gtctttgatg tatatcgtat     300
tcattcatgt tagttgcgta cgagccggaa gcataaagtg taaagcctgg ggtgcctaat     360
gagtgagcta actcacatta ttgcgttgc gctcactgcc cgctttccag tcgggaaacc      420
tgtcgtgcca gctgcattaa tgaatcggcc aacgcgcggg gagaggcggt ttgcgtattg     480
ggcgctcttc cgcttcctcg ctcactgact cgctgcgctc ggtcgttcgg ctgcggcgag     540
cggtatcagc tcactcaaag gcggtaatac ggttatccac agaatcaggg gataacgcag     600
gaaagaacat gtgagcaaaa ggccagcaaa aggccaggaa ccgtaaaaag gccgcgttgc     660
tggcgttttt ccataggctc cgcccccctg acgagcatca caaaaatcga cgctcaagtc     720
agaggtggcg aaacccgaca ggactataaa gataccaggc gtttccccct ggaagctccc     780
```

```
tcgtgcgctc tcctgttccg accctgccgc ttaccggata cctgtccgcc tttctcccttt      840
cgggaagcgt ggcgctttct catagctcac gctgtaggta tctcagttcg gtgtaggtcg       900
ttcgctccaa gctgggctgt gtgcacgaac cccccgttca gcccgaccgc tgcgccttat       960
ccggtaacta tcgtcttgag tccaacccgg taagacacga cttatcgcca ctggcagcag      1020
ccactggtaa caggattagc agagcgaggt atgtaggcgg tgctacagag ttcttgaagt      1080
ggtggcctaa ctacggctac actagaagga cagtatttgg tatctgcgct ctgctgaagc      1140
cagttacctt cggaaaaaga gttggtagct cttgatccgg caaacaaacc accgctggta      1200
gcggtggttt ttttgtttgc aagcagcaga ttacgcgcag aaaaaaagga tctcaagaag      1260
atcctttgat cttttctacg gggtctgacg ctcagtggaa cgaaaactca cgttaaggga      1320
ttttggtcat gagattatca aaaggatct tcacctagat ccttttaaat taaaaatgaa       1380
gttttaaatc aatctaaagt atatatgagt aaacttggtc tgacagttac caatgcttaa      1440
tcagtgaggc acctatctca gcgatctgtc tatttcgttc atccatagtt gcctgactcc      1500
ccgtcgtgta gataactacg atacgggagg gcttaccatc tggccccagt gctgcaatga      1560
taccgcgaga cccacgctca ccggctccag atttatcagc aataaaccag ccagccggaa      1620
gggccgagcg cagaagtggt cctgcaactt tatccgcctc catccagtct attaattgtt      1680
gccgggaagc tagagtaagt agttcgccag ttaatagttt gcgcaacgtt gttgccattg      1740
ctacaggcat cgtggtgtca cgctcgtcgt ttggtatggc ttcattcagc tccgttccc      1800
aacgatcaag gcgagttaca tgatccccca tgttgtgcaa aaaagcggtt agctccttcg      1860
gtcctccgat cgttgtcaga agtaagttgg ccgcagtgtt atcactcatg gttatggcag      1920
cactgcataa ttctcttact gtcatgccat ccgtaagatg cttttctgtg actggtgagt      1980
actcaaccaa gtcattctga aatagtgta tgcggcgacc gagttgctct tgcccggcgt       2040
caatacggga taataccgcg ccacatagca gaactttaaa agtgctcatc attggaaaac      2100
gttcttcggg gcgaaaactc tcaaggatct taccgctgtt gagatccagt tcgatgtaac      2160
ccactcgtgc acccaactga tcttcagcat cttttacttt caccagcgtt tctgggtgag      2220
caaaaacagg aaggcaaaat gccgcaaaaa agggaataag ggcgacacgg aaatgttgaa      2280
tactcatact cttccttttt caatattatt gaagcattta tcagggttat tgtctcatga      2340
gcggatacat atttgaatgt atttagaaaa ataaacaaat aggggttccg cgcacatttc      2400
cccgaaaagt gccacctgac cgccctgta gcggcgcatt aagcgcggcg ggtgtggtgg       2460
ttacgcgcag cgtgaccgct acacttgcca gcgccctagc gcccgctcct ttcgctttct      2520
tcccttcctt tctcgccacg ttcgccggct ttccccgtca gctctaaat cggggggctcc      2580
ctttagggtt ccgatttagt gctttacggc acctcgaccc caaaaaactt gattagggtg      2640
atggttcacg tagtgggcca tcgccctgat agacggtttt tcgccctttg acgttggagt      2700
ccacgttctt taatagtgga ctcttgttcc aaactggaac aacactcaac cctatctcgg      2760
tctattcttt tgatttataa gggattttgc cgatttcggc ctattggtta aaaaatgagc      2820
tgatttaaca aaaatttaac gcgaatttta acaaaatatt aacgcttaca atttccattc      2880
gccattcagg ctgcgcaact gttgggaagg gcgatcggtg cgggcctctt cgctattacg      2940
ccagctggcg aaagggggat gtgctgcaag gcgattaagt tgggtaacgc cagggttttc      3000
ccagtcacga cgttgtaaaa cgacggccag tgaattgtaa tacgactcac tatagggcga      3060
attgggtacc gggccccccc tcgaggtcga tggtgtcgat aagcttgata tcgaattcat      3120
gtcacacaaa ccgatcttcg cctcaaggaa acctaattct acatccgaga gactgccgag      3180
```

-continued

```
atccagtcta cactgattaa ttttcgggcc aataatttaa aaaaatcgtg ttatataata   3240
ttatatgtat tatatatata catcatgatg atactgacag tcatgtccca ttgctaaata   3300
gacagactcc atctgccgcc tccaactgat gttctcaata tttaagggt catctcgcat    3360 tgtttaataa taaacagact ccatctaccg cctccaaatg atgttctcaa aatatattgt   3420
atgaacttat ttttattact tagtattatt agacaactta cttgctttat gaaaaacact   3480
tcctatttag gaaacaattt ataatggcag ttcgttcatt taacaattta tgtagaataa   3540
atgttataaa tgcgtatggg aaatcttaaa tatggatagc ataaatgata tctgcattgc   3600
ctaattcgaa atcaacagca acgaaaaaaa tcccttgtac aacataaata gtcatcgaga   3660
aatatcaact atcaaagaac agctattcac acgttactat tgagattatt attggacgag   3720
aatcacacac tcaactgtct ttctctcttc tagaaataca ggtacaagta tgtactattc   3780
tcattgttca tacttctagt catttcatcc cacatattcc ttggatttct ctccaatgaa   3840
tgacattcta tcttgcaaat tcaacaatta taataagata taccaaagta gcggtatagt   3900
ggcaatcaaa aagcttctct ggtgtgcttc tcgtatttat ttttattcta atgatccatt   3960
aaaggtatat atttatttct tgttatataa tccttttgtt tattacatgg gctggataca   4020
taaaggtatt ttgatttaat ttttgctta aattcaatcc cccctcgttc agtgtcaact    4080
gtaatggtag gaaattacca tacttttgaa gaagcaaaaa aaatgaaaga aaaaaaaat    4140 cgtatttcca ggttagacgt tccgcagaat ctagaatgcg gtatgcggta cattgttctt   4200
cgaacgtaaa agttgcgctc cctgagatat tgtacatttt tgcttttaca agtacaagta   4260
catcgtacaa ctatgtacta ctgttgatgc atccacaaca gtttgtttg tttttttttg     4320 ttttttttt ttctaatgat tcattaccgc tatgtatacc tacttgtact tgtagtaagc     4380
cgggttattg gcgttcaatt aatcatagac ttatgaatct gcacggtgtg cgctgcgagt   4440
tacttttagc ttatgcatgc tacttgggtg taatattggg atctgttcgg aaatcaacgg   4500
atgctcaatc gatttcgaca gtaattaatt aagtcataca caagtcagct tcttcgagc    4560 ctcatataag tataagtagt tcaacgtatt agcactgtac ccagcatctc cgtatcgaga   4620
aacacaacaa catgccccat tggacagatc atgcggatac acaggttgtg cagtatcata   4680
catactcgat cagacaggtc gtctgaccat catacaagct gaacaagcgc tccatacttg   4740
cacgctctct atatacacag ttaaattaca tatccatagt ctaacctcta acagttaatc   4800
ttctggtaag cctcccagcc agccttctgg tatcgcttgg cctcctcaat aggatctcgg   4860
ttctggccgt acagacctcg gccgacaatt atgatatccg ttccggtaga catgacatcc   4920
tcaacagttc ggtactgctg tccgagagcg tctcccttgt cgtcaagacc caccccggg   4980 gtcagaataa gccagtcctc agagtcgccc ttaggtcggt tctgggcaat gaagccaacc   5040
acaaactcgg ggtcggatcg ggcaagctca atggtctgct ggagtactc gccagtggcc    5100 agagagccct tgcaagacag ctcggccagc atgagcagac ctctggccag cttctcgttg   5160
ggagagggga ctaggaactc cttgtactgg gagttctcgt agtcagagac gtcctccttc   5220
ttctgttcag agacagtttc ctcggcacca gctcgcaggc cagcaatgat tccggttccg   5280
ggtacaccgt gggcgttggt gatatcggac cactcggcga ttcggtgaca ccggtactgg   5340
tgcttgacag tgttgccaat atctgcgaac tttctgtcct cgaacaggaa gaaaccgtgc   5400
ttaagagcaa gttccttgag ggggagcaca gtgccggcgt aggtgaagtc gtcaatgatg   5460
tcgatatggg ttttgatcat gcacacataa ggtccgacct tatcggcaag ctcaatgagc   5520
```

```
tccttggtgg tggtaacatc cagagaagca cacaggttgg ttttcttggc tgccacgagc    5580
ttgagcactc gagcggcaaa ggcggacttg tggacgttag ctcgagcttc gtaggagggc    5640
attttggtgg tgaagaggag actgaaataa atttagtctg cagaactttt tatcggaacc    5700
ttatctgggg cagtgaagta tatgttatgg taatagttac gagttagttg aacttataga    5760
tagactggac tatacggcta tcggtccaaa ttagaaagaa cgtcaatggc tctctgggcg    5820
tcgcctttgc cgacaaaaat gtgatcatga tgaaagccag caatgacgtt gcagctgata    5880
ttgttgtcgg ccaaccgcgc cgaaaacgca gctgtcagac ccacagcctc aacgaagaa     5940
tgtatcgtca aagtgatcca agcacactca tagttggagt cgtactccaa aggcggcaat    6000
gacgagtcag acagatactc gtcgacgttt aaacagtgta cgcagatcta ctatagagga    6060
acatttaaat tgccccggag aagacggcca ggccgcctag atgacaaatt caacaactca    6120
cagctgactt tctgccattg ccactagggg ggggcctttt tatatggcca agccaagctc    6180
tccacgtcgg ttgggctgca cccaacaata aatgggtagg gttgcaccaa caaagggatg    6240
ggatggggg tagaagatac gaggataacg gggctcaatg gcacaaataa gaacgaatac     6300
tgccattaag actcgtgatc cagcgactga caccattgca tcatctaagg gcctcaaaac    6360
tacctcggaa ctgctgcgct gatctggaca ccacagaggt tccgagcact ttaggttgca    6420
ccaaatgtcc caccaggtgc aggcagaaaa cgctggaaca gcgtgtacag tttgtcttaa    6480
caaaagtga gggcgctgag gtcgagcagg gtggtgtgac ttgttatagc ctttagagct    6540
gcgaaagcgc gtatggattt ggctcatcag gccagattga gggtctgtgg acacatgtca    6600
tgttagtgta cttcaatcgc cccctggata tagccccgac aataggccgt ggcctcattt    6660
ttttgccttc cgcacatttc cattgctcga tacccacacc ttgcttctcc tgcacttgcc    6720
aaccttaata ctggtttaca ttgaccaaca tcttacaagc ggggggcttg tctagggtat    6780
atataaacag tggctctccc aatcggttgc cagtctcttt tttcctttct ttccccacag    6840
attcgaaatc taaactacac atcacagaat tccgagccgt gagtatccac gacaagatca    6900
gtgtcgagac gacgcgtttt gtgtaatgac acaatccgaa agtcgctagc aacacacact    6960
ctctacacaa actaacccag ctctggtacc atggaggtcg tgaacgaaat cgtctccatt    7020
ggccaggagg ttcttcccaa ggtcgactat gctcagctct ggtctgatgc ctcgcactgc    7080
gaggtgctgt acgggtccat cgccttcgtc atcctgaagt tcacccttgg tcctctcgga    7140
cccaagggtc agtctcgaat gaagtttgtg ttcaccaact acaacctgct catgtccatc    7200
tactcgctgg gctccttcct ctctatggcc tacgccatgt gtaccattgg tgtcatgtcc    7260
gacaactgcg agaaggcttt cgacaacaat gtcttccgaa tcaccactca gctgttctac    7320
ctcagcaagt tcctcgagta cattgactcc ttctatctgc ccctcatggg caagcctctg    7380
acctggttgc agttctttca ccatctcgga gctcctatgg acatgtggct gttctacaac    7440
taccgaaacg aagccgtttg gatctttgtg ctgctcaacg gcttcattca ctggatcatg    7500
tacggctact attggacccg actgcgaaag ctcaagttcc ctatgcccaa gtccctgatt    7560
acttctatgc agatcattca gttcaacgtt ggcttctaca tcgtctggaa gtaccggaac    7620
attccctgct accgacaaga tggaatgaga atgtttggct ggtttttcaa ctacttctac    7680
gttggtactg tcctgtgtct gttcctcaac ttctacgtga acacctacat cgtccgaaag    7740
cacaagggag ccaaaaagat tcagtgagc                                      7769
```

<210> SEQ ID NO 109
<211> LENGTH: 777

<212> TYPE: DNA
<213> ORGANISM: Euglena gracilis
<220> FEATURE:
<221> NAME/KEY: CDS
<222> LOCATION: (1)..(777)
<223> OTHER INFORMATION: mutant delta-9 elongase
    "EgD9eS-A21V/L35G/W132T/I179R/Q244N"

<400> SEQUENCE: 109

```
atg gag gtc gtg aac gaa atc gtc tcc att ggc cag gag gtt ctt ccc      48
Met Glu Val Val Asn Glu Ile Val Ser Ile Gly Gln Glu Val Leu Pro
1               5                  10                  15 aag gtc gac tat gtg cag ctc tgg tct gat gcc tcg cac tgc gag gtg      96
Lys Val Asp Tyr Val Gln Leu Trp Ser Asp Ala Ser His Cys Glu Val
            20                  25                  30 ctg tac ggg tcc atc gcc ttc gtc atc ctg aag ttc acc ctt ggt cct     144
Leu Tyr Gly Ser Ile Ala Phe Val Ile Leu Lys Phe Thr Leu Gly Pro
        35                  40                  45 ctc gga ccc aag ggt cag tct cga atg aag ttt gtg ttc acc aac tac     192
Leu Gly Pro Lys Gly Gln Ser Arg Met Lys Phe Val Phe Thr Asn Tyr
    50                  55                  60 aac ctg ctc atg tcc atc tac tcg ctg ggc tcc ttc ctc tct atg gcc     240
Asn Leu Leu Met Ser Ile Tyr Ser Leu Gly Ser Phe Leu Ser Met Ala
65                  70                  75                  80 tac gcc atg tac acc att ggt gtc atg tcc gac aac tgc gag aag gct     288
Tyr Ala Met Tyr Thr Ile Gly Val Met Ser Asp Asn Cys Glu Lys Ala
                85                  90                  95 ttc gac aac aat gtc ttc cga atc acc act cag ctg ttc tac ctc agc     336
Phe Asp Asn Asn Val Phe Arg Ile Thr Thr Gln Leu Phe Tyr Leu Ser
            100                 105                 110 aag ttc ctc gag tac att gac tcc ttc tat ctg ccc ctc atg ggc aag     384
Lys Phe Leu Glu Tyr Ile Asp Ser Phe Tyr Leu Pro Leu Met Gly Lys
        115                 120                 125 cct ctg acc acc ttg cag ttc ttt cac cat ctc gga gct cct atg gac     432
Pro Leu Thr Thr Leu Gln Phe Phe His His Leu Gly Ala Pro Met Asp
    130                 135                 140 atg tgg ctg ttc tac aac tac cga aac gaa gcc gtt tgg atc ttt gtg     480
Met Trp Leu Phe Tyr Asn Tyr Arg Asn Glu Ala Val Trp Ile Phe Val
145                 150                 155                 160 ctg ctc aac ggc ttc att cac tgg atc atg tac ggc tac tat tgg acc     528
Leu Leu Asn Gly Phe Ile His Trp Ile Met Tyr Gly Tyr Tyr Trp Thr
                165                 170                 175 cga ctg cga aag ctc aag ttc cct atg ccc aag tcc ctg att act tct     576
Arg Leu Arg Lys Leu Lys Phe Pro Met Pro Lys Ser Leu Ile Thr Ser
            180                 185                 190 atg cag atc att cag ttc aac gtt ggc ttc tac atc gtc tgg aag tac     624
Met Gln Ile Ile Gln Phe Asn Val Gly Phe Tyr Ile Val Trp Lys Tyr
        195                 200                 205 cgg aac att ccc tgc tac cga caa gat gga atg aga atg ttt ggc tgg     672
Arg Asn Ile Pro Cys Tyr Arg Gln Asp Gly Met Arg Met Phe Gly Trp
    210                 215                 220 ttt ttc aac tac ttc tac gtt ggt act gtc ctg tgt ctg ttc ctc aac     720
Phe Phe Asn Tyr Phe Tyr Val Gly Thr Val Leu Cys Leu Phe Leu Asn
225                 230                 235                 240 ttc tac gtg aac acc tac atc gtc cga aag cac aag gga gcc aaa aag     768
Phe Tyr Val Asn Thr Tyr Ile Val Arg Lys His Lys Gly Ala Lys Lys
                245                 250                 255 att cag tga                                                         777
Ile Gln
```

<210> SEQ ID NO 110

-continued

```
<211> LENGTH: 258
<212> TYPE: PRT
<213> ORGANISM: Euglena gracilis

<400> SEQUENCE: 110

Met Glu Val Val Asn Glu Ile Val Ser Ile Gly Gln Glu Val Leu Pro
1               5                   10                  15

Lys Val Asp Tyr Val Gln Leu Trp Ser Asp Ala Ser His Cys Glu Val
                20                  25                  30

Leu Tyr Gly Ser Ile Ala Phe Val Ile Leu Lys Phe Thr Leu Gly Pro
            35                  40                  45

Leu Gly Pro Lys Gly Gln Ser Arg Met Lys Val Phe Thr Asn Tyr
    50                  55                  60

Asn Leu Leu Met Ser Ile Tyr Ser Leu Gly Ser Phe Leu Ser Met Ala
65                  70                  75                  80

Tyr Ala Met Tyr Thr Ile Gly Val Met Ser Asp Asn Cys Glu Lys Ala
                85                  90                  95

Phe Asp Asn Asn Val Phe Arg Ile Thr Thr Gln Leu Tyr Leu Ser
            100                 105                 110

Lys Phe Leu Glu Tyr Ile Asp Ser Phe Tyr Leu Pro Leu Met Gly Lys
            115                 120                 125

Pro Leu Thr Thr Leu Gln Phe Phe His His Leu Gly Ala Pro Met Asp
    130                 135                 140

Met Trp Leu Phe Tyr Asn Tyr Arg Asn Glu Ala Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Arg Lys Leu Lys Phe Pro Met Pro Lys Ser Leu Ile Thr Ser
            180                 185                 190

Met Gln Ile Ile Gln Phe Asn Val Gly Phe Tyr Ile Val Trp Lys Tyr
            195                 200                 205

Arg Asn Ile Pro Cys Tyr Arg Gln Asp Gly Met Arg Met Phe Gly Trp
    210                 215                 220

Phe Phe Asn Tyr Phe Tyr Val Gly Thr Val Leu Cys Leu Phe Leu Asn
225                 230                 235                 240

Phe Tyr Val Asn Thr Tyr Ile Val Arg Lys His Lys Gly Ala Lys Lys
                245                 250                 255

Ile Gln

<210> SEQ ID NO 111
<211> LENGTH: 7769
<212> TYPE: DNA
<213> ORGANISM: Artificial Sequence
<220> FEATURE:
<223> OTHER INFORMATION: Plasmid EgD9eS-A21V/L35G/W132T/I179R/Q244N

<400> SEQUENCE: 111
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta    180
aacatactgt acatactcat actcgtaccc gggcaacggt ttcacttgag tgcagtggct    240
agtgctctta ctcgtacagt gtgcaatact gcgtatcata gtctttgatg tatatcgtat    300
tcattcatgt tagttgcgta cgagccggaa gcataaagtg taaagcctgg ggtgcctaat    360
gagtgagcta actcacatta attgcgttgc gctcactgcc cgctttccag tcgggaaacc    420
```

```
tgtcgtgcca gctgcattaa tgaatcggcc aacgcgcggg gagaggcggt ttgcgtattg    480
ggcgctcttc cgcttcctcg ctcactgact cgctgcgctc ggtcgttcgg ctgcggcgag    540
cggtatcagc tcactcaaag gcggtaatac ggttatccac agaatcaggg gataacgcag    600
gaaagaacat gtgagcaaaa ggccagcaaa aggccaggaa ccgtaaaaag gccgcgttgc    660
tggcgttttt ccataggctc cgcccccctg acgagcatca caaaaatcga cgctcaagtc    720
agaggtggcg aaacccgaca ggactataaa gataccaggc gtttccccct ggaagctccc    780
tcgtgcgctc tcctgttccg accctgccgc ttaccggata cctgtccgcc tttctccctt    840
cgggaagcgt ggcgctttct catagctcac gctgtaggta tctcagttcg gtgtaggtcg    900
ttcgctccaa gctgggctgt gtgcacgaac cccccgttca gcccgaccgc tgcgccttat    960
ccggtaacta tcgtcttgag tccaacccgg taagacacga cttatcgcca ctggcagcag   1020
ccactggtaa caggattagc agagcgaggt atgtaggcgg tgctacagag ttcttgaagt   1080
ggtggcctaa ctacggctac actagaagga cagtatttgg tatctgcgct ctgctgaagc   1140
cagttacctt cggaaaaaga gttggtagct cttgatccgg caaacaaacc accgctggta   1200
gcggtggttt ttttgtttgc aagcagcaga ttacgcgcag aaaaaaagga tctcaagaag   1260
atcctttgat cttttctacg gggtctgacg ctcagtggaa cgaaaactca cgttaaggga   1320
ttttggtcat gagattatca aaaaggatct cacctagat ccttttaaat taaaaatgaa   1380
gttttaaatc aatctaaagt atatatgagt aaacttggtc tgacagttac caatgcttaa   1440
tcagtgaggc acctatctca gcgatctgtc tatttcgttc atccatagtt gcctgactcc   1500
ccgtcgtgta gataactacg atacgggagg gcttaccatc tggccccagt gctgcaatga   1560
taccgcgaga cccacgctca ccggctccag atttatcagc aataaaccag ccagccggaa   1620
gggccgagcg cagaagtggt cctgcaactt tatccgcctc catccagtct attaattgtt   1680
gccgggaagc tagagtaagt agttcgccag ttaatagttt gcgcaacgtt gttgccattg   1740
ctacaggcat cgtggtgtca cgctcgtcgt ttggtatggc ttcattcagc tccggttccc   1800
aacgatcaag gcgagttaca tgatccccca tgttgtgcaa aaaagcggtt agctccttcg   1860
gtcctccgat cgttgtcaga agtaagttgg ccgcagtgtt atcactcatg gttatggcag   1920
cactgcataa ttctcttact gtcatgccat ccgtaagatg cttttctgtg actggtgagt   1980
actcaaccaa gtcattctga aatagtgta tgcggcgacc gagttgctct tgcccggcgt   2040
caatacggga taataccgcg ccacatagca gaactttaaa agtgctcatc attggaaaac   2100
gttcttcggg gcgaaaactc tcaaggatct taccgctgtt gagatccagt tcgatgtaac   2160
ccactcgtgc acccaactga tcttcagcat cttttacttt caccagcgtt tctgggtgag   2220
caaaaacagg aaggcaaaat gccgcaaaaa agggaataag ggcgacacgg aaatgttgaa   2280
tactcatact cttccttttt caatattatt gaagcattta tcagggttat tgtctcatga   2340
gcggatacat atttgaatgt atttagaaaa ataaacaaat aggggttccg cgcacatttc   2400
cccgaaaagt gccacctgac gcgccctgta gcggcgcatt aagcgcggcg ggtgtggtgg   2460
ttacgcgcag cgtgaccgct acacttgcca gcgccctagc gcccgctcct ttcgctttct   2520
tcccttcctt tctcgccacg ttcgccggct ttccccgtca agctctaaat cggggctcc    2580 ctttagggtt ccgatttagt gctttacggc acctcgaccc caaaaaactt gattagggtg   2640
atggttcacg tagtgggcca tcgccctgat agacggtttt tcgccctttg acgttggagt   2700
ccacgttctt taatagtgga ctcttgttcc aaactggaac aacactcaac cctatctcgg   2760
```

```
tctattctttt tgatttataa gggattttgc cgatttcggc ctattggtta aaaaatgagc    2820
tgatttaaca aaaatttaac gcgaatttta acaaaatatt aacgcttaca atttccattc    2880
gccattcagg ctgcgcaact gttgggaagg gcgatcggtg cgggcctctt cgctattacg    2940
ccagctggcg aaaggggat gtgctgcaag gcgattaagt tgggtaacgc cagggttttc    3000
ccagtcacga cgttgtaaaa cgacggccag tgaattgtaa tacgactcac tatagggcga    3060
attgggtacc gggccccccc tcgaggtcga tggtgtcgat aagcttgata tcgaattcat    3120
gtcacacaaa ccgatcttcg cctcaaggaa acctaattct acatccgaga gactgccgag    3180
atccagtcta cactgattaa ttttcgggcc aataatttaa aaaaatcgtg ttatataata    3240
ttatatgtat tatatatata catcatgatg atactgacag tcatgtccca ttgctaaata    3300
gacagactcc atctgccgcc tccaactgat gttctcaata tttaagggt catctcgcat    3360
tgtttaataa taaacagact ccatctaccg cctccaaatg atgttctcaa aatatattgt    3420
atgaacttat ttttattact tagtattatt agacaactta cttgctttat gaaaaacact    3480
tcctatttag gaaacaattt ataatggcag ttcgttcatt taacaattta tgtagaataa    3540
atgttataaa tgcgtatggg aaatcttaaa tatggatagc ataaatgata tctgcattgc    3600
ctaattcgaa atcaacagca acgaaaaaaa tcccttgtac aacataaaata gtcatcgaga    3660
aatatcaact atcaaagaac agctattcac acgttactat tgagattatt attggacgag    3720
aatcacacac tcaactgtct ttctctcttc tagaaataca ggtacaagta tgtactattc    3780
tcattgttca tacttctagt catttcatcc cacatattcc ttggatttct ctccaatgaa    3840
tgacattcta tcttgcaaat tcaacaatta taataagata taccaaagta gcggtatagt    3900
ggcaatcaaa aagcttctct ggtgtgcttc tcgtatttat ttttattcta atgatccatt    3960
aaaggtatat atttatttct tgttatataa tccttttgtt tattacatgg gctggataca    4020
taaaggtatt ttgatttaat tttttgctta aattcaatcc cccctcgttc agtgtcaact    4080
gtaatggtag gaaattacca tacttttgaa gaagcaaaaa aaatgaaaga aaaaaaaaat    4140
cgtatttcca ggttagacgt tccgcagaat ctagaatgcg gtatgcggta cattgttctt    4200
cgaacgtaaa agttgcgctc cctgagatat tgtacatttt tgcttttaca agtacaagta    4260
catcgtacaa ctatgtacta ctgttgatgc atccacaaca gtttgttttg tttttttttg    4320
ttttttttt ttctaatgat tcattaccgc tatgtatacc tacttgtact tgtagtaagc    4380
cgggttattg gcgttcaatt aatcatagac ttatgaatct gcacggtgtg cgctgcgagt    4440
tactttttagc ttatgcatgc tacttgggtg taatattggg atctgttcgg aaatcaacgg    4500
atgctcaatc gatttcgaca gtaattaatt aagtcataca caagtcagct ttcttcgagc    4560
ctcatataag tataagtagt tcaacgtatt agcactgtac ccagcatctc cgtatcgaga    4620
aacacaacaa catgccccat tggacagatc atgcggatac acaggttgtg cagtatcata    4680
catactcgat cagacaggtc gtctgaccat catacaagct gaacaagcgc tccatacttg    4740
cacgctctct atatacacag ttaaattaca tatccatagt ctaacctcta acagttaatc    4800
ttctggtaag cctcccagcc agccttctgg tatcgcttgg cctcctcaat aggatctcgg    4860
ttctggccgt acagacctcg gccgacaatt atgatatccg ttccggtaga catgacatcc    4920
tcaacagttc ggtactgctg tccgagagcg tctccctttgt cgtcaagacc caccccgggg    4980
gtcagaataa gccagtcctc agagtcgccc ttaggtcggt tctgggcaat gaagccaacc    5040
acaaactcgg ggtcggatcg ggcaagctca atggtctgct tggagtactc gccagtggcc    5100
agagagccct tgcaagacag ctcggccagc atgagcagac ctctggccag cttctcgttg    5160
```

```
ggagagggga ctaggaactc cttgtactgg gagttctcgt agtcagagac gtcctccttc    5220
ttctgttcag agacagtttc ctcggcacca gctcgcaggc cagcaatgat tccggttccg    5280
ggtacaccgt gggcgttggt gatatcggac cactcggcga ttcggtgaca ccggtactgg    5340
tgcttgacag tgttgccaat atctgcgaac tttctgtcct cgaacaggaa gaaaccgtgc    5400
ttaagagcaa gttccttgag ggggagcaca gtgccggcgt aggtgaagtc gtcaatgatg    5460
tcgatatggg ttttgatcat gcacacataa ggtccgacct tatcggcaag ctcaatgagc    5520
tccttggtgg tggtaacatc cagagaagca cacaggttgg ttttcttggc tgccacgagc    5580
ttgagcactc gagcggcaaa ggcggacttg tggacgttag ctcgagcttc gtaggagggc    5640
attttggtgg tgaagaggag actgaaataa atttagtctg cagaactttt tatcggaacc    5700
ttatctgggg cagtgaagta tatgttatgg taatagttac gagttagttg aacttataga    5760
tagactggac tatacggcta tcggtccaaa ttagaaagaa cgtcaatggc tctctgggcg    5820
tcgcctttgc cgacaaaaat gtgatcatga tgaaagccag caatgacgtt gcagctgata    5880
ttgttgtcgg ccaaccgcgc cgaaaacgca gctgtcagac ccacagcctc caacgaagaa    5940
tgtatcgtca aagtgatcca agcacactca tagttggagt cgtactccaa aggcggcaat    6000
gacgagtcag acagatactc gtcgacgttt aaacagtgta cgcagatcta ctatagagga    6060
acatttaaat tgccccggag aagacggcca ggccgcctag atgacaaatt caacaactca    6120
cagctgactt tctgccattg ccactagggg ggggcctttt tatatggcca agccaagctc    6180
tccacgtcgg ttgggctgca cccaacaata aatgggtagg gttgcaccaa caaagggatg    6240
ggatgggggg tagaagatac gaggataacg gggctcaatg gcacaaataa gaacgaatac    6300
tgccattaag actcgtgatc cagcgactga caccattgca tcatctaagg gcctcaaaac    6360
tacctcggaa ctgctgcgct gatctggaca ccacagaggt tccgagcact ttaggttgca    6420
ccaaatgtcc caccaggtgc aggcagaaaa cgctggaaca gcgtgtacag tttgtcttaa    6480
caaaaagtga gggcgctgag gtcgagcagg gtggtgtgac ttgttatagc ctttagagct    6540
gcgaaagcgc gtatggattt ggctcatcag gccagattga gggtctgtgg acacatgtca    6600
tgttagtgta cttcaatcgc cccctggata tagccccgac aataggccgt ggcctcattt    6660
ttttgccttc cgcacatttc cattgctcga tacccacacc ttgcttctcc tgcacttgcc    6720
aaccttaata ctggtttaca ttgaccaaca tcttacaagc gggggggcttg tctagggtat    6780 atataaacag tggctctccc aatcggttgc cagtctcttt tttcctttct ttccccacag    6840
attcgaaatc taaactacac atcacagaat tccgagccgt gagtatccac gacaagatca    6900
gtgtcgagac gacgcgtttt gtgtaatgac acaatccgaa agtcgctagc aacacacact    6960
ctctacacaa actaacccag ctctggtacc atggaggtcg tgaacgaaat cgtctccatt    7020
ggccaggagg ttcttcccaa ggtcgactat gtgcagctct ggtctgatgc ctcgcactgc    7080
gaggtgctgt acgggtccat cgccttcgtc atcctgaagt tcaccgttgg tcctctcgga    7140
cccaagggtc agtctcgaat gaagtttgtg ttcaccaact acaacctgct catgtccatc    7200
tactcgctgg gctccttcct ctctatggcc tacgccatgt acaccattgg tgtcatgtcc    7260
gacaactgcg agaaggcttt cgacaacaat gtcttccgaa tcaccactca gctgttctac    7320
ctcagcaagt tcctcgagta cattgactcc ttctatctgc ccctcatggg caagcctctg    7380
accaccttgc agttctttca ccatctcgga gctcctatgg acatgtggct gttctacaac    7440
taccgaaacg aagccgtttg gatctttgtg ctgctcaacg gcttcattca ctggatcatg    7500
```

```
tacggctact attggacccg actgcgaaag ctcaagttcc ctatgccaa gtccctgatt    7560 acttctatgc agatcattca gttcaacgtt ggcttctaca tcgtctggaa gtaccggaac    7620
attccctgct accgacaaga tggaatgaga atgtttggct ggtttttcaa ctacttctac    7680
gttggtactg tcctgtgtct gttcctcaac ttctacgtga acacctacat cgtccgaaag    7740
cacaagggag ccaaaaagat tcagtgagc                                      7769
```